United States Patent
Hangauer, Jr.

(10) Patent No.: US 7,838,542 B2
(45) Date of Patent: Nov. 23, 2010

(54) BICYCLIC COMPOSITIONS AND METHODS FOR MODULATING A KINASE CASCADE

(75) Inventor: David G. Hangauer, Jr., East Amherst, NY (US)

(73) Assignee: Kinex Pharmaceuticals, LLC, Buffalo, NY (US)

( * ) Notice: Subject to any disclaimer, the term of this patent is extended or adjusted under 35 U.S.C. 154(b) by 247 days.

(21) Appl. No.: 11/480,163

(22) Filed: Jun. 29, 2006

(65) Prior Publication Data

US 2008/0004241 A1 Jan. 3, 2008

(51) Int. Cl.
*A61K 31/404* (2006.01)
(52) U.S. Cl. .................................................. 514/359
(58) Field of Classification Search .................. 514/359
See application file for complete search history.

(56) References Cited

U.S. PATENT DOCUMENTS

| | | | |
|---|---|---|---|
| 5,464,861 A | 11/1995 | Dobrusin et al. | |
| 5,532,167 A | 7/1996 | Cantley et al. | |
| 5,552,534 A | 9/1996 | Hirschmann et al. | |
| 5,648,378 A | 7/1997 | Huang | |
| 5,705,585 A | 1/1998 | Hogan, Jr. et al. | |
| 5,736,412 A | 4/1998 | Zambias et al. | |
| 6,011,175 A | 1/2000 | Sebti et al. | |
| 6,420,338 B1 | 7/2002 | Schneider et al. | 514/12 |
| 6,552,066 B1 | 4/2003 | Sharpe et al. | 514/419 |
| 6,747,053 B2 * | 6/2004 | Gabriel et al. | 514/419 |
| 7,005,445 B2 | 2/2006 | Hangauer, Jr. et al. | 514/419 |
| 7,070,936 B1 | 7/2006 | Hangauer, Jr. et al. | 435/7.1 |
| 7,129,225 B2 | 10/2006 | Nicotera et al. | 514/64 |
| 7,141,596 B2 * | 11/2006 | Combs et al. | 514/372 |
| 2003/0016615 A1 | 1/2003 | Lee et al. | 369/112.24 |
| 2004/0019015 A1 | 1/2004 | Nicotera et al. | 514/64 |
| 2005/0256159 A1 * | 11/2005 | Barton et al. | 514/314 |
| 2006/0030544 A1 | 2/2006 | Hangauer, Jr. et al. | 514/80 |
| 2006/0089401 A1 | 4/2006 | Hangauer, Jr. et al. | 514/419 |
| 2006/0122197 A1 * | 6/2006 | Yao et al. | 514/256 |
| 2006/0172971 A1 | 8/2006 | Nicotera et al. | 514/64 |

FOREIGN PATENT DOCUMENTS

| | | |
|---|---|---|
| CA | 2264020 | 3/1998 |
| CA | 2360581 | 7/2000 |
| CA | 2392866 | 7/2001 |
| CA | 2407677 | 10/2002 |
| DE | 43 07 883 A1 | 9/1993 |
| EP | 0 370 381 A2 | 5/1990 |
| EP | 0 463 638 A1 | 1/1992 |
| EP | 0 846 464 A2 | 6/1998 |
| EP | 0974584 A1 | 1/2000 |
| JP | S45-39538 | 12/1970 |
| JP | 01132579 | 5/1989 |
| WO | WO 91/09849 | 7/1991 |
| WO | WO 96/35805 | 11/1996 |
| WO | WO 96/39384 | 12/1996 |
| WO | WO 96/39385 | 12/1996 |
| WO | WO 97/29091 | 8/1997 |
| WO | WO 98/07695 | 2/1998 |
| WO | WO-9915500 A1 | 4/1999 |
| WO | WO 99/48868 | 9/1999 |
| WO | WO-9954309 A1 | 10/1999 |
| WO | WO-9959973 A1 | 11/1999 |
| WO | WO 00/42213 | 7/2000 |
| WO | WO-0116097 A1 | 3/2001 |
| WO | WO 01/53274 A1 | 7/2001 |
| WO | WO 01/55111 | 8/2001 |
| WO | WO-0160814 A2 | 8/2001 |
| WO | WO 01/85726 A1 | 11/2001 |
| WO | WO 01/98290 A2 | 12/2001 |
| WO | WO 02/00661 A1 | 1/2002 |
| WO | WO 02/04459 A1 | 1/2002 |
| WO | WO 02/072548 A2 | 9/2002 |
| WO | WO 02/080926 A1 | 10/2002 |
| WO | WO 03/086385 | * 10/2003 |
| WO | WO 03/093297 A2 | 11/2003 |
| WO | WO 2004/022525 | * 3/2004 |
| WO | WO 2004/056774 A2 | 7/2004 |
| WO | WO 2005/032493 A2 | 4/2005 |
| WO | WO 2007/026920 A2 | 3/2007 |

OTHER PUBLICATIONS

Vippagunta, et al. Advanced Drug Delivery Reviews 48 (2001) 3-26.*
Diabetes Mellitus (DM) [online] retrieved on Apr. 17, 2007, retrieved from the internet URL; http://www.merck.com/mmpe/print/sec12/ch158/ch158b.html.*
Treatment of osteoporosis [online]. [Retrieved from the internet on Jan. 28, 2009] URL; http://www.emedicinehealth.com/treatment_of_osteoporosis/article_em.htm.*
Document No. 137:232908 retrieved from CAPLUS on Sep. 11, 2009.*
Document No. 131:243258 retrieved from CAPLUS on Sep. 11, 2009.*
Document No. 130:311803 retrieved from CAPLUS on Sep. 11, 2009.*
Document No. 137:185515 retrieved from CAPLUS on Sep. 11, 2009.*
Davidson et al., "Discovery and characterization of a substrate selective p38α inhibitor", *Biochemistry*, 43:11658-11671 (2004).
Duong, et al., "Inhibition of Osteoclast Function by Adenovirus Expressing Antisense Protein-tyrosine Kinase 2", *J. Biol. Chem.* 276:7484-7492 (2001).

(Continued)

*Primary Examiner*—Rebecca L Anderson
*Assistant Examiner*—Shawquia Young
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The invention relates to compounds of the class of 2-carboxamide substituted indoles and methods for modulating one or more components of a kinase cascade. The compounds of the invention are useful for osteoporosis, hepatitis B, opthalmic disease, diabetes, athrosclerosis, obesity, chronic neuropathic pain, and stroke.

18 Claims, 54 Drawing Sheets

OTHER PUBLICATIONS

Frame, M., "Src in cancer: deregulation and consequences for cell behavior", *Biochimica et Biophysica Acta* 1602:114-130 (2002).
Guo, et al., "Tyrosine Phosphorylation of the NR2B Subunit of the NMDA Receptor in the Spinal Cord during the Development and Maintenance of Inflammatory Hyperalgesia" *J. Neurosci.* 22:6208-6217 (2002).
Hadjeri, et al., "Antimitotic Activity of 5-Hydroxy-7-methoxy-2-phenyl-4-quinolones", *J. Med. Chem.* 47:4964-4970 (2004).
Martin, et al., "Discovery of a human liver glycogen phosphorylase inhibitor that lowers blood glucose in vivo" *Proc. Natl. Acad. Sci. USA*, 95:1776-1781 (1998).
Miyazaki, et al., "Src Kinase Activity Is Essential for Osteoclast Function" *J. Biol. Chem.* 279:17660-17666 (2004).
Parang, et al., "Recent advances in the discovery of Src kinase inhibitors" *Expert Opin. Ther. Patents* 15:1183-1207 (2005).
Paul, et al., "Src deficiency or blockade of Src activity in mice provides cerebral protection following stroke" *Nat. Med.*, 7:222-227 (2001).
Yu, et al., "Src, a molecular switch governing gain control of synaptic transmission mediated by *N*-methyl-D-aspartate receptors" *Proc. Natl. Acad. Sci USA.* 96:7697-7704 (1999).
Lawrence et al., "Protein Kinase Inhibitors: The Tyrosine-Specific Protein Kinases", *Pharmacol. Ther.*, 77(2):81-114 (1998).
Stahura et al., "Molecular scaffold-based design and comparison of combinatorial libraries focused on the ATP-binding site of protein kinases", *J. Mol. Graphics Modelling*, 17:1-9 (1999).
"Amersham Pharmacia Biotech to Market and Distribute BioFocus' SoftFocus(TM) Kinase Libraries in North America," News release: Nov. 23, 1999.
Abram et al., "Src Family Tyrosine Kinases and Growth Factor Signaling," *Experimental Cell Research*, 254:1-13 (2000).
Alfaro-Lopez et al., "Discovery of a Novel Series of Potent and Selective Substrate-Based Inhibitors of p60$^{c-src}$ Protein Tyrosine Kinase: Conformational and Topographical Constraints in Peptide Design," *J. Med. Chem.*, 41:2252-2260 (1998).
Al-Obeidi et al., "Protein Tyrosine Kinases: Structure, Substrate Specificity, and Drug Discovery", *Biopoly*, 47:197-223 (1998).
Bakhtiar et al., "Quantification of the Anti-Leukemia Drug STI1571 (Gleevec) and its Metabolite (CGP 74588) in Monkey Plasma Using a Semi-Automated Solid Phase Extraction Procedure and Liquid Chromatography-Tandem Mass Spectrometry," *Journal of Pharmaceutical & Biomedical Analysis*, 28(6):1183-1194 (2002) (Abstract).
Biscardi et al., "c-Src, Receptor Tyrosine Kinases and Human Cancer," *Advances in Cancer Research*, 61-119 (1999).
Biscardi et al., "Tyrosine Kinase Signaling in Breast Cancer: Epidermal Growth Factor Receptor and c-Src Interactions in Breast Cancer." *Breast Cancer Res.*, 2:203-210 (2000).
Bishop et al., "Screening a Hydroxystilbene Library for Selective Inhibition of the B Cell Antigen Receptor Kinase Cascade", *Tetrahedron*, 53(35):11995-12004 (1997).
Blume-Jensen et al., "Oncogenic Kinase Signaling," *Nature*, 411:355-365 (2001).
Bridges, "Chemical Inhibitors of Protein Kinases," *Chemical Reviews*, 101(8):2541-2571 (2001).
Budde et al., "Discovery, Development, and Testing of Substrates and Inhibitors of PP60$^{C-SRC}$", *Int. J. Pharmacognosy*, 33:27-34 (1995).
Burke et al., "Bicyclic Compounds as Ring-Constrained Inhibitors of Protein-Tyrosine Kinase p56lck," *J. Med. Chem.*, 36(4):425-432 (1993).
Burke et al., "Phosphotyrosyl Mimetics in the Development of Signal Transduction Inhibitors," *Acc. Chem. Res.*, 36:426-433 (2003).
Casnellie et al., "The Use of Synthetic Peptides for Defining the Specificity of Tyrosine Protein Kinases," *Adv. Enzyme Regul.*, 22:501-515 (1984).
Chemical Abstracts vol. 67, No. 1 (1967) abstract No. 1850x (Chi-Ting Chou) p. 166 & Yao Hsueh Ao, vol. 13, No. 6 (1966).
Choi "Development of a Cellular Mimetic Protein Kinase Assay and a Novel Methodology for Determining the Mode of Inhibition for Multisubstrate" thesis, Bell & Howell Co., (1999).
Dolle, R. E., "Discovery of enzyme inhibitors through combinatorial chemistry",*Mol. Diversity*, 2:223-236 (1996).

Druker, "STI571 (Gleevec) as a Paradigm for Cancer Therapy," *Trends in Molecular Medicine*, 8(4 Suppl):S14-18 (2002) (Abstract).
Engström et al., "Detection and Identification of Substrates for Protein Kinases: Use of Proteins and Synthetic Peptides," *Meth. Enzymol.*, 107:130-154 (1984).
Faltynek et al., "Damnacanthal is a Highly Potent, Selective Inhibitor of p56$^{lck}$ Tyrosine Kinase Activity," *Biochem.*, 34:12404-12410 (1995).
Frame, "Src in Cancer: Deregulation and Consequences for Cell Behavior," *Biochemica et Biophysica Acta*, 1602:114-130 (2002).
Fretz et al., "Structure-based Design of Compounds Inhibiting Grb2-SH2 Mediated Protein-Protein Interactions in Signal Transduction Pathways," *Current Pharmaceutical Design*, 6(18):1777-1796 (2000) (Abstract).
Fry et al., "A Specific Inhibitor of the Epidermal Growth Factor Receptor Tyrosine Kinase," *Science*, 265:1093-1095 (1994).
Fukunaga et al., "Identifying Protein Kinase Substrates by Expression Screening with Solid-Phase Phosphorylation," *Protein Phosphorylation*, Second Edition, Chapter 13, pp. 291-313 (1999).
Garcia-Echeverria et al., "ATP Site-Directed Competitive and Irreversible Inhibitors of Protein Kinases," *Med. Res. Rev.*, 20(1):28-57 (2000).
Garcia-Echeverria, "Antagonists of the Src Homology 2 (SH2) Domains of Grb2, Src, Lck and ZAP-70," *Current Medicinal Research*, 8(13):1589-1604 (2001) (Abstract).
Hanke et al., "Discovery of a Novel, Potent and Src Family-selective Tyrosine Kinase Inhibitor," *J. Biol. Chem.*, 271(2):695-701 (1996).
Haskell et al., "c-Src Tyrosine Phosphorylation of Epidermal Growth Factor Receptor, P190 RhoGAP, and Focal Adhesion Kinase Regulates Diverse Cellular Processes," *Chemical Reviews*, 101(8):2425-2440 (2001).
Hoover et al., "Indole-2-Carboxamide Inhibitors of Human Liver Glycogen Phosphorylase,"*J. Med. Chem.*, 41(16):2934-2938 (1998).
Hsiao et al., "A Facile Synthesis of *tert*-Butyl 2-[(Benzyloxycarbonyl)amino]-3-(4,4,5,5-tetramethyl-1,3,2-dioxaborolan-2-yl)Propionate: An Orthogonally Protected Boronic Acid Analog of Aspartic Acid," *Synthesis*, pp. 1043-1046 (1998).
Huang et al., "Polyhydroxylated 3-(N-Phenyl) Carbamoyl-2-Iminochromene Derivatives as Potent Inhibitors of Tyrosine Kinase p60$^{c-src}$," *Bioorg. Med. Chem. Lett.*, 5(20):2423-2428 (1995).
Hubbard, "Crystal Structure of the Activated Insulin Receptor Tyrosine Kinase in Complex With Peptide Substrate and ATP Analog," *EMBO J.*, 16(18):5572-5581 (1997).
Hubbard et al., "Protein Tyrosine Kinase Structure and Function," *Annu. Rev. Biochem.*, 69:373-398 (2000).
Irby et al., "Role of Src Expression and Activation in Human Cancer," *Oncogene*, 19:5636-5642 (2000).
Johnson et al., "Protein Tyrosine Phosphatase 1B Inhibitors for Diabetes," *Nat. Rev. Drg. Discov.*, 1(9):696-709 (2002).
Kemp et al., "Design and Use of Peptide Substrates for Protein Kinases," *Meth. Enzymol.*, 200:121-134 (1991).
Kemp et al., "Protein Kinase Recognition Sequence Motifs," *TIBS*, 15:342-346 (1990).
Kennedy, "Role of Protein Tyrosine Phosphatase-1B in Diabetes and Obesity," *Biomedicine & Pharmacotherapy*, 53(10):466-470 (1999).
Kim et al., "Tetrapeptide Tyrosine Kinase Inhibitors," *Int. J. Peptide Protein Res.*, 44:457-465 (1994).
Lai et al., Synthesis of a Vicinal Tricarbonyl Amide Derivative of L-Phenylalanine, *J. Org. Chem.*, 61:1872-1874 (1996).
Lai et al., "The Design, Synthesis and Activity of Pentapeptide pp60$^{c-src}$, Inhibitors Containing L-phosphotyrosine Mimics," *J. Peptide Res.*, 51:271-281 (1998).
Levitzki et al., "Tyrosine Kinase Inhibition: An Approach to Drug Development," *Science*, 267:1782-1788 (1995).
Levitzki, "Protein Kinase Inhibitors as a Therapeutic Modality," *Acc. Chem. Res.*, 36(6):462-469 (2003).
Lou et al., "Identification of GIYWHHY as a Novel Peptide Substrate for Human p60$^{c-src}$ Protein Tyrosine Kinase," *Bioorg. Med. Chem.*, 4(5):677-682 (1996).
Marsilje et al., "The Design, Synthesis and Activity of Non-ATP Competitive Inhibitors of pp60$^{c-src}$ Tyrosine Kinase. Part 1: Hydroxynaphthalene Derivatives," *Bioorg. Med. Chem. Lett.*, 10:477-481 (2000).

Martin, "TIMELINE: The Hunting of the Src," *Nat. Rev. Mol. Cell Biol.*, 2:467-475 (2001).

McCluskey et al., "Serine-Threonine Protein Phosphatase Inhibitors: Development of Potential Therapeutic Strategies," *Journal of Medicinal Chemistry*, 45(6):1151-1175 (2002).

McCluskey et al., "Small Molecule Inhibitors of Serine/Theonine Protein Phosphatases," *Mini-Reviews in Medicinal Chemistry*, 1(1):43-55 (2001) (Abstract).

Metcalf III et al., "Targeting Protein Kinases for Bone Disease: Discovery and Development of Src Inhibitors," *Curr. Pharm. Design*, 8:2049-2075 (2002).

Milkiewicz et al., "The Design, Synthesis and Activity of Non-ATP Competitive Inhibitors of pp60$^{c-src}$ Tyrosine Kinase. Part 2: Hydroxyindole Derivatives," *Bioorg. Med. Chem. Lett.*, 10:483-486 (2000).

Milkiewicz, "Design, Synthesis and Biological Testing of Non-ATP Competitive Inhibitors of the pp60$^{c-src}$ Protein Tyrosine Kinase," A dissertation submitted to the Faculty of the Graduate School of State University of New York at Buffalo in Partial Fulfillment of the Requirements for the Degree of Doctor of Philosophy, Department of Medicinal Chemistry (2001).

Mohammadi et al., "Structures of the tyrosine kinase domain of fibroblast growth factor receptor in complex with inhibitors," *Science*, 276:955-960 (1997).

Moller et al, "Protein Tyrosine Phosphatases (PTPs) as Drug Targets: Inhibitors of PTP-1B for the Treatment of Diabetes," *Current Opinion in Drug Discovery & Development*, 3(5):527-540 (2000) (Abstract).

Muller, "Peptidomimetic SH2 Domain Antagonists for Targeting Signal Transduction," *Topics in Current Chemistry*, 211:17-59 (2001) (Abstract).

Nair et al., "Identification of Efficient Pentapeptide Substrates for the Tyrosine Kinase pp60$^{c-src}$," *J. Med. Chem.*, 38:4276-4283 (1995).

Nair et al., "Synthesis of Orthogonally Protected L-Homocystein and L-2-Amino-4-phosphonobutanoic Acid From L-Homoserine," *Synthesis*, pp. 810-814 (1995).

Norman et al., "A Structure-Based Library Approach to Kinase Inhibitors", *J. Am. Chem. Soc.*, 118:7430-7431 (1996).

Park et al., "Metabolism of Fluorine-Containing Drugs," *Annu. Rev. Pharmacol. Toxicol.*, 41:443-470 (2001).

Patent Abstracts of Japan vol. 013, No. 384 (1989) & JP 01 132579 A (SS Pharmaceut. Co. Ltd.) abstract only (1989).

Patrick et al., "Protein Kinase Inhibitors for the Treatment of Cancer," *DDT*, 1(8):325-330 (1996).

Pearson et al., "Protein Kinase Phosphorylation Site Sequences and Consensus Specificity Motifs: Tabulations," *Meth. Enzymol.*, 200:62-81 (1991).

Pestell et al., "Small Molecule Inhibitors of Dual Specificity Protein Phosphatases," *Oncogene*, 19(56):6607-6612 (2000).

Poulain et al., "From Hit to Lead. Combining Two Complementary Methods for Focused Library Design. Application to μ Opiate Ligands," *J. Med. Chem.*, 44(21):3378-3390 (2001).

Ramdas et al., "A Tyrphostin-Derived Inhibitor of Protein Tyrosine Kinases: Isolation and Characterization," *Arch. Biochem. Biophys.*, 323(2):237-242 (1995).

Rewcastle et al., "Tyrosine Kinase Inhibitors. 10. Isomeric 4-[(3-Bromophenyl)amino]pyrido[*d*]-pyrimidines Are Potent ATP Binding Site Inhibitors of the Tyrosine Kinase Function of the Epidermal Growth Factor Receptor," *J. Med. Chem.*, 39:1823-1835 (1996).

Ripka, "Chapter 21. Protein Tyrosine Phosphatase Inhibition," *Annual Reports in Medicinal Chemistry*, 35:231-250 (2000) (Abstract).

Romero et al., "Discovery, Synthesis, and Bioactivity of Bis(heteroaryl)piperazines. 1. A Novel Class of Non-Nucleoside HIV-1 Reverse Transcriptase Inhibitors," *J. Med. Chem.*, 37(7):999-1014 (1994).

Ruzzene et al., "Assay of Protein Kinases and Phosphatases using Specific Peptide Substrates," *Protein Phosphorylation*, Second Edition, Chapter 10, pp. 221-253 (1999).

Saperstein et al., "Design of a Selective Insulin Receptor Tyrosine Kinase Inhibitor and Its Effect on Glucose Uptake and Metabolism in Intact Cells," *Biochem.*, 28:5694-5701 (1989).

Sawutz et al., "In Vitro Characterization of a Novel Series of Platelet-Derived Growth Factor Receptor Tyrosine Kinase Inhibitors," *Biochem. Pharmacol.*, 51:1631-1638 (1996).

Sawyer, "Cancer Metastasis Therapeutic Targets and Drug Discovery: Emerging Small-Molecule Protein Kinase Inhibitors," *Expert Opin. Investig. Drugs*, 13(1):1-19 (2004).

Sawyer et al., "Src Inhibitors: Genomics to Therapeutics," *Expert Opin. Investg. Drugs*, 10(7):1327-1344 (2001).

Schlessinger, "New Roles for Src Kinases in Control of Cell Survival and Angiogenesis," *Cell*, 100:293-296 (2000).

Sedlacek, "Kinase Inhibitors in Cancer Therapy." *Drugs*, 59(3):435-476 (2000).

Shoichet, "Virtual Screening of Chemical Libraries," *Nature*, 432:862-865 (2004).

Showalter et al., "Small Molecule Inhibitors of the Platelet-Derived Growth Factor Receptor, the Fibroblast Growth Factor Receptor, and Src Family Tyrosine Kinases," *Pharmacol. Ther.*, 76(1-3):55-71 (1997).

Songyang et al., "The Use of Peptide Library for the Determination of Kinase Peptide Substrates," *Meth. Mol. Biol.*, 87:87-98 (1998).

Sparks et al, "Identification and Characterization of Src SH3 Ligands from Phage-Displayed Random Peptide," *Journal of Biological Chemistry*, 269(39):23853-23856 (1994) (Abstract).

Sparks et al., "Molecular Basis for Substrate Specificity of Protein Kinases and Phosphatases," *Int. J. Biochem.*, 18(6):497-504 (1986).

Sridhar et al., "Protein Kinases as Therapeutic Targets," *Pharmaceutical Research*, 17(11):1345-1353 (2000).

Stein, "SH2 and SH3 Domains. Unraveling Signaling Networks with Peptide Antagonists," *Methods in Molecular Biology*, 88:187-195 (1998) (Abstract).

Sun et al., "CombiDOCK: Structure-based combinatorial docking and library design", *J. Computer-Aided Mol. Des.*, 12:597-604 (1998).

Susa et al., "Src Inhibitors: Drugs for the Treatment of Osteoporosis, Cancer or Both?," *TiPS*, 21:489-495 (2000).

Susa et al., "Tyrosine Kinase Src Inhibitors: Potential Therapeutic Applications," *Drug News Perspect.*, 13(3):169-175 (2000).

Taylor et al., "Protein kinase inhibition: natural and synthetic variations on a theme", *Curr. Opin. Chem. Biol.*, 1:219-226 (1997).

Tegge et al., "Analysis of protein kinase substrate specificity by the use of peptide libraries on cellulose paper (SPOT-Method)", *Meth. Mol. Biol.*, 87:99-106 (1998).

Thakkar et al., "Synthesis and Protein-Tyrosine Kinase Inhibitory Aactivity of Polyhydroxylated Stilbene Analogues of Piceatannol," *J. Med. Chem.*, 36:2950-2955 (1993).

Vu, "Recent Advances in the Design and Synthesis of SH2 Inhibitors of Src, Grb2 and ZAP-70," *Current Medicinal Chemistry*, 7(10):1081-1100 (2000) (Abstract).

Xu et al., "Three-Dimensional Structure of the Tyrosine Kinase c-Src," *Nature*, 385:595-602 (1997).

Zhang, "Protein Tyrosine Phosphatases: Prospects for Therapeutics," *Current Opinion in Chemical Biology*, 5(4):416-423 (2001) (Abstract).

Zhang, "Protein Tyrosine Phosphatases: Structure and Function, Substrate Specificity, and Inhibitor Development," *Annual Review of Pharmacology and Toxicology*, 42:209-234 (2002) (Abstract).

Zheng et al., "Crystal Structure of the Catalytic Subunit of cAMP-Dependent Protein Kinase Complexed with MgATP and Peptide Inhibitor," *Biochem.*, 32:2154-2161 (1993).

Wright, W.B. et al, Central Nervous System Depressants, IV, Nov. 1968, p. 1164-67.

\* cited by examiner

FIG. 5  Binding interactions of src substrate Ac-Ile-Tyr-Gly-Glu-Phe-NH₂ in model src active site.

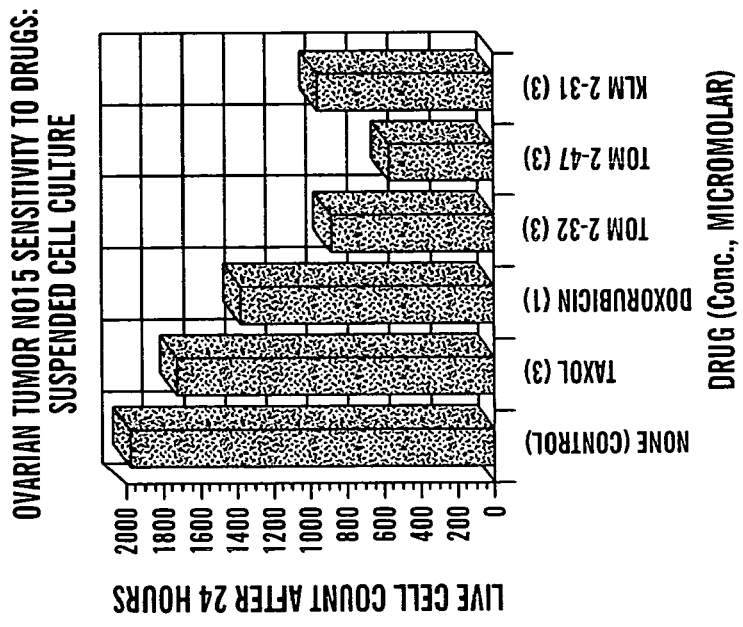
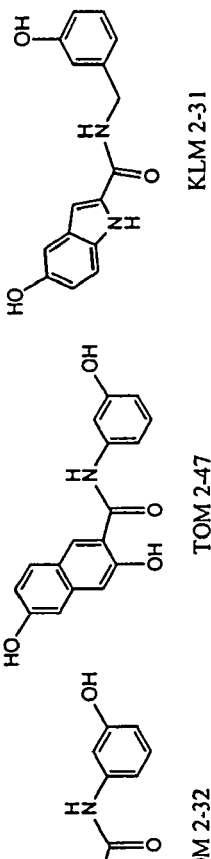
FIG. 15B
FIG. 15A
FIG. 15C

Figure 29
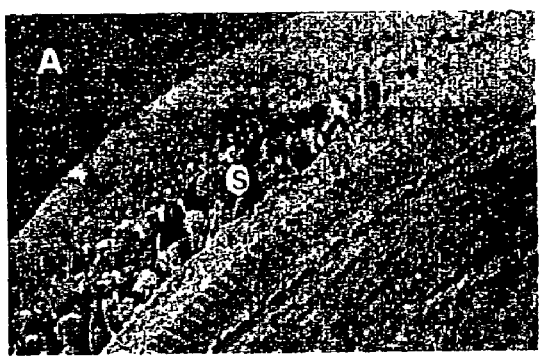
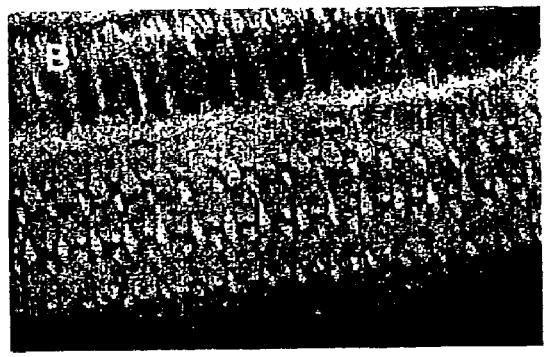
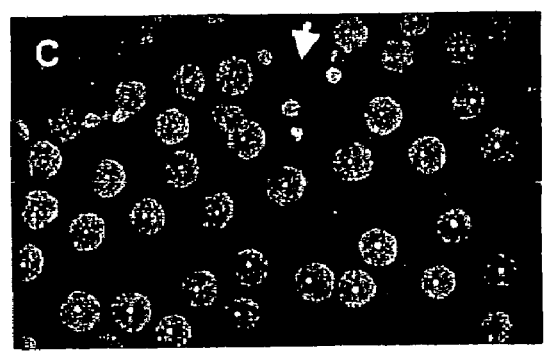
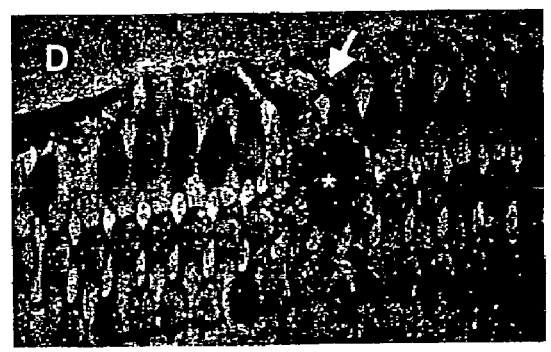
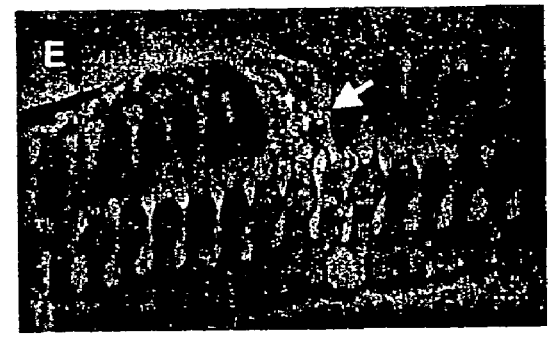
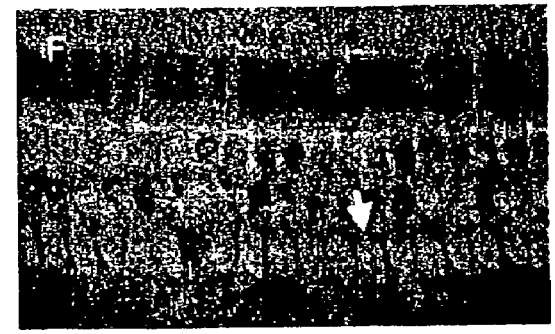

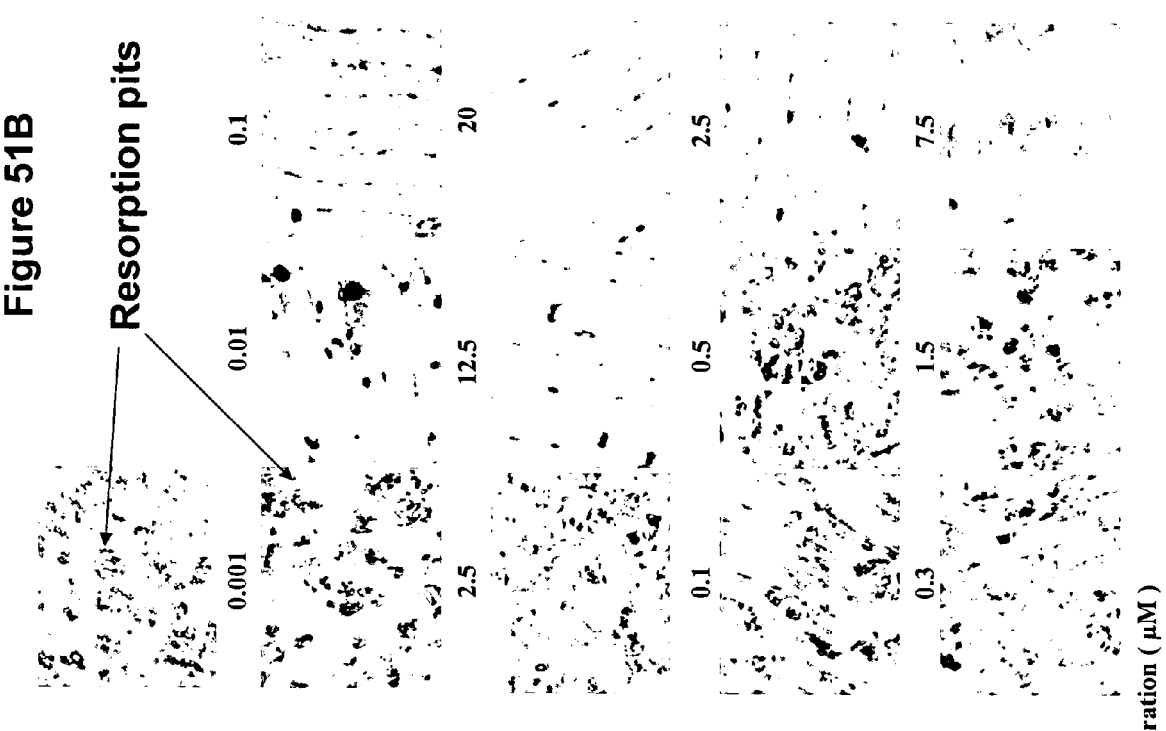
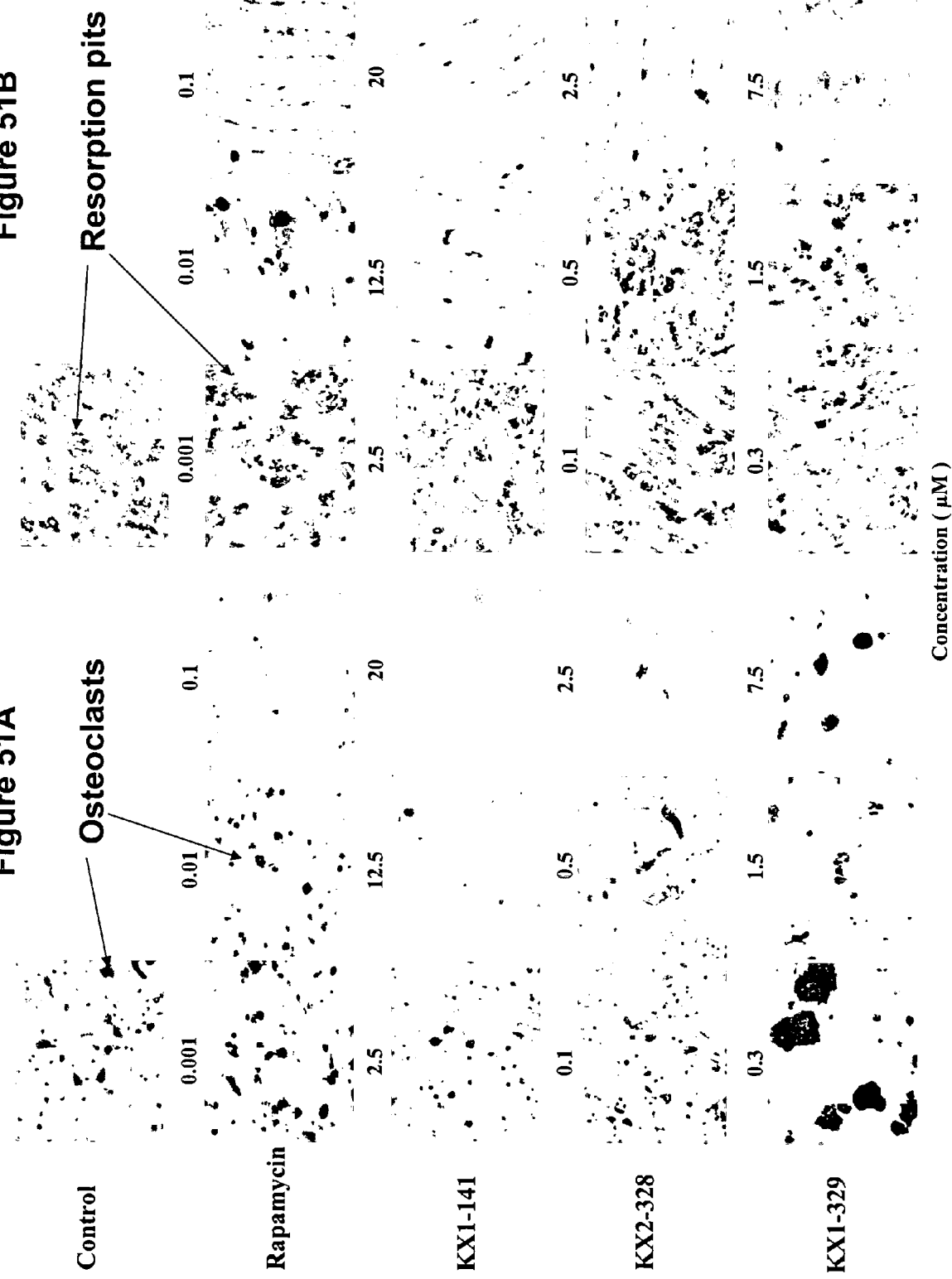

BICYCLIC COMPOSITIONS AND METHODS FOR MODULATING A KINASE CASCADE

BACKGROUND OF THE INVENTION

Signal transduction is any process by which a cell converts one kind of signal or stimulus into another. Processes referred to as signal transduction often involve a sequence of biochemical reactions inside the cell, which are carried out by enzymes and linked through second messengers. In many transduction processes, an increasing number of enzymes and other molecules become engaged in the events that proceed from the initial stimulus. In such cases the chain of steps is referred to as a "signaling cascade" or a "second messenger pathway" and often results in a small stimulus eliciting a large response. One class of molecules involved in signal transduction is the kinase family of enzymes. The largest group of kinases are protein kinases, which act on and modify the activity of specific proteins. These are used extensively to transmit signals and control complex processes in cells.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate, ATP, in a highly conserved pocket. Protein phosphatases catalyze the transfer of phosphate in the opposite direction.

A tyrosine kinase is an enzyme that can transfer a phosphate group from ATP to a tyrosine residue in a protein. Phosphorylation of proteins by kinases is an important mechanism in signal transduction for regulation of enzyme activity. The tyrosine kinases are divided into two groups; those that are cytoplasmic proteins and the transmembrane receptor-linked kinases. In humans, there are 32 cytoplasmic protein tyrosine kinases and 58 receptor-linked protein-tyrosine kinases. The hormones and growth factors that act on cell surface tyrosine kinase-linked receptors are generally growth-promoting and function to stimulate cell division (e.g., insulin, insulin-like growth factor 1, epidermal growth factor).

Inhibitors of various known protein kinases or protein phosphatases have a variety of therapeutic applications. One promising potential therapeutic use for protein kinase or protein phosphatase inhibitors is as anti-cancer agents. About 50% of the known oncogene products are protein tyrosine kinases (PTKs) and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products). There are at least 9 members of the Src family of non-receptor PTK's with pp60$^{c-src}$ (hereafter referred to simply as "Src") being the prototype PTK of the family wherein the approximately 300 amino acid catalytic domains are highly conserved. The hyperactivation of Src has been reported in a number of human cancers, including those of the colon, breast, lung, bladder, and skin, as well as in gastric cancer, hairy cell leukemia, and neuroblastoma. Overstimulated cell proliferation signals from transmembrane receptors (e.g. EGFR and p185HER2/Neu) to the cell interior also appear to pass through Src. Consequently, it has recently been proposed that Src is a universal target for cancer therapy, because hyperactivation (without mutation) is involved in tumor initiation, progression, and metastasis for many important human tumor types.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders.

An important contribution to the protein kinase field has been the x-ray structural work with the serine kinase cAMP-dependent protein kinase ("PKA") bound to the 20-residue peptide derived from the heat stable inhibitor protein, PKI(5-24), and Mg$_2$ATP (Taylor et al., 1993). This structural work is particularly valuable because PKA is considered to be a prototype for the entire family of protein kinases since they have evolved from a single ancestral protein kinase. Sequence alignments of PKA with other serine and tyrosine kinases have identified a conserved catalytic core of about 260 residues and 11 highly conserved residues within this core (Taylor et al., 1993). Two highly conserved residues of particular note for the work proposed herein are the general base Asp-166 which is proposed to interact with the substrate OH and the positively charged residue, Lys-168 for serine kinases and an Arg for tyrosine kinases (Knighton et al., 1993), which is proposed to interact with the γ-phosphate of ATP to help catalyze transfer of this phosphate. Two additional important PKA crystal structures have been reported (Madhusudan et al., 1994), one for the ternary PKA:ADP:PKI(5-24) complex wherein the PKI Ala 21 has been replaced with Ser (thereby becoming a substrate), and one for the binary PKA:PKI(5-24) complex wherein the PKI Ala 21 has been replaced with phosphoserine (an end product inhibitor). The ternary complex shows the serine OH donating a H-bond to Asp-166 and accepting a H-bond from the side chain of Lys 168. The binary complex shows the phosphate group of phosphoserine forming a salt bridge with the Lys-168 side chain and within H-bonding distance of the Asp-166 carboxyl group. These structures support the earlier proposed roles for Asp-166 and Lys-168 in the catalytic mechanism.

The x-ray structures of PKA show that the enzyme consists of two lobes wherein the smaller lobe binds ATP and the larger lobe the peptide substrate. Catalysis occurs at the cleft between the lobes. The crystallographic and solution structural studies with PKA have indicated that the enzyme undergoes major conformational changes from an "open" form to the "closed" catalytically active form as it binds the substrates (Cox et al., 1994). These conformational changes are presumed to involve the closing of the cleft between the two lobes as the substrates bind bringing the γ-phosphate of ATP and the Ser OH in closer proximity for direct transfer of the phosphate.

However, many inhibitors of protein kinases and protein phosphatases still lack the specificity and potency desired for therapeutic use. Due to the key roles played by protein kinases and protein phosphatases in a number of different diseases, including cancer, psoriasis, arthrosclerosis, Type II diabetes, obesity, and their role in regulating immune system activity, modulators of protein kinase cascades are needed.

SUMMARY OF THE INVENTION

One aspect of the invention provides a compound having the Formula I:

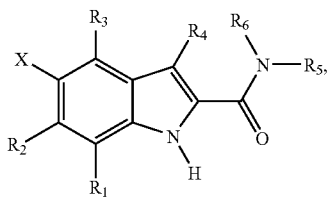

(Formula I)

wherein X is a halogen, and $R_1$, $R_2$, $R_3$, $R_4$, $R_5$, and $R_6$ are the same or different, and selected from H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_b OR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), having from 1 to 20 carbon atoms, optionally containing a double or triple bond and optionally substituted with a heteroatom or other functional groups, such as a carboxylic acid, carboxylic ester, alcohol, alkoxy, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl, or $R_5$ and $R_6$ together form a heterocyclic compound. $R_a$, $R_b$, and $R_c$ are the same or different and selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, alkoxy, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

In one embodiment, at least one of $R_5$ or $R_6$ is

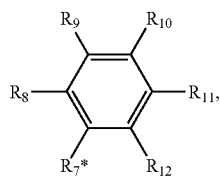

wherein $R_7^*$ is the point of attachment and is $(CH_2)_x$, wherein X is selected from 0, 1, 2, 3, 4, 5, 6, 7, 8, 9, and 10, $CH_2CHOH$, $CH(CH_3)$(R-isomer), or $CH(CH_3)$(S-isomer), and each of $R_8$, $R_9$, $R_{10}$, $R_{11}$, and $R_{12}$ are the same or different and selected from H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_8$, $R_9$, $R_{10}$, $R_{11}$, and $R_{12}$ are substituted or unsubstituted.

In another embodiment, at least one of $R_5$ or $R_6$ is

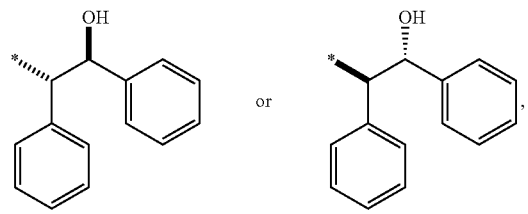

wherein the asterisk indicates the point of attachment to the nitrogen.

Another aspect of the invention is a compound having the Formula II:

(Formula II)

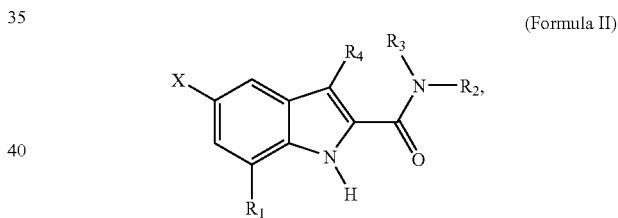

wherein X is a halogen, e.g., fluorine, and $R_1$, $R_2$, $R_3$, and $R_4$ are specificity side chain elements and defined as described above. In one embodiment, $R_1$ is H, $R_2$ is

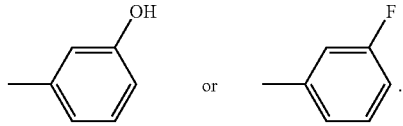

$R_3$ is H, and $R_4$ is H. In another embodiment, the compound is substituted at any other position on the indole ring.

Another aspect of the invention is a method for identifying inhibitors of protein kinases. The method involves providing at least one first module having one or more functional groups each capable of covalently or non-covalently binding to catalytic residues of the protein kinase, wherein at least one of the one or more functional groups is a halogen, combining at least one first module with at least one second module which provides a non-peptide scaffold to form one or more combinations of the first and second modules, screening the one or more combinations of the first and second modules for protein kinase inhibition, and selecting combinations of the first and second modules which inhibit protein kinase activity. As used herein, a module is a single molecular entity or a collection of functional groups. As used herein, a non-peptide scaffold is a molecule which may include peptide bonds, so long as a part of the molecule is not a peptide.

Another aspect of the invention is a method of inhibiting a protein kinase. The protein kinase is contacted by a compound comprising at least one first module having one or more functional groups each capable of covalently or non-covalently binding to catalytic residues of the protein kinase, wherein the one or more functional groups comprise a halogen, and a second module which provides a non-peptide scaffold. The combination of at least one first module and second module inhibits the protein kinase activity.

Another aspect of the invention is a method of treating a condition, responsive to a protein kinase inhibitor, in a subject. A protein kinase inhibitor is administered to a subject. The protein kinase inhibitor has at least one first module having one or more functional groups each capable of covalently or non-covalently binding to catalytic residues of the protein kinase, wherein the one or more functional groups comprise a halogen, and a second module which provides a non-peptide scaffold. The combination of at least one first module and second module inhibits protein kinase activity in the subject.

Another aspect of the invention is a method for identifying inhibitors of protein phosphatases. The method involves providing at least one first module having one or more functional groups each capable of covalently or non-covalently binding to catalytic residues of the protein phosphatase, combining at least one first module with at least one second module which provides a non-peptide scaffold to form one or more combinations of the first and second modules, screening the one or more combinations of the first and second modules for phosphatase inhibition, and selecting combinations of the first and second modules which inhibit protein phosphatase activity.

Another aspect of the present invention is a method of inhibiting a protein phosphatase. The protein phosphatase is contacted by a compound comprising at least one first module having one or more functional groups each capable of covalently or non-covalently binding to catalytic residues of the protein phosphatase, and a second module which provides a non-peptide scaffold. The combination of at least one first module and second module inhibits the protein phosphatase activity.

Another aspect of the invention is a method of treating a condition, responsive to a protein phosphatase inhibitor, in a subject. A protein phosphatase inhibitor is administered to a subject. The protein phosphatase inhibitor has at least one first module having one or more functional groups each capable of covalently or non-covalently binding to catalytic residues of the protein phosphatase, and a second module which provides a non-peptide scaffold. The combination of at least one first module and second module inhibits protein phosphatase activity in the subject.

Another aspect of the invention is a compound according to Formula V:

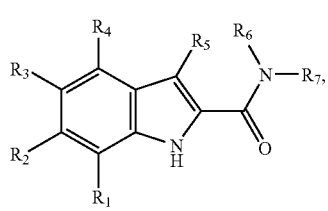

(Formula V)

or a salt, solvate, hydrate, or prodrug thereof. $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, and branched, unbranched, or cyclic alkyl. $R_6$ and $R_7$ are the same or different and are independently H, branched or unbranched, or $(CH_2)_t$-Z, wherein Z is aryl, heteroaryl, biaryl, cyclic alkyl, or heterocycle, or $R_6$ and $R_7$ together form a heterocycle. t is 0, 1, 2, 3, 4, 5, 6, 7, 8, 9, or 10. $R_a$, $R_b$, and $R_c$ are the same or different and are independently H, aryl, heteroaryl, biaryl, heterobiaryl, or branched, unbranched, or cyclic alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

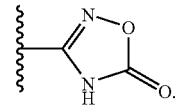

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

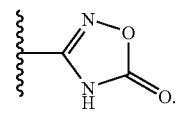

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

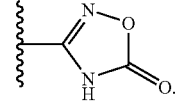

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. Any of $R_1$, $R_2$, $R_3$, $R_4$, $R_5$, $R_6$, and $R_7$ and $R_a$, $R_b$, and $R_c$ is substituted or unsubstituted. At least one of $R_1$, $R_2$, $R_3$, $R_4$, $R_5$, and $R_6$ is P.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further where K is $SO_3H$, $OSO_3H$, $PO_3H_2$, $OPO_3H_2$, $NH_2$, $NHR_{19}$, $NR_{19}R_{20}$, glycoside, and heterocycle; further where L is $SO_3H$, $OSO_3H$, $PO_3H_2$, $OPO_3H_2$, $NH_2$, $NHR_{19}$, $NR_{19}R_{20}$, glycoside, and heterocycle; and further where M is $SO_3H$, $OSO_3H$, $PO_3H_2$, $OPO_3H_2$, $NH_2$, $NHR_{19}$, $NR_{19}R_{20}$, glycoside, and heterocycle.

In one embodiment, at least one of $R_1$, $R_2$, $R_3$, $R_4$, and $R_5$ is selected from halogen, boronic acid, hydroxyl, phosphonic acid, sulfamic acid, guanidine, carboxylic acid, aldehyde, amide, and hydroxymethylphosphonic acid. In another embodiment, at least one of $R_1$, $R_2$, $R_3$, $R_4$, and $R_5$ is halogen. In another embodiment, at least one of $R_1$, $R_2$, $R_3$, $R_4$, and $R_5$ is boronic acid. In another embodiment, at least one of $R_1$, $R_2$, $R_3$, $R_4$, and $R_5$ is hydroxyl. In another embodiment, at least one of $R_1$, $R_2$, $R_3$, $R_4$, and $R_5$ is amide. For example, amide is vicinal tricarbonyl amide. In one embodiment, $R_3$ is halogen. For example, $R_3$ is fluorine. In another embodiment, $R_3$ is hydroxyl.

In one embodiment, at least one of $R_6$ and $R_7$ is

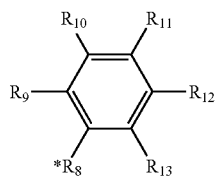

where $*R_8$ is the point of attachment. In one embodiment $R_8$ is $(CH_2)_x$, where X is 0, 1, 2, 3, 4, 5, 6, 7, 8, 9, or 10. In another embodiment $R_8$ is $CH_2CHOH$, $CH(CH_3)$(R-isomer), or $CH(CH_3)$(S-isomer). In another embodiment, each of $R_9$, $R_{10}$, $R_{11}$, $R_{12}$, and $R_{13}$ are the same or different and each of $R_9$, $R_{10}$, $R_{11}$, $R_{12}$, and $R_{13}$ independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, P', aryl, heteroaryl, biaryl, heterobiaryl, heterocycle, or branched, cyclic, or unbranched alkyl, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q', further where lower ($C_1$, $C_2$, $C_3$, $C_4$, $C_5$, or $C_6$) alkyl is linear or branched alkyl. K' is $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

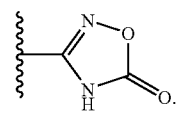

L' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

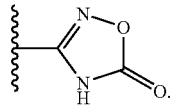

M' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

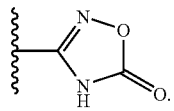

Q' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

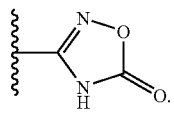

$R_{22}$, $R_{23}$ and $R_{24}$ are independently $C_1$, $C_2$, $C_3$, $C_4$, $C_5$, or $C_6$ alkyl or $R_{22}$ and $R_{23}$ taken together with the attached nitrogen atom form a five membered ring. $R_a$, $R_b$, and $R_c$ are the same or different and independently are H, aryl, heteroaryl, biaryl, heterobiaryl, branched, cyclic, or unbranched alkyl;

wherein any of $R_9$, $R_{10}$, $R_{11}$, $R_{12}$, and $R_{13}$ are substituted or unsubstituted; and provided that if one of $R_1$, $R_2$, $R_3$, $R_4$, or $R_5$ is not P, then at least one of $R_9$, $R_{10}$, $R_{11}$, $R_{12}$, and $R_{13}$ is P'.

In another embodiment, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q'. K' is $SO_3H$, $OSO_3H$, $PO_3H_2$, $OPO_3H_2$, $NH_2$, $NHR_{22}$, $NR_{22}R_{23}$, glycoside, or heterocycle. L' is $SO_3H$, $OSO_3H$, $PO_3H_2$, $OPO_3H_2$, $NH_2$, $NHR_{22}$, $NR_{22}R_{23}$, glycoside, or heterocycle. M' is $SO_3H$, $OSO_3H$, $PO_3H_2$, $OPO_3H_2$, $NH_2$, $NHR_{22}$, $NR_{22}R_{23}$, glycoside, or heterocycle. In another embodiment, at least one of $R_6$ and $R_7$ is

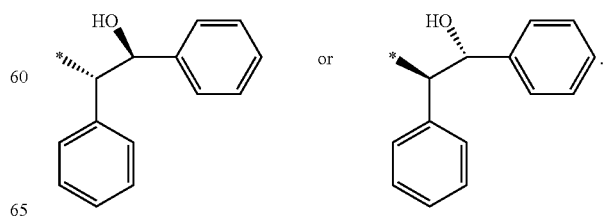

Another aspect of the invention includes a compound of Formula VI:

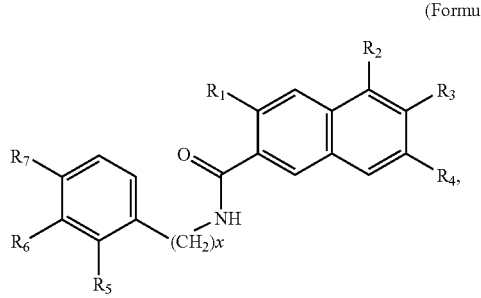
(Formula VI)

or a salt, solvate, hydrate, or prodrug. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further where lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

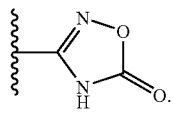

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

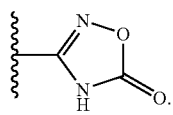

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

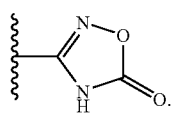

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

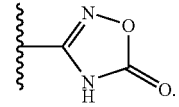

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. X is 1, 2, 3, 4, 5, 6, 7, 8, 9, or 10. At least one of $R_1$, $R_2$, $R_3$, $R_4$, $R_5$, $R_6$, and $R_7$ is P.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, $OSO_3H$, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

Another aspect of the invention includes a method of protecting against or treating hearing loss in a subject comprising administering a compound having the Formula V:

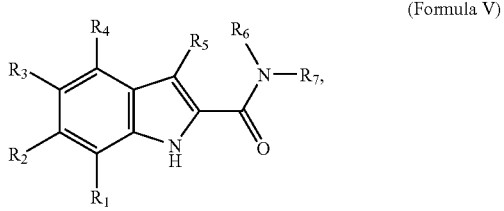
(Formula V)

or a salt, solvate, hydrate, or prodrug thereof. $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, and branched, unbranched, or cyclic alkyl. $R_6$ and $R_7$ are the same or different and are independently H, branched or unbranched or $(CH_2)_t$-Z, wherein Z is aryl, heteroaryl, biaryl, cyclic alkyl, or heterocycle, or $R_6$ and $R_7$ together form a heterocycle. t is 0, 1, 2, 3, 4, 5, 6, 7, 8, 9, or 10. $R_a$, $R_b$, and $R_c$ are the same or different and are independently H, aryl, heteroaryl, biaryl, heterobiaryl, or branched, unbranched, or cyclic alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

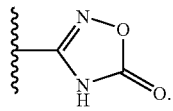

L is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

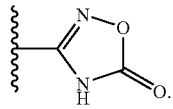

M is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

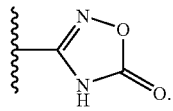

Q is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

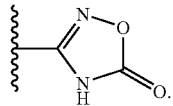

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring. Any of R$_1$, R$_2$, R$_3$, R$_4$, R$_5$, R$_6$, and R$_7$ and R$_a$, R$_b$, and R$_c$ is substituted or unsubstituted. At least one of R$_1$, R$_2$, R$_3$, R$_4$, R$_5$, R$_6$, and R$_7$ is P.

In one embodiment, P is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q. K is SO$_3$H, OSO$_3$H, PO$_3$H$_2$, OPO$_3$H$_2$, NH$_2$, NHR$_{19}$, NR$_{19}$R$_{20}$, glycoside, or heterocycle. L is SO$_3$H, OSO$_3$H, PO$_3$H$_2$, OPO$_3$H$_2$, NH$_2$, NHR$_{19}$, NR$_{19}$R$_{20}$, glycoside, or heterocycle. M is SO$_3$H, OSO$_3$H, PO$_3$H$_2$, OPO$_3$H$_2$, NH$_2$, NHR$_{19}$, NR$_{19}$R$_{20}$, glycoside, or heterocycle.

In one embodiment, the compound inhibits one or more components of a protein kinase signaling pathway. In another embodiment, the compound is an allosteric inhibitor. In another embodiment, the compound does not inhibit ATP binding to a protein kinase. In one embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops into the ear), intraarterially, intralesion-ally, by metering pump, or by application to mucous membranes. In one embodiment, the compound is administered in combination with a drug that causes hearing loss e.g., cis platinum or an aminoglycoside antibiotic. In another embodiment, the compound is administered in combination with a drug that targets hairy cells. In one embodiment, the compound is administered with a pharmaceutically acceptable carrier. In one embodiment, the compound is administered before initiation of hearing loss. In another embodiment, the compound is administered after inititiation of hearing loss.

In one embodiment, at least one of R$_1$, R$_2$, R$_3$, R$_4$, and R$_5$ is selected from halogen, boronic acid, hydroxyl, phosphonic acid, sulfamic acid, guanidine, carboxylic acid, aldehyde, amide, and hydroxymethylphosphonic acid. In another embodiment, at least one of R$_1$, R$_2$, R$_3$, R$_4$, and R$_5$ is a halogen. In another embodiment, at least one of R$_1$, R$_2$, R$_3$, R$_4$, and R$_5$ is boronic acid. In another embodiment, at least one of R$_1$, R$_2$, R$_3$, R$_4$, and R$_5$ is hydroxyl. In another embodiment, at least one of R$_1$, R$_2$, R$_3$, R$_4$, and R$_5$ is amide. For example, amide is vicinal tricarbonyl amide. In one embodiment, R$_3$ is halogen. For example, R$_3$ is fluorine. In one embodiment, R$_3$ is hydroxyl.

In one embodiment, at least one of R$_6$ and R$_7$ is

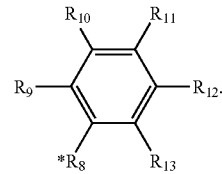

*R$_8$ is the point of attachment and is (CH$_2$)$_x$, wherein X is 0, 1, 2, 3, 4, 5, 6, 7, 8, 9, or 10, CH$_2$CHOH, CH(CH$_3$)(R-isomer), or CH(CH$_3$)(S-isomer). Each of R$_9$, R$_{10}$, R$_{11}$, R$_{12}$, and R$_{13}$ is the same or different and independently are H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, P', aryl, heteroaryl, biaryl, heterobiaryl, heterocycle, or branched, cyclic, or unbranched alkyl. P' is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K', O—C(O)-lower (C$_1$, C$_2$, C$_3$, C$_4$, C$_5$, or C$_6$) alkyl-L', NH-lower (C$_1$, C$_2$, C$_3$, C$_4$, C$_5$, or C$_6$) alkyl-M', or O-aryl-Q', further where lower (C$_1$, C$_2$, C$_3$, C$_4$, C$_5$, or C$_6$) alkyl is linear or branched alkyl. K' is C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

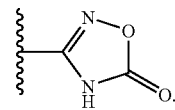

L' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

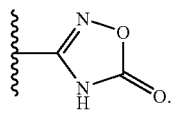

M' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

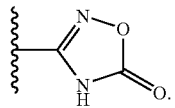

Q' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

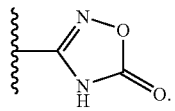

R$_{22}$, R$_{23}$ and R$_{24}$ are independently C$_1$, C$_2$, C$_3$, C$_4$, C$_5$, or C$_6$ alkyl or R$_{22}$ and R$_{23}$ taken together with the attached nitrogen atom form a five membered ring. R$_a$, R$_b$, and R$_c$ are the same or different and independently are H, aryl, heteroaryl, biaryl, heterobiaryl, branched, cyclic, or unbranched alkyl. Any of R$_9$, R$_{10}$, R$_{11}$, R$_{12}$, and R$_{13}$ are substituted or unsubstituted. If one of R$_1$, R$_2$, R$_3$, R$_4$, or R$_5$ is not P, then at least one of R$_9$, R$_{10}$, R$_{11}$, R$_{12}$, and R$_{13}$ is P'.

In one embodiment, P' is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K', O—C(O)-lower (C$_1$, C$_2$, C$_3$, C$_4$, C$_5$, or C$_6$) alkyl-L', NH-lower (C$_1$, C$_2$, C$_3$, C$_4$, C$_5$, or C$_6$) alkyl-M', or O-aryl-Q'. K' is SO$_3$H, OSO$_3$H, PO$_3$H$_2$, OPO$_3$H$_2$, NH$_2$, NHR$_{22}$, NR$_{22}$R$_{23}$, glycoside, or heterocycle. L' is SO$_3$H, OSO$_3$H, PO$_3$H$_2$, OPO$_3$H$_2$, NH$_2$, NHR$_{22}$, NR$_{22}$R$_{23}$, glycoside, or heterocycle. M' is SO$_3$H, OSO$_3$H, PO$_3$H$_2$, OPO$_3$H$_2$, NH$_2$, NHR$_{22}$, NR$_{22}$R$_{23}$, glycoside, or heterocycle. In another embodiment, at least one of R$_6$ or R$_7$ and

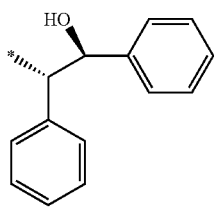 or 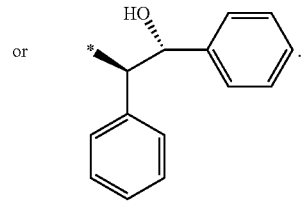.

Another aspect of the invention includes a method of preventing or treating a proliferative disease in a subject comprising administering a compound having the Formula V:

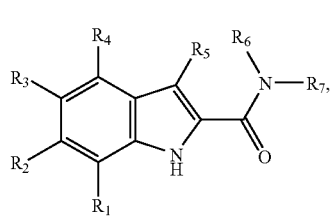

(Formula V)

or a salt, solvate, hydrate, or prodrug thereof. R$_1$, R$_2$, R$_3$, R$_4$, and R$_5$ are the same or different and are independently H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, P, halogen, aryl, benzyl, heteroaryl, biaryl, heterobiaryl, heterocycle, and branched, unbranched, or cyclic alkyl. R$_6$ and R$_7$ are the same or different and are independently H, branched or unbranched, or (CH$_2$)$_t$-Z, wherein Z is aryl, heteroaryl, biaryl, cyclic alkyl, or heterocycle, or R$_6$ and R$_7$ together form a heterocycle. t is 0, 1, 2, 3, 4, 5, 6, 7, 8, 9, or 10. R$_a$, R$_b$, and R$_c$ are the same or different and are independently H, aryl, heteroaryl, biaryl, heterobiaryl, or branched, unbranched, or cyclic alkyl. P is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q, further wherein lower (C$_1$, C$_2$, C$_3$, C$_4$, C$_5$, or C$_6$) alkyl is linear or branched alkyl. K is C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

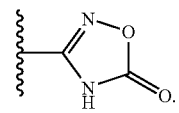

L is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

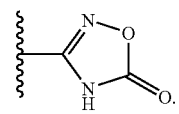

M is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

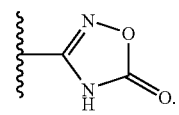

Q is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

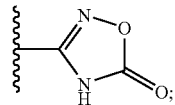

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring;

wherein any of R$_1$, R$_2$, R$_3$, R$_4$, R$_5$, R$_6$, and R$_7$ and R$_a$, R$_b$, and R$_c$ is substituted or unsubstituted. At least one of R$_1$, R$_2$, R$_3$, R$_4$, R$_5$, and R$_6$ is P.

In one embodiment, P is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q. K is SO$_3$H, OSO$_3$H, PO$_3$H$_2$, OPO$_3$H$_2$, NH$_2$, NHR$_{19}$, NR$_{19}$R$_{20}$, glycoside, and heterocycle. L is SO$_3$H, OSO$_3$H, PO$_3$H$_2$, OPO$_3$H$_2$, NH$_2$, NHR$_{19}$, NR$_{19}$R$_{20}$, glycoside, and heterocycle. M is SO$_3$H, OSO$_3$H, PO$_3$H$_2$, OPO$_3$H$_2$, NH$_2$, NHR$_{19}$, NR$_{19}$R$_{20}$, glycoside, and heterocycle.

In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membrane. In another embodiment, the compound is administered with a pharmaceutically acceptable carrier. In one embodiment, the compound is administered before initiation of the proliferative disease. In another embodiment, the compound is administered after inititiation of the proliferative disease.

In one embodiment, at least one of R$_1$, R$_2$, R$_3$, R$_4$, and R$_5$ is selected from halogen, boronic acid, hydroxyl, phosphonic acid, sulfamic acid, guanidine, carboxylic acid, aldehyde, amide, and hydroxymethylphosphonic acid. In another embodiment, at least one of R$_1$, R$_2$, R$_3$, R$_4$, and R$_5$ is halogen. In another embodiment, at least one of R$_1$, R$_2$, R$_3$, R$_4$, and R$_5$ is boronic acid. In another embodiment, at least one of R$_1$, R$_2$, R$_3$, R$_4$, and R$_5$ is hydroxyl. In another embodiment, at least one of R$_1$, R$_2$, R$_3$, R$_4$, and R$_5$ is amide. For example, the amide is vicinal tricarbonyl amide. In one embodiment, R$_3$ is halogen. For example, R$_3$ is fluorine. In one embodiment, R$_3$ is hydroxyl. In one embodiment, at least one of R$_6$ and R$_7$ is

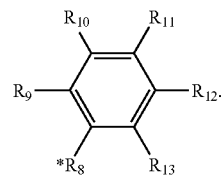

*R$_8$ is the point of attachment and is (CH$_2$)$_x$, wherein X is 0, 1, 2, 3, 4, 5, 6, 7, 8, 9, or 10, CH$_2$CHOH, CH(CH$_3$)(R-isomer), or CH(CH$_3$)(S-isomer). Each of R$_9$, R$_{10}$, R$_{11}$, R$_{12}$, and R$_{13}$ is the same or different and independently are H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, P', aryl, heteroaryl, biaryl, heterobiaryl, heterocycle, or branched, cyclic, or unbranched alkyl. P' is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K', O—C(O)-lower (C$_1$, C$_2$, C$_3$, C$_4$, C$_5$, or C$_6$) alkyl-L', NH-lower (C$_1$, C$_2$, C$_3$, C$_4$, C$_5$, or C$_6$) alkyl-M', or O-aryl-Q', further wherein lower (C$_1$, C$_2$, C$_3$, C$_4$, C$_5$, or C$_6$) alkyl is linear or branched alkyl. K' is C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

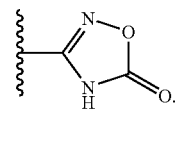

L' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

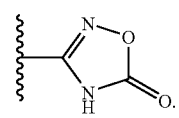

M' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

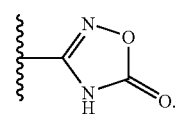

Q' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

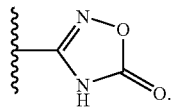

$R_{22}$, $R_{23}$ and $R_{24}$ are independently $C_1$, $C_2$, $C_3$, $C_4$, $C_5$, or $C_6$ alkyl or $R_{22}$ and $R_{23}$ taken together with the attached nitrogen atom form a five membered ring. $R_a$, $R_b$, and $R_c$ are the same or different and independently are H, aryl, heteroaryl, biaryl, heterobiaryl, branched, cyclic, or unbranched alkyl. $R_9$, $R_{10}$, $R_{11}$, $R_{12}$, and $R_{13}$ are substituted or unsubstituted. If one of $R_1$, $R_2$, $R_3$, $R_4$, or $R_5$ is not P, then at least one of $R_9$, $R_{10}$, $R_{11}$, $R_{12}$, and $R_{13}$ is P'.

In one embodiment, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q'. K' is $SO_3H$, $OSO_3H$, $PO_3H_2$, $OPO_3H_2$, $NH_2$, $NHR_{22}$, $NR_{22}R_{23}$, glycoside, or heterocycle. L' is $SO_3H$, $OSO_3H$, $PO_3H_2$, $OPO_3H_2$, $NH_2$, $NHR_{22}$, $NR_{22}R_{23}$, glycoside, or heterocycle. M' is $SO_3H$, $OSO_3H$, $PO_3H_2$, $OPO_3H_2$, $NH_2$, $NHR_{22}$, $NR_{22}R_{23}$, glycoside, or heterocycle.

In one embodiment, at least one of $R_6$ and $R_7$ is

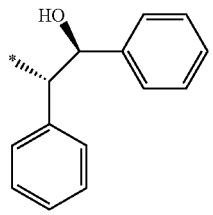 or 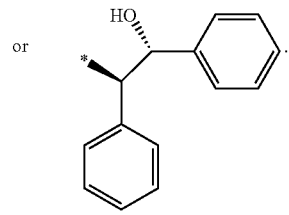.

Another aspect of the invention includes a method of protecting against or treating osteoporosis in a subject comprising administering a compound of Formula VII:

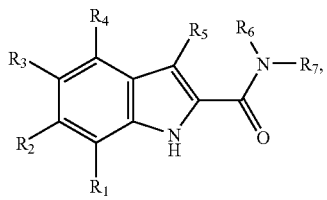

(Formula VII)

or a salt, solvate, hydrate, or prodrug thereof. $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, and branched, unbranched, or cyclic alkyl. $R_6$ and $R_7$ are the same or different and are independently H, branched or unbranched or $(CH_2)_t$-Z, wherein Z is aryl, heteroaryl, biaryl, cyclic alkyl, or heterocycle, or $R_6$ and $R_7$ together form a heterocycle. t is 0, 1, 2, 3, 4, 5, 6, 7, 8, 9, or 10. $R_a$, $R_b$, and $R_c$ are the same or different and are independently H, aryl, heteroaryl, biaryl, heterobiaryl, or branched, unbranched, or cyclic alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

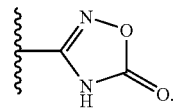

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

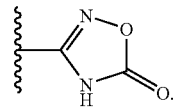

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

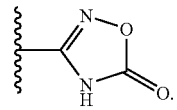

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

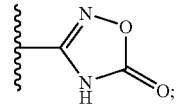;

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

wherein any of $R_1$, $R_2$, $R_3$, $R_4$, $R_5$, $R_6$, and $R_7$ and $R_a$, $R_b$, and $R_c$ is substituted or unsubstituted.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, $OSO_3H$, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase. For example, the Src family protein kinase is pp60$^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before initiation of osteoporosis. In another embodiment, the compound is administered after inititiation of osteoporosis.

In another embodiment, at least one of $R_1$, $R_2$, $R_3$, $R_4$, and $R_5$ is selected from halogen, boronic acid, hydroxyl, phosphonic acid, sulfamic acid, guanidine, carboxylic acid, aldehyde, amide, and hydroxymethylphosphonic acid.

In another embodiment, at least one of $R_1$, $R_2$, $R_3$, $R_4$, and $R_5$ is a halogen. In one embodiment, at least one of $R_1$, $R_2$, $R_3$, $R_4$, and $R_5$ is a boronic acid. In another embodiment, at least one of $R_1$, $R_2$, $R_3$, $R_4$, and $R_5$ is hydroxyl. In another embodiment, at least one of $R_1$, $R_2$, $R_3$, $R_4$, and $R_5$ is amide. For example, the amide group is vicinal tricarbonyl amide. In one embodiment, $R_3$ is halogen. For example, $R_3$ is fluorine. In one embodiment, $R_3$ is hydroxyl.

In one embodiment, at least one of $R_6$ and $R_7$ is

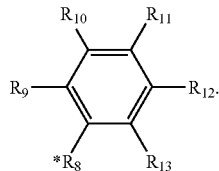

*$R_8$ is the point of attachment and is $(CH_2)_x$, wherein X is 0, 1, 2, 3, 4, 5, 6, 7, 8, 9, or 10, $CH_2CHOH$, $CH(CH_3)$(R-isomer), or $CH(CH_3)$(S-isomer). Each of $R_9$, $R_{10}$, $R_{11}$, $R_{12}$, and $R_{13}$ is the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)_2OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, P', aryl, heteroaryl, biaryl, heterobiaryl, heterocycle and branched, cyclic, or unbranched alkyl, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q', further wherein lower ($C_1$, $C_2$, $C_3$, $C_4$, $C_5$, or $C_6$) alkyl is linear or branched alkyl. K' is $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

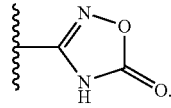

L' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

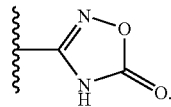

M' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

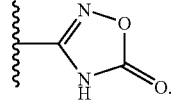

Q' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

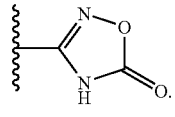

$R_{22}$, $R_{23}$ and $R_{24}$ are independently $C_1$, $C_2$, $C_3$, $C_4$, $C_5$, or $C_6$ alkyl or $R_{22}$ and $R_{23}$ taken together with the attached nitrogen atom form a five membered ring. $R_a$, $R_b$, and $R_c$ are the same or different and independently are H, aryl, heteroaryl, biaryl, heterobiaryl, branched, cyclic, or unbranched alkyl; and wherein any of $R_9$, $R_{10}$, $R_{11}$, $R_{12}$, and $R_{13}$ are substituted or unsubstituted.

In one embodiment, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q'. K' is $SO_3H$, $OSO_3H$, $PO_3H_2$, $OPO_3H_2$, $NH_2$, $NHR_{22}$, $NR_{22}R_{23}$, glycoside, or heterocycle. L' is $SO_3H$, $OSO_3H$, $PO_3H_2$, $OPO_3H_2$, $NH_2$, $NHR_{22}$, $NR_{22}R_{23}$, glycoside, or heterocycle; and further wherein M' is $SO_3H$, $OSO_3H$, $PO_3H_2$, $OPO_3H_2$, $NH_2$, $NHR_{22}$, $NR_{22}R_{23}$, glycoside, or heterocycle. In one embodiment, at least one of $R_6$ and $R_7$ is

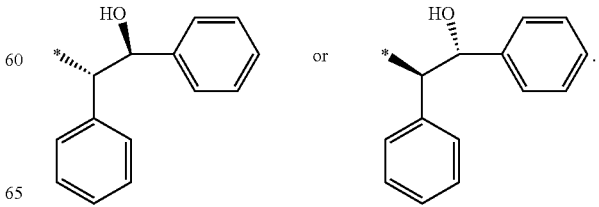

In another embodiment, the compound is

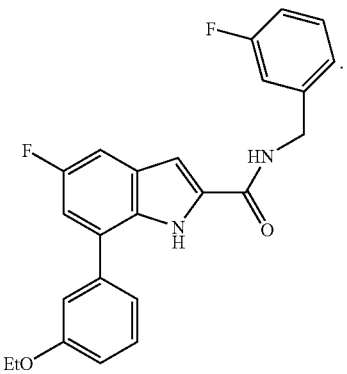

Another aspect of the invention includes a method of protecting against or treating hearing loss in a subject comprising administering a compound of Formula VI:

(Formula VI)

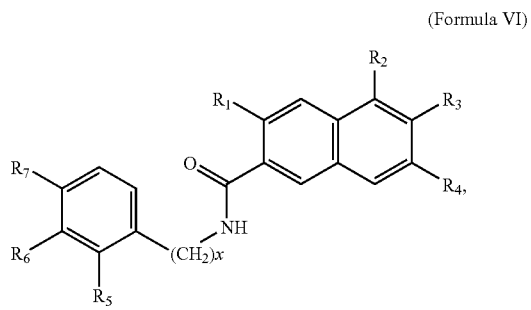

or a salt, solvate, hydrate, or prodrug thereof. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl;

P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

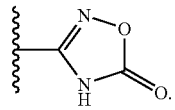

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

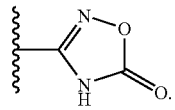

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

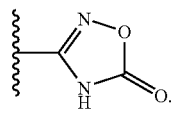

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

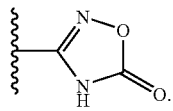

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. x is 1, 2, 3, 4, 5, 6, 7, 8, 9, or 10. At least one of $R_1$, $R_2$, $R_3$, $R_4$, $R_5$, $R_6$, and $R_7$ is P.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, $OSO_3H$, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

In one embodiment, the compound inhibits one or more components of a protein kinase signaling pathway. In another embodiment, the compound is an allosteric inhibitor. In one embodiment, the compound is a peptide substrate inhibitor. In another embodiment, the compound does not inhibit ATP binding to a protein kinase. In another embodiment, the compound inhibits a Src family protein kinase. For example, the Src family protein kinase is $pp60^{c\text{-}src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops into the ear), intraarterially, intralesionally, by metering pump, or by application to mucous membranes. In one embodiment, the compound is administered in combination with a drug that causes hearing loss. In another embodiment, the compound is administered with a pharmaceutically acceptable carrier. In another embodiment, the compound is administered before initiation of hearing loss. In another embodiment, the compound is administered after inititiation of hearing loss.

Another aspect of the invention includes a method of protecting against or treating osteoporosis in a subject comprising administering a compound of Formula VIII:

(Formula VIII)

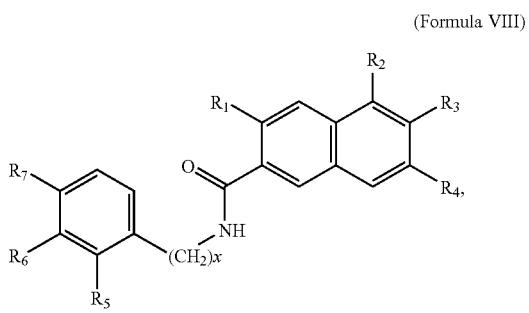

or a salt, solvate, hydrate, or prodrug thereof. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_b$ $OR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

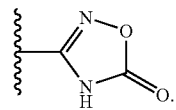

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

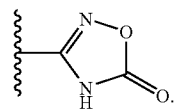

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

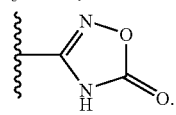

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

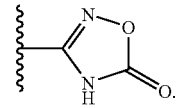

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. x is 1, 2, 3, 4, 5, 6, 7, 8, 9, or 10.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, 3H, H, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase. For example, the Src family protein kinase is $pp60^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of osteoporosis. In another embodiment, the compound is administered after onset of osteoporosis.

A method of preventing or treating a proliferative disorder in a subject comprising administering a compound of Formula VIII:

(Formula VIII)

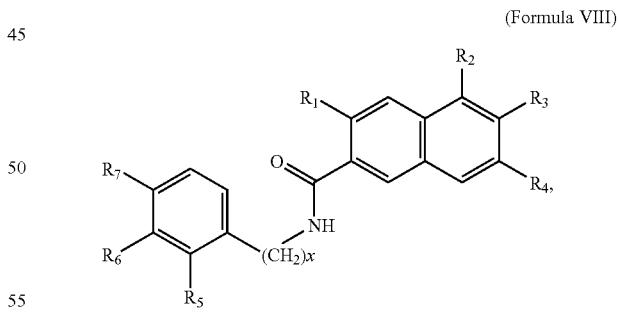

or a salt, solvate, hydrate, or prodrug thereof. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_b$ $OR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

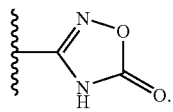

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

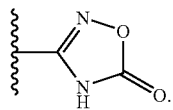

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

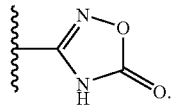

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

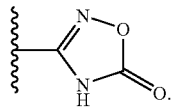

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. x is 1, 2, 3, 4, 5, 6, 7, 8, 9, or 10.

In one embodiment, the compound inhibits one or more components of a protein kinase signaling pathway. In another embodiment, the compound is an allosteric inhibitor. In another embodiment, the compound is a peptide substrate inhibitor. In one embodiment, the compound does not inhibit ATP binding to a protein kinase. In another embodiment, the compound inhibits a Src family protein kinase. For example, the Src family protein kinase is pp60$^{c-src}$ tyrosine kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before onset of the proliferative disease. In another embodiment, the compound is administered after onset of the proliferative disease.

Another aspect of the invention includes a method of protecting against or treating ophthalmic disease (e.g., macular degeneration, retinopathy, macular edema, etc.) in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically (e.g., by administration of drops or a cream to the eye), intraarterially, intralesionally, by metering pump, or by application to mucous membranes. In one embodiment, the compound is administered with a pharmaceutical acceptable carrier. In another embodiment, the compound is administered before initiation of ophthalmic disease. In another embodiment, the compound is administered after inititiation of ophthalmic disease.

Another aspect of the invention includes a method of protecting against or treating diabetes in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before the onset of diabetes. In another embodiment, the compound is administered after the onset of diabetes.

Another aspect of the invention includes a method of protecting against or treating obesity in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before the onset of obesity. In another embodiment, the compound is administered after the onset of obesity.

Another aspect of the invention includes a method of protecting against or treating stroke in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before a stroke occurs in a subject. In another embodiment, the compound is administered after a stroke has occurred in a subject.

Another aspect of the invention includes a method of protecting against or treating athrosclerosis in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before the onset of athrosclerosis. In another embodiment, the compound is administered after the onset of athrosclerosis.

Another aspect of the invention includes a method of regulating immune system activity in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of protecting against or treating chronic neuropathic pain in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of chronic neuropathic pain. In another embodiment, the compound is administered after the onset of chronic neuropathic pain.

Another aspect of the invention includes a method of protecting against or treating hepatitis B in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of hepatitis B. In another embodiment, the compound is administered after the onset of hepatitis B.

BRIEF DESCRIPTION OF THE DRAWINGS

FIG. 15 is a graph showing the maximum tolerated dose (MTD) of two Src inhibitors (1a from Example 1 and 2k from Example 4) in SCID mice.

FIGS. 29A-F are SEM images of chinchilla cochleas. FIG. 29A shows a split (marked by S) of the reticular lamina after exposure to an impulse noise. FIG. 29B shows focal adhesion kinase (FAK) staining in a cochlea exposed to an octave band noise centered at 4 kHz (OBN) at 105 dB (SPL). FIG. 29C shows a small lesion with a few apoptotic nuclei (marked with arrow) from a cochlea exposed to an OBN at 110 dB. FIG. 29D shows FAK staining for the lesion shown in FIG. 29C. FIG. 29E shows a confocal scanning level a few microns lower than in FIG. 29D, demonstrating that the lesion extends well below the cuticular plate and into the cell body (marked with arrow). FIG. 29F shows FAK staining in a cochlea exposed to impulse noise at 155 dB (SPL). In this figure, many outer hair cells have lost their cuticular plate integrity. The remaining outer hair cells show strong FAK fluorescence in the cuticular plates.

In FIG. 30A, the chinchilla cochlea was pre-treated with CH-65. In FIG. 30B, the chinchilla cochlea was left untreated.

FIG. 51A is a series of illustrations depicting the effect of compounds on osteoclast formation on bone slices.

FIG. 51B is a series of illustrations demonstrating the effect of compounds on the formation of resorption pits on bone slices.

DETAILED DESCRIPTION OF THE INVENTION

Figure 1:
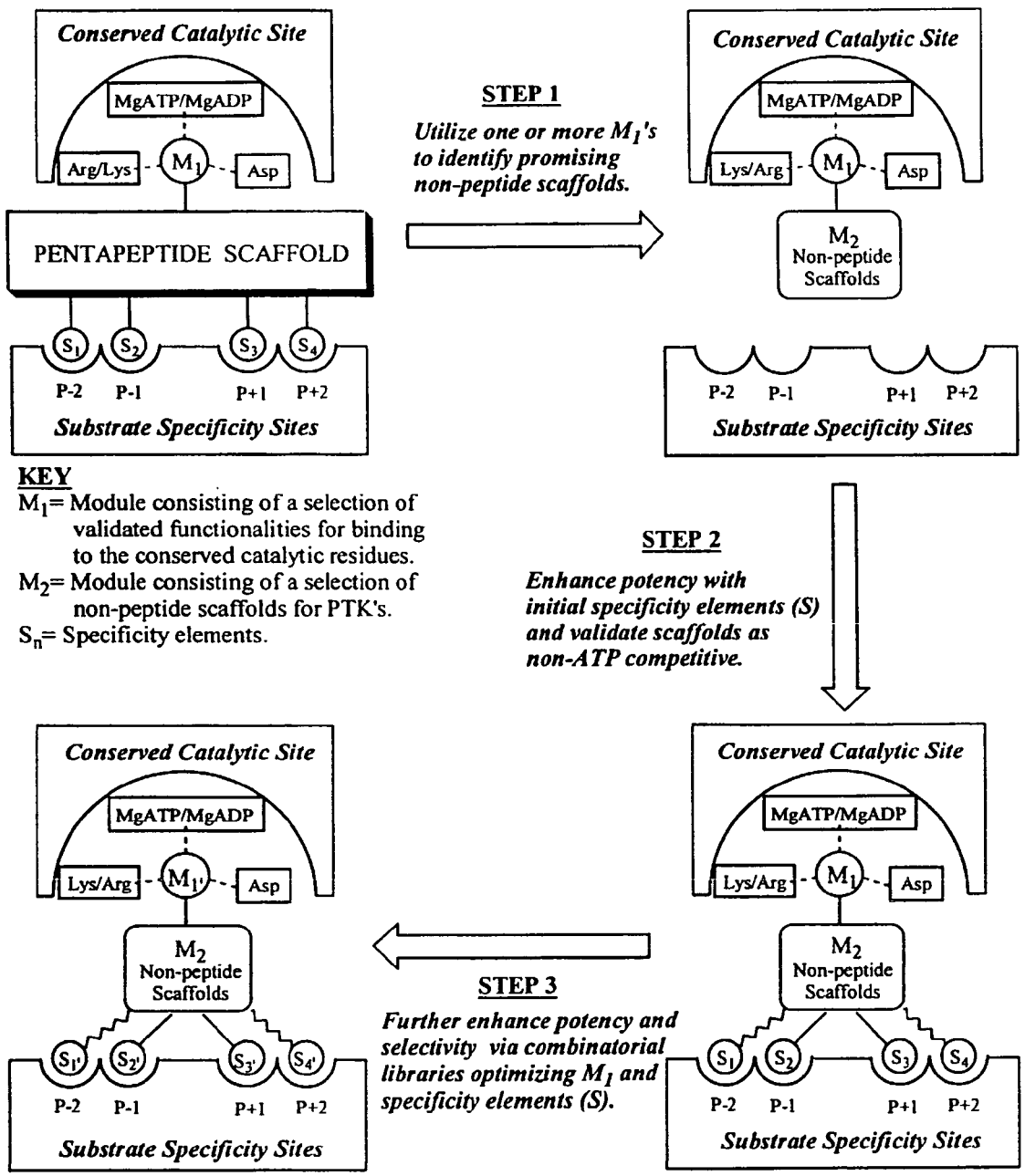
FIG. 1 depicts the modular strategy for developing non-peptide protein kinase inhibitors. Step 1 utilizes one or more first modules ("$M_1$'s") to identify promising non-peptide scaffolds. Step 2 enhances the potency by adding specificity elements. During this step the scaffolds are validated. Whether the inhibitor is non-ATP competitive can also be determined. In step 3, the potency and selectivity are further enhanced using combinatorial libraries to optimize $M_1$ and specificity elements.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders. Such diseases and disorders include, for example, cancers, osteoporosis, cardiovascular disorders, immune system dysfunction, type II diabetes, obesity, and transplant rejection.

Compounds of the invention are useful in modulation a component of the kinase signaling cascade. Some compounds may be useful in modulation of more than one component of a kinase signaling cascade. The phrase "modulates one or more components of a protein kinase signaling cascade" means that one or more components of the kinase signaling cascade are affected such that the functioning of a cell changes. Components of a protein kinase signaling cascade include any proteins involved directly or indirectly in the kinase signaling pathway including second messengers and upstream and downstream targets.

A number of protein kinases and phosphatases are known, and are targets for the development of therapeutics. See, e.g., Hidaka and Kobayashi, Annu. Rev. Pharmacol. Toxicol, 1992, 32:377-397; Davies et al., Biochem. J., 2000, 351:95-105, each of which is incorporated by reference herein.

One family of kinases, the protein tyrosine kinases are divided into two large families: receptor tyrosine kinases, or RTKs (e.g., insulin receptor kinase (IRK), epidermal growth factor receptor (EGFR), basic fibroblast growth factor receptor (FGFR), platelet-derived growth factor receptor (PDGFR), vascular endothelial growth factor receptor (VEGFR-2 or Flk1/KDR), and nerve growth factor receptor (NGFR)) and nonreceptor tyrosine kinases, or NRTKs (e.g., the Src family (Src, Fyn, Yes, Blk, Yrk, Fgr, Hck, Lck, and Lyn), Fak, Jak, Abl and Zap70). See, for example, Parang and Sun, Expert Opin. Ther. Patents, 2005, 15:1183-1207, incorporated by reference herein.

Because of the role of Src kinases in a variety of cancers, these kinases are the subject of a number of studies relating to the development of Src inhibitors as cancer therapeutics, including highly metastatic cancer cell growth. Src inhibitors are sought as therapeutics for a variety of cancers, including, for example, colon cancer, precancerous colon lesions, ovarian cancer, breast cancer, epithelial cancers, esophageal cancer, non-small cell lung cancer, pancreatic cancer, and others. See, e.g., Frame, Biochim. Biophys. Acta, 2002, 1602:114-130 and Parang and Sun, Expert Opin. Ther. Patents, 2005, 15:1183-1207.

Inhibition of other kinases may be useful in the treatment and modulation of other types of diseases and disorders. For example, various eye diseases may be inhibited or prevented by administration of VEGF receptor tyrosine kinase inhibitors. Inhibitors of the tyrosine phosphatase PTP-1B and/or glycogen phosphorylase may provide treatments for Type II diabetes or obesity. Inhibitors of p56lck may be useful in treating immune system disorders. Other targets include HIV reverse transcriptase, thromboxane synthase, EGFRTK, p55 fyn, etc.

Compounds of the invention may be Src signaling inhibitors that bind in the Src peptide substrate site. The activity of various compounds of the invention has been studied in c-Src (527F, constitutively active and transforming) transformed NIH3T3 cells and in human colon cancer cells (HT29). For example, in these cell lines, KX2-391 was shown to reduce the phosphorylation level of known Src protein substrates in a dose-dependent fashion and in good correlation with growth inhibitory effects. Thus, in some embodiments, compounds of the invention may directly inhibit Src, and may do so by binding in the peptide binding site (as opposed to binding at an allosteric site).

Molecular modeling experiments have been performed which show that compounds of the invention fit into the model Src substrate site (See, e.g., U.S. Pat. Nos. 7,005,445 and 7,070,936). Modeling is also used to retool the Src kinase inhibitor scaffolds in order to target other kinases, simply by using a different set of side chains present on the molecules and/or modifying the scaffold itself.

Without wishing to be bound by theory, it is believed that the conformation of some kinases (e.g., Src) outside cells relative to the conformation inside cells is markedly different, because inside cells, many kinases are is embedded in multi-protein signaling complexes. Thus, because the peptide substrate binding site is not well formed in an isolated kinase (as shown by Src x-ray structures), it is believed that the activity against isolated kinase for a peptide substrate binding inhibitor would be weak. Binding to this site in an isolated kinase assay requires the inhibitor to capture the very small percentage of total protein in an isolated enzyme assay that is in the same conformation that exists inside cells. This requires a large excess of the inhibitor to drain significant amounts of the enzyme from the catalytic cycle in the assay in order to be detectable.

However, for cell-based assays, a large inhibitor excess is not needed because the peptide binding site is expected to be formed. In cell-based Src assays, SH2 & SH3 domain binding proteins have already shifted the Src conformation so that the peptide substrate binding site is fully formed. Thus, low concentrations of the inhibitor can remove the enzyme from the catalytic cycle since all of the enzyme is in the tight binding conformation.

The vast majority of known kinase inhibitors are ATP competitive and show poor selectivity in a panel of isolated kinase assays. However, many of the compounds of the invention are thought to be peptide substrate binding inhibitors. Thus, traditional high throughput screening of compounds against isolated enzymes, such as Src, would not result in the discovery of compounds of the invention.

There is considerable recent literature support for targeting pp60c-src (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al. (1999) Oncogene 18(33): 4654-4662). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano, et al., Proc. Annu. Meet. Am. Assoc. Cancer Res. 38:A1925 (1997)). Additionally, reduced VEGF mRNA expression was noted upon Src inhibition and tumors derived from these Src-inhibited cell lines showed reduced angiogenic development (Ellis et al., Journal of Biological Chemistry 273 (2):1052-1057 (1998)).

For example, a knock-out of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., (1997) Genes & Development 11: 2835-2844). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be overactivated in a growing number of human tumors (Levitzki, Current Opinion in Cell Biology, 8, 239-244 (1996); Levitzki, Anti-Cancer Drug Design, 11, 175-182 (1996)). The potential benefits of Src inhibition for cancer therapy appear to be four-fold inhibition of uncontrolled cell growth caused by autocrine growth factor loop effects, inhibition of metastasis due to triggering apoptosis upon breaking free from the cell matrix, inhibition of tumor angiogenesis via reduced VEGF levels, low toxicity.

Prostate cancer cells have been reported to have both an over expression of paxillin and p130cas and are hyperphosphorylated (Tremblay et al., Int. J. Cancer, 68, 164-171, 1996) and may thus be a prime target for Src inhibitors.

As described herein, a compound of the invention may be used to protect against or prevent hearing loss in a subject. In order to protect against hearing loss, the compound may be administered prior to noise exposure or exposure to a drug which induces hearing loss. Such drugs may include chemotherapeutic drugs (e.g., platinum-based drugs which target hair cells) and aminoglycoside antibiotics. A compound of the invention may provide a synergistic effect with certain cancer drugs. For example, promising inhibitors can be screened in primary human tumor tissue assays, particularly to look for synergy with other known anti-cancer drugs. In addition, the protein kinase inhibitors may reduce toxicity of certain cancer drugs (e.g., platinum-based drugs which are toxic to the cochlea and kidney), thereby allowing increased dosage.

Alternatively, a compound of the invention may be used to treat hearing loss in a subject. In this embodiment, the compound is administered to the subject subsequent to the initiation of hearing loss to reduce the level of hearing loss. A compound of the invention may be involved in modulating a kinase cascade, e.g. a kinase inhibitor, a non-ATP competitive inhibitor, a tyrosine kinase inhibitor, a Src inhibitor or a focal adhesion kinase (FAK) modulator. Although not wishing to be bound by theory, it is believed that the administration of kinase inhibitors prevents apoptosis of cochlear hair cells, thereby preventing hearing loss. In one embodiment, administration of a compound of the invention is administered to a subject suffering from hearing loss in order to prevent further hearing loss. In another embodiment, administration of a compound of the invention is administered to a subject suffering from hearing loss in order to restore lost hearing. In particular, following noise exposure, the tight cell junctures between the cochlear hair cells, as well as the cell-extracellular matrix interaction, are torn and stressed. The stressing of these tight cell junctures initiates apoptosis in the cells through a complex signaling pathway in which tyrosine kinases act as molecular switches, interacting with focal adhesion kinase to transduce signals of cell-matrix disruptions to the nucleus. It is believed that the administration of kinase inhibitors prevents the initiation of apoptosis in this cascade.

The identification of apoptosis in the noise-exposed cochlea has generated a number of new possibilities for the prevention of noise-induced hearing loss (NIHL) (Hu, et al.; 2000, Acta. Otolaryngol., 120, 19-24). For example, the ear can be protected from NIHL by administration of antioxidant drugs to the round window of the ear (Hight, et al.; 2003, Hear. Res., 179, 21-32; Hu, et al.; Hear. Res. 113, 198-206). Specifically, NIHL has been reduced by the administration of FDA-approved antioxidant compounds (N-L-acetylcysteine (L-NAC) and salicylate) in the chinchilla (Kopke, et al.; 2000, Hear. Res., 149, 138-146). Moreover, Harris et al. have recently described prevention of NIHL with Src-PTK inhibitors (Harris, et al.; 2005, Hear. Res., 208, 14-25). Thus, it is hypothesized that the administration of a compound of the instant invention which modulates the activity of kinases, is useful for treating hearing loss.

Changes in cell attachment or cell stress can activate a variety of signals through the activation of integrins and through the phosphorylation of PTKs, including the Src family of tyrosine kinases. Src interactions have been linked to signaling pathways that modify the cytoskeleton and activate a variety of protein kinase cascades that regulate cell survival and gene transcription (reviewed in Giancotti and Ruoslahti; 1999, Science, 285, 1028-1032). In fact, recent results have indicated that outer hair cells (OHC), which had detached at the cell base following an intense noise exposure, underwent apoptotic cell death. Specifically, the Src PTK signaling cascade is thought to be involved in both metabolic- and mechanically-induced initiation of apoptosis in sensory cells of the cochlea. In a recent study, Src inhibitors provided protection from a 4 hour, 4 kHz octave band noise at 106 dB, indicating that Src-PTKs might be activated in outer hair cells following noise exposure (Harris, et al.; 2005, Hear. Res., 208, 14-25). Thus, compounds of the instant invention that modulate the activity of Src, are useful in treating hearing loss.

The present invention relates to a method for protecting against or treating osteoporosis in a subject. This method involves administering an effective amount of a compound of the invention to the subject to protect against or to treat osteoporosis. In order to protect against osteoporosis, the compound may be administered prior to the development of osteoporosis. Alternatively, the compound may be used to treat osteoporosis in a subject. In this embodiment, the compound is administered to the subject subsequent to the initiation of osteoporosis to reduce the level of osteoporosis.

A compound of the invention can be, e.g. a non-ATP competitive inhibitor. The compound of the invention can modulate a kinase signaling cascade, depending upon the particular side chains and scaffold modifications selected. The compound of the invention can be a kinase inhibitor. For example, the compound can be a protein tyrosine kinase (PTK) inhibitor. The proline-rich tyrosine kinase (PYK2; also known as cell adhesion kinase p, related adhesion focal tyrosine kinase, or calcium-dependent tyrosine kinase) and focal adhesion kinase (FAK) are members of a distinct family of non receptor protein-tyrosine kinases that are regulated by a variety of extracellular stimuli (Avraham, et al.; 2000, Cell Signal., 12, 123-133; Schlaepfer, et al.; 1999, Prog. Biophys. Mol. Biol., 71, 435-478). The compound of the invention can be a Src inhibitor. It has been shown that Src deficiency is associated with osteoporosis in mice, because of loss of osteoclast function (Soriano, et al.; 1991, Cell, 64, 693-702). Alternatively, the compound of the invention can modulate the expression of interleukin-1 receptor associated kinase M (IRAK-M). Mice that lack IRAK-M develop severe osteoporosis, which is associated with the accelerated differentiation of osteoclasts, an increase in the half-life of osteoclasts, and their activation (Hongmei, et al.; 2005, J. Exp. Med., 201, 1169-1177).

Multinucleated osteoclasts originate from the fusion of mononuclear phagocytes and play a major role in bone development and remodeling via the resorption of bone. Osteoclasts are multinucleated, terminally differentiated cells that degrade mineralized matrix. In normal bone tissue, there is a balance between bone formation by osteoblasts and bone resorption by osteoclasts. When the balance of this dynamic and highly regulated process is disrupted, bone resorption can exceed bone formation resulting in quantitative bone loss. Because osteoclasts are essential for the development and remodeling of bone, increases in their number and/or activity lead to diseases that are associated with generalized bone loss (e.g., osteoporosis) and others with localized bone loss (e.g., rheumatoid arthritis, periodontal disease).

Osteoclasts and osteoblasts both command a multitude of cellular signaling pathways involving protein kinases. Osteoclast activation is initiated by adhesion to bone, cytoskeletal rearrangement, formation of the sealing zone, and formation of the polarized ruffled membrane. It is believed that protein-tyrosine kinase 2 (PYK2) participates in the transfer of signals from the cell surface to the cytoskeleton, as it is tyrosine phosphorylated and activated by adhesion-initiated signaling in osteoclasts (Duong, et al.; 1998, J. Clin. Invest., 102, 881-892). Recent evidence has indicated that the reduction of PYK2 protein levels results in the inhibition of osteoclast formation and bone resorption in vitro (Duong, et al.; 2001, J. Bio. Chem., 276, 7484-7492). Therefore, the inhibition of PYK2 or other protein tyrosine kinases might reduce the level of osteoporosis by decreasing osteoclast formation and bone resorption. Thus, without wishing to be bound by theory, it is hypothesized that the administration of a compound of the instant invention will modulate kinase (e.g. PTK) activity and therefore result in the inhibition of osteoclast formation and/or bone resorption, thereby treating osteoporosis.

Src tyrosine kinase stands out as a promising therapeutic target for bone disease as validated by Src knockout mouse studies and in vitro cellular experiments, suggesting a regulatory role for Src in both osteoclasts (positive) and osteoblasts (negative). In osteoclasts, Src plays key roles in motility, polarization, survival, activation (ruffled border formation) and adhesion, by mediating various signal transduction pathways, especially in cytokine and integrin signaling (Parang and Sun; 2005, Expert Opin. Ther. Patents, 15, 1183-1207). Moreover, targeted disruption of the src gene in mice induces osteopetrosis, a disorder characterized by decreased bone resorption, without showing any obvious morphological or functional abnormalities in other tissues or cells (Soriano, et al.; 1991, Cell, 64, 693-702). The osteopetrotic phenotype of src$^{-/-}$ mice is cell-autonomous and results from defects in mature osteoclasts, which normally express high levels of Src protein (Home, et al.; 1991, Cell, 119, 1003-1013). By limiting the effectiveness of Src tyrosine kinase, which triggers osteoclast activity and inhibits osteoblasts, Src inhibitors are thought to lessen bone break down and encourage bone formation. Because osteoclasts normally express high levels of Src, inhibition of Src kinase activity might be useful in the treatment of osteoporosis (Missbach, et al.; 1999, Bone, 24, 437-449). Thus, the PTK inhibitors of the instant invention that modulate the activity of Src, are useful in treating osteoporosis.

As described herein, a compound of the invention may be used to protect against or prevent obesity in a subject. In order to protect against obesity, the compound may be administered prior to the development of obesity in a subject. Alternatively, the compound may be used to treat obesity in a subject. A compound of the instant invention may be involved in modulating a kinase signaling cascade, e.g., a kinase inhibitor, a non-ATP competitive inhibitor, a tyrosine kinase inhibitor, a protein tyrosine phosphatase inhibitor, or a protein-tyrosine phosphatase 1B inhibitor.

Obesity is associated with diabetes and increased insulin resistance in insulin responsive tissues, such as skeletal muscle, liver, and white adipose tissue (Klaman, et al.; 2000, Mol. Cell. Biol., 20, 5479-5489). Insulin plays a critical role in the regulation of glucose homeostasis, lipid metabolism, and energy balance. Insulin signaling is initiated by binding of insulin to the insulin receptor (IR), a receptor tyrosine kinase. Insulin binding evokes a cascade of phosphorylation events, beginning with the autophosphorylation of the IR on multiple tyrosyl residues. Autophosphorylation enhances IR kinase activity and triggers downstream signaling events. The stimulatory effects of protein tyrosine kinases and the inhibitory effects of protein tyrosine phosphatases largely define the action of insulin. Appropriate insulin signaling minimizes large fluctuations in blood glucose concentrations and ensures adequate delivery of glucose to cells. Since insulin stimulation leads to multiple tyrosyl phosphorylation events, enhanced activity of one or more protein-tyrosine phosphatases (PTPs) could lead to insulin resistance, which may lead to obesity. Indeed, increased PTP activity has been reported in several insulin-resistant states, including obesity (Ahmad, et al.; 1997, Metabolism, 46, 1140-1145). Thus, without wishing to be bound by theory, the administration of a compound of the instant invention modulates kinase (e.g., PTP) activity, thereby treating obesity in a subject.

Insulin signaling begins with the activation of the IR via tyrosine phosphorylation and culminates in the uptake of glucose into cells by the glucose transporter, GLUT4 (Saltiel and Kahn; 2001, Nature, 414, 799-806). The activated IR must then be deactivated and returned to a basal state, a process that is believed to involve protein-tyrosine phosphatase-1B (PTP-1B) (Ahmad, et al; 1997, *J. Biol. Chem.,* 270, 20503-20508). Disruption of the gene that codes for PTP-1B in mice results in sensitivity to insulin and increased resistance to diet-induced obesity (Elchebly, et al.; 1999, *Science,* 283, 1544-1548; Klaman, et al.; 2000, *Mol. Cell. Biol.,* 20, 5479-5489). The decreased adiposity in PTP-1B deficient mice was due to a marked reduction in fat cell mass without a decrease in adipocyte number (Klaman, et al.; 2000, *Mol. Cell. Biol.,* 20, 5479-5489). Moreover, leanness in PTP-1B-deficient mice was accompanied by increased basal metabolic rate and total energy expenditure, without marked alteration of uncoupling protein mRNA expression. The disruption of the PTP-1B gene demonstrated that altering the activity of PTP-1B can modulate insulin signaling and dietary-induced obesity in vivo. Thus, without wishing to be bound by theory, the administration of a compound of the instant invention that modulates insulin signaling (e.g., PTP-1B activity), is useful in treating obesity in a subject.

As described herein, a compound of the invention may be used to protect against or prevent diabetes in a subject. In order to protect against diabetes, the compound may be administered prior to the development of diabetes in a subject. Alternatively, the compound may be used to treat diabetes in a subject. The compound of the instant invention may be involved in modulating a kinase signaling cascade, e.g. a kinase inhibitor, a non-ATP competitive inhibitor, a tyrosine kinase inhibitor, a phosphatase and tension homologue on chromosome 10 (PTEN) inhibitor, or a sequence homology 2-containing inositol 5'-phosphatase 2 (SHIP2) inhibitor.

Type 2 diabetes mellitus (T2DM) is a disorder of dysregulated energy metabolism. Energy metabolism is largely controlled by the hormone insulin, a potent anabolic agent that promotes the synthesis and storage of proteins, carbohydrates and lipids, and inhibits their breakdown and release back into the circulation. Insulin action is initiated by binding to its tyrosine kinase receptor, which results in autophosphorylation and increased catalytic activity of the kinase (Patti, et al.; 1998, *J. Basic Clin. Physiol. Pharmacol.* 9, 89-109). Tyrosine phosphorylation causes insulin receptor substrate (IRS) proteins to interact with the p85 regulatory subunit of phosphatidylinositol 3-kinase (PI3K), leading to the activation of the enzyme and its targeting to a specific subcellular location, depending on the cell type. The enzyme generates the lipid product phosphatidylinositol-3,4,5-trisphosphate (PtdIns(3,4,5)$P_3$), which regulates the localization and activity of numerous proteins (Kido, et al.; 2001, *J. Clin. Endocrinol. Metab.,* 86, 972-979). PI3K has an essential role in insulin-stimulated glucose uptake and storage, inhibition of lipolysis and regulation of hepatic gene expression (Saltiel, et al.; 2001, *Nature,* 414, 799-806). Overexpression of dominant-interfering forms of PI3K can block glucose uptake and translocation of glutamate transporter four, GLUT4, to the plasma membrane (Quon, et al.; 1995, *Mol. Cell. Biol.,* 15, 5403-5411). Thus, the administration of a compound of the instant invention that modulates kinase (e.g. PI3K) activity, and therefore results in increased glucose uptake, is useful in treating diabetes.

PTEN is a major regulator of PI3K signaling in may cell types, and functions as a tumor suppressor due to antagonism of the anti-apoptotic, proliferative and hypertrophic activities of the PI3K pathway (Goberdhan, et al.; 2003, *Hum. Mol Genet.,* 12, R239-R248; Leslie, et al.; 2004, *J. Biochem.,* 382, 1-11). Although not wishing to be bound by theory, it is believed that PTEN attenuates the PI3K pathway by dephosphorylation of the PtdIns(3,4,5)$P_3$ molecule, degrading this important lipid second messenger to PtdIns(4,5)$P_2$. In a recent study, reduction of endogenous PTEN protein by 50% using small interfering RNA (siRNA) enhanced insulin-dependent increases in PtdIns(3,4,5)$P_3$ levels, and glucose uptake (Tang, et al.; 2005, *J. Biol. Chem.,* 280, 22523-22529). Thus, without wishing to be bound by theory, it is hypothesized that the administration of a compound of the instant invention that modulates PTEN activity, and therefore results in increased glucose uptake, is useful for treating diabetes.

PtdIns(3,4,5)$P_3$ levels are also controlled by the family of SRC homology 2 (SH2)-containing inositol 5'-phosphatase (SHIP) proteins, SHIP1 and SHIP2 (Lazar and Saltiel; 2006, *Nature Reviews,* 5, 333-342). SHIP2, expressed in skeletal muscle, among other insulin-sensitive tissues, catalyzes the conversion of PtdIns(3,4,5)$P_3$ into PtdIns(3,4)$P_2$ (Pesesse, et al.; 1997; *Biochem Biophys. Res. Commun.,* 239, 697-700; Backers, et al.; 2003, *Adv. Enzyme Regul.,* 43, 15-28; Chi, et al.; 2004, *J. Biol. Chem.,* 279, 44987-44995; Sleeman, et al.; 2005, *Nature Med.,* 11, 199-205). Overexpression of SHIP2 markedly reduced insulin-stimulated PtdIns(3,4,5)$P_3$ levels, consistent with the proposed capacity of SHIP2 to attenuate the activation of downstream effectors of PI3K (Ishihara, et al.; 1999, *Biochem. Biophys. Res. Commun.,* 260, 265-272). Thus, without wishing to be bound by theory, it is hypothesized that the administration of a compound of the instant invention which modulates SHIP2 activity, and therefore results in increased glucose uptake, is useful for treating diabetes.

As described herein, a compound of the invention may be used to protect against or prevent eye disease in a subject. In order to protect against eye disease, the compound may be administered prior to the development of eye disease in a subject. Alternatively, the compound may be used to treat eye disease in a subject, e.g. macular degeneration, retinopathy, and macular edema. The compound of the instant invention may be involved in modulating a kinase cascade, e.g. a kinase inhibitor, a non-ATP competitive inhibitor, a tyrosine kinase inhibitor, e.g. a vascular endothelial growth factor (VEGF) receptor tyrosine kinase inhibitor.

Vision-threatening neovascularization of the physiologically avascular cornea can occur. The proliferative retinopathies, principally diabetic retinopathy and age-related macular degeneration, are characterized by increased vascular permeability, leading to retinal edema and subretinal fluid accumulation, and the proliferation of new vessels that are prone to hemorrhage. Angiogenesis, the formation of new blood vessels from preexisting capillaries, is an integral part of both normal development and numerous pathological processes. VEGF, a central mediator of the complex cascade of angiogenesis and a potent permeability factor, is an attractive target for novel therapeutics. VEGF is the ligand for two membrane-bound tyrosine kinase receptors, VEGFR-1 and VEGFR-2. Ligand binding triggers VEGFR dimerization and transphosphorylation with subsequent activation of an intracellular tyrosine kinase domain. The ensuing intracellular signaling axis results in vascular endothelial cell proliferation, migration, and survival. Thus, without wishing to be bound by theory, it is hypothesized that the administration of a compound of the instant invention which modulates kinase activity, e.g. tyrosine kinase activity, and results in the inhibition of angiogenesis and/or neovascularization, is useful for treating an eye disease, e.g. macular degeneration, retinopathy and/or macular edema.

Macular degeneration is characterized by VEGF-mediated retinal leakage (an increase in vascular permeability) and by the abnormal growth of small blood vessels in the back of the eye (angiogenesis). VEGF has been identified in neovascular membranes in both diabetic retinopathy and age-related macular degeneration, and intraocular levels of the factor correlate with the severity of neovascularization in diabetic retinopathy (Kvanta, et al.; 1996, *Invest. Ophthal. Vis. Sci.,* 37, 1929-1934.; Aiello, et al.; 1994, *N. Engl. J. Med.,* 331, 1480-1487). Therapeutic antagonism of VEGF in these models results in significant inhibition of both retinal and choroidal neovascularization, as well as a reduction in vascular permeability (Aiello, et al.; 1995, *Proc. Natl. Acad. Sci. USA.,* 92, 10457-10461; Krzystolik, et al.; 2002, *Arch. Ophthal.,* 120, 338-346; Qaum, et al.; 2001, *Invest. Ophthal. Vis. Sci.,* 42, 2408-2413). Thus, without wishing to be bound by theory, it is hypothesized that the administration of a compound of the instant invention which modulates VEGF activity, and results in the inhibition of angiogenesis and/or neovascularization, is useful for treating an eye disease, e.g. macular degeneration, retinopathy and/or macular edema.

The compounds of the invention are used in methods of treating, preventing, ameliorating a stroke in a subject who is at risk of suffering a stroke, is suffering from a stroke or has suffered a stroke. The compounds of the invention are useful in methods of treating patients who are undergoing post-stroke rehabilitation.

A stroke, also known as a cerebrovascular accident (CVA), is an acute neurological injury whereby the blood supply to a part of the brain is interrupted due to either blockage of an artery or rupture of a blood vessel. The part of the brain in which blood supply is interrupted no longer receives oxygen and/or nutrients carried by the blood. The brain cells become damaged or necrotic, thereby impairing function in or from that part of the brain. Brain tissue ceases to function if deprived of oxygen for more than 60 to 90 seconds and after a few minutes will suffer irreversible injury possibly leading to a death of the tissue, i.e., infarction.

Strokes are classified into two major types: ischemic, i.e., blockage of a blood vessel supplying the brain, and hemorrhagic, i.e., bleeding into or around the brain. The majority of all strokes are ischemic strokes. Ischemic stroke is commonly divided into thrombotic stroke, embolic stroke, systemic hypoperfusion (Watershed stroke), or venous thrombosis. In thrombotic stroke, a thrombus-forming process develops in the affected artery, the thrombus, i.e., blood clot, gradually narrows the lumen of the artery, thereby impeding blood flow to distal tissue. These clots usually form around atherosclerotic plaques. There are two types of thrombotic strokes, which are categorized based on the type of vessel on which the thrombus is formed. Large vessel thrombotic stroke involves the common and internal carotids, vertebral, and the Circle of Willis. Small vessel thrombotic stroke involves the intracerebral arteries, branches of the Circle of Willis, middle cerebral artery stem, and arteries arising from the distal vertebral and basilar artery.

A thrombus, even if non-occluding, can lead to an embolic stroke if the thrombus breaks off, at which point it becomes an embolus. An embolus refers to a traveling particle or debris in the arterial bloodstream originating from elsewhere. Embolic stroke refers to the blockage of arterial access to a part of the brain by an embolus. An embolus is frequently a blood clot, but it can also be a plaque that has broken off from an atherosclerotic blood vessel or a number of other substances including fat, air, and even cancerous cells. Because an embolus arises from elsewhere, local therapy only solves the problem temporarily. Thus, the source of the embolus must be identified. There are four categories of embolic stroke: those with a known cardiac source; those with a potential cardiac or aortic source (from trans-thoracic or trans-esophageal echocardiogram); those with an arterial source; and those with unknown source.

Systemic hypoperfusion is the reduction of blood flow to all parts of the body. It is most commonly due to cardiac pump failure from cardiac arrest or arrhythmias, or from reduced cardiac output as a result of myocardial infarction, pulmonary embolism, pericardial effusion, or bleeding. Hypoxemia (i.e., low blood oxygen content) may precipitate the hypoperfusion. Because the reduction in blood flow is global, all parts of the brain may be affected, especially the "watershed" areas which are border zone regions supplied by the major cerebral arteries. Blood flow to these area has not necessary stopped, but instead may have lessened to the point where brain damage occurs.

Veins in the brain function to drain the blood back to the body. When veins are occluded due to thrombosis, the draining of blood is blocked and the blood backs up, causing cerebral edema. This cerebral edema can result in both ischemic and hemorrhagic strokes. This commonly occurs in the rare disease sinus vein thrombosis.

Stroke is diagnosed in a subject or patient using one or more of a variety of techniques known in the art, such as, for example, neurological examination, blood tests, CT scans (without contrast enhancements), MRI scans, Doppler ultrasound, and arteriography (i.e., roentgenography of arteries after injection of radiopacque material into the blood stream). If a stroke is confirmed on imaging, various other studies are performed to determine whether there is a peripheral source of emboli. These studies include, e.g., an ultrasound/doppler study of the carotid arteries (to detect carotid stenosis); an electrocardiogram (ECG) and echocardiogram (to identify arrhythmias and resultant clots in the heart which may spread to the brain vessels through the bloodstream); a Holter monitor study to identify intermittent arrhythmias and an angiogram of the cerebral vasculature (if a bleed is thought to have originated from an aneurysm or arteriovenous malformation).

Compounds useful in these methods of treating, preventing or ameliorating stroke or a symptom associated with stroke are compounds that modulate kinase signaling cascade preceding, during or after a stroke. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating stroke or a symptom associated with stroke described herein is an allosteric inhibitor of kinase signaling cascade preceding, during or after a stroke. Preferably, the compound used in the methods of treating, preventing or ameliorating stroke or a symptom associated with stroke described herein is a non-ATP competitive inhibitor of kinase signaling cascade preceding, during or after a stroke.

Inhibition of Src activity has been shown to provide cerebral protection during stroke. (See Paul et al., Nature Medicine, vol. 7(2):222-227 (2001), which is hereby incorporated by reference in its entirety). Vascular endothelia growth factor (VEGF), which is produced in response to the ischemic injury, has been shown to promote vascular permeability. Studies have shown that the Src kinase regulates VEGF-mediated VP in the brain following stroke, and administration of an Src inhibitor before and after stroke reduced edema, improved cerebral perfusion and decreased infarct volume after injury occurred. (Paul et al., 2001). Thus, Src inhibition may be useful in the prevention, treatment or amelioration of secondary damage following a stroke.

The compounds of the invention prevent, treat or ameliorate stroke or a symptom associated with stroke. Symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause.

Generally there are three treatment stages for stroke: prevention, therapy immediately after the stroke, and post-stroke rehabilitation. Therapies to prevent a first or recurrent stroke are based on treating the underlying risk factors for stroke, such as, e.g., hypertension, high cholesterol, atrial fibrillation, and diabetes. Acute stroke therapies try to stop a stroke while it is happening by quickly dissolving the blood clot causing an ischemic stroke or by stopping the bleeding of a hemorrhagic stroke. Post-stroke rehabilitation helps individuals overcome disabilities that result from stroke damage. Medication or drug therapy is the most common treatment for stroke. The most popular classes of drugs used to prevent or treat stroke are anti-thrombotics (e.g., anti-platelet agents and anticoagulants) and thrombolytics. The compounds are administered to a patient who is at risk of suffering a stroke, is suffering from a stroke or has suffered a stroke at a time before, during, after, or any combination thereof, the occurrence of a stroke. The compounds of the invention are administered alone, in pharmaceutical compositions, or in combination with any of a variety of known treatments, such as, for example, an anti-platelet medication (e.g., aspirin, clopidogrel, dipyridamole), an anti-coagulant (e.g., warfarin), or a thrombolytic medication (e.g., tissue plasminogen activator (t-PA), reteplase, Urokinase, streptokinase, tenectaplase, lanoteplase, or anistreplase.

The compounds of the invention are used in methods of treating, preventing, ameliorating atherosclerosis or a symptom thereof in a subject who is at risk for or suffering from atherosclerosis.

Atherosclerosis is a disease affecting the arterial blood vessel and is commonly referred to as a "hardening" of the arteries. It is caused by the formation of multiple plaques within the arteries. Atherosclerotic plaques, though compensated for by artery enlargement, eventually lead to plaque ruptures and stenosis (i.e., narrowing) of the artery, which, in turn, leads to an insufficient blood supply to the organ it feeds. Alternatively, if the compensating artery enlargement process is excessive, a net aneurysm results. These complications are chronic, slowly progressing and cumulative. Most commonly, soft plaque suddenly ruptures, causing the formation of a blood clot (i.e., thrombus) that rapidly slows or stops blood flow, which, in turn, leads to death of the tissues fed by the artery. This catastrophic event is called an infarction. For example, coronary thrombosis of a coronary artery causes a myocardial infarction, commonly known as a heart attack. A myocardial infarction occurs when an atherosclerotic plaque slowly builds up in the inner lining of a coronary artery and then suddenly ruptures, totally occluding the artery and preventing blood flow downstream.

Atherosclerosis and acute myocardial infarction are diagnosed in a patient using any of a variety of clinical and/or laboratory tests such as, physical examination, radiologic or ultrasound examination and blood analysis. For example, a doctor or clinical can listen to a subject's arteries to detect an abnormal whooshing sound, called a bruit. A bruit can be heard with a stethoscope when placed over the affected artery. Alternatively, or in addition, the clinician or physician can check pulses, e.g., in the leg or foot, for abnormalities such as weakness or absence. The physician or clinical may perform blood work to check for cholesterol levels or to check the levels of cardiac enzymes, such as creatine kinase, troponin and lactate dehydrogenase, to detect abnormalities. For example, troponin sub-units I or T, which are very specific for the myocardium, rise before permanent injury develops. A positive troponin in the setting of chest pain may accurately predict a high likelihood of a myocardial infarction in the near future. Other tests to diagnose atherosclerosis and/or myocardial infarction include, for example, EKG (electrocardiogram) to measure the rate and regularity of a subject's heartbeat; chest X-ray, measuring ankle/brachial index, which compares the blood pressure in the ankle with the blood pressure in the arm; ultrasound analysis of arteries; CT scan of areas of interest; angiography; an exercise stress test, nuclear heart scanning; and magnetic resonance imaging (MRI) and positron emission tomography (PET) scanning of the heart.

Compounds useful in these methods of treating, preventing or ameliorating atherosclerosis or a symptom thereof are compounds that modulate kinase signaling cascade in a patient at risk for or suffering from atherosclerosis. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating atherosclerosis or a symptom thereof described herein is an allosteric inhibitor of kinase signaling cascade involved in atherosclerosis. Preferably, the compound used in the methods of treating, preventing or ameliorating atherosclerosis or a symptom associated with atherosclerosis described herein is a non-ATP competitive inhibitor of kinase signaling cascade involved in atherosclerosis.

Cellular signal transduction by Src is believed to play a key role in increased permeability of vessels, known as vascular permeability (VP). Vascular endothelia growth factor (VEGF), which is produced in response to the ischemic injury, including, e.g., myocardial infarction, has been shown to promote vascular permeability. Studies have shown that the inhibition of Src kinase decreases VEGF-mediated VP. (See Parang and Sun, Expert Opin. Ther. Patents, vol. 15(9): 1183-1206 (2005), which is hereby incorporated by reference in its entirety). Mice treated with an Src inhibitor demonstrated reduced tissue damage associated with trauma or injury to blood vessels after myocardial infarction, as compared to untreated mice. (See e.g., U.S. Patent Publication Nos. 20040214836 and 20030130209 by Cheresh et al., the contents of which are hereby incorporated by reference in their entirety). Thus, Src inhibition may be useful in the prevention, treatment or amelioration of secondary damage following injury due to atherosclerosis, such as, for example, myocardial infarction.

The compounds of the invention prevent, treat or ameliorate stroke or a symptom associated with atherosclerosis. Atherosclerosis generally does not produce symptoms until it severely narrows the artery and restricts blood flow, or until it causes a sudden obstruction. Symptoms depend on where the plaques and narrowing develop, e.g., in the heart, brain, other vital organs and legs or almost anywhere in the body. The initial symptoms of atherosclerosis may be pain or cramps when the body requires more oxygen, for example during exercise, when a person may feel chest pain (angina) because of lack of oxygen to the heart or leg cramps because of lack of oxygen to the legs. Narrowing of the arteries supplying blood to the brain may cause dizziness or transient ischaemic attacks (TIA's) where the symptoms and signs of a stroke last less than 24 hours. Typically, these symptoms develop gradually.

Symptoms of myocardial infarction are characterized by varying degrees of chest pain, discomfort, sweating, weakness, nausea, vomiting, and arrhythmias, sometimes causing loss of consciousness. Chest pain is the most common symptom of acute myocardial infarction and is often described as a tightness, pressure, or squeezing sensation. Pain may radiate to the jaw, neck, arms, back, and epigastrium, most often to the left arm or neck. Chest pain is more likely caused by myocardial infarction when it lasts for more than 30 minutes. Patients suffering from a myocardial infarction may exhibit shortness of breath (dyspnea) especially if the decrease in myocardial contractility due to the infarct is sufficient to cause left ventricular failure with pulmonary congestion or even pulmonary edema.

The compounds of the invention are administered alone, in pharmaceutical compositions, or in combination with any of a variety of known treatments for atherosclerosis, such as, for example, cholesterol-lowering drugs (e.g., statins), anti-platelet medications, or anti-coagulants.

The compounds of the invention are used in methods of treating, preventing, ameliorating neuropathic pain, such as chronic neuropathic pain, or a symptom thereof in a subject who is at risk of suffering from, is suffering from, or has suffered neuropathic pain.

Neuropathic pain, also known as neuralgia, is qualitatively different from ordinary nociceptive pain. Neuropathic pain usually presents as a steady burning and/or "pins and needles" and/or "electric shock" sensations. The difference between nociceptive pain and neuropathic pain is due to the fact that "ordinary", nociceptive pain stimulates only pain nerves, while a neuropathy often results in the stimulation of both pain and non-pain sensory nerves (e.g., nerves that respond to touch, warmth, cool) in the same area, thereby producing signals that the spinal cord and brain do not normally expect to receive.

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury.

Neuropathic pain is diagnosed in a subject or patient using one or more of a variety of laboratory and/or clinical techniques known in the art, such as, for example, physical examination.

Compounds useful in these methods of treating, preventing or ameliorating neuropathic pain, such as chronic neuropathic pain, or a symptom associated with neuropathic pain are compounds that modulate kinase signaling cascade involved in neuropathic pain. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating neuropathic pain or a symptom thereof is an allosteric inhibitor of kinase signaling cascade involved in neuropathic pain. Preferably, the compound used in the methods of treating, preventing or ameliorating neuropathic pain or a symptom thereof is a non-ATP competitive inhibitor of kinase signaling cascade involved in neuropathic pain.

c-Src has been shown to regulate the activity of N-methyl-D-aspartate (NMDA) receptors. (See Yu et al., Proc. Natl. Acad. Sci. USA, vol. 96:7697-7704 (1999), which is hereby incorporated by reference in its entirety). Studies have shown that PP2, a low molecular weight Src kinase inhibitor, decreases phosphorylation of the NMDA receptor NM2 subunit. (See Guo et al., J. Neuro., vol. 22:6208-6217 (2002), which is hereby incorporated by reference in its entirety). Thus, Src inhibition, which in turn, inhibits the activity NMDA receptors, may be useful in the prevention, treatment or amelioration of neuropathic pain, such as chronic neuropathic pain.

The compounds of the invention prevent, treat or ameliorate neuropathic pain, such as chronic neuropathic pain, or a symptom associated with neuropathic pain. Symptoms of neuropathic pain include shooting and burning pain, tingling and numbness.

The compounds of the invention are administered alone, in pharmaceutical compositions, or in combination with any of a variety of known treatments, such as, for example, analgesics, opioids, tricyclic antidepressants, anticonvulsants and serotonin norepinephrine reuptake inhibitors The compounds of the invention are used in methods of treating, preventing, ameliorating hepatitis B or a symptom thereof in a subject who is at risk for or suffering from hepatitis B.

The hepatitis B virus, a member of the Hepadnavirus family, consists of a proteinaceous core particle containing the viral genome in the form of double stranded DNA with single-stranded regions and an outer lipid-based envelope with embedded proteins. The envelope proteins are involved in viral binding and release into susceptible cells. The inner capsid relocates the DNA genome to the cell's nucleus where viral mRNAs are transcribed. Three subgenomic transcripts encoding the envelope proteins are made, along with a transcript encoding the X protein. A fourth pre-genomic RNA is transcribed, which is exported to the cytosol and translates the viral polymerase and core proteins. Polymerase and pre-genomic RNA are encapsidated in assembling core particles, where reverse transcription of the pre-genomic RNA to genomic DNA occurs by the polymerase protein. The mature core particle then exits the cell via normal secretory pathways, acquiring an envelope along the way.

Hepatitis B is one of a few known non-retroviral viruses that employ reverse transcription as part of the replication process. Other viruses which use reverse transcription include, e.g., HTLV or HIV.

During HBV infection, the host immune response is responsible for both hepatocellular damage and viral clearance. While the innate immune response does not play a significant role in these processes, the adaptive immune response, particularly virus-specific cytotoxic T lymphocytes (CTLs), contributes to nearly all of the liver injury associated with HBV infection. By killing infected cells and by producing antiviral cytokines capable of purging HBV from viable hepatocytes, CTLs also eliminate the virus. Although liver damage is initiated and mediated by the CTLs, antigen-non-specific inflammatory cells can worsen CTL-induced immunopathology and platelets may facilitate the accumulation of CTLs into the liver.

Hepatitis B is diagnosed in a patient using any of a variety of clinical and/or laboratory tests such as, physical examination, and blood or serum analysis. For example, blood or serum is assayed for the presence of viral antigens and/or antibodies produced by the host. In a common test for Hepatitis B, detection of hepatitis B surface antigen (HBsAg) is used to screen for the presence of infection. It is the first detectable viral antigen to appear during infection with this virus; however, early in an infection, this antigen may not be present and it may be undetectable later in the infection as it is being cleared by the host. During this 'window' in which the host remains infected but is successfully clearing the virus, IgM antibodies to the hepatitis B core antigen (anti-HBc IGM) may be the only serologic evidence of disease.

Shortly after the appearance of the HBsAg, another antigen named as the hepatitis B e antigen (HBeAg) will appear.

Traditionally, the presence of HBeAg in a host's serum is associated with much higher rates of viral replication; however, some variants of the hepatitis B virus do not produce the "e" antigen at all. During the natural course of an infection, the HBeAg may be cleared, and antibodies to the "e" antigen (anti-HBe) will arise immediately afterward. This conversion is usually associated with a dramatic decline in viral replication. If the host is able to clear the infection, eventually the HBsAg will become undetectable and will be followed by antibodies to the hepatitis B surface antigen (anti-HBs). A person negative for HBsAg but positive for anti-HBs has either cleared an infection or has been vaccinated previously. A number of people who are positive for HBsAg may have very little viral multiplication, and hence may be at little risk of long-term complications or of transmitting infection to others.

Compounds useful in these methods of treating, preventing or ameliorating hepatitis B or a symptom thereof are compounds that modulate kinase signaling cascade in a patient at risk for or suffering from hepatitis B. In some embodiments, the compound is a kinase inhibitor. For example, the compound is a tyrosine kinase inhibitor. In an embodiment, the tyrosine kinase inhibitor is an Src inhibitor. Preferably, the compound used in the methods of treating, preventing or ameliorating hepatitis B or a symptom thereof described herein is an allosteric inhibitor of kinase signaling cascade involved in hepatitis B. Preferably, the compound used in the methods of treating, preventing or ameliorating hepatitis B or a symptom associated with hepatitis B described herein is a non-ATP competitive inhibitor of kinase signaling cascade involved in hepatitis B.

Src plays a role in the replication of the hepatitis B virus. The virally encoded transcription factor HBx activates Src in a step that is required from propagation of the HBV virus. (See e.g., Klein et al., EMBO J., vol. 18:5019-5027 (1999); Klein et al., Mol. Cell. Biol., vol. 17:6427-6436 (1997), each of which is hereby incorporated by reference in its entirety). Thus, Src inhibition, which in turn, inhibits Src-mediated propagation of the HBV virus, may be useful in the prevention, treatment or amelioration of hepatitis B or a symptom thereof.

The compounds of the invention prevent, treat or ameliorate hepatitis B or a symptom associated with hepatitis B. Symptoms of hepatitis B typically develop within 30-180 days of exposure to the virus. However, up to half of all people infected with the hepatitis B virus have no symptoms. The symptoms of hepatitis B are often compared to flu, and include, e.g., appetite loss; fatigue; nausea and vomiting; itching all over the body; pain over the liver (e.g., on the right side of the abdomen, under the lower rib cage), jaundice, and changes in excretory functions.

The compounds of the invention are administered alone, in pharmaceutical compositions, or in combination with any of a variety of known treatments for hepatitis B, such as, for example, interferon alpha, lamivudine (Epivir-HBV) and baraclude (entecavir).

As described herein, the compounds of the invention may be used to regulate immune system activity in a subject, thereby protecting against or preventing autoimmune disease, e.g., rheumatoid arthritis, multiple sclerosis, sepsis and lupus as well as transplant rejection and allergic diseases. Alternatively, the compound may be used to treat autoimmune disease in a subject. For example, the compound may result in reduction in the severity of symptoms or halt impending progression of the autoimmune disease in a subject. The compound of the invention may be involved in modulating a kinase signaling cascade, e.g., a kinase inhibitor, a non-ATP competitive inhibitor, a tyrosine kinase inhibitor, e.g., a Src inhibitor, a p59fyn (Fyn) inhibitor or a p56lck (Lck) inhibitor.

Autoimmune diseases are diseases caused by a breakdown of self-tolerance such that the adaptive immune system responds to self antigens and mediates cell and tissue damage. Autoimmune diseases can be organ specific (e.g., thyroiditis or diabetes) or systemic (e.g., systemic lupus erythematosus). T cells modulate the cell-mediated immune response in the adaptive immune system. Under normal conditions, T cells express antigen receptors (T cell receptors) that recognize peptide fragments of foreign proteins bound to self major histocompatibility complex molecules. Among the earliest recognizable events after T cell receptor (TCR) stimulation are the activation of Lck and Fyn, resulting in TCR phosphorylation on tyrosine residues within immunoreceptor tyrosine-based activation motifs (Zamoyska, et al.; 2003, *Immunol. Rev.*, 191, 107-118). Tyrosine kinases, such as Lck (which is a member of the Src family of protein tyrosine kinases) play an essential role in the regulation of cell signaling and cell proliferation by phosphorylating tyrosine residues of peptides and proteins (Levitzki; 2001, *Top. Curr. Chem.*, 211, 1-15; Longati, et al.; 2001, *Curr. Drug Targets*, 2, 41-55; Qian, and Weiss; 1997, *Curr. Opin. Cell Biol.*, 9, 205-211). Thus, although not wishing to be bound by theory, it is hypothesized that the administration of a compound of the instant invention which modulates tyrosine kinase (e.g., Src) activity is useful in the treatment of autoimmune disease.

The tyrosine kinases lck and fyn are both activated in the TCR pathway; thus, inhibitors of lck and/or fyn have potential utility as autoimmune agents (Palacios and Weiss; 2004, *Oncogene*, 23, 7990-8000). Lck and Fyn are predominantly expressed by T cells through most of their lifespan. The roles of Lck and Fyn in T cell development, homeostasis and activation have been demonstrated by animal and cell line studies (Parang and Sun; 2005, *Expert Opin. The. Patents*, 15, 1183-1207). Lck activation is involved in autoimmune diseases and transplant rejection (Kamens, et al.; 2001, *Curr. Opin. Investig. Drugs*, 2, 1213-1219). Results have shown that the lck (−) Jurkat cell lines are unable to proliferate, produce cytokines, and generate increases in intracellular calcium, inositol phosphate, and tyrosine phosphorylation in response to T cell receptor stimulation (Straus and Weiss; 1992, *Cell.*, 70, 585-593; Yamasaki, et al.; 1996, *Mol. Cell. Biol.*, 16, 7151-7160). Therefore, an agent inhibiting lck would effectively block T cell function, act as an immunosuppressive agent, and have potential utility in autoimmune diseases, such as rheumatoid arthritis, multiple sclerosis, and lupus, as well as in the area of transplant rejection and allergic diseases (Hanke and Pollok; 1995, *Inflammation Res.*, 44, 357-371). Thus, although not wishing to be bound by theory, it is hypothesized that the administration of a compound of the instant invention which modulates one or more members of the Src family of protein tyrosine kinases (e.g., lck and/or fyn) is useful in the treatment of autoimmune disease.

The present invention provides inhibitors of protein kinases and/or protein phosphatases. In one embodiment, the protein kinase and/or protein phosphatase inhibitor is a non-peptide inhibitor having the following Formula I:

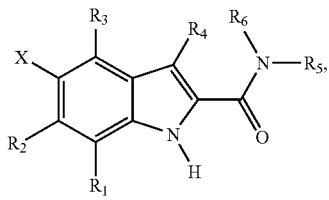

(Formula I)

wherein X is a halogen, and $R_1$, $R_2$, $R_3$, $R_4$, $R_5$, and $R_6$ are the same or different, and selected from H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $OSO_3H$, $OPO_3H_2$, $P(O)OR_aOR_b$, $B(OH)_2$, halogen, aryl, O-aryl-Q, heteroaryl, biaryl, heterobiaryl, heterocyclic compound, and alkyl (branched, cyclic, or unbranched), having from 1 to 20 carbon atoms, optionally containing a double or triple bond and optionally substituted with a heteroatom or other functional groups, such as a carboxylic acid, carboxylic ester, alcohol, alkoxy, thioether, amide, $C(O)NH_2$, thioamide, urea, urethane, sulfoxide, sulfone, $SO_3H$, $OSO_3H$, phosphonic acid, phosphonic ester, phosphinic acid, phosphinic ester, $PO_3H_2$, $OPO_3H_2$, boronic acid, aryl, heteroaryl, biaryl, heterocycle, $NH_2$, alkyl and dialkyl amine, glucoside, and heterobiaryl, or $R_5$ and $R_6$ together form a heterocyclic compound. $R_a$, $R_b$, and $R_c$ are the same or different and selected from H, aryl, heteroaryl, biaryl, heterobiaryl, and alkyl (branched, cyclic, or unbranched), optionally substituted with a heteroatom or other functional groups such as a carboxylic acid, carboxylic ester, alcohol, alkoxy, thioether, amide, $C(O)NH_2$, thioamide, urea, urethane, sulfoxide, sulfone, $SO_3H$, $OSO_3H$, phosphonic acid, phosphonic ester, phosphinic acid, phosphinic ester, $PO_3H_2$, $OPO_3H_2$, boronic acid, aryl, heteroaryl, biaryl, heterocycle, NH2, alkyl and dialkyl amine, glucoside, and heterobiaryl. Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glucoside, alkoxy, or

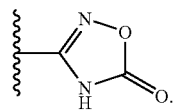

It is understood that all open substitution positions in the above side chains can contain further substitutions. Examples of suitable R groups are provided in Table VI, below.

In one embodiment, at least one of $R_5$ or $R_6$ is

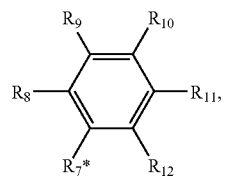

wherein $R_7^*$ is the point of attachment and is $(CH_2)_x$, wherein X is 0, 1, 2, 3, 4, 5, 6, 7, 8, 9, and 10, $CH_2CHOH$, $CH(CH_3)$ (R-isomer), or $CH(CH_3)$(S-isomer), and each of $R_8$, $R_9$, $R_{10}$, $R_{11}$, and $R_{12}$ are the same or different and selected from H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $OSO_3H$, $OPO_3H_2$, $P(O)OR_aOR_b$, $B(OH)_2$, halogen, aryl, O-aryl-Q, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, alkoxy, thioether, amide, $C(O)NH_2$, thioamide, urea, urethane, sulfoxide, sulfone, $SO_3H$, $OSO_3H$, phosphonic acid, phosphonic ester, phosphinic acid, phosphinic ester, boronic acid, aryl, heteroaryl, biaryl, heterocycle, $NH_2$, alkyl and dialkyl amine, glucoside, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, alkoxy, thioether, amide, $C(O)NH_2$, thioamide, urea, urethane, sulfoxide, sulfone, $SO_3H$, $OSO_3H$, phosphonic acid, phosphonic ester, phosphinic acid, phosphinic ester, $PO_3H_2$, $OPO_3H_2$, boronic acid, aryl, heteroaryl, biaryl, heterocycle, $NH_2$, alkyl and dialkyl amine, glucoside, and heterobiaryl. Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glucoside, alkoxy, or

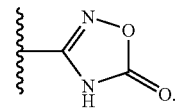

It is understood that all open substitution positions in the above side chains can contain further substitutions. In one embodiment, each of $R_8$, $R_9$, $R_{10}$, $R_{11}$, and $R_{12}$ is selected from $OCH_3$, $OCH_2CH_3$, H, $CH_3$, OH, $CH_2OH$, $CF_3$, $OCF_3$, CFO, $C_6H_5$, $OC_6H_5$, $OCH_2C_6H_5$, $OCH_2CH_2CH_3$, CHO, $CO_2H$, $CO_2CH_3$, $CH_2CO_2H$, $CH_2CO_2CH_3$, $NO_2$, and halogen.

In another embodiment, at least one of $R_5$ or $R_6$ is

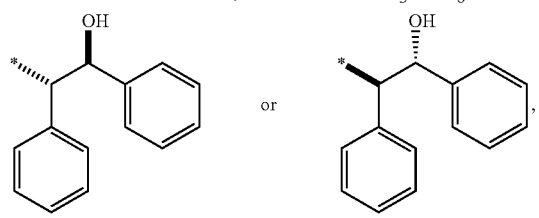

wherein the asterisk indicates the point of attachment to the nitrogen.

In a preferred embodiment, the non-peptide inhibitor inhibits the activity of $pp60^{c-src}$ tyrosine kinase, $pp56^{lck}$ tyrosine kinase, or $pp55^{fyn}$ tyrosine kinase.

In another preferred embodiment, the non-peptide inhibitor inhibits the activity of protein tyrosine phosphatase 1B (PTP-1B).

Another compound of the present invention has the following Formula II:

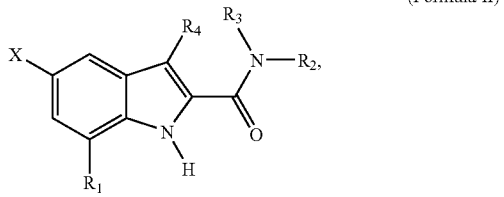

(Formula II)

wherein X is a halogen, e.g., fluorine, and $R_1$, $R_2$, $R_3$, and $R_4$ are specificity elements. As used herein, specificity elements or specificity side chains are side chains which will bind in unique binding pockets for individual proteins. Thus, the side chains used will depend on the particular protein to be inhibited. To identify suitable side chains, known peptide binding side chains may be used to identify analogues which are then used in combinatorial chemistry techniques to expand the library of possible side chains.

In one embodiment, $R_1$ is H, $R_2$ is

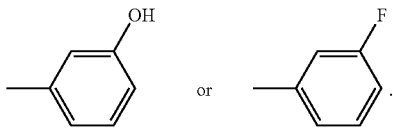

$R_3$ is H, and $R_4$ is H. In another embodiment, the compound is substituted at any other position on the indole ring.

The compounds of the present invention provide activity against tyrosine kinases, such as $pp60^{c\text{-}src}$, and are expected to improve the ability of the compound to inhibit tyrosine kinases in vivo, since one easily metabolized OH group has been removed. In particular, an OH group at the 5-position on the indole ring has been substituted with a halogen. The halogen is a hydrogen bond acceptor, useful with catalytic residues which are hydrogen bond donors. In addition, the halogen is not metabolized in phase II metabolism and is electronegative, leading to in vivo benefits (see, e.g., Park et al., 2001). Some members of this class are also inhibitors of the opposing enzymes, i.e., phosphotyrosine phosphatases. These compounds are inhibitors of $pp60^{c\text{-}src}$, of highly metastatic prostate cancer cell growth, and are non-toxic in mice upon high dose acute i.p. administration, as described in Example 1, below. Some of these compounds may be found to have other biological activities upon broader testing (e.g., inhibit glycogen phosphorylase for Type II diabetes, HIV reverse transcriptase, or thromboxane synthase). Thus, these compounds may be used as tyrosine kinase inhibitors for therapeutic applications, such as cancer. Tyrosine kinase inhibitors have other potential therapeutic applications as well (e.g., immunosuppressants in the case of p56lck) and inhibitors of the tyrosine phosphatase PTP-1B may provide drugs for treating Type II diabetes or obesity.

The present invention also provides a method for identifying inhibitors of protein kinases. The general modular strategy for the development of non-peptide PTK inhibitors is outlined in FIG. 1. Basically, at least one first module having a one or more functional groups for binding to catalytic residues of the protein kinase (in a preferred embodiment, at least one of the functional groups is a halogen) is combined with at least one second module which provides a non-peptide scaffold. The functional group(s) of the at least one first module are each capable of covalently or non-covalently binding with catalytic residues of the protein kinase. Thus, each functional group of each first module is capable of reversible or irreversible bond formation, either covalently or non-covalently, to catalytic residues of the protein kinase when the protein kinase the first module are combined under conditions effective for such binding. Combinations of the first and second modules which inhibit protein kinase activity are then selected. Step 1 begins with protein kinase inhibitor information which was already generated, i.e. pentapeptide scaffolds which bind in the substrate specificity sites of PKA or Src have already been used to position various rationally designed functional groups (i.e. module "$M_1$" or "first module") to interact with the conserved catalytic residues, MgATP or MgADP. A selection of preferred functional groups have now been identified in this fashion to serve as the initial $M_1$ module for Step 1. These $M_1$ functional groups have been utilized to identify promising non-peptide scaffolds for Src inhibitors in Step 1. It was anticipated that these bare non-peptide scaffolds, with only an $M_1$ appendage, would have low binding affinity and be relatively non-selective among the protein tyrosine kinases (PTKs). A lack of selectivity at the level of Step 1 is viewed as an advantage for the development of a general strategy which can be reapplied to additional PTKs. Therefore, the suite of non-peptide scaffolds identified in Step 1 can be recycled for use against additional PTKs by re-screening them and carrying the better ones through Steps 2 and 3, all using the new PTK target. The potency of these bare scaffolds from Step 1 may be increased enough by the attachment of one or two initial specificity elements ($S_n$) to allow for the validation of the scaffold as non-ATP competitive and amenable to further potency enhancements using combinatorial chemistry in a rationally guided fashion. Promising Src non-peptide $M_2$ (second module) scaffolds identified in Step 1 have undergone Step 2 and displayed a one to two order-of-magnitude increase in potency against Src as well as non-competitive binding relative to ATP.

Validation of the scaffolds at the level of Step 2 before undertaking the resource intensive combinatorial library synthesis and testing of Step 3 is important for three reasons: 1) to develop the chemistry for appending the specificity element ($S_n$) side chains; 2) to determine that these inhibitors are not ATP-competitive; and 3) to determine that the potency is responding to the side chain $S_n$ properties and attachment points as would be expected based upon the working model for the Src:inhibitor complex (this provides some confidence that rationally guided choices can be made for the ranges of individual selectivity elements $S_n$ to include in the focused libraries of Step 3).

It is in Step 3 that high potency and specificity for a particular PTK is anticipated because numerous combinations of $M_1$ functional groups (and close analogs $M_1$') with selectivity elements ($S_n$) will be evaluated experimentally via combinatorial chemistry and high-throughput screening. Potency and selectivity may be further increased if necessary by appending additional specificity elements (see optional $S_n$'s in FIG. 1).

In each of the Steps 1-3, molecular modeling studies with the IRTK:peptide:AMP-PNP crystal structure, the model of the Src:peptide complex and the models for the Src complex with the individual families of inhibitors based upon a particular scaffold will be used as qualitative guides. These modeling studies have been remarkably helpful thus far in guiding the inhibitor design efforts as detailed later. Combining structure-based design and combinatorial chemistry technologies in this fashion provides a synergy wherein the major individual deficiencies of these technologies used in isolation are addressed by the strengths of the other. The major deficiency of structure-based design is the difficulty in quantitatively predicting ligand binding affinities, which is particularly challenging due to the complex effects of solvation and entropy (Ajay & Murcko, 1995). The major strength of structure-based design is its capability to predict what types of molecules are likely to be good ligands. Structure-based design can determine the rough boundaries (proteins have some flexibility which need to be taken into account) for molecular size and shape as well as indicate where hydrophobic, H-bonding, and ionic interactions are likely to occur. On the other hand, the major deficiency of combinatorial chemistry is that "molecular space" for drug-sized molecules (i.e. MW ca. 500 or less) is so large that one could not hope to sample all of this molecular space with a high density of coverage in a reasonable sized combinatorial library. A recent estimate (Bohacek et al., 1996) of the number of possible compounds containing up to 30 atoms chosen only from carbon, nitrogen, oxygen and sulfur (in addition to H's) is $10^{60}$ compounds. This is in the molecular weight range of typical drug molecules and still does not include additional diversity provided by other atoms, e.g. halogens. Consequently, additional constraints need to be used to identify regions of molecular space wherein particular drug candidates are likely to be located. Structure-based design can drastically reduce the volume of molecular space to be explored by identifying the types of molecules which have a higher probability of being good ligands. The inability to quantitatively predict which of these "focused" combinatorial library members will in fact be the tightest binding ligands (i.e. the quantitation problem) is then resolved by employing an efficient combinatorial synthesis and high-throughput testing of the library.

In the earlier peptide based serine and tyrosine kinase inhibitor design efforts, PKA was used as a convenient qualitative model for designing the protein kinase inhibitor module $M_1$ for interaction with the conserved catalytic residues. There is much more structural and kinetic information available for PKA than any other protein kinase.

Figure 2:
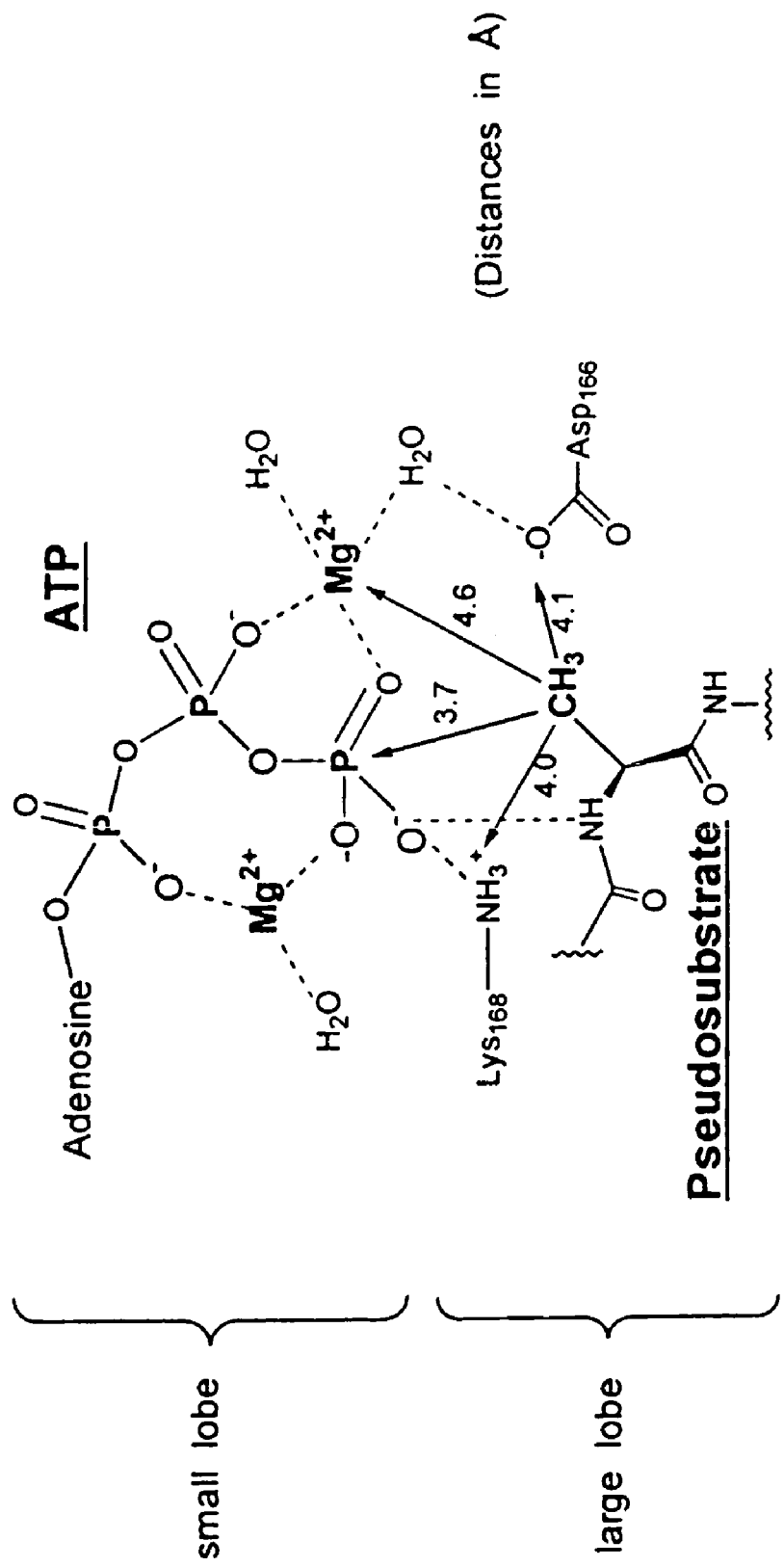
FIG. 2 provides a depiction of the x-ray structure of (PKA): $Mg_2ATP$:pseudosubstrate inhibitor.

The crystal structure of PKA complexed with $Mg_2ATP$ and a pseudosubstrate (i.e. OH replaced with H) peptide inhibitor (PKI 5-24 amide) has been solved (Zheng et al., 1993) and the active site interactions near the P 0 Ala of this inhibitor are shown in FIG. 2.

This crystal structure shows $Mg_2ATP$ bound to the small lobe of PKA and a 20-residue pseudosubstrate peptide inhibitor bound to the large lobe with the overall conformation of the enzyme in the closed (i.e. the two lobes are touching) and activated state. The distances between the P 0 Ala side chain carbon and the nearby heavy atoms in the complex are shown in Å in FIG. 2. These distances show that the Ala side chain is within van der Waals contact distance of the surrounding atoms and indicates that there is little space for appending bulky $M_1$ functional groups to the Ala side chain. However, PKA is a flexible enzyme with open, closed and intermediate conformations (Cox et al., 1994) and these more open conformations would result in a retraction back of the ATP γ-phosphate from the inhibitor Ala thereby creating a binding cavity for appended $M_1$ functional groups. Furthermore, PKA binds MgADP with the same affinity as MgATP (Whitehouse et al., 1983) and the ratio of ATP/ADP in cells is typically 10/1 (Alberts, et al. 1994). Therefore, at equilibrium, ca. 10% of the cellular protein kinase is in the MgADP bound state and this form of the enzyme can also be targeted with an inhibitor to drain all of the enzyme from the catalytic cycle into a PKA:MgADP:inhibitor inactive complex.

Since the PKA catalytic residues Asp-166 and Lys-168 are completely conserved in all serine kinases, and the tyrosine kinases only differ by the substitution of Arg for Lys-168 (Taylor et al., 1993), this region of the active site was chosen, along with the adjoining MgATP or MgADP, to target a selection of inhibitor functional groups which could serve as $M_1$ and be broadly useful for developing inhibitors for the entire protein kinase family. By targeting $M_1$ to the region of the active site adjacent to the nucleotide, an orientation point is provided for the non-peptide inhibitors which can extend into the peptide binding specificity sites without always competing with ATP/ADP binding.

A selection of functional groups which could be utilized as $M_1$ was identified first because, although this region of the active site is very highly conserved, it was expected that each particular protein kinase will still display some differing preferences across this selection due to small variations in the active site conformations and adjoining residues. Furthermore, the rank order preference among this selection of $M_1$'s may change somewhat as the $M_1$ module is appended to different non-peptide scaffolds. This expectation is based upon the potential for each non-peptide scaffold to bind in somewhat different orientations with each individual protein kinase and with each particular set of selectivity element ($S_n$) side chains. Pentapeptide scaffolds were chosen for the initial screening of functional groups for $M_1$ because the binding orientation of these larger peptide scaffolds is likely to be very consistent and predictable (i.e. closely resembling that observed by x-ray) throughout the series and could be more confidently assumed to position each tested $M_1$ functionality adjacent to the conserved catalytic residues as intended. Consequently, the goal of this earlier peptide-based work was to identify a collection of $M_1$ functional groups which can be used, not only for the initial screening of non-peptide scaffolds (Step 1), but also as an initial set of $M_1$ side chains which can be further expanded via close analogs and thereby optimized simultaneously with the other side chains in the final non-peptide combinatorial libraries (Step 3).

Figure 3:
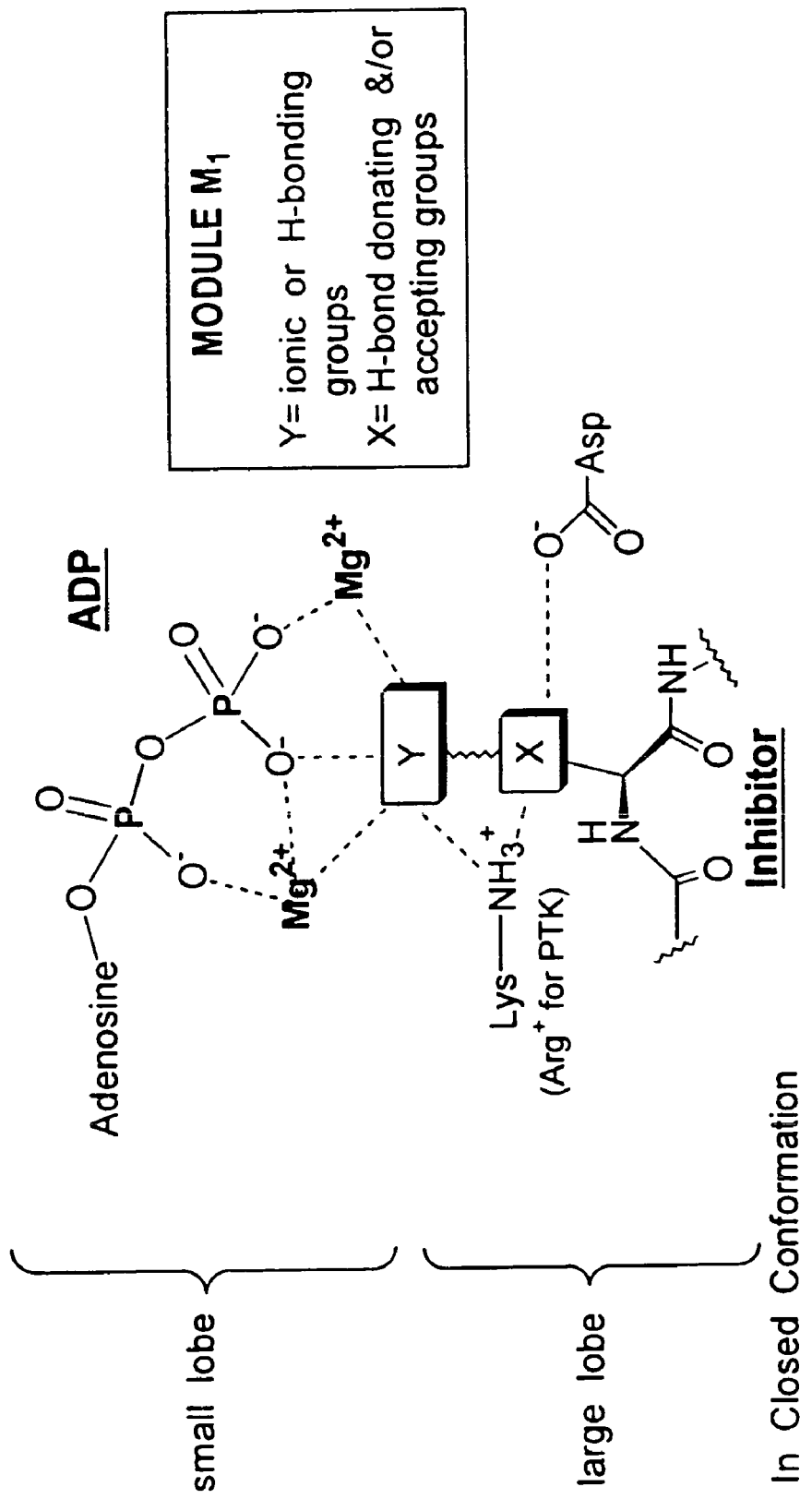
FIG. 3 provides a general module $M_1$ design features for binding to the conserved protein kinase catalytic region.

In order to model the candidate $M_1$ functional groups in this conserved catalytic region of the PKA active site, they were built onto the P 0 Ala position in the PKA ternary structure using the SYBYL molecular modeling package (Tripos) on a Silicone Graphics workstation as indicated in FIG. 3.

A crystal structure of PKA with MgATP and an inhibitor bound in a more "open" conformation was not available, so initial modeling studies were carried out on the MgADP bound form of PKA derived from the ternary complex illustrated in FIG. 2 by simply deleting the ATP γ-phosphate. Initial modeling studies were used to provide qualitative guidance for identifying interesting potential $M_1$ functional groups for the protein kinase family before synthesis and testing. The most advanced computational algorithms for quantitatively predicting the free energy of binding, such as Free Energy Perturbation methods, are computationally intensive methods which are not practical at this point in time for routine use by the non-specialist. Even the most advanced methods can be inaccurate due to difficulties in sampling, inadequacies in the molecular mechanics force fields/parameters, and an incomplete understanding of electrostatics in water (Ajay & Murcko, 1995). Less rigorous (and easier to use) computational methods tend to be unreliable in making quantitative predictions of binding affinities, especially when dealing with multiple polar and ionic interactions such as those involved in $M_1$ binding.

In order to allow molecular mechanics calculations to be done with the Silicone Graphics workstation in a reasonable amount of time, two layers of residues were carved out from the PKA ternary structure which are surrounding the PKA active site, along with the peptide inhibitor and Mg$_2$ADP. The M$_1$ functional groups were then appended to the P 0 Ala side chain and the entire PKA active site:Mg$_2$ADP:modified peptide inhibitor complex was then subjected to 300 iterations of molecular mechanics minimization using the Tripos force field with a distance dependent dielectric constant after assigning appropriate formal charges and calculating Gasteiger Marsili point charges using SYBYL. Setting the maximum number of iterations at 300 was sufficient to remove any serious strain in the complexes and yet not allow the overall structure to "drift" significantly from the starting x-ray structure if convergence is not reached. These minimized complexes were then visually evaluated to determine if the appended individual M$_1$ functional groups were able to engage in favorable interactions with the conserved catalytic residues and/or Mg$_2$ADP. This visual evaluation involved, among other standard interaction evaluations, measuring atom-atom distances to determine if hydrogen bonds and ionic interactions were being favorably formed.

Favorable intermolecular interactions between an individual M$_1$ functionality and the conserved catalytic residues or Mg$_2$ADP does not necessarily mean enhanced binding affinity will be observed for the new inhibitor. Unfavorable desolvation of both the polar M$_1$ functionality and the polar PKA active site residues (as well as complex entropy effects) are not included in this analysis and may reduce the net binding affinity to the point that the modified inhibitor may even be less potent that the corresponding P 0 Ala inhibitor, even though the appended M$_1$ functionality is interacting with the conserved catalytic residues and/or MgADP (or MgATP) as intended. Even in cases where this desolvation penalty results in no net increase in binding affinity, these M$_1$ functional groups are still useful as an orienting groups for correctly positioning the non-peptide inhibitor analogs in the protein kinase active site. Positioning these polar functional groups elsewhere within the active site (assuming they are tethered so as not to be able to extend into bulk solvent while the scaffold is favorably bound in the active site) is likely to result in a reduced binding affinity because they were specifically designed and selected based upon their demonstrated ability (while appropriately tethered to pentapeptide scaffolds) to be accepted adjacent to the conserved catalytic residues and MgADP/MgATP. If a particular M$_1$ functionality does not correctly position a non-peptide scaffold in Step 1 then attempts to improve the potency by rationally appending initial specificity elements in Step 2 would likely fail.

None of the literature protein kinase assay procedures contain added ADP. A typical PKA literature assay procedure (Glass et al., 1989) was modified by adding 10% as much ADP as the ATP concentration used to reflect the natural 1/10 ratio in the cell. This protein kinase assay is hereinafter referred to as the "Literature Mimetic" assay. It has been used for PKA as well as the Src. An examination of the literature, and commercially available protein kinase assays, showed that there is poor consistency from lab to lab and company to company and that all of these assays use physical chemical conditions which differ considerably from those known to exist inside cells. Since inhibition of intracellular protein kinases is the ultimate goal for drug discovery, new protein kinase assays have been developed which come much closer to mimicking the overall cytosolic physical chemical conditions known to exist inside cells. The development of these "Cellular Mimetic" protein kinase assays, is described herein, along with a novel method for determining which form of a protein kinase a given inhibitor binds best to (the STAIRe method). Data was collected correlating the activity of the new non-peptide Src inhibitors in the Cellular Mimetic assay with that obtained in the LA25 Src transformed cell line (see below).

When these two assay conditions were applied to some of the pentapeptide-based PKA inhibitors, which were designed as illustrated in FIG. 3, the results shown in Table I were obtained. The same assay conditions were also applied to the analogously designed pentapeptide-based Src inhibitors and obtained the results shown in Table II.

TABLE I

INITIAL M$_1$ SCREENING RESULTS WHILE APPENDED TO THE PKA PENTAPEPTDE SCAFFOLD

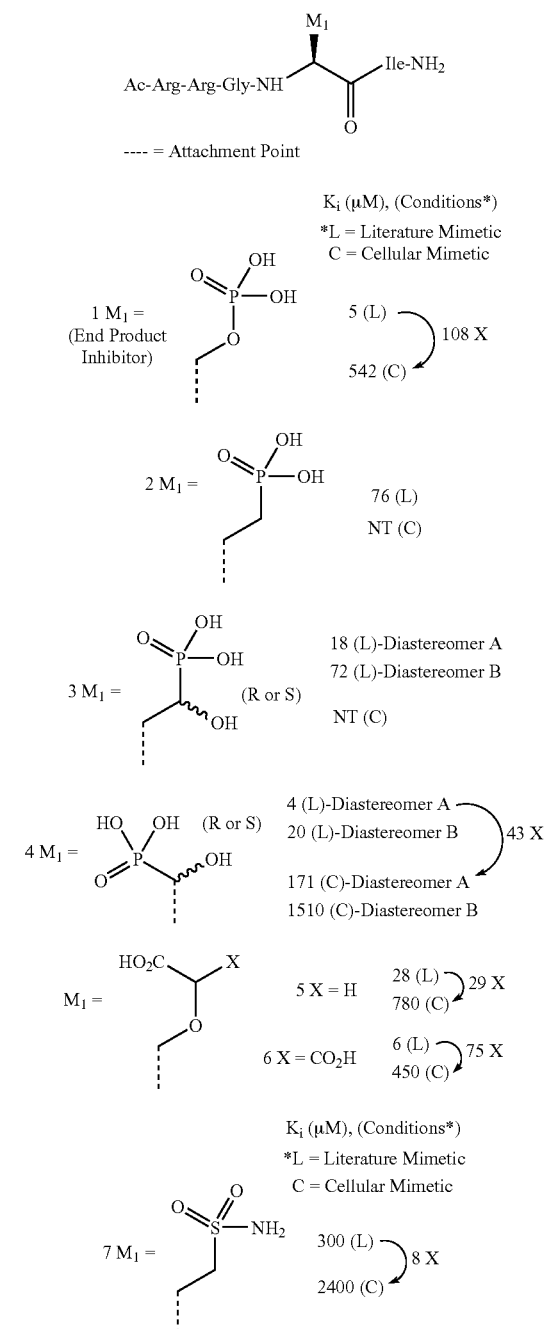

TABLE I-continued

INITIAL $M_1$ SCREENING RESULTS WHILE APPENDED TO THE PKA PENTAPEPTDE SCAFFOLD

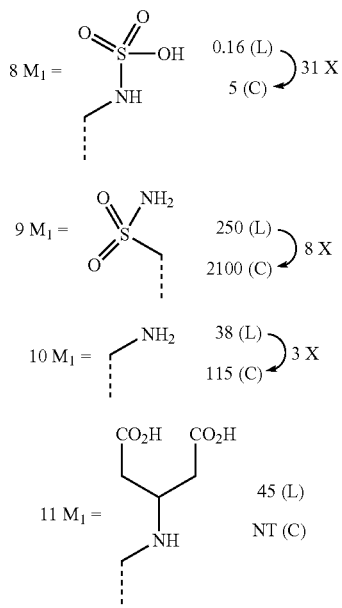

| | | |
|---|---|---|
| 8 $M_1$ = | (sulfamic acid structure) | 0.16 (L), 5 (C) } 31 X |
| 9 $M_1$ = | (sulfonamide structure) | 250 (L), 2100 (C) } 8 X |
| 10 $M_1$ = | (aminoethyl structure) | 38 (L), 115 (C) } 3 X |
| 11 $M_1$ = | (dicarboxylate structure) | 45 (L), NT (C) |

The structure identified in Table I as Ac-Arg-Arg-Gly-Ala bonded to $M_1$-Ile-$NH_2$ is SEQ. ID. No. 2.

TABLE II

INITIAL $M_1$ SCREENING RESULTS WHILE APPENDED TO THE SRC PENTAPEPTIDE SCAFFOLD

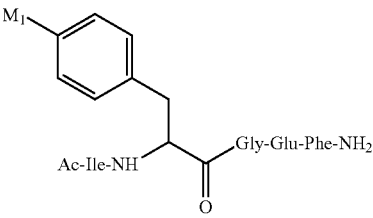

% Inhibition of 2 mM RR-src phosphorylation by src Assay Conditions

| Inhibitor (1 mM) | Literature Mimetic | Cellular Mimetic |
|---|---|---|
| 12 $M_1$ = O—P(=O)(OH)(OH) | 36 | 0 |
| 13 $M_1$ = HC(OH)—P(=O)(OH)(OH) | 51 | 0 |
| 14 $M_1$ = P(=O)(OH)(OH) | 83 | 88 |
| 15 $M_1$ = C(=O)OH | 68 | 59 |

TABLE II-continued

INITIAL $M_1$ SCREENING RESULTS WHILE APPENDED TO THE SRC PENTAPEPTIDE SCAFFOLD

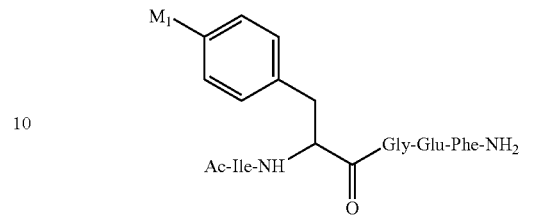

% Inhibition of 2 mM RR-src phosphorylation by src Assay Conditions

| Inhibitor (1 mM) | Literature Mimetic | Cellular Mimetic |
|---|---|---|
| 16 $M_1$ = NH—C(=O)—$NH_2$ | 60 | 8 |
| 17 $M_1$ = NH—C(=O)—$CH_2$—C(=O)OH | 20 | 28 |
| 18 $M_1$ = NH—C(=O)—CH(OH)—C(=O)OH | 64 | 5 |
| 19 $M_1$ = NH—C(=O)—CH($NH_2$)—C(=O)OH | 24 | 0 |

The structure identified in Table II as Ac-Ile-Tyr bonded to $M_1$-Gly-Glu-Phe-$NH_2$ is SEQ. ID. No. 3.

The standard pentapeptide sequence chosen for the majority of PKA inhibitors in Table I was derived from the pseudosubstrate sequence of the peptide inhibitor which was bound to PKA, when the crystal structure illustrated in FIG. 1 was solved. The standard pentapeptide sequence used for Src in Table II, Ac-Ile-Xaa-Gly-Glu-Phe-$NH_2$ (SEQ. ID. No. 3), was described in Nair, Kim et al., 1995. Some of the chemistry used to prepare the PKA inhibitors is described in Nair, Lee & Hangauer 1995. The synthetic methodology used to develop a number of the Src inhibitors is described in Lai et al., 1998.

The collective results in Tables I and II show that both the serine kinase PKA and the PTK Src can accommodate a variety of large polar $M_1$ functional groups at the P 0 phosphorylation position. Furthermore, using the STAIRe methodology (see Choi et al. 1996), the sulfamic acid inhibitor 8, and related inhibitors, were shown to actually bind best when MgATP (not MgADP or no nucleotide) is also bound. This was a somewhat surprising result since these inhibitors are analogs of the "end product inhibitors" 1 and 12 which must bind simultaneously with MgADP just following phosphate transfer in the generally accepted reaction mechanism for protein kinases.

These results also demonstrate that both PKA and Src can show a large difference in binding affinity for structurally very similar inhibitors. For example, the sulfamic acid PKA inhibitor 8 (Table I) has a $K_i$ of 0.16 μM under Literature Mimetic assay conditions (L) whereas the isosteric sulfonamide 7 is 1,875× less potent ($K_i$=300 μM). The sulfamic acid inhibitor 8 is also isosteric with the end product phosphate inhibitor 1 yet it binds much more tightly under both Literature Mimetic assay conditions (31×) and Cellular Mimetic (C) assay conditions (108×). The beneficial effect of an oxygen atom positioned analogously to that in the substrate Ser is illustrated by comparison of phosphonate 2 to phosphate 1 and also ether 6 to phosphate 1. This oxygen atom can also be positioned as a serine-like OH side chain and enhance binding (compare 2 to 3A and 4A) wherein the closer serine mimic 4A is the more active. The difference in activity of the diastereomeric inhibitors 3A or B and 4A or B suggests a specific interaction with the active site catalytic residue Asp-166 may in fact be occurring as intended in the $M_1$ design (FIG. 3).

The Src inhibition results (Table II) show that the end product inhibitor 12 drops in activity upon going from Literature Mimetic assay conditions to the higher ionic strength Cellular Mimetic assay conditions, analogous to the PKA end product inhibitor 1. However, whereas all of the PKA inhibitors with polar $M_1$ functional groups were less active under Cellular Mimetic assay conditions, three of the Src inhibitors 14, 15, and 17 held their activity under these higher ionic strength assay conditions. Also, the hydroxyphosphonate Src inhibitor 13 (a mixture of the R and S diastereomers) is analogous to the PKA inhibitor 3A and both are roughly in the same activity range as their corresponding end product inhibitors, 12 and 1 respectively, under Literature Mimetic assay conditions. Shortening the side chain length in the phosphonate Src inhibitor 13 by one carbon atom (and necessarily removing the attached OH at the same time) to give 14 improved the activity (analogous to the PKA inhibitor comparison 3 to 4) and, more importantly, resulted in equivalent activity under Cellular Mimetic assay conditions. The Src results with 16-19 (particularly 17, see later for an analogous α-tricarbonyl acid $M_1$ analog appended to non-peptide Src inhibitors) also suggests that similar amides may be useful $M_1$ functional groups to explore with non-peptide Src inhibitors.

Non-peptide Src inhibitors are preferred to peptide scaffold based compounds, partly because some of these inhibitors have a dual effect on Src. For example, phosphonate inhibitor 14 not only inhibits Src by competitively binding in the active site but it also activates Src by binding to the $SH_2$ site thereby releasing the intramolecular autoinhibition mechanism (Xu et al., 1997). This opposing effect gives an unusual $IC_{50}$ curve for 14, wherein at low inhibitor concentrations Src is stimulated (to a maximum of 70%) in a smooth dose-response fashion (due to initial tighter SH2 binding) followed by a typical $IC_{50}$ inhibition curve at higher inhibitor concentrations (due to lower affinity blockade of the active site). This opposing activation effect of the pentapeptide inhibitors makes them appear to be less potent active site inhibitors than they in fact are, and makes it difficult to accurately rank $M_1$ groups while appended to this pentapeptide scaffold. However, the better $M_1$ groups identified with the Src pentapeptide scaffold must still be accommodated in the catalytic region of the active site and hence are useful orienting groups for the ongoing non-peptide Src inhibitor studies as intended. Since PKA does not have an SH2 domain, this complication is not a factor in interpreting the PKA pentapeptide inhibitor $M_1$ testing data.

The results in Tables I and II also show how much effect the assay conditions can have on both inhibitor potencies and the rank order of activity. For example, as shown in Table I, switching from the Literature Mimetic (L) assay conditions to the Cellular Mimetic (C) assay conditions can change the potency from as little as 3-fold (inhibitor 10) to as much as 108-fold (inhibitor 1). Also, whereas inhibitor 10 is less potent than 1 under Literature Mimetic conditions, it is more potent under Cellular Mimetic conditions. The Src inhibitor data presented in Table II show that many of the inhibitors lose their potency upon going from Literature Mimetic assay conditions to Cellular Mimetic assay conditions. The rank order of potency against Src is also sensitive to the assay conditions. Whereas inhibitor 18 is more potent than inhibitor 17 under Literature Mimetic conditions, the opposite is true under Cellular Mimetic conditions. Since activity within cells is the goal, the Cellular Mimetic Src assay was selected as the standard assay for testing potential non-peptide Src inhibitors. Activity within the Cellular Mimetic assay is a necessary, but not sufficient, condition for activity within cells. As will be described later, the Cellular Mimetic Src assay will be followed up with cell culture assays wherein cell penetration, metabolism, and binding to other cellular components are also factors in the measured potency.

The next class of $M_1$ functionality which was explored was the boronic acid group. This functional group is an intriguing candidate for $M_1$ for a number of reasons: 1) It can exist in a non-ionic state so that it should not prevent passive absorption of non-peptide inhibitors across cell membranes. 2) The planar, trigonal, boron acids might form reversible tetrahedral covalent borate complexes (a well known property of boronic acids, see Loomis & Durst, 1992) through their vacant 2p orbitals with anions present in the protein kinase active site, such as the catalytic Asp carboxyl group, or the ATP/ADP terminal phosphate oxygens. This ability to form borate complexes with active site nucleophiles has been extensively utilized to develop slow binding inhibitors of serine proteases (e.g. see Kettner & Shenvi, 1984), wherein the nucleophilic serine OH forms a covalent bond with the vacant 2p orbital in the boronic acid resulting in a tetrahedral borate complex (e.g. see Skordalakes et al., 1997). Also, an intramolecular complex of a boronic acid with a urea $NH_2$ was used to prepare transition state analogs inhibitors of dihydroorotase (Kinder et al., 1990). 3) Boronic acids act as Lewis acids and are converted to tetrahedral hydrates in water by forming borate complexes with water or hydroxide ions. Therefore, it is also possible that these boronic acid hydrates may function as phosphate mimics and $M_1$ modules as proposed in FIG. 2. This hydration property was utilized by Baggio et al. (1997) wherein a hydrated boronic acid functioned as a transition state analog inhibitor functionality for arginase. These researchers evaluated the inhibited complex by x-ray and showed that the hydrated boronic acid functionality formed two hydrogen bonds with the active site catalytic Glu-277 carboxyl side chain and one of the other hydrated boronic acid OH's interacted with two catalytic $Mn^{2+}$'s in the active site. These binding interactions are closely analogous to those proposed in protein kinase active sites, i.e. H-bonds to the catalytic Asp side chain carboxyl group and interactions with the active site $Mg^{2+}$'s (see FIGS. 2 and 4). The use of boronic acids or protein kinase inhibitors has not been explored previously.

In the area of pentapeptide-based PKA inhibitors, the boronic acid functionality has been prepared and tested as a potential $M_1$ module utilizing the four inhibitors 21-24 shown in Table III (see Hsiao & Hangauer, 1998, for some of the chemistry used to prepare these compounds).

TABLE III

PKA INHIBITION RESULTS WITH BORONIC ACID-CONTAINING PEPTIDE INHIBITORS

| Ac-RRGXI-NH$_2$, X = | $IC_{50}$ μM (cond. L, 0 h preincubation) | $IC_{50}$ μM (cond. L, 4 h preincubation) | $IC_{50}$ μM (cond. C, 0 h preincubation) | $IC_{50}$ μM (cond. C, 4 h preincubation) |
|---|---|---|---|---|
| 20 Ala | 278 ($K_i$ = 9 μM) | 417 | 41 ($K_i$ = 25 μM) | 50 |
| 21 (L-boronic acid sidechain) | 249 | * 500 μM 34% inh | 764 | * 2000 μM 19% sti |
| 22 (D-boronic acid sidechain) | 81 | * 65 | * 1753 | * 2000 μM 71% sti |
| 23 (dihydroxy boronic sidechain) | 398 | 133 | 2000 μM 16% inh | * 2000 μM 5% inh |
| 24 (longer boronic sidechain) | 1000 μM 33% inh | 1000 μM 44% inh | 2000 μM 6% sti | 1734 μM |

\* Very distorted $IC_{50}$ curve: Suggests Inhibitor is also a substrate.
L = Literature Mimetic Assay Conditions.
C = Cellular Mimetic Assay Conditions.
Inh = Inhibition.
Sti = Stimulation.

The structure identified in Table III as Ac-RRGXI-NH$_2$ is SEQ. ID. No. 4.

While testing these boronic acid-containing PKA inhibitors, the corresponding pentapeptide pseudosubstrate inhibitor 20 was included as an internal control while investigating time-dependent inhibition as shown in Table III. Under Literature Mimetic assay conditions, and no preincubation, the initial results suggested that the shortest chain L-amino acid 21 was binding with the same affinity as the pseudosubstrate inhibitor 20 (i.e. $K_i$ ca. 9 μM). As this side chain was increased in length (to 23 and then 24) binding affinity appeared to decrease. When the stereochemistry of the unnatural amino acid was inverted from L in 21 to D in 22, binding affinity appeared to increase 3-fold. This improvement in binding may occur as a result that the boronic acid OH in 21 is positioned at the same chain length as L-homoserine whereas the natural substrate, L-serine, has a one carbon shorter side chain. Modeling results with the PKA ternary structure indicated that the boronic acid OH can be retracted back somewhat by inverting the α-carbon stereochemistry from L in 21 to D in 22 and then repositioning the side chain to more closely mimic the positioning of the natural substrate L-serine OH adjacent to the catalytic residues (Asp-166 and Arg-168). The modeling results were subsequently supported by the finding that, upon incubation of PKA with these inhibitors for up to four hours without adding the competing peptide substrate (Kemptamide: LRRASLG-NH$_2$ (SEQ. ID. No. 5)), both 21 and 22 function as substrates with the D-diastereomer 22 being phosphorylated faster.

The fact that these boronic acid inhibitors are also substrates, became much more obvious by the greatly distorted $IC_{50}$ curves obtained under the Cellular Mimetic conditions, both with and without preincubation (both PKA and Src are more active enzymes under the Cellular Mimetic conditions than under Literature Mimetic conditions). In the assay used to obtain these results, the $P^{32}$ phosphorylated Kemptamide product (25 generated from γ-$P^{32}$ ATP) was isolated at the end of the substrate incubation period by binding to phosphocellulose filter paper via the three cationic groups (two Arg's and the N-terminus) and the level of phosphorylated product isolated on the paper is then measured by liquid scintillation counting (cpm's). The boronic acid inhibitors 21-24 have two Arg's in their sequence also and therefore will bind to the phosphocellulose paper in addition to Kemptamide (although not as consistently or completely due to one less positive charge). Consequently, when analyzed as inhibitors, the amount of phosphorylated Kemptamide produced was not only counted, but also the amount of phosphorylated inhibitor simultaneously produced (e.g. see 26 below). The net result is that distorted $IC_{50}$ curves are obtained which show net "stimulation" at higher inhibitor concentrations in some cases. The D diastereomer 22 gives the greatest apparent "stimulation" (71%) when preincubated with PKA for four hours under Cellular Mimetic conditions followed by the L diastereomer 21 (19%) and then the one carbon homolog 23 (5%), indicating all three are substrates for PKA (Table III). The underlying substrate behavior of these "inhibitors" makes an accurate measurement of their inhibition potency impossible with the current assay. However, it does appear from the data that homologating the boronic acid functionality out with only $CH_2$ groups (homologations with boronic acid non-peptide Src inhibitors may also be carried out) decreases the binding affinity and ability to function as a substrate.

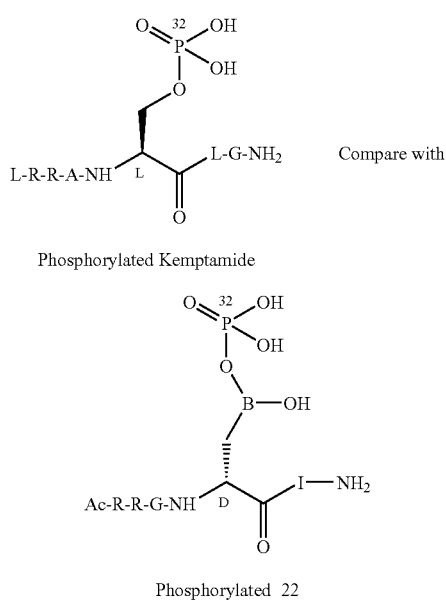

Figure 4:
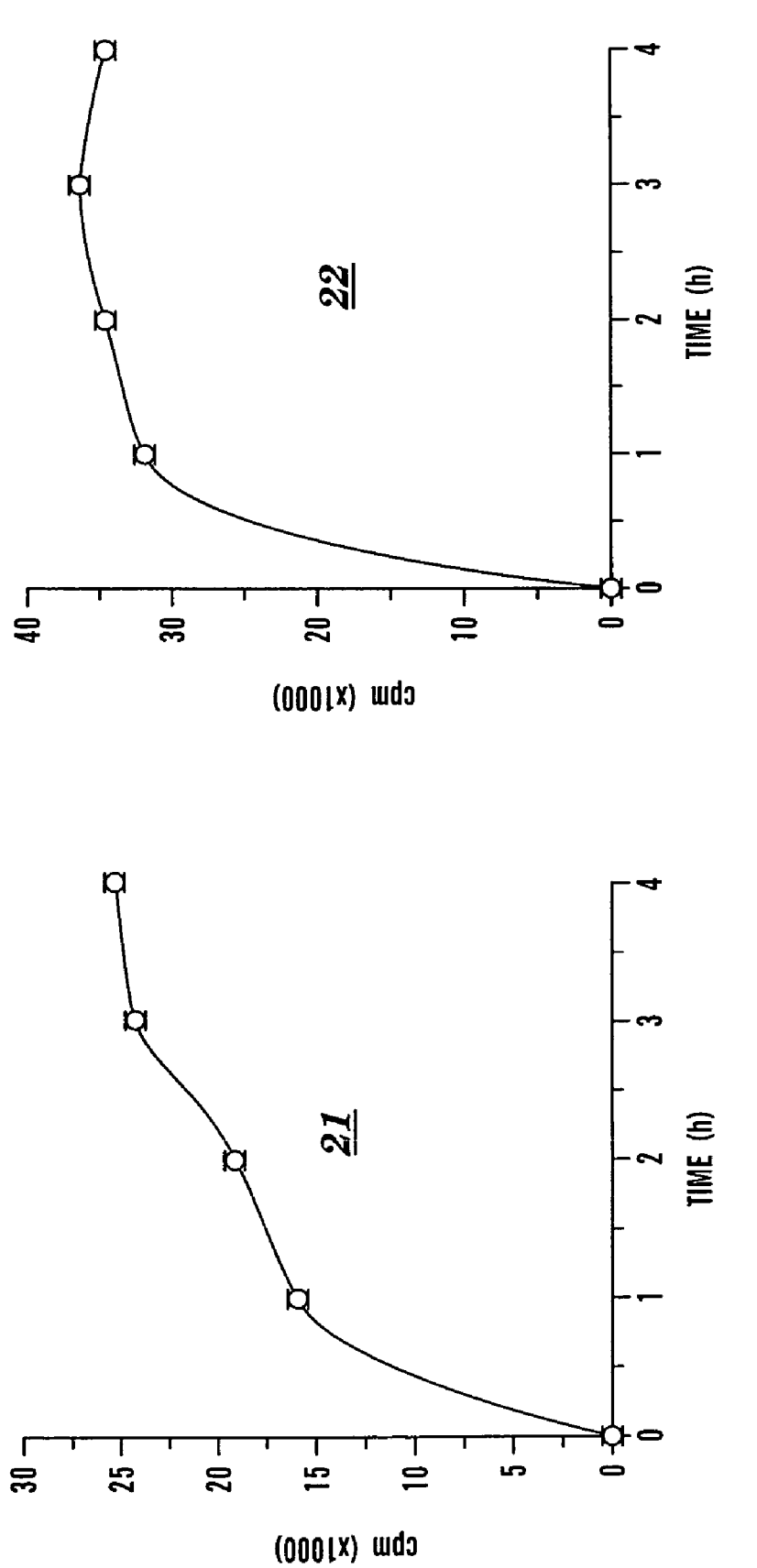
FIG. 4 shows that the boronic acid "inhibitors" 21 and 22 were shown to be substrates for PKA.

Phosphorylated Kemptamide is SEQ. ID. No. 6. Phosphorylated 22 is SEQ. ID. No. 4. The boronic acid "inhibitors" 21 and 22 were shown to be substrates for PKA by running the same assay, but without adding Kemptamide, and stopping the reaction at various time points as shown in FIG. 4. The graphs show their respective rates and levels of phosphorylation with the typical loss of initial velocity kinetics with time (due to substrate depletion and end product inhibition), analogous to a standard L-Ser substrate such as Kemptamide. The comparison of 21 to 22 shown was done in the same assay run, at identical boronic acid substrate concentrations, and with identical Cellular Mimetic assay solutions so that the cpm's could be directly compared. The graphs show that initial velocity conditions were lost within one hour for D isomer 22 whereas the linearity appears to have been lost somewhat slower with the L isomer 21 suggesting a slower consumption of starting material. That the boronic acid moiety would be phosphorylated by PKA was surprising, but it is even more surprising that the phosphonic-boronic acid mixed anhydride produced (e.g. 26) was stable enough to survive the pH 7.2/37° C. assay incubation and then be isolated by binding to phosphocellulose paper after acid quenching of the reaction with 10% TCA and washing the phosphocellulose paper with 25 mM phosphoric acid (3×). An STN substructure search was run on mixed anhydrides of phosphoric and boronic acids and found only three references to experiments and theoretical calculations for the analogous putative (but not proven) anhydride formed from boric acid and phosphoric acid as a solid surface impregnated catalyst for the partial oxidation of ethane to acetaldehyde at 823° K (Zhanpeisov & Otsuka, 1992, Otsuka et al., 1992, Murakami et al., 1990). However, this highly unusual anhydride has never before been synthesized free of a solid surface, isolated, or characterized. Thus, this is a novel enzymatic reaction and chemical entity with interesting possibilities for protein kinase inhibitor designs.

The next class of $M_1$ functionality which was explored was the halogen group. This functional group is an intriguing candidate for $M_1$ for a number of reasons: 1) it is a good hydrogen bond acceptor; and 2) it reduces the rate of metabolism, leading to in vivo benefits.

The halogen functionality has been prepared and tested as a potential $M_1$ module utilizing the inhibitor shown below (see Example 1, for the chemistry used to prepare this compound):

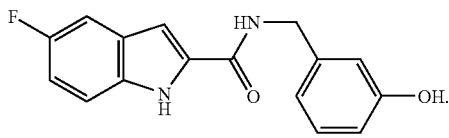

This inhibitor was tested for Src inhibition using the assay procedure set forth in Example 1. The results obtained are shown in Table VII, which indicates an $IC_{50}$ of 40 µM for the above inhibitor (1a in Table VII). This inhibitor includes a non-peptide scaffold (indole) which was chosen based on the screening method described below.

The Src and PKA pentapeptide scaffold tethered $M_1$ evaluations described above have resulted in identifying a variety of orienting $M_1$ groups which could be used for screening potential non-peptide scaffolds as indicated in Step 1 (FIG. 1). The boronic acid (from 22), the phosphonate (from 14), and the sulfamic acid (from 8) were chosen from the menu of potential $M_1$'s for the Src non-peptide scaffold screening. Among these choices, the boronic acid $M_1$ group has proven effective for Step 1 screening of non-peptide scaffolds.

The most useful crystal structures available for the design of non-peptide Src inhibitors, which do not compete with ATP, are the native Src structure and the IRTK:peptide:AMP-PNP ternary structure. For all of the modeling studies discussed below, the SYBYL molecular modeling software package is used on a Silicone Graphics Workstation.

Since the Src and IRTK structures are only used as qualitative guides in designing the non-peptide scaffolds and combinatorial libraries, the active sites along with two layers of surrounding residues were carved out from the native Src and IRTK ternary structures, analogous to the previous PKA modeling studies. The IRTK:peptide:AMP-PNP ternary structure active site region was used as the template structure to guide the building of the Src residue sequence 424-418 back onto the Src structure using the comparative homology modeling technique (see Hutchins & Greer, 1991). These residues were disordered in the native Src crystal structure and therefore not visible by x-ray. They were reintroduced because they help form the P+1 to P+3 binding sites for peptide substrates which are important for some of the modeling studies. The analogous residues in the IRTK ternary structure are seen by x-ray and directly interact with the bound peptide substrate. In fact, it is probably the presence of the bound peptide substrate which induces order in the positioning of this sequence so that it is visible by x-ray. The Src pentapeptide substrate Ac-Ile-Tyr-Gly-Glu-Phe-NH$_2$ (SEQ. ID. No. 1) (Nair et al., 1995) was then docked into the Src active site again using the IRTK ternary structure as a template. Small adjustments were then manually made to partially clean up this complex, all of the hydrogen atoms were added, appropriate formal and partial charges (calculated via the Gasteiger Marsili method) were added, and then the entire complex was subjected to 300 iterations of molecular mechanics minimization using the Tripos force field, analogous to the previous PKA modeling procedure. A schematic representation of this modeled complex is given in FIG. 5. Any inaccuracies in this Src:peptide and the Src:inhibitor models are accommodated by experimentally evaluating a range of side chains, the number and diversity of which is scaled roughly to the level of uncertainty for the structure of their particular binding region in the Src model active site (see later), in a combinatorial fashion.

Figure 5:
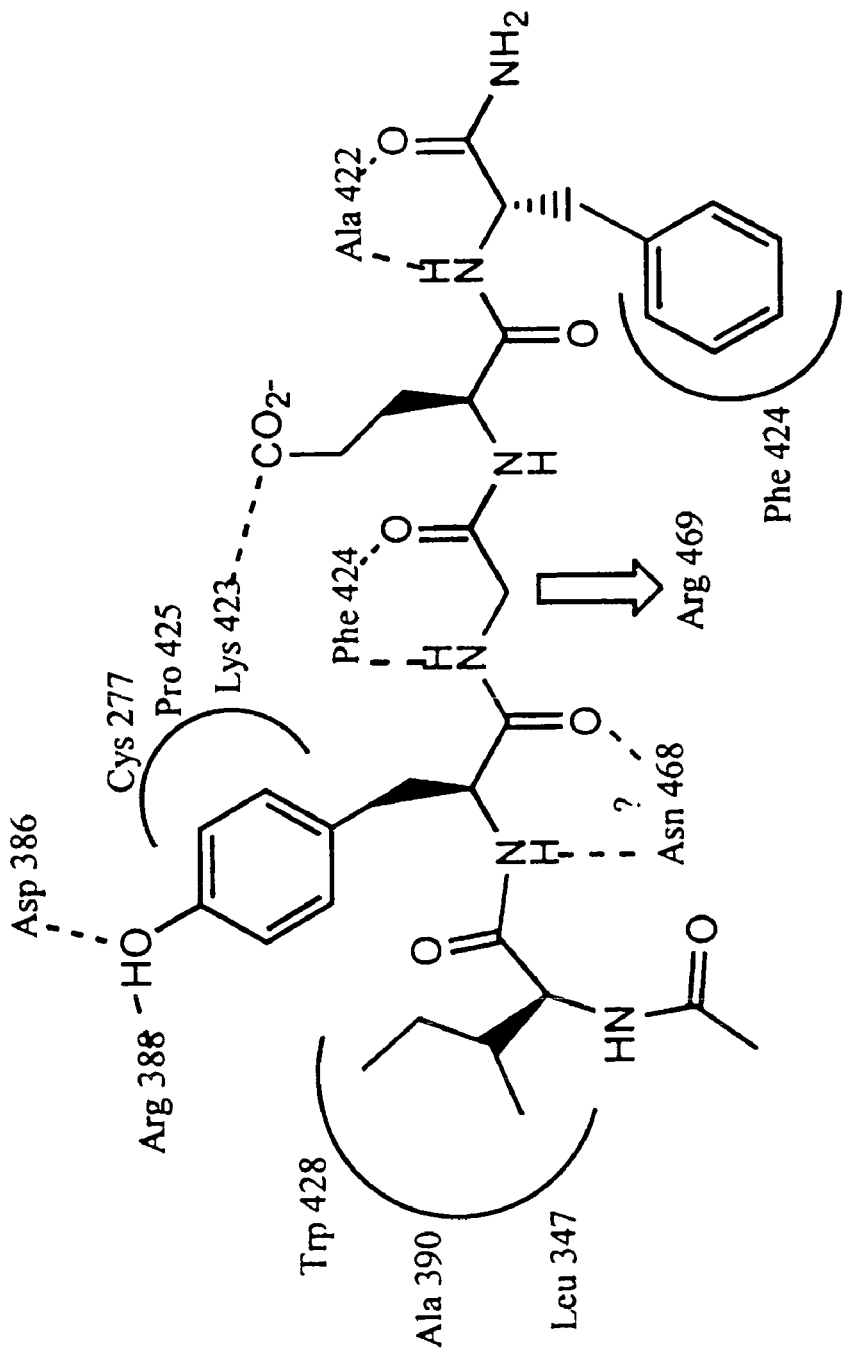
FIG. 5 demonstrates the binding interactions of Src substrate Ac-Ile-Tyr-Gly-Glu-Phe-$NH_2$ (SEQ. ID. No. 1) in model Src active site.

As shown in FIG. 5 the residues 424-418 built back into the Src interact with the P+1 to P+3 substrate residues, Gly-Glu-Phe-NH$_2$ respectively, through beta sheet type hydrogen bonding interactions with the substrate main chain (analogous to the IRTK peptide substrate). Lys 423 engages in two important interactions: 1) the $\beta$ and $\gamma$ CH$_2$'s fold over the top of the P O Tyr phenyl ring engaging in a hydrophobic binding interaction and then 2) the remaining CH$_2$—CH$_2$—NH$_3^+$ of this side chain extends away to form a salt bridge with the P+2 Glu side chain as indicated. The rest of the P 0 Tyr hydrophobic binding pocket is formed by Pro 425 under the phenyl ring and part of the Cys 277 side chain above the phenyl ring. Using a large combinatorial peptide Src substrate library, Songyang et al. (1995) found that the most commonly chosen side chain for the P+1 position was Gly followed by Glu. The present model indicates that a P+1 Glu side chain may form a salt bridge with nearby Arg 469 as indicated in FIG. 5. Previously, researchers found that only Glu was chosen for the P+2 position and the present model indicates that this side chain forms a salt bridge with the Lys 423 side chain. At the P+3 position Phe was very strongly preferred and the model indicates that this side chain forms a stacking interaction with the Phe 424 side chain. At the P−1 position Songyang et al. found that Ile was the most preferred residue followed by Val and then Leu. The model shows a hydrophobic pocket for binding the P−1 side chain formed mainly by Trp 428, Ala 390 and Leu 347. One might expect that the P 0 Tyr side main chain will strongly interact (though hydrogen bonding) with the active site in a catalytically competent complex because enzymes often form more critical interactions in this region close to where the reaction will be occurring. The IRTK ternary complex does not show a good hydrogen bond to either the P 0 Tyr NH or carbonyl. The nearest candidate residue for this interaction in the IRTK structure is Asn 1215 wherein the side chain NH$_2$ is 3.71 Å from the Tyr carbonyl oxygen. When the IRTK ternary structure is overlayed onto the Src native structure, using the four residues mentioned in the Background and Significance section, Asn 468 from the Src structure was found to be positioned very close to the analogous IRTK Asn 1215. This suggests that this conserved residue is performing an important role and might move a little closer (i.e. about 1 Å) to the substrate P 0 NH and carbonyl in a catalytically active complex and form the hydrogen bonding interactions indicated in FIG. 5. Finally, the catalytic Arg 388 and Asp 386 are correctly positioned in the Src model to catalyze the transfer of the $\gamma$-phosphate from ATP to the Tyr OH.

The Src:peptide substrate complex can now be used to model potential non-peptide scaffolds and determine preferred substitution positions for the specificity elements, all with an appropriately attached M$_1$ functionality, before choosing new scaffolds to experimentally evaluate. The IRTK:peptide:AMP-PNP ternary structure can also be used to model these potential scaffolds and preferred substitution positions. These scaffolds have broad utility for the development of selective PTK inhibitors by further developing them with appropriate specificity elements following the strategy outlined in FIG. 1.

Figure 6:
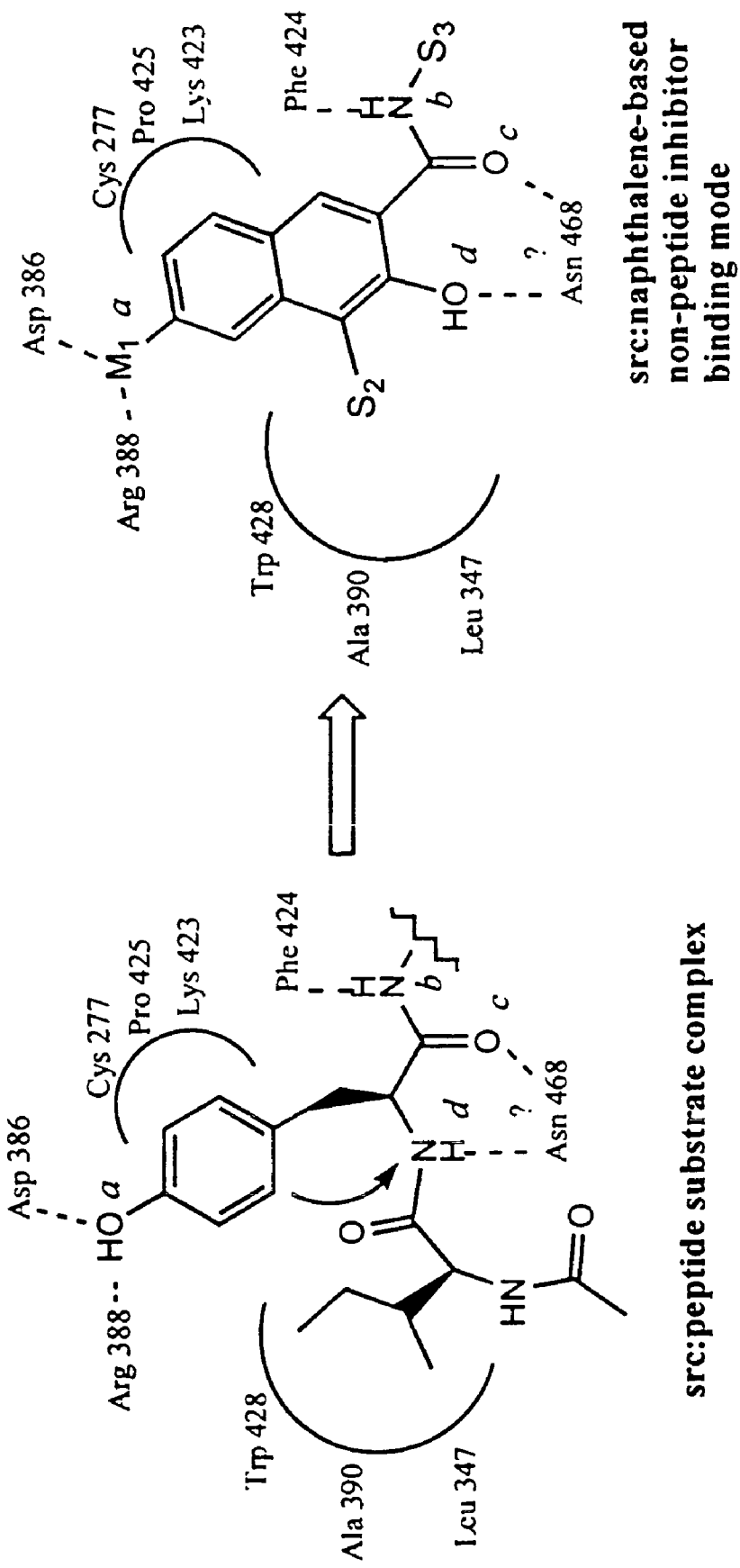
FIG. 6 shows the design of naphthalene-based Src inhibitor scaffolds.
Figure 7:
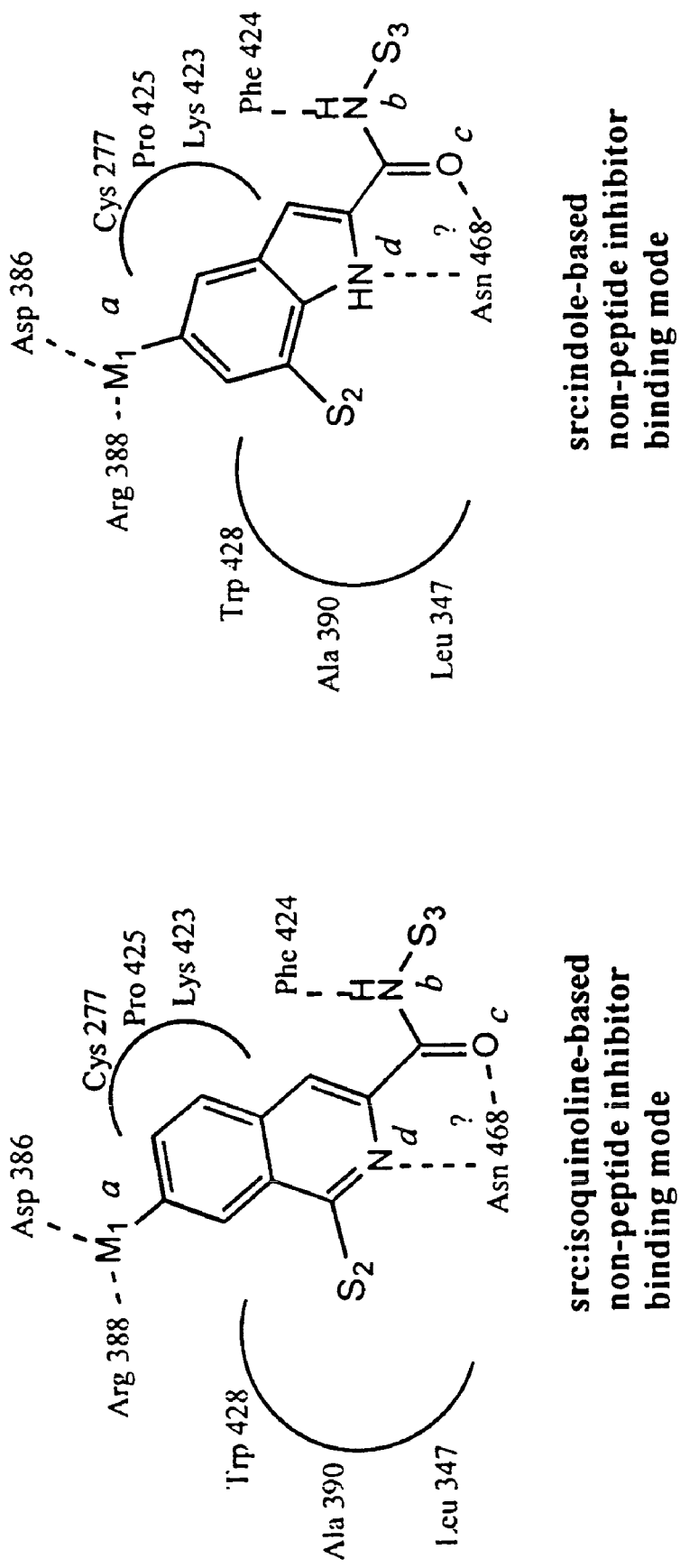
FIG. 7 shows the design of isoquinoline and indole-based Src inhibitor scaffolds.

The first non-peptide scaffold evaluated with this Src:peptide substrate model was the naphthalene scaffold. This is the first use of bicyclic aromatic scaffolds for non-peptide PTK inhibitors, which do not compete with ATP. The naphthalene scaffold's utility for this purpose was demonstrated by developing a non-peptide inhibitor of the IRTK and EGF receptor PTK (Saperstein et al., 1989). The IRTK ternary complexes were subsequently used to adapt this scaffold for Src inhibition (see Marsilje et al., 2000). The naphthalene scaffold was docked into the Src active site by first carrying out a least squares fitting of atoms a-d onto the peptide substrate as indicated in FIG. 6. In this way the naphthalene scaffold is related to the peptide substrate by the cyclization shown by the arrow in FIG. 6 and an appended OH as a substitute for the substrate Tyr NH. This is essentially the same process used to dock this scaffold into the IRTK structure as described in Marsilje 2000. The peptide substrate was then deleted from the active site, various M$_1$ functional groups and specificity elements S$_2$ and S$_3$ were then added to the scaffold as indicated and the complexes were then individually minimized for 300 iterations. This same process was also used to design the isoquinoline and indole scaffolds whose binding modes are indicated in FIG. 7.

In all of these modeled complexes, selectivity element S$_2$ consists of various hydrophobic side chains which can bind in the same pocket as the substrate P−1 Ile side chain and selectivity element S$_3$ consists of various molecular fragments which can bind in the P+1 to P+3 region of the peptide substrate binding sites (FIG. 5). Since the active site region where M$_1$ binds is highly conserved among all of the protein kinases, the small menu of M$_1$ functional groups previously identified using peptide scaffolds served as the initial M$_1$ groups for attachment to the scaffolds at the indicated positions. Of the two selectivity elements binding sites, the structure of the hydrophobic binding cavity for S$_2$ is known with greater confidence in the Src model than is the P+1 to P+3 binding region for S$_3$. This is because the S$_3$ binding site was constructed partially by comparative homology modeling whereas the S$_2$ site is largely unchanged from the structure determined by x-ray for native Src. In view of these varied levels of confidence in the modeled binding sites for M$_1$, S$_2$ and S$_3$, the combinatorial library diversity is scaled such that the greatest variety and number of side chains in the combinatorial libraries are at the S$_3$ site followed by the S$_2$ site and then M$_1$.

The Src results using M$_1$ functional groups to experimentally identify promising non-peptide scaffolds are listed in Table IV.

TABLE IV

INITIAL STEP 1 RESULTS
% SRC INHIBITION IN CELLULAR MIMETIC ASSAY

| Inhibitor | % Inhibition of 2 mM RR-src at Inhibitor Concentration O | |
|---|---|---|
| $M_1$-2-naphthyl | - - - = Attaching bond. | |
| 27  $M_1$-B(OH)$_2$ | 59 (1 mM)<br>13 (100 μM)<br>$IC_{50}$ = 950 μM<br>$K_i$ = 554 μM | NON-ATP COMPETITIVE |
| 28  HO-S(O)$_2$-NH- | 31 (1 mM)<br>$IC_{50}$ = 1.6 mM<br>$K_i$ = 963 μM | NON-ATP COMPETITIVE |
| 29  HO-S(O)$_2$- | 0 (1 mM) | |
| 30  (HO)$_2$P(O)- | 14 (1 mM) | |
| 31  H$_2$N-S(O)$_2$- | 0 (100 μM) | |
| $M_1$-1-naphthyl | | |
| 32  $M_1$-B(OH)$_2$ | 0 (100 μM) | |
| 33  (HO)$_2$P(O)- | 1 (1 mM) | |
| 34  H$_2$N-S(O)$_2$- | 0 (100 μM) | |

TABLE IV-continued
INITIAL STEP 1 RESULTS
% SRC INHIBITION IN CELLULAR MIMETIC ASSAY
| Inhibitor | % Inhibition of 2 mM RR-src at Inhibitor Concentration O |
|---|---|
| 35 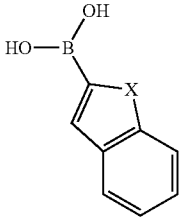 X = O | 10 (100 μM) |
| 36 X = S | 12 (100 μM) |
| 37 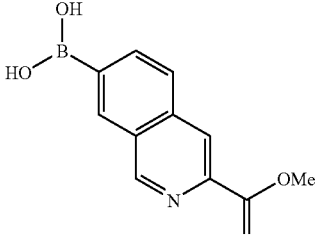 | 13 (500 μM) |
| 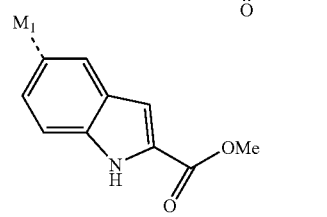 | |
| 38 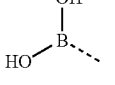 NON-ATP COMPETITIVE | 62 (500 μM) |
| 39 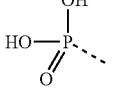 | 11 (500 μM) |
| 40 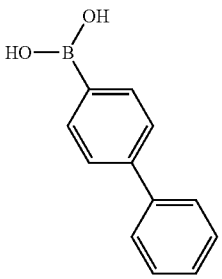 | 13 (100 μM) |

TABLE IV-continued

INITIAL STEP 1 RESULTS
% SRC INHIBITION IN CELLULAR MIMETIC ASSAY

| Inhibitor | % Inhibition of 2 mM RR-src at Inhibitor Concentration O |
|---|---|
| 41  HO-B(OH)-biphenyl (meta) | 14 (100 µM) |

The data in Table IV allows a number of conclusions to be drawn: 1) Low, but measurable, inhibition potency can be obtained with an appropriate $M_1$ group attached to a scaffold (e.g. 27 and 38). 2) 1 mM inhibitor concentrations for this type of screening is higher than desirable but 100 µM is too low. Screening of scaffolds bearing an $M_1$ group would optimally be conducted at 500 µM. 3) The boronic acid, sulfamic acid, and phosphonic acid $M_1$ functional groups, which had been identified using the PKA pentapeptide scaffold (22, Table III and 8, Table I) or the Src pentapeptide scaffold (14, Table II), respectively, give measurable activity when placed at the 2 position of the naphthalene ring (27, 28, and 30, respectively), the preferred position for $M_1$ identified in the model naphthalene inhibitor:Src complex (FIG. 6). Moving the boronic acid or phosphonic acid $M_1$ groups to the 1 position (32 or 33) reduced activity. 4) The related $M_1$ sulfonamide functionality, which was poor on the PKA pentapeptide scaffold (7 & 9, Table I) is also poor when appended to the 2 (31) or 1 (34) position of the naphthalene scaffold. The sulfonic acid analog at the naphthalene 2 position (29) is completely inactive, even at 1 mM. 5) The naphthalene scaffold can be replaced with a benzofuran (35) or a benzothiophene (36) scaffold without a noticeable reduction in activity when the boronic acid $M_1$ group is positioned analogous to the 2 position on a naphthalene. 6) The boronic acid $M_1$ group also provides active compounds when appended to the isoquinoline (37) or indole (38) scaffolds at the positions indicated by modeling results (FIG. 7). However, the indole scaffold is clearly favored over the isoquinoline scaffold suggesting that a hydrogen bond donating ability to Asn 468 (see FIG. 7) is important for higher activity (this would require the protonated isoquinoline which is disfavored by the adjacent electron withdrawing ester group). This conclusion is also supported by considering that a peptide substrate may position a hydrogen bond donating peptide bond NH at a similar position (FIG. 6) and by finding that an equivalently positioned phenolic OH (FIG. 6) improves potency (phenolic OH's are much better H-bond donors than acceptors). 8) When directly compared to other $M_1$ groups, the boronic acid group is superior (e.g. 27 vs. 28-31, 38 vs. 39). 9) A biphenyl scaffold modeled into the Src and IRTK active sites and found promising binding modes for this scaffold. Combinatorial libraries were developed with the biphenyl scaffold (see Pavia et al., 1996), and the modeling results were encouraging. Therefore, the para (40) and meta (41) isomers were evaluated with the boronic acid $M_1$ group. Both biphenyl compounds showed potency equivalent to the best naphthalene boronic acid (27) and therefore provide another scaffold geometry (the two phenyl rings are not planar) for further evaluation and development.

Since the bare scaffolds, with only an $M_1$ group appended, often have low binding affinity, the $IC_{50}$'s and $K_i$'s for the 2-naphthalene boronic acid and sulfamic acid inhibitors were determined to ensure that a typical dose/response $IC_{50}$ curve is obtained. This analysis provided the typical shape dose/response curves seen with more potent inhibitors. The $IC_{50}$'s and $K_i$'s of these simple inhibitors also confirmed that the boronic acid inhibitor 27 is more potent than the sulfamic acid analog 28 and has a $K_i$ of about 554 µM.

The next issue addressed with these simple inhibitors before proceeding to elaborate them further was their mode of inhibition, specifically whether they are ATP-competitive inhibitors. In the case of the naphthalene inhibitors 27 and 28, their $IC_{50}$'s were monitored as the ATP concentration was increased in three steps up to 1 mM. As a comparison, the $IC_{50}$ of the pentapeptide phosphonic acid Src inhibitor 14 (Table II) was also monitored. If any of these inhibitors were competing with ATP, then their $IC_{50}$'s should have increased proportionally with the ATP concentration (i.e. the dashed line). As shown, the $IC_{50}$'s for all three inhibitors remained essentially constant as the ATP concentration was increased demonstrating that they are not ATP-competitive inhibitors. A very similar, but much less costly (commercial Src is expensive), analysis was conducted with the indole boronic acid inhibitor 38. In this case, the % inhibition was monitored with 38 at a constant 500 µM inhibitor concentration but with increasing ATP concentrations of 200, 500 and 1,000 µM. Once again the inhibitor potency was not reduced by the increasing ATP concentration demonstrating that 38 is also non-ATP competitive.

The initial results obtained in Step 1 suggests that it is possible to identify promising scaffolds for further elaboration with this procedure. The biggest uncertainty with Step 1 is that some of the scaffolds identified in this way might not be binding in the fashion suggested by the prior modeling evaluations. This is essentially a "false positive" problem. These "false positives" will likely fail in Step 2, when they are evaluated for improved binding using the modeled complexes as a guide. Some false positive results can be accepted in Step 1 because the bare scaffolds with only the $M_1$ group attached are easily obtained. For further inhibitor development, one may return to Step 1 each time new scaffolds are needed to carry through Steps 2 and 3. The best $M_1$ generated can be used each time Step 1 is repeated. Currently, the boronic acid $M_1$ group has been used since it has a proven ability to give measurable activity with bare scaffolds. Also the boronic acid $M_1$ group offers multiple interesting possibilities for covalent and non-covalent interactions with the conserved catalytic residues since it can: 1) hydrate, 2) form borate complexes with electron rich active site atoms, and/or 3) be phosphorylated and then react with active site nucleophiles or engage in additional non-covalent interactions. From the data in Table IV, the naphthalene and indole scaffolds were chosen as $M_2$ for the first efforts in Step 2 (the biphenyl scaffold is also a preferred scaffold). It is also worth mentioning that naphthylalanine and analogs can be successfully substituted for the P 0 tyrosine in Src peptide substrates (e.g. see Alfaro-Lopez et al., 1998) further supporting the notion that naphthalene and related scaffolds can bind at the P 0 site.

In comparing the naphthalene vs. indole scaffold results with a boronic acid $M_1$ group (i.e. 27 vs. 38, Table IV) the indole hydrogen bond donating NH and/or the adjacent ester group appeared to be the reason for the enhanced potency.

Consequently, for Step 2 one of the first attempts was to add a hydroxyl group and an amide (with $S_2$) to the naphthalene scaffold at the adjacent positions suggested by the modeling results (FIG. 6). For the indole scaffold one priority was to prepare some amide analogs to see if potency can be increased with the $S_2$ specificity element (FIG. 7). In order to facilitate the synthesis of these initial analogs, an OH was temporarily substituted for the boronic acid $M_1$ group. The OH group is also known to interact with the catalytic residues, as required for an $M_1$ group, because it is the natural substrate $M_1$ whose phosphorylation rate is accelerated by interactions with the catalytic residues. The results obtained for some of the initial analogs are given in Table V along with a side by side comparison, in the Cellular Mimetic Src assay, to two literature Src inhibitors 50 and 51 which are reported be non-ATP competitive. Some of these results and additional analogs are described in Marsilje 2000.

TABLE V

INITIAL STEP 2 RESULTS
% SRC INHIBITION IN CELLULAR MIMETIC ASSAY

| Inhibitor | % Inhibition of 2 mM RR-src at Inhibitor Concentration O |
|---|---|
| 42 ($M_1$) [naphthalene with HO, OH, and C(O)OMe substituents] | 47 (100 μM) |
| 43 ($M_1$) [naphthalene with HO, OH, and C(O)NH-phenyl-OH substituents] NON-ATP COMPETITIVE | Ortho: 39 (100 μM) <br> Meta: 89 (100 μM) <br> $IC_{50}$ = 18 μM, $K_i$ = 10 μM <br> Para: 23 (100 μM) |
| 44 ($M_1$) [naphthalene with HO and C(O)NH-phenyl-OH substituents] | 45 (100 μM) |

TABLE V-continued
INITIAL STEP 2 RESULTS
% SRC INHIBITION IN CELLULAR MIMETIC ASSAY
| Inhibitor | % Inhibition of 2 mM RR-src at Inhibitor Concentration O |
|---|---|
| 45 ($M_1$) 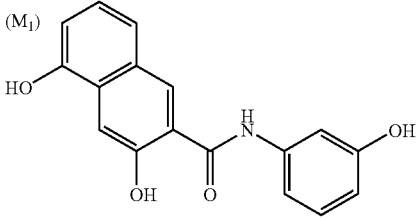 NON-ATP COMPETITIVE | 51 (100 µM) <br> $IC_{50}$ = 170 µM |
| 46 ($M_1$) 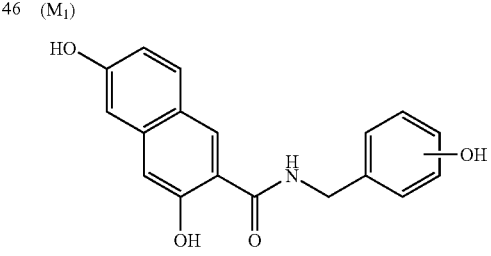 | Ortho: 42 (100 µM) <br> Meta: In progress <br> Para: 42 (100 µM) |
| 47 ($M_1$) 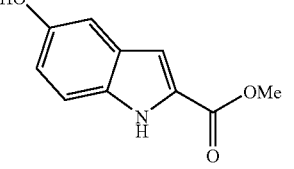 | 40 (500 µM) |
| 48 ($M_1$) 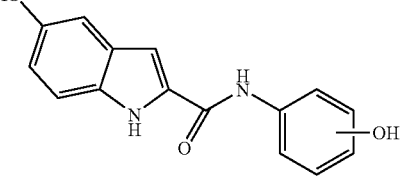 | Ortho: 43 (100 µM) <br> Meta: 30 (100 µM) <br> Para: 45 (100 µM) |
| 49 ($M_1$) 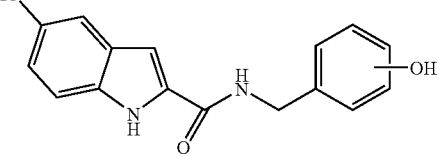 | Ortho: 24 (100 µM) <br> Meta: 74 (100 µM) <br> Para: 54 (100 µM) |

TABLE V-continued

INITIAL STEP 2 RESULTS
% SRC INHIBITION IN CELLULAR MIMETIC ASSAY

| Inhibitor | % Inhibition of 2 mM RR-src at Inhibitor Concentration O |
|---|---|
| 50 ($M_1$?) Huang et al | 30 (100 μM) Lit. $IC_{50}$ = 118 nM |
| 51 ($M_1$?) ST 638 | 37 (100 μM) Lit. $IC_{50}$ = 18 μM |
| 52 ($M_1$?) Piceatannol | 41 (100 μM) Lit. $IC_{50}$ = 66 μM for p56$^{lck}$ |

Inhibitor 50, and analogs (Huang et al., 1995), were of particular interest because the iminochromene scaffold is closely related to the naphthalene scaffold and it's binding mode would be expected to be very similar based upon the model (FIG. 6). Partly because of this close analogy, the amides of hydroxyanilines with the naphthalene and indole scaffolds were examined as shown in Table V. Also, the modeling studies with these hydroxyaniline amide derivatives in the Src active site indicated that the hydroxyl group may be able to engage in hydrogen bonding interactions with the Src Phe 424-Ala 422 backbone peptide bonds analogous to peptide substrates (see FIG. 5). These modeling studies also indicated that the homologous hydroxybenzylamides should be active and, more importantly, provide a substitution position (i.e. the benzylic carbon) for appending side chains to bind in the P–1 side chain pocket (e.g. to Arg 469, FIG. 5).

The data in Table V allow the following conclusions to be drawn: 1) Adding an amide extension onto both the naphthalene and indole scaffolds can increase potency as predicted by the models for these scaffolds bound in the Src active site (ca. 5-fold in the cases of 42 vs. 43-meta & 47 vs 48). 2) Adding a hydroxyl group to the naphthalene scaffold adjacent to the amide increases potency (about 5-fold, 43-meta vs. 44) as predicted by the Src model, and also suggests Asn 468 does hydrogen bond with this OH. 3) Moving the $M_1$ OH group from the position predicted to be best in the Src model to the adjacent position reduces potency by one order of magnitude (43-meta to 45). 4) The indole scaffold is less responsive than the naphthalene scaffold to regiochemistry of the hydroxyaniline extension (48 vs. 43). 5) The naphthalene and the indole scaffolds accept the one carbon homologation provided by using hydroxybenzylamides (46 vs. 43 & 49 vs. 48). 6) The two $M_1$ hydroxy regioisomers of the naphthalene scaffold are both non-ATP competitive (see Marsilje 2000). 7) All of the methyl hydroxyaniline and hydroxybenzylamide inhibitors were found to be less active suggesting that the hydroxyl group in the amide extension is functioning as a hydrogen bond donor. In this regard it is worth mentioning that in another Src peptide substrate combinatorial library study, Ser and Thr were identified as two of the most preferred residues at the P+2 position (Alfaro-Lopez et al., 1998), suggesting that there are other binding opportunities for an amide extension OH other than to the Phe 424-Ala 422 peptide bonds suggested by the modeling studies. 8) The most potent non-ATP competitive, non-peptide, Src inhibitor previously disclosed in the literature (50) is not nearly as potent as reported when tested under the Cellular Mimetic assay conditions ($IC_{50}$=118 nM reported by Huang et al., 1995 vs only 30% inhibition at 100 µM) and is less potent than a number of the current inhibitors (especially 43-meta) including the most analogous inhibitor (50 vs. 45). The structure-activity-relationship (SAR) reported for hydroxy regioisomers of 50 in their assay (Huang et al., 1995) also does not correspond with the SAR which was obtained for the related naphthalene inhibitors. For example, their iminochromene analog of the most potent naphthalene inhibitor 43-meta is 230-fold less potent than 50 in their Src assay. An important advantage of the naphthalene scaffold over the iminochromene scaffold is that it allows a highly desirable $S_2$ specificity element to be added for accessing the P-1 hydrophobic site (see FIG. 6) whereas the analogous position can not be substituted on the iminochromene scaffold because it is occupied by the ring oxygen atom.

The inhibitor potencies in the Src Cellular Mimetic assay can be further calibrated against other literature non-ATP, non-peptide Src inhibitors. Two additional examples are 51 (ST 638, Shiraishi et al., 1989) which is a member of the "tyrphostin" family of erbstatin analogs (see Lawrence & Niu, 1998) and the natural product PTK inhibitor piceatannol 52 (Thakkar et al., 1993). In the Cellular Mimetic assay all of these known inhibitors are less potent than had been reported suggesting that the assay is particularly demanding in terms of achieving high potency. The initial testing of Src inhibitors is carried out using a single concentration (in triplicate) because commercial Src is too expensive to do full $IC_{50}$ curves on every inhibitor. It should be mentioned, however, that an $IC_{50}$ dose response curve is not linear and the difference between ca. 50% inhibition at 100 µM and a ca. 90% inhibition at 100 µM is actually a factor of 10 and not a factor of 2 (e.g. 45 vs. 43-meta). Consequently, the literature Src inhibitors 50-52 are greater than an order-of-magnitude less active than the currently most potent inhibitor 43-meta.

The discrepancies found within the literature reporting the potency of these inhibitors, the sensitivity to assay conditions described earlier with the PKA inhibitors, and the lack of consistency among numerous labs and commercial protein kinase assay kits highlights this overlooked, but crucial, problem in the field. Although the inhibitors produced by the present invention may be more potent under other assay conditions, the Cellular Mimetic assay should be used, which mimics the intracellular physical chemical conditions as closely as possible, as the primary potency and rank order guide for evaluating the inhibitors before choosing compounds to proceed to whole cell or tissue assays. As will be discussed in more detail later, the most potent naphthalene-based inhibitor thus far from the Cellular Mimetic assay (i.e. 43-meta, $IC_{50}$=18 µM and $K_i$=10 µM) is also effective in specifically blocking pp60$^{v\text{-}src}$ stimulated cell proliferation with a similar $IC_{50}$ of ca. 25 µM. This suggests that not only is the Cellular Mimetic Src assay predictive, but also that this class of naphthalene-based inhibitors can readily pass through cell membranes and inhibit intracellular Src.

Analogs of a number of the naphthalene and indole inhibitors above can be prepared with the boronic acid or halogen $M_1$ group in place of the $M_1$ OH and/or with a $S_2$ hydrophobic specificity element attached for binding in the Src P-1 site as illustrated in FIGS. 6 and 7. The naphthalene and indole scaffolds can then be taken through to Step 3 as described below. Each time Step 2 is repeated with new scaffolds from Step 1, the best selectivity elements $S_2$ and/or $S_3$ which have discovered with previous scaffolds will be used in the combinatorial libraries of Step 3. Even though the optimal combination of $M_1$, $S_2$, and $S_3$ is likely to be different for each scaffold, those found optimal with the previous related scaffold (e.g. going from the naphthalene to the indole scaffold) should be suitable for utilization as better initial specificity elements in Step 2 with the new scaffold. The same process will be repeated each time there is a need to try another scaffold until sufficient potency, selectivity, and suitable pharmaceutical properties are achieved for the Src inhibitors or, subsequently, for inhibitors of additional therapeutically important PTK's.

Some of the chemistry used to prepare the naphthalene inhibitors is described in Marsilje 2000. For attaching a boronic acid functionality in place of a $M_1$ hydroxyl group in the Src inhibitors from Table V, the Pd (0)-catalyzed cross-coupling methodology was used wherein either an aryl triflate (Ishiyama et al., 1997) or an aryl halide (Ishiyama, 1995) can be coupled with the commercially available pinacol ester of diboron. An illustrative example recently completed is given in FIG. 8.

Figure 8:
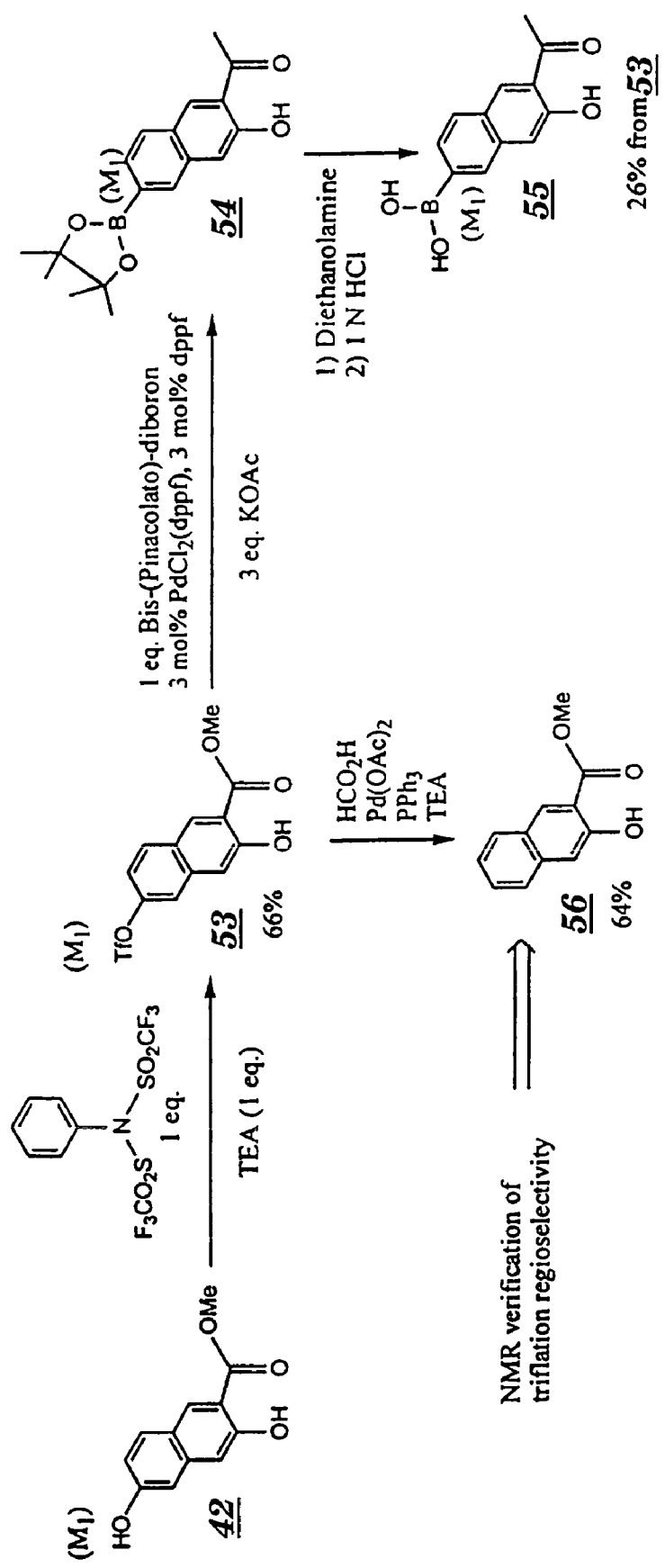
FIG. 8 provides an example of the chemistry used to prepare the naphthalene inhibitors, which is described in Marsilje 2000. A boronic acid functionality can be put in place of a $M_1$ hydroxyl groups in the Src inhibitors from Table V using the Pd (0)-catalyzed cross-coupling methodology wherein either an aryl triflate (Ishiyama et al, 1997) or an aryl halide (Ishiyama, 1995) can be coupled with the commercially available pinacol ester of diboron.
Figure 9:
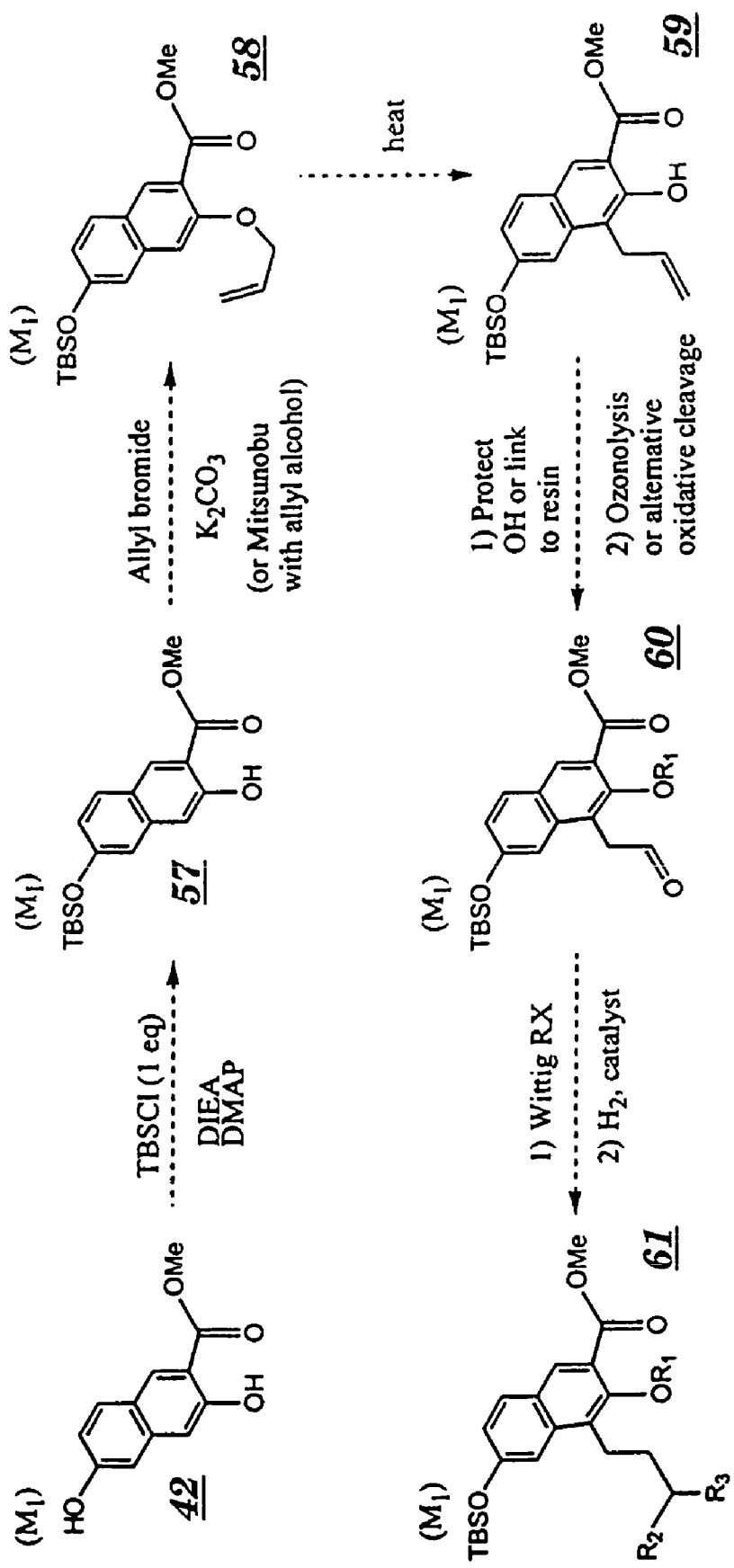
FIG. 9 shows a synthetic scheme that can be followed, in order to attach hydrophobic $S_2$ selectivity elements to the naphthalene scaffold.

The example shown in FIG. 8 demonstrates that it is possible to selectively triflate the less hindered OH at the $M_1$ position and this has been proven by its removal to 56 with subsequent $^1$H NMR verification of the substitution pattern. The monotriflate 53 was then taken on to the desired boronic acid 55 as indicated. The same reaction sequence also works well for the regioisomer of 42 which corresponds to inhibitor 45 from Table V. The synthetic scheme shown in FIG. 9 can be followed, in order to attach hydrophobic $S_2$ selectivity elements to the naphthalene scaffold.

Figure 10:
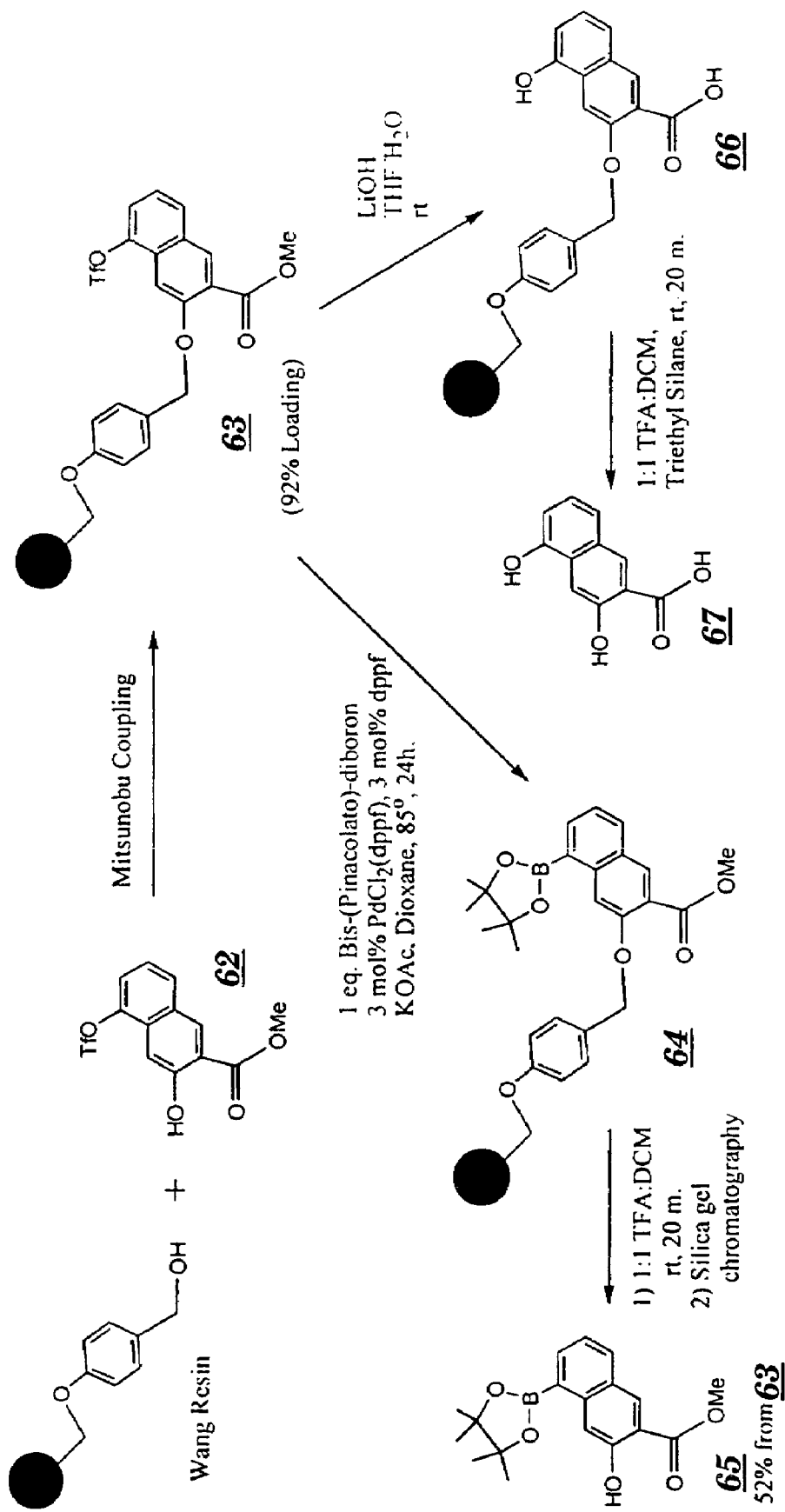
FIG. 10 shows successful model reactions with naphthalene chemistry, which can be converted to the solid phase in preparation for synthesizing combinatorial libraries of this scaffold in a 96-well plate format. The chemistry has been carried out on the less active naphthalene regioisomer represented by 44 because this compound is readily obtained from commercially available 3,5-dihydroxy-2-naphthoic acid, as described in Marsilje 2000.

The naphthalene chemistry can be converted to the solid phase in preparation for synthesizing combinatorial libraries of this scaffold in a 96-well plate format. Thus far, model chemistry has been carried out on the less active naphthalene regioisomer represented by 44 because this compound is readily obtained from commercially available 3,5-dihydroxy-2-naphthoic acid as described in Marsilje 2000. The successful model reactions to date are shown in FIG. 10.

These model reactions demonstrate that it is possible to couple the naphthalene scaffold to the Wang resin (63) and then carry out chemistry on the triflate [in this case the Pd (0)-catalyzed cross-coupling to the boronic ester 64] followed by cleavage under mild conditions (65). The ester in 63 can also be saponified for subsequent coupling reactions to form amides containing the $S_3$ selectivity elements.

Figure 11:
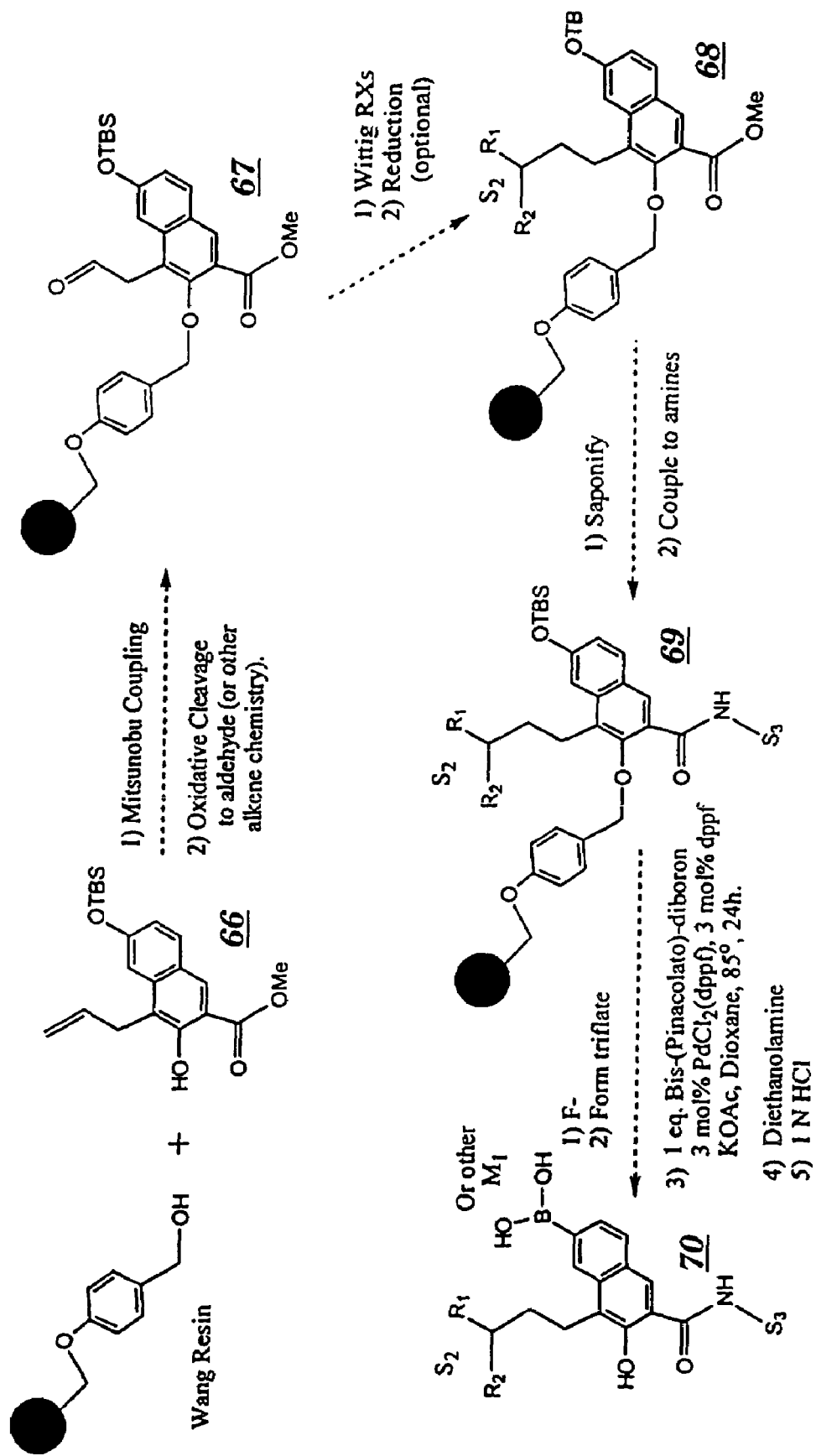
FIG. 11 provides a possible strategy for modifying the naphthalene scaffold in combinatorial libraries.

The naphthalene scaffold currently provides three diversity sites to be explored in the combinatorial libraries, $M_1$, $S_2$, and $S_3$. Solid phase combinatorial chemistry with 96-well plate reactors similar to that used in previous studies may be used (Pavia et al., 1996). The greatest number and diversity of side chains will be used for $S_3$ followed by $S_2$ and then $M_1$ for the reasons discussed earlier. One possible overall synthetic strategy, based upon the synthetic model studies above, for preparing these libraries is shown in FIG. 11.

Of course if problems arise with this route there are many other possibilities. For example, if the Mitsunobu coupling to give 67 proceeds in too low a yield (due to the increased steric congestion of the added adjacent allyl group—but perhaps not a problem given the 92% loading obtained in FIG. 10), then the scaffold could be tethered to a resin through the carboxyl group, rather than the OH, using the acylsulfonamide "safety catch" linker (Backes et al., 1996) and form the amides last (the excess amines can be removed after cleavage by filtering through an acidic resin). Likewise, other linkers and/or resins can be used if the reduction of the alkene in the presence of benzylic ethers (67 to 68) is desired but problematic. The first use of the chemistry proposed in FIG. 11 will be to simply prepare a library of 96 amides, containing the boronic acid $M_1$ group, without having the allyl side chain in place so that these two potential complications will not be a problem initially and the most promising $S_3$ elements can be quickly identified.

At least 14 $S_2$ hydrophobic side chains (includes linear, branched and cyclic) are identified for further study (28 if the corresponding alkenes are also explored) based upon the modeling of candidate side chains into the P–1 site of the Src model (FIG. 6) and on the commercial availability of the needed halides to prepare the corresponding Wittig reagents. At least 96 commercially available amines are available which will provide potential $S_3$ specificity elements including: 1) hydrocarbons (4), 2) alkyl groups containing hydrogen bond acceptors (4), 3) alkyl groups containing both hydrogen bond acceptors and donors (19), 4) alkyl/aryl groups containing hydrogen bond acceptors and donors (25), 5) aryl hydrogen bond acceptors and donors (10), 6) heterocyclic hydrogen bond acceptors and donors (20), 7) side chains containing cationic groups (4), 8) side chains containing anionic groups (9), and the 3-amino phenol side chain from inhibitor 43-meta as an internal control for Src activity. A broad range of amines were included for $S_3$, in order not to overly bias the library here due to the higher level of uncertainty for this binding site in the Src model.

The indole scaffold can be developed into a combinatorial library in much the same fashion. In this case, the indole NH would be used as the tether point for attachment to the Wang (or other) resin since the analogous Mitsunobu reaction is known (Bhagwat & Gude, 1994). A large amount of synthetic methodology has been developed for the synthesis of substituted indoles and have designed a route to include the $S_2$ hydrophobic side chain (see FIG. 7) (Ezquerra et al., 1996).

Figure 12:
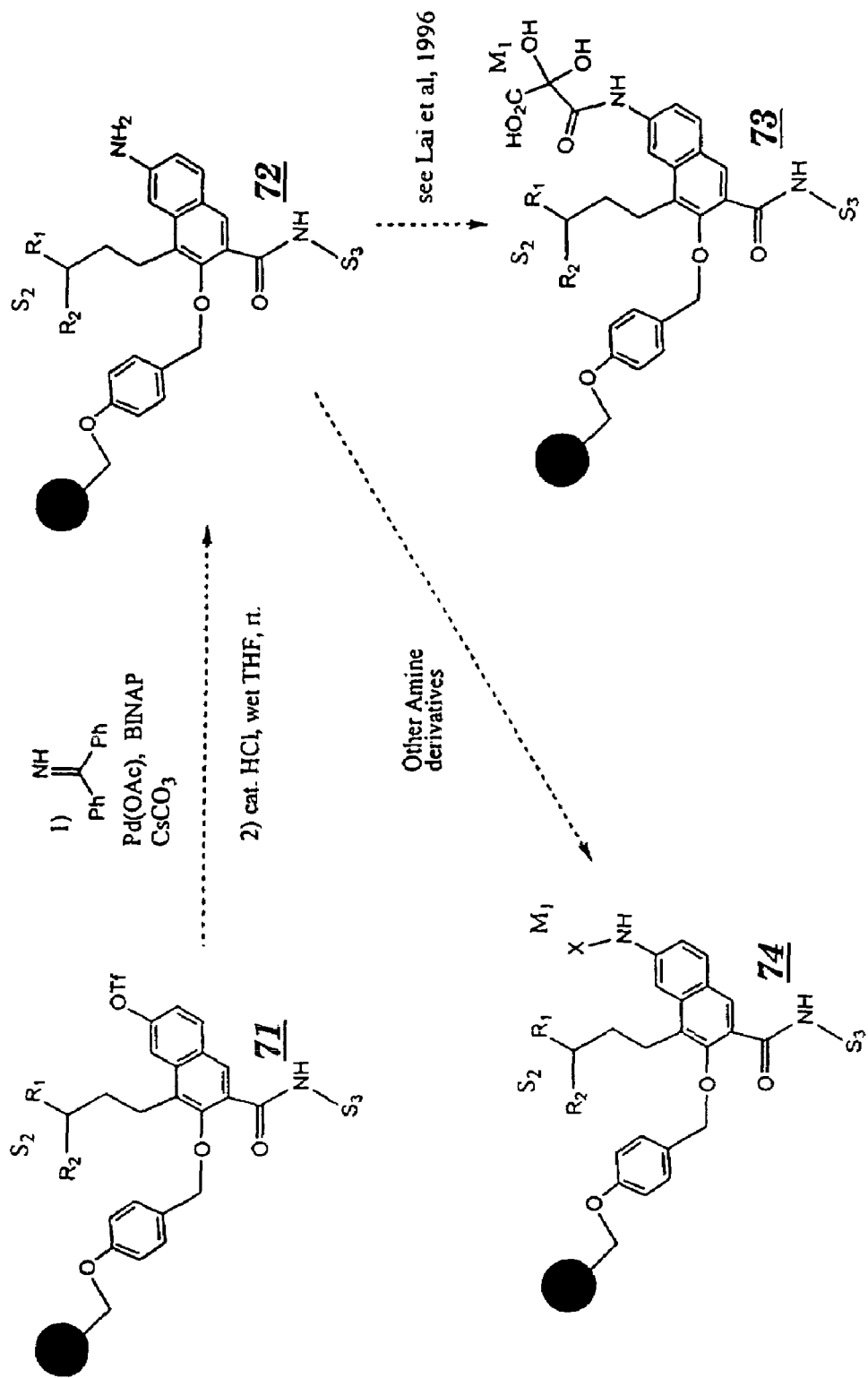
FIG. 12 shows the conversion of the triflate functionality formed in reaction 2 from intermediate 69 (FIG. 11) to an amine (Wolfe et al, 1997) and then a series of amides or other amine derivatives.

The triflate functionality formed in reaction 2 from intermediate 69 (FIG. 11) can be converted to an amine (Wolfe et al., 1997) and then a series of amides or other amine derivatives following the reaction sequence shown in FIG. 12. In fact, the triflate is a versatile synthetic handle and could be converted into other functional groups as well.

When the amine 72 is available, the known $M_1$'s (e.g. the sulfamic acid from Src inhibitor 28 Table V and amide-acid 17 Table III) can be evaluated with this more developed scaffold and evaluate some new amine derivatives as potential $M_1$'s. For example the hydrated tricarbonyl amide $M_1$ group shown in structure 73 (and it's non-hydrated precursor) is accessible via the synthetic methodology (see Lai et al., 1996) and could form a variety of interesting interactions with the conserved catalytic residues.

Figure 13:
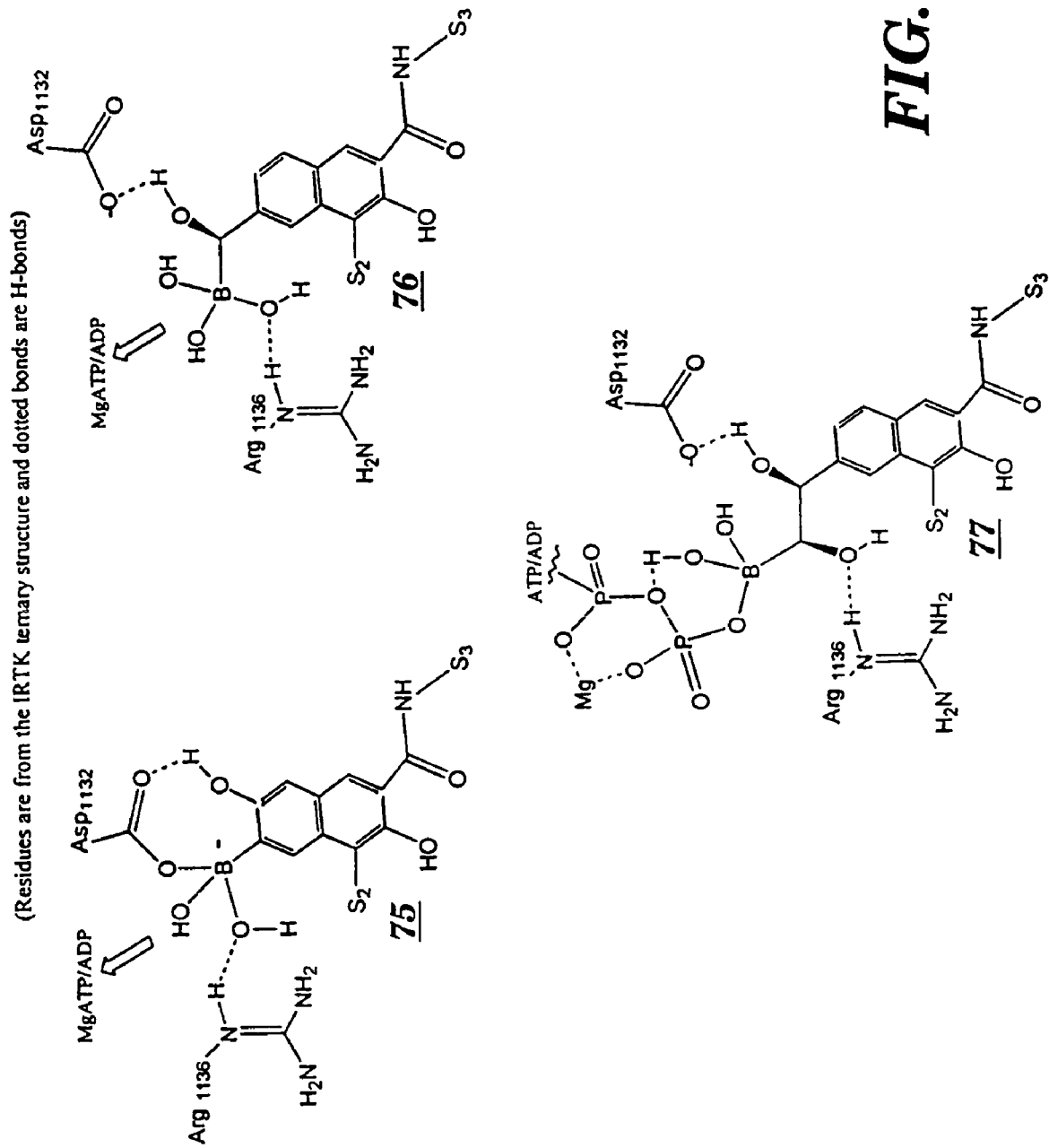
FIG. 13 shows modeling a series of hydroxy-containing analogs of the boronic acid $M_1$ group shown in the Src and IRTK (insulin receptor protein tyrosine kinase) active sites.

Following the modeling procedure described above, a series of hydroxy-containing analogs of the boronic acid $M_1$ group shown in FIG. 13 were modeled in the Src and IRTK active sites and the illustrated interactions/binding modes were found as some of the interesting possibilities. By phosphorylating the boronic acid, additional interesting possibilities are available (e.g. suicide type inhibition via reaction of the resulting mixed anhydride with an active site nucleophile). The presence of additional hydroxyl groups on the Tyr-mimetic phenyl ring is necessary and common among many PTK inhibitors (e.g. Piceatannol 52, Table V) and was shown to be beneficial on the side chain with the PKA phosphonate inhibitors (e.g. 2 vs. 3 and 4, Table I). Consequently, adding one or more OH's to the boronic acid inhibitor $M_1$ design as illustrated in FIG. 13 may considerably enhance potency. These OH groups would also extend the boronic acid side chain past the catalytic Asp and Arg residues without suffering a penalty for covering them with hydrocarbon as was probably the case with the PKA boronic acid homologs (23 and 24, Table III). One possible route to the hydroxyboronic acids 76 and 77 utilizes the chiral boronic ester homologation methodology of Matteson (e.g. see Matteson et al., 1987, 1988 & 1990).

Thus, in a preferred embodiment of the invention, the first module is produced by attaching the first module to a peptide scaffold. One or more functional groups are identified which preferentially bind to catalytic residues of the protein kinase, wherein at least one of the one or more functional groups is a halogen. Further, the first module is combined with the second module so that the second module substitutes for the peptide scaffold.

Preferred first modules have a two or more functional groups, including a halogen and one or more additional functional groups such as a boronic acid group, a hydroxyl group, phosphonic acid, sulfamic acid, a guanidino group, carboxylic acid, an aldehyde, an amide, and hydroxymethylphosphonic acid. More preferred additional functional groups are boronic acid groups, a hydroxyl group, or an amide group. An even more preferred amide group is a vicinal tricarbonyl amide.

Preferred second modules include indole, naphthalene, biphenyl, isoquinoline, benzofuran, and benzothiophene. More preferred second modules are an indole or naphthalene. In some embodiments of the invention more than one first module may be bound to the second module. In addition, the first module may have a linear chain comprising between one and three carbon atoms which links the first module to the second module. In alternative embodiments, one of the carbon atoms in the linear chain is substituted with a nitrogen, oxygen or sulfur atom.

The methods and compounds of the invention are broadly applicable to any protein kinase. Preferred protein kinases are protein tyrosine kinases and protein serine kinases (a.k.a. serine-threonine kinases). Preferred protein tyrosine kinases are $pp60^{c-src}$, $p56^{lck}$, $p55^{fyn}$, ZAP kinase, platelet derived growth factor receptor tyrosine kinase, Bcr-Abl, VEGF (vascular endothelial growth factor) receptor tyrosine kinase, epidermal growth factor receptor tyrosine kinase, and epidermal growth factor receptor-like tyrosine kinases. A more preferred protein tyrosine kinase is $pp60^{c-src}$. Preferred serine protein kinases include MAP (mitogen activated protein) kinase, protein kinase C, and CDK (cyclin dependent protein kinase).

The method of the present invention may further consist of adding one or more specificity side chain elements to the combination of the first and second modules, as described above. Specificity side chains can increase potency and specificity of the inhibitor. Suitable specificity side chains are described above (R groups for above structures) and in the Examples, which follow.

Once a promising second module is identified it is not necessary to repeat all the steps of the method. Rather, the first module, specificity side chains, or a combination the two may be modified to improve the original inhibitor, i.e an inhibitor which has an increased ability to inhibit protein kinase activity when compared to the unmodified first inhibitor.

The present method is designed to preferentially provide protein kinase inhibitors which do not act by inhibiting ATP binding to the protein kinase. Inhibitors of protein kinases which act by inhibiting ATP binding may be potent but often lack specificity and are therefore often not good drug candidates. Therefore, protein kinase inhibitors which inhibit protein kinase activity but do not inhibit or only weakly inhibit ATP binding to the protein kinase are preferred.

In another embodiment, the present invention provides a method of inhibiting a protein kinase. The protein kinase is contacted with a compound having at least one first module which has one or more functional groups capable of covalently or non-covalently binding to catalytic residues of the protein kinase, wherein the one or more functional groups comprise a halogen, and a second module which provides a non-peptide scaffold. The combination of the at least one first module and second module inhibits the protein kinase activity.

The present invention further provides a method of treating a condition, responsive to a protein kinase inhibitor, in a subject. An effective dose of a protein kinase inhibitor is administered to a subject. The protein kinase inhibitor has at least one first module having one or more functional groups each capable of covalently or non-covalently binding to catalytic residues of the protein kinase, wherein the one or more functional groups comprise a halogen, and a second module which provides a non-peptide scaffold, where the combination of the at least one first module and second module inhibits protein kinase activity.

Another aspect of the present invention is a method for identifying inhibitors of protein phosphatases. The method involves providing at least one first module having one or more functional groups each capable of covalently or non-covalently binding to catalytic residues of the protein phosphatase, combining at least one first module with at least one second module which provides a non-peptide scaffold to form one or more combinations of the first and second modules, screening the one or more combinations of the first and second modules for protein phosphatase inhibition, and selecting combinations of the first and second modules which inhibit protein phosphatase activity.

Suitable first and second modules and functional groups are described above. In a preferred embodiment, the at least one first module comprises a halogen, most preferably, fluorine. Examples of suitable non-peptide protein phosphatase inhibitors are shown in Table VIII, below.

Suitable protein phosphatases include, but are not limited to, PTP-1B. Other suitable protein phosphatases are described, for example, in Zhang, 2002; McCluskey et al., 2002a; Zhang 2001; McCluskey et al., 2001; Pestell et al., 2000; Moller et al., 2000; Ripka, 2000; Kennedy, 1999; Johnson et al., 2002; McCluskey 2002b.

As described above, this method is designed to preferentially provide phosphatase inhibitors which bind to the substrate peptide binding site.

The present invention also relates to a method of inhibiting a protein phosphatase. The protein phosphatase is contacted by a compound comprising at least one first module having one or more functional groups each capable of covalently or non-covalently binding to catalytic residues of the protein phosphatase, and a second module which provides a non-peptide scaffold. The combination of at least one first module and second module inhibits the protein phosphatase activity.

In one embodiment, the compound has the following Formula III:

(Formula III)

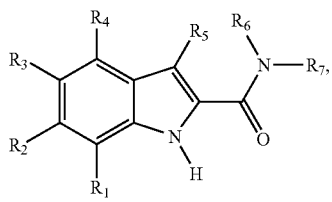

wherein $R_1$ through $R_7$ may be the same or different, and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl, or $R_5$ and $R_6$ together form a heterocyclic compound. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_1$ through $R_7$ and $R_a$ through $R_c$ may be substituted or unsubstituted. In a preferred embodiment, $R_3$ is a halogen, most preferably, fluorine.

In another embodiment, at least one of $R_6$ or $R_7$ is

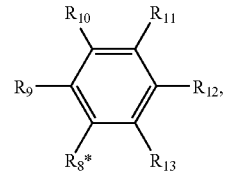

wherein $R_8^*$ is the point of attachment and is $(CH_2)_x$, wherein X is from 0 to 10, $CH_2CHOH$, $CH(CH_3)$(R-isomer), or $CH(CH_3)$(S-isomer), and each of $R_9$ through $R_{13}$ may be the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_9$ through $R_{13}$ and $R_a$ through $R_c$ may be substituted or unsubstituted. In a preferred embodiment, each of $R_9$ through $R_{13}$ may be selected from the group consisting of $OCH_3$, $OCH_2CH_3$, H, $CH_3$, OH, $CH_2OH$, $CF_3$, $OCF_3$, CFO, $C_6H_5$, $OC_6H_5$, $OCH_2C_6H_5$, $OCH_2CH_2CH_3$, CHO, $CO_2H$, $CO_2CH_3$, $CH_2CO_2H$, $CH_2CO_2CH_3$, $NO_2$, and halogen.

In a further embodiment, at least one of $R_6$ or $R_7$ is

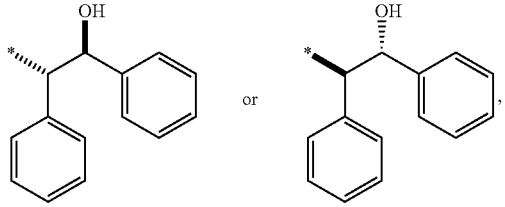

or wherein the asterisk indicates the point of attachment to the nitrogen.

In yet a further embodiment, the compound has the Formula IV:

(Formula IV)

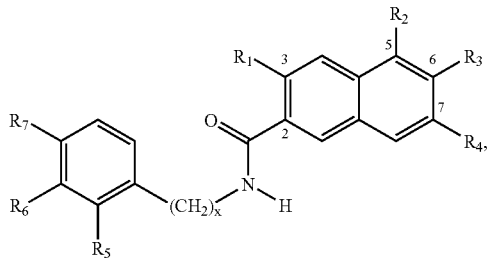

wherein $R_1$ through $R_7$ are each the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

Another aspect of the present invention relates to a method of treating a condition, responsive to a protein phosphatase inhibitor, in a subject. A protein phosphatase inhibitor is administered to a subject. The protein phosphatase inhibitor has at least one first module having one or more functional groups each capable of covalently or non-covalently binding to catalytic residues of the protein phosphatase, and a second module which provides a non-peptide scaffold. The combination of at least one first module and second module inhibits protein phosphatase activity in the subject.

Protein phosphatase inhibitors may be used in various therapeutic techniques, including, but not limited to, treatment of Type II diabetes, obesity, and cancer (Zhang, 2002; McCluskey et al., 2002a; Zhang 2001; McCluskey et al., 2001; Pestell et al., 2000; Moller et al., 2000; Ripka, 2000; Kennedy, 1999; Johnson et al., 2002; McCluskey 2002b).

Examples of other suitable compounds for the above-described methods include:

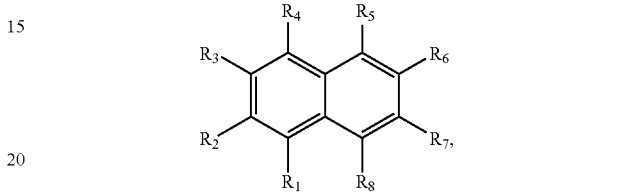

wherein any of the individual R's can be a halogen-containing $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

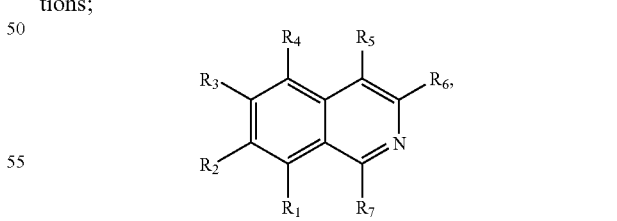

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

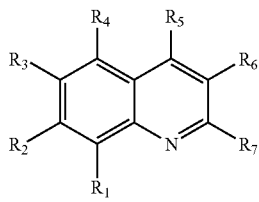

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

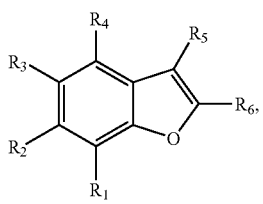

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

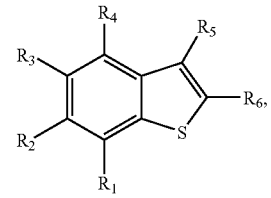

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

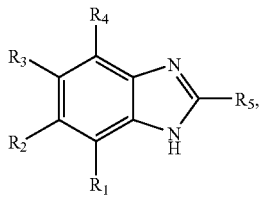

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

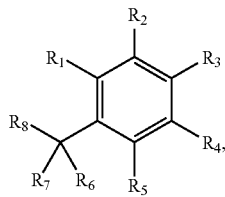

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

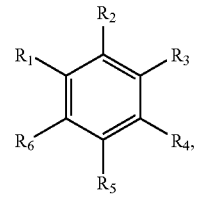

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

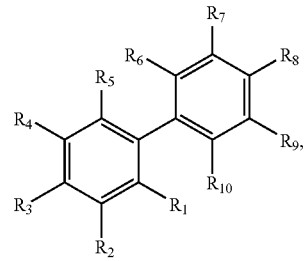

wherein any of the individual R's can be $M_1$, and the remaining R groups can be H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

Another aspect of the invention is a compound according to Formula V:

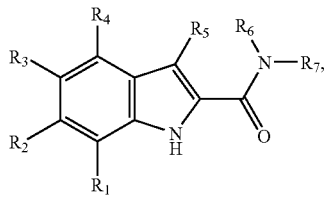

(Formula V)

or a salt, solvate, hydrate, or prodrug thereof. $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, and branched, unbranched, or cyclic alkyl. $R_6$ and $R_7$ are the same or different and are independently H, branched or unbranched or $(CH_2)_t$—Z, wherein Z is aryl, heteroaryl, biaryl, cyclic alkyl, or heterocycle, or $R_6$ and $R_7$ together form a heterocycle. t is 0, 1, 2, 3, 4, 5, 6, 7, 8, 9, or 10. $R_a$, $R_b$, and $R_c$ are the same or different and are independently H, aryl, heteroaryl, biaryl, heterobiaryl, or branched, unbranched, or cyclic alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

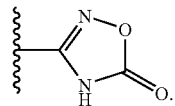

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

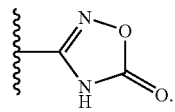

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

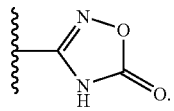

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

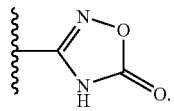

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. Any of $R_1$, $R_2$, $R_3$, $R_4$, $R_5$, $R_6$, and $R_7$ and $R_a$, $R_b$, and $R_c$ is substituted or unsubstituted. At least one of $R_1$, $R_2$, $R_3$, $R_4$, $R_5$, and $R_6$ is P.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further where K is $SO_3H$, $OSO_3H$, $PO_3H_2$, $OPO_3H_2$, $NH_2$, $NHR_{19}$, $NR_{19}R_{20}$, glycoside, and heterocycle; further where L is $SO_3H$, $OSO_3H$, $PO_3H_2$, $OPO_3H_2$, $NH_2$, $NHR_{19}$, $NR_{19}R_{20}$, glycoside, and heterocycle; and further where M is $SO_3H$, $OSO_3H$, $PO_3H_2$, $OPO_3H_2$, $NH_2$, $NHR_{19}$, $NR_{19}R_{20}$, glycoside, and heterocycle.

In one embodiment, at least one of $R_1$, $R_2$, $R_3$, $R_4$, and $R_5$ is selected from halogen, boronic acid, hydroxyl, phosphonic acid, sulfamic acid, guanidine, carboxylic acid, aldehyde, amide, and hydroxymethylphosphonic acid. In another embodiment, at least one of $R_1$, $R_2$, $R_3$, $R_4$, and $R_5$ is halogen. In another embodiment, at least one of $R_1$, $R_2$, $R_3$, $R_4$, and $R_5$ is boronic acid. In another embodiment, at least one of $R_1$, $R_2$, $R_3$, $R_4$, and $R_5$ is hydroxyl. In another embodiment, at least one of $R_1$, $R_2$, $R_3$, $R_4$, and $R_5$ is amide. For example, amide is vicinal tricarbonyl amide. In one embodiment, $R_3$ is halogen. For example, $R_3$ is fluorine. In another embodiment, $R_3$ is hydroxyl.

In one embodiment, at least one of $R_6$ and $R_7$ is $(CH_2)_t$-Z. In another embodiment, Z is aryl. In one embodiment, aryl is unsubstituted. In one embodiment aryl is monosubstituted. In another embodiment, aryl is disubstituted. In another embodiment, aryl is trisubstituted. In one embodiment aryl is substituted with hydroxyl, halogen, phenoxy (—$OC_6H_5$), alkoxy, $CF_3$, alkyl, hydroxymethyl, aryl, $OCF_3$, benzyloxy (—$OCH_2C_6H_5$), nitro, aldehyde, or alkoxycarboxy (also referred to as ester e.g., —C(O)OEt). In one embodiment, ($CH_2$) is substituted, wherein one or more of the hydrogen atoms of the methylene group are replaced with one or more substituents. Methylene substitutents are selected from hydroxmethyl, alkyl (e.g., methyl), hydroxyl, and aryl. In another embodiment, at least one of $R_6$ and $R_7$ is branched or unbranched alkyl. In one embodiment, branched or unbranched alkyl is unsubstituted. In another embodiment, branched or unbranched alkyl is substituted with hydroxyl. In another embodiment, Z is cyclic alkyl. In one embodiment, cyclic alkyl is substituted. In another embodiment, cyclic alkyl is substituted with hydroxyl. In another embodiment, cyclic alkyl is unsubstituted. In one embodiment, t is 0. In another embodiment, t is 1. In another embodiment, t is 2.

In one embodiment, $R_6$ and $R_7$ form a ring, where the ring is selected from pyrrolidine, piperidine, and morpholine.

In one embodiment, at least one of $R_6$ and $R_7$ is

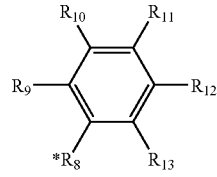

where $*R_8$ is the point of attachment. In one embodiment $R_8$ is $(CH_2)_x$, where X is 0, 1, 2, 3, 4, 5, 6, 7, 8, 9, or 10. In another embodiment $R_8$ is $CH_2CHOH$, $CH(CH_3)$(R-isomer), or $CH(CH_3)$(S-isomer). In another embodiment, each of $R_9$, $R_{10}$, $R_{11}$, $R_{12}$, and $R_{13}$ are the same or different and each of $R_9$, $R_{10}$, $R_{11}$, $R_{12}$, and $R_{13}$ independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, P', aryl, heteroaryl, biaryl, heterobiaryl, heterocycle, or branched, cyclic, or unbranched alkyl, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q', further where lower ($C_1$, $C_2$, $C_3$, $C_4$, $C_5$, or $C_6$) alkyl is linear or branched alkyl. K' is $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

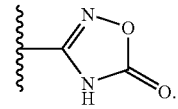

L' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

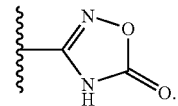

M' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

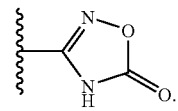

Q' is aryl, OH, $C(O)NH_2$, COOH, $SO_3H$, $OSO_3H$, $PO_3H_2$, $OPO_3H_2$, $NH_2$, $NHR_{22}$, $NR_{22}R_{23}$, $SO_2R_{24}$, glycoside, lower $C_1$, $C_2$, $C_3$, $C_4$, $C_5$, $C_6$ alkoxy, or

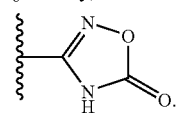

$R_{22}$, $R_{23}$ and $R_{24}$ are independently $C_1$, $C_2$, $C_3$, $C_4$, $C_5$, or $C_6$ alkyl or $R_{22}$ and $R_{23}$ taken together with the attached nitrogen atom form a five membered ring. $R_a$, $R_b$, and $R_c$ are the same or different and independently are H, aryl, heteroaryl, biaryl, heterobiaryl, branched, cyclic, or unbranched alkyl;

wherein any of $R_9$, $R_{10}$, $R_{11}$, $R_{12}$, and $R_{13}$ are substituted or unsubstituted; and provided that if one of $R_1$, $R_2$, $R_3$, $R_4$, or $R_5$ is not P, then at least one of $R_9$, $R_{10}$, $R_{11}$, $R_{12}$, and $R_{13}$ is P'.

In another embodiment, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q'. K' is $SO_3H$, $OSO_3H$, $PO_3H_2$, $OPO_3H_2$, $NH_2$, $NHR_{22}$, $NR_{22}R_{23}$, glycoside, or heterocycle. L' is $SO_3H$, $OSO_3H$, $PO_3H_2$, $OPO_3H_2$, $NH_2$, $NHR_{22}$, $NR_{22}R_{23}$, glycoside, or heterocycle. M' is $SO_3H$, $OSO_3H$, $PO_3H_2$, $OPO_3H_2$, $NH_2$, $NHR_{22}$, $NR_{22}R_{23}$, glycoside, or heterocycle.

In another embodiment, at least one of $R_6$ and $R_7$ is

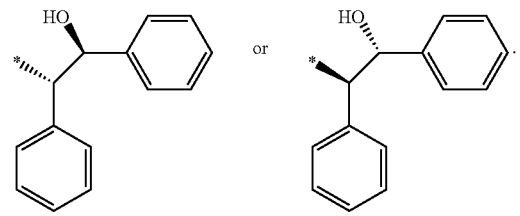

Another aspect of the invention includes a compound of Formula VI:

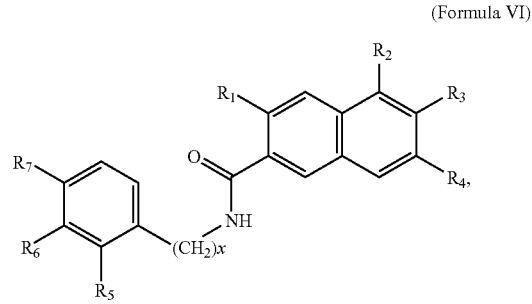

(Formula VI)

or a salt, solvate, hydrate, or prodrug. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further where lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

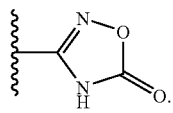

L is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

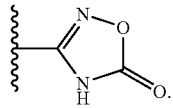

M is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

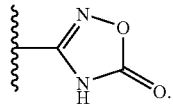

Q is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

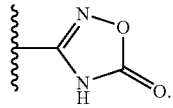

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring. X is 1, 2, 3, 4, 5, 6, 7, 8, 9, or 10. At least one of R$_1$, R$_2$, R$_3$, R$_4$, R$_5$, R$_6$, and R$_7$ is P.

In one embodiment, P is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q. K is SO$_3$H, OSO$_3$H, PO$_3$H$_2$, OPO$_3$H$_2$, NH$_2$, NHR$_{19}$, NR$_{19}$R$_{20}$, glycoside, or heterocycle. L is SO$_3$H, OSO$_3$H, PO$_3$H$_2$, OPO$_3$H$_2$, NH$_2$, NHR$_{19}$, NR$_{19}$R$_{20}$, glycoside, or heterocycle. M is SO$_3$H, OSO$_3$H, PO$_3$H$_2$, OPO$_3$H$_2$, NH$_2$, NHR$_{19}$, NR$_{19}$R$_{20}$, glycoside, or heterocycle.

Another aspect of the invention includes a method of protecting against or treating hearing loss in a subject comprising administering a compound having the Formula V:

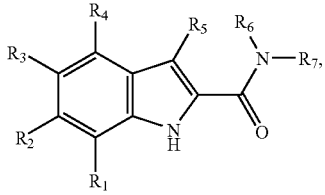

(Formula V)

or a salt, solvate, hydrate, or prodrug thereof. R$_1$, R$_2$, R$_3$, R$_4$, and R$_5$ are the same or different and are independently H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, P, halogen, aryl, benzyl, heteroaryl, biaryl, heterobiaryl, heterocycle, and branched, unbranched, or cyclic alkyl. R$_6$ and R$_7$ are the same or different and are independently H, branched or unbranched, or (CH$_2$)$_t$—Z, wherein Z is aryl, heteroaryl, biaryl, cyclic alkyl, or heterocycle, or R$_6$ and R$_7$ together form a heterocycle. t is 0, 1, 2, 3, 4, 5, 6, 7, 8, 9, or 10. R$_a$, R$_b$, and R$_c$ are the same or different and are independently H, aryl, heteroaryl, biaryl, heterobiaryl, or branched, unbranched, or cyclic alkyl. P is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q, further wherein lower (C$_1$, C$_2$, C$_3$, C$_4$, C$_5$, or C$_6$) alkyl is linear or branched alkyl. K is C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

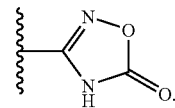

L is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

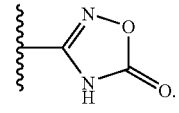

M is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

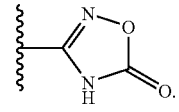

Q is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

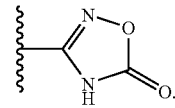

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring. Any of R$_1$, R$_2$, R$_3$, R$_4$, R$_5$, R$_6$, and R$_7$ and R$_a$, R$_b$, and R$_c$ is substituted or unsubstituted. At least one of R$_1$, R$_2$, R$_3$, R$_4$, R$_5$, R$_6$, and R$_7$ is P.

In one embodiment, P is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K, O—C(O)-lower (C$_1$, C$_2$, C$_3$, C$_4$, C$_5$, or C$_6$) alkyl-L, NH-lower (C$_1$, C$_2$, C$_3$, C$_4$, C$_5$, or C$_6$) alkyl-M, or O-aryl-Q. K is SO$_3$H, OSO$_3$H, PO$_3$H$_2$, OPO$_3$H$_2$, NH$_2$, NHR$_{19}$, NR$_{19}$R$_{20}$, glycoside, or heterocycle. L is SO$_3$H, OSO$_3$H, PO$_3$H$_2$, OPO$_3$H$_2$, NH$_2$, NHR$_{19}$, NR$_{19}$R$_{20}$, glycoside, or heterocycle. M is SO$_3$H, OSO$_3$H, PO$_3$H$_2$, OPO$_3$H$_2$, NH$_2$, NHR$_{19}$, NR$_{19}$R$_{20}$, glycoside, or heterocycle.

In one embodiment, the compound inhibits one or more components of a protein kinase signaling pathway. In another embodiment, the compound is an allosteric inhibitor. In another embodiment, the compound does not inhibit ATP binding to a protein kinase. In one embodiment, the compound binds to a peptide binding site. In one embodiment, the compound inhibits a Src family protein kinase. For example, the Src family protein kinase is pp60$^{c\text{-}src}$ tyrosine kinase. In another embodiment, the Src family protein kinase is PYK2.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops into the ear), intraarterially, intralesionally, by metering pump, or by application to mucous membranes. In one embodiment, the compound is administered in combination with a drug that causes hearing loss e.g., cis platinum or an aminoglycoside antibiotic. In another embodiment, the compound is administered in combination with a drug that targets hairy cells. In one embodiment, the compound is administered with a pharmaceutically acceptable carrier. In one embodiment, the compound is administered before initiation of hearing loss. In another embodiment, the compound is administered after inititiation of hearing loss.

In one embodiment, at least one of $R_1$, $R_2$, $R_3$, $R_4$, and $R_5$ is selected from halogen, boronic acid, hydroxyl, phosphonic acid, sulfamic acid, guanidine, carboxylic acid, aldehyde, amide, and hydroxymethylphosphonic acid. In another embodiment, at least one of $R_1$, $R_2$, $R_3$, $R_4$, and $R_5$ is a halogen. In another embodiment, at least one of $R_1$, $R_2$, $R_3$, $R_4$, and $R_5$ is boronic acid. In another embodiment, at least one of $R_1$, $R_2$, $R_3$, $R_4$, and $R_5$ is hydroxyl. In another embodiment, at least one of $R_1$, $R_2$, $R_3$, $R_4$, and $R_5$ is amide. For example, amide is vicinal tricarbonyl amide. In one embodiment, $R_3$ is halogen. For example, $R_3$ is fluorine. In one embodiment, $R_3$ is hydroxyl.

In one embodiment, at least one of $R_6$ and $R_7$ is $(CH_2)_t$-Z. In another embodiment, Z is aryl. In one embodiment, aryl is unsubstituted. In one embodiment aryl is monosubstituted. In another embodiment, aryl is disubsituted. In another embodiment, aryl is trisubstituted. In one embodiment aryl is substituted with hydroxyl, halogen, phenoxy (—$OC_6H_5$), alkoxy, $CF_3$, alkyl, hydroxymethyl, aryl, $OCF_3$, benzyloxy (—$OCH_2C_6H_5$), nitro, aldehyde, or alkoxycarboxy (also referred to as ester e.g., —C(O)OEt). In one embodiment, ($CH_2$) is substituted, wherein one or more of the hydrogen atoms of the methylene group are replaced with one or more substituents. Methylene substitutents are selected from hydroxmethyl, alkyl (e.g., methyl), hydroxyl, and aryl. In another embodiment, at least one of $R_6$ and $R_7$ is branched or unbranched alkyl. In one embodiment, branched or unbranched alkyl is unsubstituted. In one embodiment, branched or unbranched alkyl is substituted with hydroxyl. In another embodiment, Z is cyclic alkyl. In one embodiment, cyclic alkyl is substituted. In another embodiment, cyclic alkyl is substituted with hydroxyl. In another embodiment, cyclic alkyl is unsubstituted. In one embodiment, t is 0. In another embodiment, t is 1. In another embodiment, t is 2.

In one embodiment, $R_6$ and $R_7$ form a ring, where the ring is selected from pyrrolidine, piperidine, and morpholine.

In one embodiment, at least one of $R_6$ and $R_7$ is

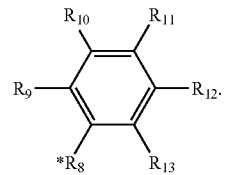

*$R_8$ is the point of attachment and is $(CH_2)_x$, wherein X is 0, 1, 2, 3, 4, 5, 6, 7, 8, 9, or 10, $CH_2CHOH$, $CH(CH_3)$(R-isomer), or $CH(CH_3)$(S-isomer). Each of $R_9$, $R_{10}$, $R_{11}$, $R_{12}$, and $R_{13}$ is the same or different and independently are H, C(O)$R_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, P', aryl, heteroaryl, biaryl, heterobiaryl, heterocycle, or branched, cyclic, or unbranched alkyl. P' is SO$_3$H, OSO$_3$H, OPO$_3$H$_2$, OPO$_3$H$_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q', further where lower ($C_1$, $C_2$, $C_3$, $C_4$, $C_5$, or $C_6$) alkyl is linear or branched alkyl. K' is C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

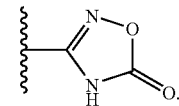

L' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

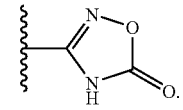

M' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

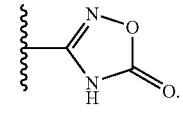

Q' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

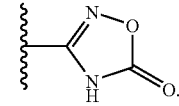

$R_{22}$, $R_{23}$ and $R_{24}$ are independently $C_1$, $C_2$, $C_3$, $C_4$, $C_5$, or $C_6$ alkyl or $R_{22}$ and $R_{23}$ taken together with the attached nitrogen atom form a five membered ring. $R_a$, $R_b$, and $R_c$ are the same or different and independently are H, aryl, heteroaryl, biaryl, heterobiaryl, branched, cyclic, or unbranched alkyl. Any of $R_9$, $R_{10}$, $R_{11}$, $R_{12}$, and $R_{13}$ are substituted or unsubstituted. If one of $R_1$, $R_2$, $R_3$, $R_4$, or $R_5$ is not P, then at least one of $R_9$, $R_{10}$, $R_{11}$, $R_{12}$, and $R_{13}$ is P'.

In one embodiment, P' is $SO_3H$, $OSO_3H$, $OPO_3H_2$, $OPO_3H_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q'. K' is $SO_3H$, $OSO_3H$, $PO_3H_2$, $OPO_3H_2$, $NH_2$, $NHR_{22}$, $NR_{22}R_{23}$, glycoside, or heterocycle. L' is $SO_3H$, $OSO_3H$, $PO_3H_2$, $OPO_3H_2$, $NH_2$, $NHR_{22}$, $NR_{22}R_{23}$, glycoside, or heterocycle. M' is $SO_3H$, $OSO_3H$, $PO_3H_2$, $OPO_3H_2$, $NH_2$, $NHR_{22}$, $NR_{22}R_{23}$, glycoside, or heterocycle. In another embodiment, at least one of $R_6$ or $R_7$ and

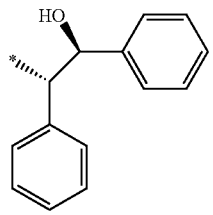 or 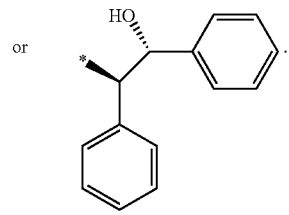.

Another aspect of the invention includes a method of preventing or treating a proliferative disease in a subject comprising administering a compound having the Formula V:

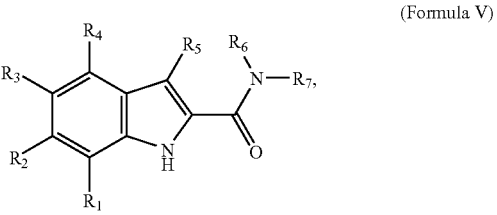

(Formula V)

or a salt, solvate, hydrate, or prodrug thereof. $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_b R_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, and branched, unbranched, or cyclic alkyl. $R_6$ and $R_7$ are the same or different and are independently H, branched or unbranched, or $(CH_2)_t$-Z, wherein Z is aryl, heteroaryl, biaryl, cyclic alkyl, or heterocycle, or $R_6$ and $R_7$ together form a heterocycle. t is 0, 1, 2, 3, 4, 5, 6, 7, 8, 9, or 10. $R_a$, $R_b$, and $R_c$ are the same or different and are independently H, aryl, heteroaryl, biaryl, heterobiaryl, or branched, unbranched, or cyclic alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

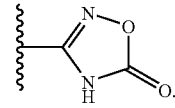

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

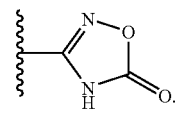

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

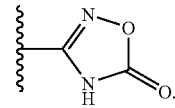

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or $R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

wherein any of $R_1$, $R_2$, $R_3$, $R_4$, $R_5$, $R_6$, and $R_7$ and $R_a$, $R_b$, and $R_c$ is substituted or unsubstituted. At least one of $R_1$, $R_2$, $R_3$, $R_4$, $R_5$, and $R_6$ is P.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, and heterocycle. L is $SO_3H$, $OSO_3H$, $PO_3H_2$, $OPO_3H_2$, $NH_2$, $NHR_{19}$, $NR_{19}R_{20}$, glycoside, and heterocycle. M is $SO_3H$, $OSO_3H$, $PO_3H_2$, $OPO_3H_2$, $NH_2$, $NHR_{19}$, $NR_{19}R_{20}$, glycoside, and heterocycle.

In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In another embodiment, the compound binds to a peptide binding site. In another embodiment, the compound inhibits a Src family protein kinase. For example, the Src family protein kinase is $pp60^{c-src}$ tyrosine kinase. In another embodiment, the Src family protein kinase is PYK2.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membrane. In another embodiment, the compound is administered with a pharmaceutically acceptable carrier. In one embodiment, the compound is administered before initiation of the proliferative disease. In another embodiment, the compound is administered after inititiation of the proliferative disease.

In one embodiment, at least one of $R_1$, $R_2$, $R_3$, $R_4$, and $R_5$ is selected from halogen, boronic acid, hydroxyl, phosphonic acid, sulfamic acid, guanidine, carboxylic acid, aldehyde, amide, and hydroxymethylphosphonic acid. In another embodiment, at least one of $R_1$, $R_2$, $R_3$, $R_4$, and $R_5$ is halogen. In another embodiment, at least one of $R_1$, $R_2$, $R_3$, $R_4$, and $R_5$ is boronic acid. In another embodiment, at least one of $R_1$, $R_2$, $R_3$, $R_4$, and $R_5$ is hydroxyl. In another embodiment, at least one of $R_1$, $R_2$, $R_3$, $R_4$, and $R_5$ is amide. For example, the amide is vicinal tricarbonyl amide. In one embodiment, $R_3$ is halogen. For example, $R_3$ is fluorine. In one embodiment, $R_3$ is hydroxyl.

In one embodiment, at least one of $R_6$ and $R_7$ is $(CH_2)_t$-Z. In another embodiment, Z is aryl. In one embodiment, aryl is unsubstituted. In one embodiment aryl is monosubstituted. In another embodiment, aryl is disubsituted. In another embodiment, aryl is trisubstituted. In one embodiment aryl is substituted with hydroxyl, halogen, phenoxy (—$OC_6H_5$), alkoxy, $CF_3$, alkyl, hydroxymethyl, aryl, $OCF_3$, benzyloxy (—$OCH_2C_6H_5$), nitro, aldehyde, or alkoxycarboxy (also referred to as ester e.g., —C(O)OEt). In one embodiment, ($CH_2$) is substituted, wherein one or more of the hydrogen atoms of the methylene group are replaced with one or more substituents. Methylene substitutents are selected from hydroxmethyl, alkyl (e.g., methyl), hydroxyl, and aryl. In another embodiment, at least one of $R_6$ and $R_7$ is branched or unbranched alkyl. In one embodiment, branched or unbranched alkyl is unsubstituted. In another embodiment, branched or unbranched alkyl is substituted with hydroxyl. In another embodiment, Z is cyclic alkyl. In one embodiment, cyclic alkyl is substituted. In another embodiment, cyclic alkyl is substituted with hydroxyl. In another embodiment, cyclic alkyl is unsubstituted. In one embodiment, t is 0. In another embodiment, t is 1. In another embodiment, t is 2.

In one embodiment, $R_6$ and $R_7$ form a ring, where the ring is selected from pyrrolidine, piperidine, and morpholine.

In one embodiment, at least one of $R_6$ and $R_7$ is

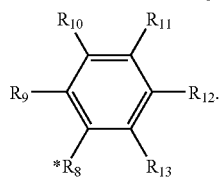

*$R_8$ is the point of attachment and is $(CH_2)_x$, wherein X is 0, 1, 2, 3, 4, 5, 6, 7, 8, 9, or 10, $CH_2CHOH$, $CH(CH_3)$(R-isomer), or $CH(CH_3)$(S-isomer). Each of $R_9$, $R_{10}$, $R_{11}$, $R_{12}$, and $R_{13}$ is the same or different and independently are H, C(O)$R_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, P', aryl, heteroaryl, biaryl, heterobiaryl, heterocycle, or branched, cyclic, or unbranched alkyl. P' is SO$_3$H, OSO$_3$H, OPO$_3$H$_2$, OPO$_3$H$_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q', further wherein lower ($C_1$, $C_2$, $C_3$, $C_4$, $C_5$, or $C_6$) alkyl is linear or branched alkyl. K' is C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

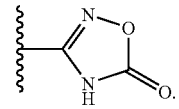

L' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

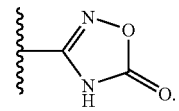

M' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

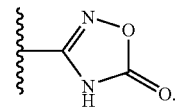

Q' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower $C_1$, $C_2$, $C_3$, $C_4$, $C_5$, $C_6$ alkoxy, or

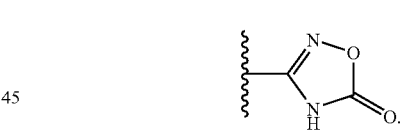

$R_{22}$, $R_{23}$ and $R_{24}$ are independently $C_1$, $C_2$, $C_3$, $C_4$, $C_5$, or $C_6$ alkyl or $R_{22}$ and $R_{23}$ taken together with the attached nitrogen atom form a five membered ring. $R_a$, $R_b$, and $R_c$ are the same or different and independently are H, aryl, heteroaryl, biaryl, heterobiaryl, branched, cyclic, or unbranched alkyl. $R_9$, $R_{10}$, $R_{11}$, $R_{12}$, and $R_{13}$ are substituted or unsubstituted. If one of $R_1$, $R_2$, $R_3$, $R_4$, or $R_5$ is not P, then at least one of $R_9$, $R_{10}$, $R_{11}$, $R_{12}$, and $R_{13}$ is P'.

In one embodiment, P' is SO$_3$H, OSO$_3$H, OPO$_3$H$_2$, OPO$_3$H$_2$, O-lower ($C_1$, $C_2$, $C_3$, $C_4$, $C_5$, or $C_6$) alkyl-K', O—C(O)-lower ($C_1$, $C_2$, $C_3$, $C_4$, $C_5$, or $C_6$) alkyl-L', NH-lower ($C_1$, $C_2$, $C_3$, $C_4$, $C_5$, or $C_6$) alkyl-M', or O-aryl-Q'. K' is SO$_3$H, OSO$_3$H, PO$_3$H$_2$, OPO$_3$H$_2$, NH$_2$, NHR$_{22}$, NR$_{22}$R$_{23}$, glycoside, or heterocycle. L' is SO$_3$H, OSO$_3$H, PO$_3$H$_2$, OPO$_3$H$_2$, NH$_2$, NHR$_{22}$, NR$_{22}$R$_{23}$, glycoside, or heterocycle. M' is SO$_3$H, OSO$_3$H, PO$_3$H$_2$, OPO$_3$H$_2$, NH$_2$, NHR$_{22}$, NR$_{22}$R$_{23}$, glycoside, or heterocycle.

In one embodiment, at least one of $R_6$ and $R_7$ is

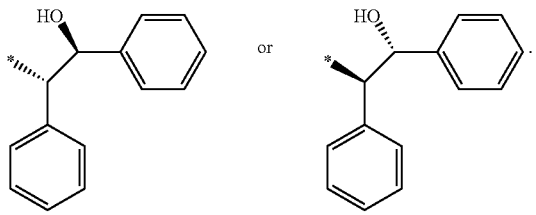

Another aspect of the invention includes a method of protecting against or treating osteoporosis in a subject comprising administering a compound of Formula VII:

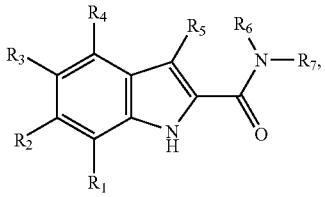

(Formula VII)

or a salt, solvate, hydrate, or prodrug thereof. $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, and branched, unbranched, or cyclic alkyl. $R_6$ and $R_7$ are the same or different and are independently H, branched or unbranched, or $(CH_2)_t$-Z, wherein Z is aryl, heteroaryl, biaryl, cyclic alkyl, or heterocycle, or $R_6$ and $R_7$ together form a heterocycle. t is 0, 1, 2, 3, 4, 5, 6, 7, 8, 9, or 10. $R_a$, $R_b$, and $R_c$ are the same or different and are independently H, aryl, heteroaryl, biaryl, heterobiaryl, or branched, unbranched, or cyclic alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

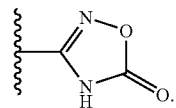

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

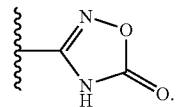

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

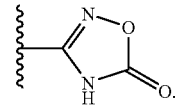

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

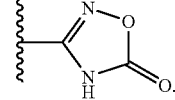

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring;

wherein any of $R_1$, $R_2$, $R_3$, $R_4$, $R_5$, $R_6$, and $R_7$ and $R_a$, $R_b$, and $R_c$ is substituted or unsubstituted.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, $OSO_3H$, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase. For example, the Src family protein kinase is pp60$^{c-src}$ tyrosine kinase. In another embodiment, the Src family protein kinase is PYK2.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before initiation of osteoporosis. In another embodiment, the compound is administered after inititiation of osteoporosis.

In another embodiment, at least one of $R_1$, $R_2$, $R_3$, $R_4$, and $R_5$ is selected from halogen, boronic acid, hydroxyl, phosphonic acid, sulfamic acid, guanidine, carboxylic acid, aldehyde, amide, and hydroxymethylphosphonic acid.

In another embodiment, at least one of $R_1$, $R_2$, $R_3$, $R_4$, and $R_5$ is a halogen. In one embodiment, at least one of $R_1$, $R_2$, $R_3$, $R_4$, and $R_5$ is a boronic acid. In another embodiment, at least one of $R_1$, $R_2$, $R_3$, $R_4$, and $R_5$ is hydroxyl. In another embodiment, at least one of $R_1$, $R_2$, $R_3$, $R_4$, and $R_5$ is amide. For example, the amide group is vicinal tricarbonyl amide. In one embodiment, $R_3$ is halogen. For example, $R_3$ is fluorine. In one embodiment, $R_3$ is hydroxyl.

In one embodiment, at least one of $R_6$ and $R_7$ is $(CH_2)_t$-Z. In another embodiment, Z is aryl. In one embodiment, aryl is unsubstituted. In one embodiment aryl is monosubstituted. In another embodiment, aryl is disubsituted. In another embodiment, aryl is trisubstituted. In one embodiment aryl is substituted with hydroxyl, halogen, phenoxy (—OC$_6$H$_5$), alkoxy, CF$_3$, alkyl, hydroxymethyl, aryl, OCF$_3$, benzyloxy (—OCH$_2$C$_6$H$_5$), nitro, aldehyde, or alkoxycarboxy (also referred to as ester e.g., —C(O)OEt). In one embodiment, (CH$_2$) is substituted, wherein one or more of the hydrogen atoms of the methylene group are replaced with one or more substituents. Methylene substitutents are selected from hydroxmethyl, alkyl (e.g., methyl), hydroxyl, and aryl. In another embodiment, at least one of R$_6$ and R$_7$ is branched or unbranched alkyl. In one embodiment, branched or unbranched alkyl is unsubstituted. In another embodiment, branched or unbranched alkyl is substituted with hydroxyl. In another embodiment, Z is cyclic alkyl. In one embodiment, cyclic alkyl is substituted. In another embodiment, cyclic alkyl is substituted with hydroxyl. In another embodiment, cyclic alkyl is unsubstituted. In one embodiment, t is 0. In another embodiment, t is 1. In another embodiment, t is 2.

In one embodiment, R$_6$ and R$_7$ form a ring, where the ring is selected from pyrrolidine, piperidine, and morpholine.

In one embodiment, at least one of R$_6$ and R$_7$ is

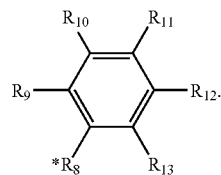

*R$_8$ is the point of attachment and is (CH$_2$)$_x$, wherein X is 0, 1, 2, 3, 4, 5, 6, 7, 8, 9, or 10, CH$_2$CHOH, CH(CH$_3$)(R-isomer), or CH(CH$_3$)(S-isomer). Each of R$_9$, R$_{10}$, R$_{11}$, R$_{12}$, and R$_{13}$ is the same or different and independently are H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, P', aryl, heteroaryl, biaryl, heterobiaryl, heterocycle and branched, cyclic, or unbranched alkyl, P' is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K', O—C(O)-lower (C$_1$, C$_2$, C$_3$, C$_4$, C$_5$, or C$_6$) alkyl-L', NH-lower (C$_1$, C$_2$, C$_3$, C$_4$, C$_5$, or C$_6$) alkyl-M', or O-aryl-Q', further wherein lower (C$_1$, C$_2$, C$_3$, C$_4$, C$_5$, or C$_6$) alkyl is linear or branched alkyl. K' is C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

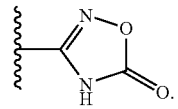

L' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

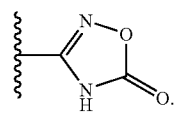

M' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

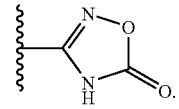

Q' is aryl, OH, C(O)NH$_2$, COOH, SO$_3$H, OSO$_3$H, PO$_3$H$_2$, OPO$_3$H$_2$, NH$_2$, NHR$_{22}$, NR$_{22}$R$_{23}$, SO$_2$R$_{24}$, glycoside, lower C$_1$, C$_2$, C$_3$, C$_4$, C$_5$, C$_6$ alkoxy, or

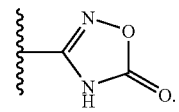

R$_{22}$, R$_{23}$ and R$_{24}$ are independently C$_1$, C$_2$, C$_3$, C$_4$, C$_5$, or C$_6$ alkyl or R$_{22}$ and R$_{23}$ taken together with the attached nitrogen atom form a five membered ring. R$_a$, R$_b$, and R$_c$ are the same or different and independently are H, aryl, heteroaryl, biaryl, heterobiaryl, branched, cyclic, or unbranched alkyl; and wherein any of R$_9$, R$_{10}$, R$_{11}$, R$_{12}$, and R$_{13}$ are substituted or unsubstituted.

In one embodiment, P' is SO$_3$H, OSO$_3$H, OPO$_3$H$_2$, OPO$_3$H$_2$, O-lower (C$_1$, C$_2$, C$_3$, C$_4$, C$_5$, or C$_6$) alkyl-K', O—C(O)-lower (C$_1$, C$_2$, C$_3$, C$_4$, C$_5$, or C$_6$) alkyl-L', NH-lower (C$_1$, C$_2$, C$_3$, C$_4$, C$_5$, or C$_6$) alkyl-M', or O-aryl-Q'. K' is SO$_3$H, OSO$_3$H, PO$_3$H$_2$, OPO$_3$H$_2$, NH$_2$, NHR$_{22}$, NR$_{22}$R$_{23}$, glycoside, or heterocycle. L' is SO$_3$H, OSO$_3$H, PO$_3$H$_2$, OPO$_3$H$_2$, NH$_2$, NHR$_{22}$, NR$_{22}$R$_{23}$, glycoside, or heterocycle; and further wherein M' is SO$_3$H, OSO$_3$H, PO$_3$H$_2$, OPO$_3$H$_2$, NH$_2$, NHR$_{22}$, NR$_{22}$R$_{23}$, glycoside, or heterocycle. In one embodiment, at least one of R$_6$ and R$_7$ is

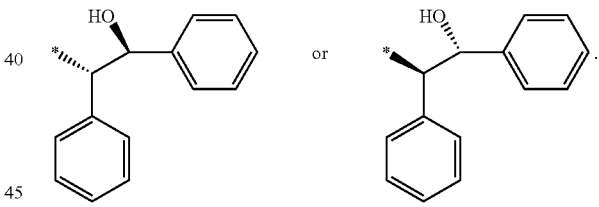

In another embodiment, the compound is

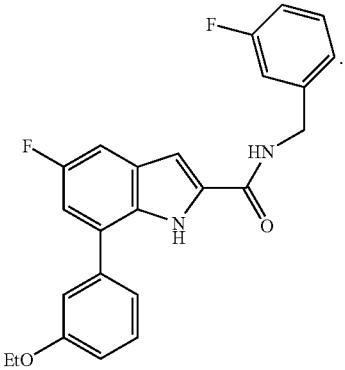

Another aspect of the invention includes a method of protecting against or treating hearing loss in a subject comprising administering a compound of Formula VI:

(Formula VI)

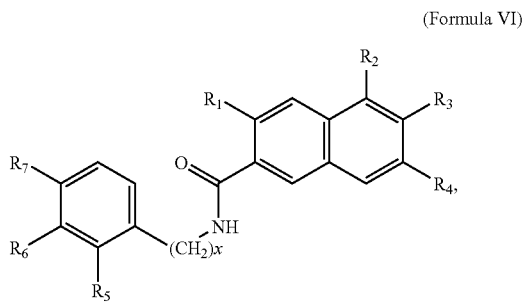

or a salt, solvate, hydrate, or prodrug thereof. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_b$ $OR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl;

P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

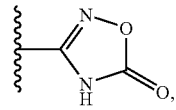

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

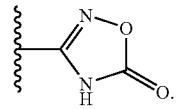

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

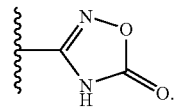

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

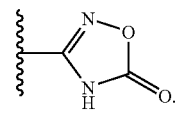

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. x is 1, 2, 3, 4, 5, 6, 7, 8, 9, or 10. At least one of $R_1$, $R_2$, $R_3$, $R_4$, $R_5$, $R_6$, and $R_7$ is P.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, $OSO_3H$, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

In one embodiment, the compound inhibits one or more components of a protein kinase signaling pathway. In another embodiment, the compound is an allosteric inhibitor. In one embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase. For example, the Src family protein kinase is pp60$^{c-src}$ tyrosine kinase. In another embodiment, the Src family protein kinase is PYK2.

In one embodiment, the administration of the compound is carried out orally, parentally, subcutaneously, intravenously, intramuscularly, intraperitoneally, by intranasal instillation, by intracavitary or intravesical instillation, topically (e.g., by administering drops into the ear), intraarterially, intralesionally, by metering pump, or by application to mucous membranes. In one embodiment, the compound is administered in combination with a drug that causes hearing loss. In another embodiment, the compound is administered with a pharmaceutically acceptable carrier. In another embodiment, the compound is administered before initiation of hearing loss. In another embodiment, the compound is administered after inititiation of hearing loss.

Another aspect of the invention includes a method of protecting against or treating osteoporosis in a subject comprising administering a compound of Formula VIII:

(Formula VIII)

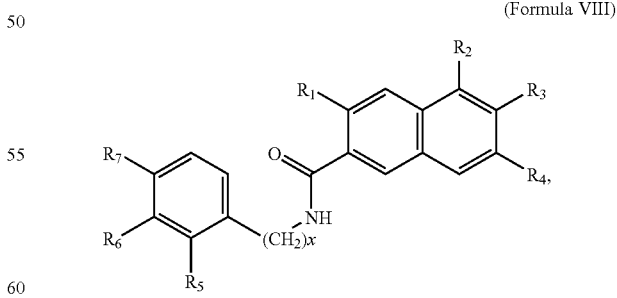

or a salt, solvate, hydrate, or prodrug thereof. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_b$ $OR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

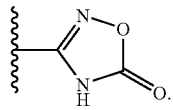

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

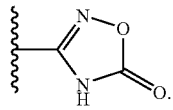

M is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

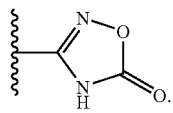

Q is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

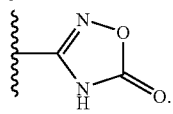

$R_{19}$, $R_{20}$ and $R_{21}$ are independently $C_1$, $C_2$, $C_3$, $C_4$, $C_5$, or $C_6$ alkyl or $R_{19}$ and $R_{20}$ taken together with the attached nitrogen atom form a five membered ring. x is 1, 2, 3, 4, 5, 6, 7, 8, 9, or 10.

In one embodiment, P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q. K is $SO_3H$, $OSO_3H$, $PO_3H_2$, $OPO_3H_2$, $NH_2$, $NHR_{19}$, $NR_{19}R_{20}$, glycoside, or heterocycle. L is $SO_3H$, $OSO_3H$, $PO_3H_2$, $OPO_3H_2$, $NH_2$, $NHR_{19}$, $NR_{19}R_{20}$, glycoside, or heterocycle. M is $SO_3H$, $OSO_3H$, $PO_3H_2$, $OPO_3H_2$, $NH_2$, $NHR_{19}$, $NR_{19}R_{20}$, glycoside, or heterocycle.

In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase. For example, the Src family protein kinase is pp60$^{c\text{-}src}$ tyrosine kinase. In another embodiment, the Src family protein kinase is PYK2.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of osteoporosis. In another embodiment, the compound is administered after onset of osteoporosis.

A method of preventing or treating a proliferative disorder in a subject comprising administering a compound of Formula VIII:

(Formula VIII)

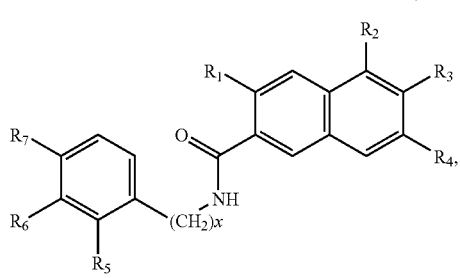

or a salt, solvate, hydrate, or prodrug thereof. $R_1$, $R_2$, $R_3$, $R_4$, $R_5$, $R_6$, and $R_7$ are each the same or different and independently are H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_b$ $OR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, heteroaryl, biaryl, heterobiaryl, heterocycle, and branched, cyclic, or unbranched alkyl. $R_a$, $R_b$, and $R_c$ are the same or different and are independently H, aryl, heteroaryl, biaryl, heterobiaryl, and branched, cyclic, or unbranched alkyl. P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl. K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

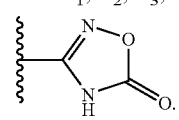

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

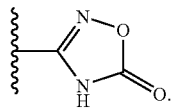

M is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

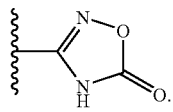

Q is aryl, OH, C(O)NH$_2$, COOH, SO$_3$H, OSO$_3$H, PO$_3$H$_2$, OPO$_3$H$_2$, NH$_2$, NHR$_{19}$, NR$_{19}$R$_{20}$, SO$_2$R$_{21}$, glycoside, lower C$_1$, C$_2$, C$_3$, C$_4$, C$_5$, C$_6$ alkoxy, or

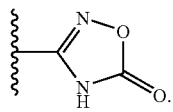

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring. x is 1, 2, 3, 4, 5, 6, 7, 8, 9, or 10.

In one embodiment, the compound inhibits one or more components of a protein kinase signaling pathway. In another embodiment, the compound is an allosteric inhibitor. In another embodiment, the compound is a peptide substrate inhibitor. In one embodiment, the compound does not inhibit ATP binding to a protein kinase. In one embodiment, the compound binds to a peptide binding site. In another embodiment, the compound inhibits a Src family protein kinase. For example, the Src family protein kinase is pp60$^{c-src}$ tyrosine kinase. In another embodiment, the Src family protein kinase is PYK2.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before onset of the proliferative disease. In another embodiment, the compound is administered after onset of the proliferative disease.

Another aspect of the invention includes a method of protecting against or treating ophthalmic disease (e.g., macular degeneration, retinopathy, macular edema, etc.) in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically (e.g., by administration of drops or a cream to the eye), intraarterially, intralesionally, by metering pump, or by application to mucous membranes. In one embodiment, the compound is administered with a pharmaceutical acceptable carrier. In another embodiment, the compound is administered before initiation of ophthalmic disease. In another embodiment, the compound is administered after inititiation of ophthalmic disease.

Another aspect of the invention includes a method of protecting against or treating diabetes in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before the onset of diabetes. In another embodiment, the compound is administered after the onset of diabetes.

Another aspect of the invention includes a method of protecting against or treating obesity in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before the onset of obesity. In another embodiment, the compound is administered after the onset of obesity.

Another aspect of the invention includes a method of protecting against or treating stroke in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before a stroke occurs in a subject. In another embodiment, the compound is administered after a stroke has occurred in a subject.

Another aspect of the invention includes a method of protecting against or treating athrosclerosis in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In another embodiment, the compound is administered before the onset of athrosclerosis. In another embodiment, the compound is administered after the onset of athrosclerosis.

Another aspect of the invention includes a method of regulating immune system activity in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier.

Another aspect of the invention includes a method of protecting against or treating chronic neuropathic pain in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of chronic neuropathic pain. In another embodiment, the compound is administered after the onset of chronic neuropathic pain.

Another aspect of the invention includes a method of protecting against or treating hepatitis B in a subject comprising administering a compound of Formula VII or VIII. In one embodiment, the compound inhibits one or more components of a protein kinase signaling pathway. In another embodiment, the compound is an allosteric inhibitor. In another embodiment, the compound is a peptide substrate inhibitor. In another embodiment, the compound does not inhibit ATP binding to a protein kinase. In one embodiment, the compound binds to a peptide binding site. In another embodiment, the compound inhibits a Src family protein kinase.

In one embodiment, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In one embodiment, the compound is administered with a pharmaceutically acceptable carrier. In one embodiment, the compound is administered before the onset of hepatitis B. In another embodiment, the compound is administered after the onset of hepatitis B.

The present invention also provides a method for testing compounds for an ability to inhibit protein kinase or protein phosphatase activity. Compounds are produced as described above. The activity of the protein kinase or protein phosphatase is measured in the presence of the inhibitor at the same temperature, pH, ionic strength, osmolarity, and free magnesium concentration as found in a cell which expresses the protein kinase or protein phosphatase. The level of protein kinase or protein phosphatase activity is compared to the level of activity from the protein kinase or protein phosphatase without the presence of the inhibitor. Such an assay system which mimics physiological conditions provides the most relevant inhibition data. The assay may be conducted in an automated assay system. Furthermore, the assay may be combined with a combinatorial chemistry method to rapidly screen numerous candidates.

The Pierce 96-well plate non-radioactive ELISA PTK assay method may be adapted to the Cellular Mimetic assay conditions for initial Src screening of the 96-well plate combinatorial libraries. This high throughput assay utilizes the same RR-SRC peptide substrate, except that it is biotinylated so that it can be attached to the NeutrAvidin-coated wells in their commercial 96-well plates. This high throughput inhibition assay can be run by incubating Src with the RR-SRC substrate prebound to the wells followed by adding their anti-phosphotyrosine antibody (PY20)-horseradish peroxidase (HRP) conjugate and their HRP substrate to quantitate the level of phospho-RR-SRC produced via measuring the level of HRP product with a 96-well plate UV reader. Standard low throughput $P^{32}$-ATP radioactive assays have been used, but a 96-well plate format is preferred, especially with a non-radioactive assay if possible. As very potent Src inhibitors are developed, a panel of protein kinase assays could be set up with commercially available protein kinases, using the Cellular Mimetic protein kinase assay conditions, and test these inhibitors across the panel to obtain an initial assessment of specificity. A more complete specificity assessment, involving the full ca. 2,000 protein kinases, will need to be conducted in cell culture and in vivo.

Figure 14:
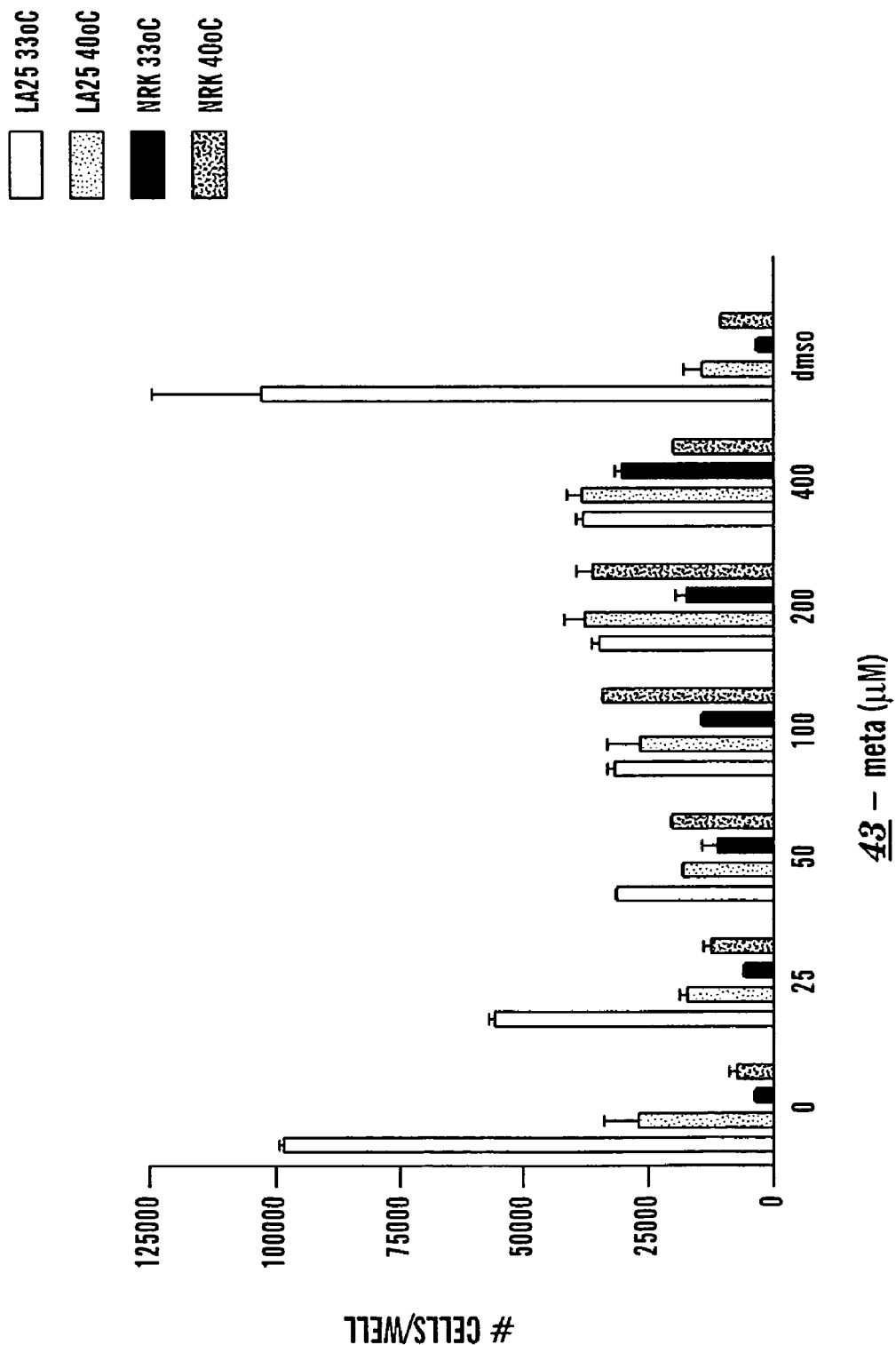
FIG. 14 shows results from testing of the non-peptide Src inhibitor 43-meta (Table V) in the LA25 and NRK cell lines.

Active Src inhibitors can be studied in a set of side-by-side cell-based assays using normal rat kidney (NRK) cells and a temperature-sensitive $pp60^{v\text{-}Src}$ transformant of this cell line (LA25). The LA25 transformant engages in anchorage- and serum-independent growth at the "permissive" temperature of 33° C. due to activation of pp60$^{v\text{-}src}$ but not at the "non-permissive" temperature of 40° C. at which pp60$^{v\text{-}src}$ is not activated (Li et al., 1996). The use of this pair of closely related cell lines for testing the Src inhibitors at both the permissive and non-permissive temperatures allows one to determine if a given Src inhibitor is blocking cell growth due to specific blockade of the Src signaling pathway, by a different mechanism or by a general cytotoxic effect. Results from initial testing of the non-peptide Src inhibitor 43-meta (Table V) in this pair of cell lines are shown in FIG. 14.

As shown in this graph the growth of the LA25 cells at the permissive temperature of 33° C. is inhibited by ca. 50% at a 25 μM concentration of 43-meta relative to the LA25 cell growth at the non-permissive 40° C. as a control. The lack of cell toxicity of 43-meta is evidenced by the fact that as its concentration is increased up to 400 μM, the basal growth of the NRK non-transformed cells, the LA25 cells at the non-permissive 40° C., and the LA25 cells at the permissive temperature of 33° C. (but with pp60$^{v\text{-}src}$ fully inhibited by 43-meta) not only does not decrease but actually increases somewhat (presumably due to a non-Src related activity of this compound). Since the 43-meta solutions were prepared with a low concentration of DMSO for solubilization, a DMSO control was also run at the same concentration.

Moreover, promising Src inhibitors can be screened in primary human tumor tissue assays, particularly to look for synergy with other known anti-cancer drugs.

Definitions

For convenience, certain terms used in the specification, examples and appended claims are collected here.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate ATP in a highly conserved pocket. About 50% of the known oncogene products are protein tyrosine kinases (PTKs), and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products and focal adhesion kinase (FAK)). The hyperactivation of Src has been reported in a number of human cancers, including those of the colon, breast, lung, bladder, and skin, as well as in gastric cancer, hairy cell leukemia, and neuroblastoma.

"inhibits one or more components of a protein kinase signaling cascade" means that one or more components of the kinase signaling cascade are effected such that the functioning of the cell changes. Components of a protein kinase signaling cascade include any proteins involved directly or indirectly in the kinase signaling pathway including second messengers and upstream and downstream targets.

"Treating", includes any effect, e.g., lessening, reducing, modulating, or eliminating, that results in the improvement of the condition, disease, disorder, etc. "Treating" or "treatment" of a disease state includes: (1) preventing the disease state, i.e. causing the clinical symptoms of the disease state not to develop in a subject that may be exposed to or predisposed to the disease state, but does not yet experience or display symptoms of the disease state; (2) inhibiting the disease state, i.e., arresting the development of the disease state or its clinical symptoms; or (3) relieving the disease state, i.e., causing temporary or permanent regression of the disease state or its clinical symptoms.

"Disease state" means any disease, disorder, condition, symptom, or indication.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the terms "psoriatic condition" or "psoriasis" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. The proliferative diseases can include dysplasias and disorders of the like.

An "effective amount" of a compound of the disclosed invention is the quantity which, when administered to a subject having a disease or disorder, results in regression of the disease or disorder in the subject. Thus, an effective amount of a compound of the disclosed invention is the quantity which, when administered to a subject having a cell proliferation disorder, results in regression of cell growth in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present invention effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as e.g., anti-cancer activity or anti-neoplastic activity. The combination of compounds optionally is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased anti-proliferative effect, or some other beneficial effect of the combination compared with the individual components.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the present invention can be used to coat or impregnate a medical device, e.g., a stent.

The term "prophylactically effective amount" means an effective amount of a compound or compounds, of the present invention that is administered to prevent or reduce the risk of unwanted cellular proliferation.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

With respect to the chemical compounds useful in the present invention, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R^1$ at each occurrence is selected independently from the definition of $R_1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

Compounds of the invention include water solubilizing groups Wermuth, *The Practice of Medicinal* Chemistry 2003, p. 617. e.g., $SO_3H$, $OSO_3H$, $OPO_3H_2$, $OPO_3H_2$, amines,

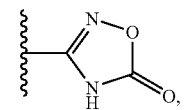

tetrazole, etc.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, 1-propyl, n-butyl, s-butyl, t-butyl, n-pentyl, s-pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in another embodiment, cycloalkyls have five or six carbons in the ring structure.

Unless the number of carbons is otherwise specified, "lower alkyl" includes an alkyl group, as defined above, but having from one to ten, or in another embodiment from one to six, carbon atoms in its backbone structure. "Lower alkenyl" and "lower alkynyl" have chain lengths of, for example, 2-5 carbon atoms.

The term "substituted alkyl" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

The term "substituted alkenyl" refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "substituted alkynyl" refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics" or the entire compound may be referred to as "heterocyclic compound". The aromatic ring can be substituted at one or more ring positions with such substituents as described above, as for example, halogen, hydroxyl, aldehyde, alkoxy, alkylcarbonyloxy, arylcarbonyloxy, alkoxycarbonyloxy, aryloxycarbonyloxy, O-benzyl, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylhydroxy, alkylthiocarbonyl, phenoxy (O—$C_6H_5$), phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, —OCF$_3$, cyano, azido, heterocyclyl, alkylaryl, or an aromatic (e.g., phenyl) or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

"Counterion" is used to represent a small, negatively charged species such as chloride, bromide, hydroxide, acetate, and sulfate.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a C$_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "glycoside" means any molecule in which a sugar group is bonded through its anomeric carbon to another group. Examples of glycosides include, for example methyl α-D-glucopyranoside,

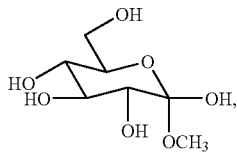

and methyl β-D-glucopyranoside,

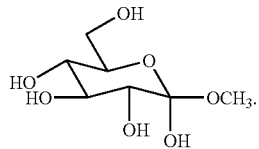

Because a glycoside is bonded through its anomeric carbon to another group, it is also known as a non-reducing sugar (i.e., it is not subject to attack by reagents that attack carbonyl groups).

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Acyl" includes compounds and moieties that contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and The term "thiocarbonyl" or "thiocarboxy" includes compounds and moieties which contain a carbon connected with a double bond to a sulfur atom.

The term "ether" or "alkoxy" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). In one embodiment, an anionic group is a carboxylate.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine. Examples include:

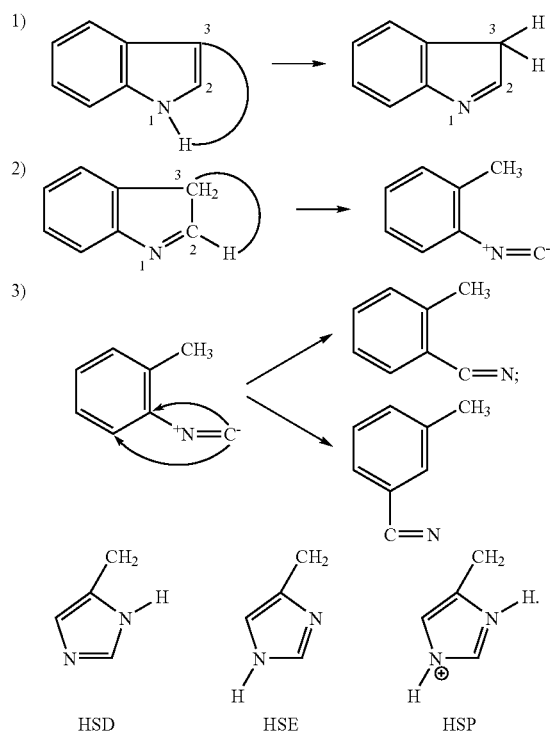

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. The compounds of this invention may exist in stereoisomeric form, therefore can be produced as individual stereoisomers or as mixtures.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by formula I are indole derivatives, and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

"Protecting group" refers to a grouping of atoms that when attached to a reactive group in a molecule masks, reduces or prevents that reactivity. Examples of protecting groups can be found in Green and Wuts, *Protective Groups in Organic Chemistry*, (Wiley, $2^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Stable compound" and "stable structure" are meant to indicate a compound that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The compounds, or pharmaceutically acceptable salts thereof, is administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, the compound is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, tautomers or polymorphs thereof, can be combined with sterile aqueous or organic media to form injectable solutions or suspensions. In one embodiment, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the invention are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/ disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Synthesis and Activity of Indole Derivative Protein Kinase and/or Protein Phosphatase Inhibitors The following results show the solution phase synthesis of 5-fluoroindole-2-carbaxamide libraries and testing of indole derived protein kinase and/or protein phosphatase inhibitors. These final products are examples of indole-based inhibitors wherein synthesis with a 5-fluoro group is illustrated.

A. Synthesis of Intermediates and Sample Reagents:

5-fluoro-3-phenylindole-2-carboxylic acid

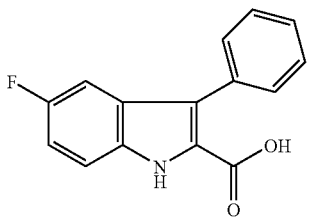

(a) Preparation of Methyl Ester

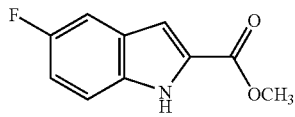

A mixture of 5-fluoroindole-2-carboxylic acid (6 g, 33.5 mmol) and a freshly prepared methanolic HCl (100 mL) was stirred overnight at room temperature. The precipitated ester was collected by filtration, washed with $NaHCO_3$ saturated solution, water, and MeOH. The filtrate was treated with saturated $NaHCO_3$ and extracted with EtOAc. The organic layer was washed with brine, dried ($MgSO_4$), and evaporated in vacuo. The product ester (6 g) was an off white solid and it was used for the next step without further purification: MP 200-201° C.; $^1$H NMR ($CDCl_3$, 500 MHz) δ 8.94 (br, 1H), 7.33 (dd, 1H, J=9.2 and 4.3 Hz), 7.30 (dd, 1H, J=2.2 and 9.2), 7.15 (d, 1H, J=2.1 Hz), 7.07 (ddd, 1H, J=2.5, 8.9 and 9.1 Hz), 3.92 (s, 3H)

(b) Preparation of the 3-iodo Derivative

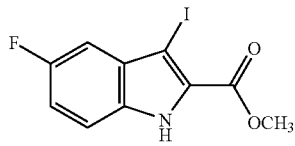

4.22 g (21.8 mmol) of the methyl ester was dissolved in DMF (25 mL). In another flask, a solution of iodine (6.09 g, 24 mmol) and KOH (4.65 g, 82.9 mmol) in DMF (25 mL) was stirred for 30 minutes and added dropwise to the ester solution over 5 minutes. After stirring for 10 minutes at room temperature, the reaction was quenched by pouring into a solution of $NaHSO_3$ (2.2 g), $NH_4OH$ (25% solution in $H_2O$) in 300 mL water. The mixture was stirred for 30 minutes then the precipitated solid product was collected by filtration and washed with $H_2O$: $^1$H NMR ($CDCl_3$, 500 MHz) δ 9.17 (br, 1H), 7.33 (dd, 1H, J=9.0 and 4.2 Hz) 7.21 (dd, 1H J=9.0 and 2.0 Hz), 7.12 (dt, 1H, J=9.0 and 2.0 Hz), 3.81 (s, 3H).

(c) Suzuki Coupling

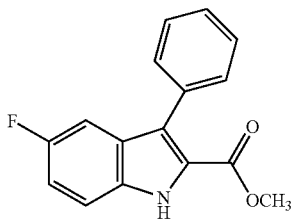

The iodo derivative was mixed with benzeneboronic acid (2.76 g, 22 mmol), $PdCl_2(PPh_3)_2$ (0.7 g, 1 mmol), and 50 mL of 2M $Na_2CO_3$ in dioxane (200 mL). The mixture was stirred at 90° C. overnight. The solvent was evaporated under vacuum. The product was extracted with EtOAc (3×200 mL). The combined extract was washed with brine, dried with $MgSO_4$, and purified by crystallization ($CH_2Cl_2$-hexane) and silica gel chromatography (Hexane-EtOAc 4:1): MP 189° C.; $^1$H NMR ($CDCl_3$, 500 MHz) δ 8.94 (br, 1H), 7.51 (dd, 2H, J=1.5 and 7.9 Hz), 7.45 (ddd, 2H, J=1.8, 7.3 and 7.8), 7.39-7.34 (complex, 2H), 7.25 (dd, 1H, J=2.5 and 8.7 Hz), 7.10 (ddd, 1H, J=2.5, 8.9 and 9.1 Hz), 3.80 (s, 3H).

(d) Saponification of Methyl Ester

The ester described above (2.5 g, 9.28 mmol) was dissolved in THF (30 mL). A solution of LiOH (2.4 g, 100 mmol) in water (20 mL) was added and the mixture was heated at reflux for 1 hour. The mixture was cooled to room temperature and THF was removed by vacuum evaporation. The mixture was treated with 2M HCl until it became acidic. The product was extracted with EtOAc. The organic layer was washed, dried (brine, $Na_2SO_4$), and concentrated under vacuum. The crude solid product was redissolved in $NaHCO_3$ (saturated solution) and washed several times with $CH_2Cl_2$. The aqueous layer was acidified with ice and 2M HCl and extracted with EtOAc. After washing, drying, and rotavaping, the product was collected as white solid (yield 2.3 g, 97%): MP 195-196° C.; $^1$H NMR ($CDCl_3$, 500 MHz) δ 8.94 (br, 1H), 7.52 (dd, 2H, J=1.8 and 7.9 Hz), 7.46 (ddd, 2H, J=1.8, 7.3 and 7.6), 7.40 (ddd, 1H, J=1.8, 7.4 and 7.8 Hz), 7.37 (dd, 1H, J=9.0 and 4.2 Hz), 7.25 (dd, 1H, J=2.5 and 8.7 Hz), 7.12 (ddd, 1H, J=2.4, 8.8 and 8.9. Hz).

3-benzyloxy-5-hydroxybenzonitrile

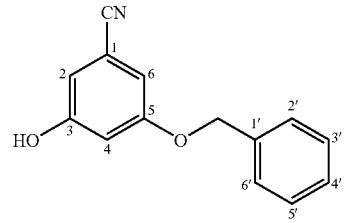

To a mixture of 3,5-dihydroxybenzonitrile (1.08 g, 8 mmol) and $K_2CO_3$ (1.104 g, 8 mmol) in $CH_3CN$ (50 mL), benzyl bromide (1.438 g, 8 mmol) was added. The mixture was heated to reflux for 2 hours. Solvent was evaporated under vacuum. The residue was treated with EtOAc (200 mL) and 1M HCl (200 mL). The organic layer was washed, dried, and evaporated in vacuo. The residue was chromatographed (gradient, Hexanes-CH$_2$Cl$_2$-MeOH) to give 3-benzyloxy-5-hydroxybenzonitrile (529 mg, 29%), 3,5-dibenzyloxybenzonitryl (784 mg, 31%) and 256 mg (23.7 mg, 24%) of the starting material. The product 3-benzyloxy-5-hydroxybenzonitrile had: MP 144-145° C.; $^1$H NMR δ 9.15 (s, 1H, OH), 7.47 (d, 2H, J=7.0 Hz, 2' and 6'), 7.40 (ddd, 2H, J=7.0, 7.0, 2.0 Hz, 3' and 5'), 7.34 (dd, 1H, J=7.7 and 2.1 Hz, 4'), 6.89 (dd, 1H, J=1.5 Hz, 4), 6.78 (d, 2H, J=1.8 Hz), 5.16 (s, 2H).

3,5-dibenzyloxybenzonitryl

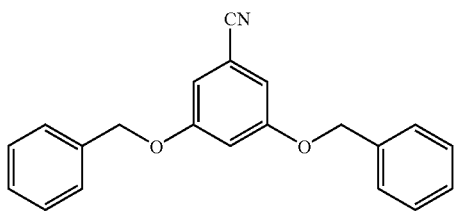

This compound had MP 106° C.; $^1$H NMR (CDCl$_3$, 500 MHz) δ 7.38 (complex, 10H), 6.83 (d, 2H, J=2.1 Hz), 6.79 (d, 1H, J=2.1 Hz).

4-benzyloxy-3-hydroxybenzonitrile

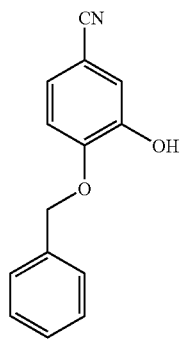

A mixture of 3,4-dihydroxybenzonitrile (540 mg, 4 mmol), K$_2$CO$_3$ (552 mg, 4 mmol) and benzyl bromide (476 mg, 4 mmol) in acetone (20 mL) was stirred at room temperature for 3 days. The mixture was evaporated under vacuum and subjected to flash column chromatography (2% MeOH in toluene-hexane, 2:1) to give the desired product (224 mg, 25%): MP 101° C.; $^1$H NMR (Acetone-d$_6$, 500 MHz) δ 8.55 (s, 1H), 7.50 (d, 2H, J=7.3 Hz), 7.39 (dd, 2H, J=7.0 and 7.3), 7.34 (dd, 1H, J=7.0 and 7.3), 7.2 (m, complex, 3H), 5.25 (s, 2H).

3-hydroxy-4-propyloxybenzonitrile

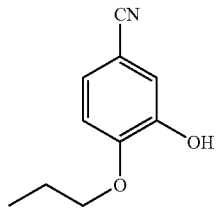

This compound was prepared following a similar procedure used to prepare 4-benzyloxy-3-hydroxybenzonitrile in 27% yield: MP 99° C.; $^1$H NMR (Acetone-d$_6$, 500 MHz) δ 8.33 (s, 1H), 7.21 (dd, 1H, J=8.2 and 1.8 Hz), 7.13 (d, 1H, J=1.8 Hz), 7.08 (d, 1H, J=8.3 Hz), 4.07 (t, 2H, J=6.4 Hz), 1.80 (m, 2H), 1.01 (t, 3H, J=7.3 Hz).

3-benzyloxy-5-hydroxybenzylamine

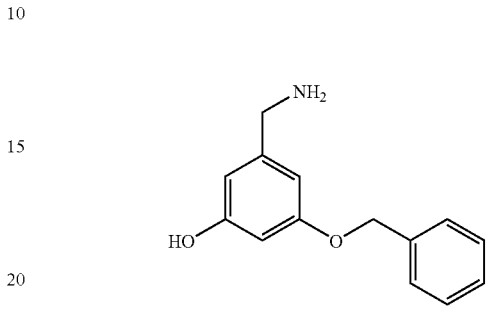

3-benzyloxy-5-hydroxybenzonitrile (225 mg, 1 mmol) was dissolved in 2 mL THF. 2 mL of BH$_3$-THF (1.5 M in THF and ether) was added dropwise, then the mixture was heated at reflux temperature for 3 hours. After cooling, the mixture was carefully poured to 3M HCl (ice cooled) and allowed to stir for 20 hours at room temperature. The mixture was neutralized with solid NaHCO$_3$, thus the product precipitated as a white solid. The product was collected by filtration, washed with water, and dried (140 mg, 61%): MP 164-166° C. (dec); $^1$H NMR (DMSO-d$_6$, 400 MHz) δ 9.28 (br, 1H), 7.41 (d, 2H, J=6.9 Hz), 7.36 (dd, 2H, J=7.0 and 7.6 Hz), 7.30 (dd, 1H, J=7.0 and 6.6 Hz), 6.43 (s, 1H), 6.32 (s, 1H), 6.21 (dd, 1H, J=2.2 and 2.0 Hz), 4.99 (S, 2H), 3.57 (S, 2H).

3,5-dibenzyloxybenzylamine

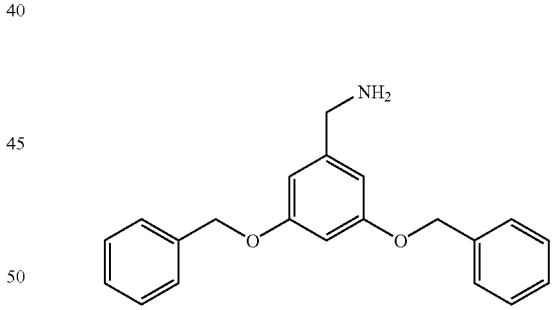

This compound was prepared according to the procedure used in preparation of 3-benzyloxy-5-hydroxybenzylamine. The reaction was quenched via addition of MeOH and the mixture was left to stir overnight. The solvent was removed and the product was obtained by flash column chromatography (CH$_2$Cl$_2$-Hexanes containing 5% MeOH) as clear thick oil (90%): $^1$H NMR (Acetone-d$_6$, 500 MHz) δ 7.46 (d, 4H, J=7.6), 7.37 (dd, 4H, J=7.3 and 7.6), 7.31 (dd, 2H, J=7.3 and 7.0), 6.65 (d, 1H, J=2.1 Hz), 6.64 (d, 1H, J=2.0 Hz), 6.52 (dd, 1H, J=2.0 and 2.2 Hz), 5.07 (s, 4H), 4.35 (s, 2H), 1.97 (br, 1H), 1.85 (br, 1H).

4-benzyloxy-3-hydroxybenzylamine

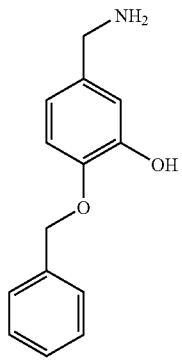

This compound was prepared according to procedure used in preparation of 3,5-dibenzyloxybenzylamine, starting from 4-benzyloxy-3-hydroxybenzonitrile. Yield was 33%. MP 122-125° C.; $^1$H NMR (DMSO-d$_6$, 400 MHz) δ 8.9 (br, 1H), 7.44 (d, 2H, J=7.4 Hz), 7.35 (dd, 2H, J=7.0 and 7.7 Hz), 7.28 (dd, 1H, J=7.0 and 7.3), 6.85 (d, 1H, J=7.6 Hz), 6.77 (d, 1H, J=2.1 Hz), 6.61 (dd, 1H, J=7.4 and 2.2 Hz), 5.05 (s, 2H), 3.55 (s, 1H), 2.50 (br, 2H).

3-hydroxy-4-propyloxybenzylamine

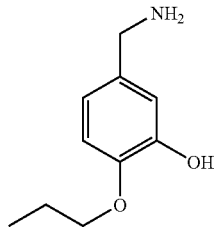

This compound was prepared by reduction of 3-hydroxy-4-propyloxybenzonitrile according to procedure described in preparation of 3,5-dibenzyloxybenzylamine. Yield was 48%: MP 110-113° C. (dec.); $^1$H NMR (CDCl$_3$, 400 MHz) δ 6.86 (s, 1H), 6.77 (d, 1H, J=8.4 Hz), 6.74 (d, 1H, J=8.1 Hz), 3.95 (t, 1H, J=6.6 Hz), 3.74 (s, 2H), 2.01 (br, 2H), 1.82 (m, 2H), 1.02 (t, 3H, J=7.4 Hz).

4-hydroxymethylbenzylamine

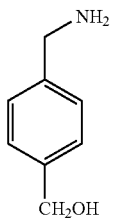

This compound was prepared by reduction of 4-cyanobenzaldehyde according to the procedure described in preparation of 3,5-dibenzyloxybenzylamine. Yield was 46%: MP 102-123° C.; $^1$H NMR (Acetone-d$_6$, 500 MHz) 7.27 (m, complex 4H), 4.58 (s, 2H), 3.72 (s, 2H), 3.69 (s, 1H) 2.77 (br, 1H), 2.45 (br, 1H).

3-hydroxymethylbenzylamine

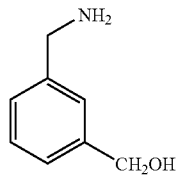

This compound was prepared by reduction of 3-cyanobenzaldehyde according to the procedure described in preparation of 3,5-dibenzyloxybenzylamine. Yield was 66%; $^1$H NMR (Acetone-d$_6$, 500 MHz) δ 7.32 (s, 1H), 7.23 (dd, 1H, J=7.6 and 7.0), 7.19, complex, 2H), 4.59 (s, 2H), 4.40 (s, 2H), 4.10 (br, 1H), 1.96 (br, 1H), 1.88 (br, 1H).

2-methoxy-5-nitrobenzaldehyde methyl hemiacetal

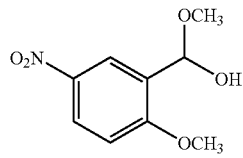

2-hydroxy-5-nitrobenzaldehyde (3.34 g, 20 mmol) was dissolved in acetone (70 mL); k$_2$CO$_3$ (5.53 g, 40 mmol) and iodomethane (14.19 g, 100 mmol) was added and the solution heated to reflux overnight. Solvent was removed in vacuo and residue was dissolved in EtOAc. The resulting product was washed with 2M NaOH, water, and brine and dried. Removal of solvent resulted in a solid product (2.5 g, 69%) of 2-methoxy-5-nitrobenzaldehyde methyl hemiacetal: MP 147-148° C. (89° C. reported for the aldehyde); $^1$H NMR (CDCl$_3$, 400 MHz) δ 8.43 (d, 1H, J=2.9 Hz), 8.24 (dd, 1H, J=2.6 and 9.1 Hz), 7.78 (d, 1H, 16.5 Hz), 6.99 (d, 1H, J=9.1 Hz), 6.83 (d, 1H, J=16.4 Hz). NOTE: This NMR was taken after about 10 months and the hemiacetal was still existing and pure.

5-nitro-2-propyloxybenzaldehyde

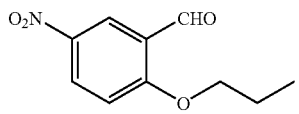

This compound was prepared by the reaction of 2-hydroxy-5-nitrobenzaldehyde and 1-iodopropane using a similar procedure as described in the preparation of 2-methoxy-5-nitrobenzaldehyde methyl hemiacetal. Yield was 72%: MP (51-52° C.); $^1$H NMR (500 MHz, CDCl$_3$) δ 10.46 (s, 1H), 8.68 (d, 1H, J=2.9 Hz), 8.39 (dd, 1H, J=2.7 and 9.1 Hz), 7.08 (d, 1H, J=9.1 Hz), 4.16 (t, 2H, J=6.2), 1.93 (m, 2H), 1.98 (t, 3H, J=7.37).

2-hydroxymethyl-4-nitrophenol

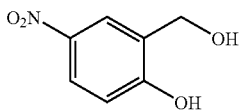

A solution of 2-hydroxy-5-nitrobenzaldehyde (5.01 g, 30 mmol) in a mixture of 60 mL 1M NaOH and 30 mL MeOH was cooled to 0° C. NaBH$_4$ (1.13 g, 30 mmol) solution in 15 mL 1M NaOH and 5 mL MeOH was added slowly. The reaction mixture was stirred for 24 hours at room temperature. The mixture was poured into ice cooled 2M HCl and extracted with EtOAc. The organic layer was washed, dried, and evaporated in vacuo to give the alcohol as a yellow solid (5.1 g, 100%): MP (112-114° C.); $^1$H NMR (DMSO-d$_6$, 400 MHz) δ 11.08 (s, 1H), 8.18 (d, 1H, J=2.5 Hz), 8.00 (dd, 1H, J=2.5 and 8.7 Hz), 6.92 (d, 1H, J=8.8 Hz), 5.20 (br, 1H), 4.49 (s, 2H).

2-methoxy-5-nitrobenzylalcohol

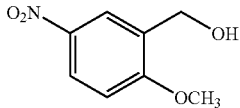

This compound was prepared by reduction of 2-methoxy-5-nitrobenzaldehyde methyl hemiacetal using a method similar to that described for preparing 2-hydroxymethyl-4-nitrophenol in 76% yield: MP 121-122° C.; $^1$H NMR (DMSO-d$_6$, 500 MHz) δ 8.22 (d, 1H, J=1.22 Hz), 8.16 (dd, 1H, J=2.7 and 9.1), 7.16 (d, 1H, J=8.9 Hz), 4.50 (s, 2H), 3.90 (s, 3H).

5-nitro-2-propyloxy-benzylalcohol

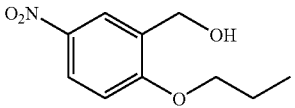

This compound was prepared by reduction of 5-nitro-2-propyloxybenzaldehyde using a method similar to that described for preparing 2-hydroxymethyl-4-nitrophenol in 93% yield: MP (No Sample left for MP); $^1$H NMR (400 MHz, DMSO-d$_6$) 8.22 (d, 1H, J=2.6 Hz), 8.13 (dd, 1H, J=2.9 and 9.2 Hz), 7.14 (d, 1H, J=9.2 Hz), 5.41 (t, 1H, J=5.5 Hz), 4.52 (d, 2H, J=5.8 Hz), 4.08 (t, 2H, J=6.2), 1.75 (m, 2H), 0.98 (t, 3H, J=7.6 Hz).

2-benzyloxy-5-nitrobenzylalcohol

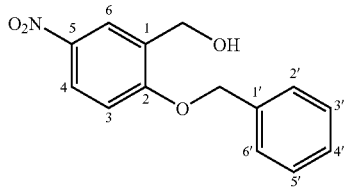

This intermediate was prepared by alkylation of 2-hydroxymethyl-4-nitrophenol with benzyl bromide following the method described for preparation of 2-methoxy-5-nitrobenzaldehyde methyl hemiacetal in a yield of 84%: MP 81-83° C.; $^1$H NMR δ (DMSO-d$_6$, 500 MHz) 8.26 (d, 1H, J=2.9 Hz H-6), 8.15 (dd, 1H, J=2.9 and 9.1 Hz, H-4), 7.46 (d, 2H, J=7.0, 2',6'-Hs) 7.41 (dd, 2H, J=7.0 and 7.7, 3',5'-Hs), 7.34 (d, 1H, J=7 Hz, 4'-H), 7.25 (d, 1H, J=9.1 Hz, 3-H), 5.4 (br, 1H, OH), 5.29 (s, 2H, CH$_2$), 4.57 (s, 2H, CH$_2$).

3-hydroxymethyl-4-methoxyaniline

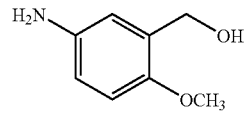

A mixture of 2-methoxy-5-nitrobenzylalcohol (1.02 g, 6.03 mmol) and SnCl$_2$.H$_2$O (6.8 g, 30.15 mmol) in EtOH (20 mL) was heated at 70° C. for 1 hour. After cooling, the mixture was treated with 2M NaOH and extracted with ether. The organic layer was washed with water, dried, and evaporated under vacuum to provide 2.18 g (84%) of the aniline 3-hydroxymethyl-4-methoxyaniline: $^1$H NMR (DMSO-d$_6$, 500 MHz) δ 6.66 (d, 1H, J=2.2 Hz), 6.61 (d, 1H, J=8.6 Hz), 6.38 (dd, 1H, J=2.4 and 8.2 Hz), 4.81 (t, 1H, J=5.5 Hz), 4.54 (br, 2H), 4.37 (d, 2H, J=5.8 Hz), 3.61 (s, 3H).

3-hydroxymethyl-4-propyloxyaniline

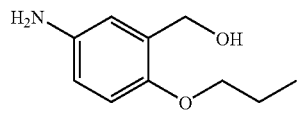

This compound was prepared by reduction of 5-nitro-2-propyloxy-benzylalcohol using the method described for the preparation of 3-hydroxymethyl-4-methoxyaniline in 37% yield: $^1$H NMR (DMSO-d$_6$, 500 MHz) δ 6.66 (d, 1H, J=2.5 Hz), 6.60 (d, 1H, J=8.6 Hz), 6.35 (dd, 1H, J=2.7 and 8.5 Hz), 4.79 (t, 1H, J=5.8 Hz), 4.54 (br, 2H), 4.37 (d, 2H, J=6.1 Hz), 3.74 (t, 2H, J=6.4 Hz), 1.65 (m, 2H), 0.94 (t, 3H, J=7.4 Hz).

4-benzyloxy-3-hydroxymethylaniline

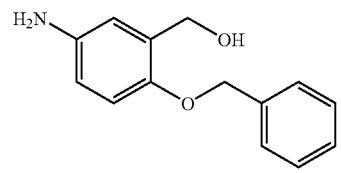

This compound was prepared by reduction of 2-benzyloxy-5-nitrobenzylalcohol using the method described for preparation of 3-hydroxymethyl-4-methoxyaniline in 86% yield: $^1$H NMR (DMSO-d$_6$, 500 MHz) δ 7.40 (d, 2H, J=7.3 Hz), 7.36 (dd, 2H, J=7.3 and 7.6 Hz), 7.28 (dd, 1H, J=7.0 and 7.4), 6.70 (d, 1H, J=8.5 Hz), 6.68 (d, 1H, J=2.4 Hz), 6.35 (dd, 1H, J=2.8 and 8.3 Hz), 4.92 (s, 2H), 4.84 (t, 1H, J=5.8 Hz), 4.59 (br, 2H), 4.44 (d, 2H, J=6.4 Hz).

B. Formation of Libraries

General Structure

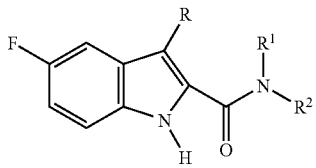

R = H, Ph
R[1], R[2] = H, alkyl, aryl, aralkyl, heterocyclic

1. General Procedures for Amide Coupling a. Method A

To a cold mixture (at 0° C.) of an amine (see Table VI below for amines) (0.15 mL of 1M solution in $CH_2Cl_2$, 0.15 mmol), an acid (5-fluoroindole-2-carboxylic acid or 5-fluoro-3-phenylindole-2-carboxylic acid) (0.15 mmol as 0.15 mL of 1M solution in THF) in $CH_2Cl_2$ (0.5 mL) was added and cooled to 0° C. Subsequently, a mixture of 1-(3-dimethylaminopropyl)-3-ethylcarbodiimide (EDCI) (0.15 mmol) and $Et_3N$ (0.06 mmol) in $CH_2Cl_2$ (0.5 mL) was added and the reaction was shaken in a Bohdan orbital shaker (Mettler-Toledo Bohdan, Vernon Hills, Ill.) at 0° C. for 30 minutes then at room temperature for 18 hours. After adding 0.5 mL of $CH_2Cl_2$ and 0.5 mL MeOH, the mixture was passed through a cartridge charged with a cationic exchange resin (Dowex 50wX4-200, Aldrich Chemical Co., Milwaukee, Wis., pre-washed with 1M HCl, $H_2O$, $H_2O$-MeOH, MeOH, MeOH—$CH_2Cl_2$). The eluent was directly passed through a chromatography cartridge containing silica gel mixed with 10% $Na_2CO_3$. The product was eluted with 2 mL $CH_2Cl_2$-MeOH (2 mL), $CH_2Cl_2$ (2 mL), and $CH_2Cl_2$-MeOH (2 mL). The fraction(s) containing pure product was identified by TLC (EtOAc-Hexane, 1:1). The compounds were characterized and their relative purity was estimated using $^1H$ NMR.

b. Method B

A mixture of an amine (see Table VI below for amines) (0.1 mmol), an acid (5-fluoroindole-2-carboxylic acid or 5-fluoro-3-phenylindole-2-carboxylic acid) (0.1 mmol as 0.1 mL of 1M solution in DMF), and diisopropylethylamine (DIEA) (0.05 mL, 0.3 mmol) was cooled to 0° C. (benzotriazol-1-yloxy)tripyrrolidino-phosphonium-hexafluorophosphate (PyBOP) (0.1 mmol as 0.1 mL of 1M solution in DMF) was added. The reaction mixture was shaken using an orbital shaker at 0° C. for 30 minutes then at room temperature for 18 hours. EtOAc was added to the mixture and the organic solution was washed with 1M HCl (2×1 mL), brine (1 mL) $NaHCO_3$ (2×1 mL), and brine (1 mL). The organic layer was passed through a silica gel cartridge containing a top layer of anhydrous $MgSO_4$ and moistened with hexane. The product amide was eluted with hexane (1×1 mL), hexane-EtOAc 2:1 (3×1 mL), hexane-EtOAc 1:1 (2×2 mL), and hexane-EtOAc 1:2 (1×2 mL). The fraction(s) containing pure product was identified by TLC (EtOAc-hexane 1:1 and EtOAc-hexane 1:2 in the case of 5-fluoro-3-phenylindole-2-carboxylic acid amide derivatives). The compounds were characterized and their relative purity was estimated using $^1H$ NMR.

c. Method C

A mixture of an amine (see Table VI below for amines) (0.1 mmol), an acid (5-fluoroindole-2-carboxylic acid or 5-fluoro-3-phenylindole-2-carboxylic acid) (0.1 mmol as 0.1 mL of 1M solution in THF), and DIEA (0.05 mL, 0.3 mmol) in 0.4 mL of $CH_2Cl_2$-THF (3:1) was cooled to 0° C. PyBrOP (0.1 mmol) was added. The reaction mixture was shaken using an orbital shaker at 0° C. for 30 minutes then at room temperature for 48 hours (0.1 mL THF and 0.2 mL $CH_2Cl_2$ were added after 24 hours). EtOAc was added to the mixture and the organic solution was washed with 1M HCl (2×1 mL), brine (1 mL) $NaHCO_3$ (2×1 mL), and brine (1 mL). The organic layer was passed through a silica gel cartridge containing a top layer of anhydrous $MgSO_4$ and moistened with hexane. The product amide was eluted with hexane (1×1 mL), hexane-EtOAc 2:1 (3×1 mL), hexane-EtOAc 1:1 (2×2 mL), and hexane-EtOAc 1:2 (1×2 mL). The fraction(s) containing pure product was identified by TLC (EtOAc-hexane 1:1 and EtOAc-hexane 1:2 in the case of 5-fluoro-3-phenylindole-2-carboxylic acid amide derivatives). The compounds were characterized by $^1H$ NMR.

d. Method D

Preparation of 5-fluoroindole-2-carboxylic acid chloride 5-fluoroindole-2-carboxylic acid (537 mg, 3 mmol) was dissolved in DME (8 mL). 0.6 mL triethylamine was added and the mixture cooled to 0° C. Thionyl chloride (0.44 mL, 6 mmol) mixed with 4 mL DME was added cautiously using addition funnel over 10 minutes while stirring. The mixture was left to stir for 30 minutes. The formed precipitate was filtered off, and the solvent was evaporated under reduced pressure to give yellow solid of the acid chloride.

Reaction of Amines with 5-fluoroindole-2-carboxylic acid chloride

A mixture of an amine (see Table VI below for amines) (1 mmol) and pyridine (0.18 mL) in 1 mL DCM was cooled to 0° C. 5-fluoroindole-2-carboxylic acid chloride (19.8 mg, 1 mmol) was added, then reaction was stirred at room temperature for 1 hour. The resulting amide (in DCM) was washed with 1M HCl, then with Brine. The crude product was purified by silica gel chromatography.

e. Representative Examples of Amide Coupling Methods

Synthesis of Compound 1z

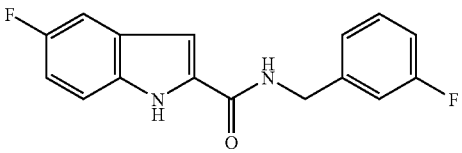

To a mixture of 3-fluorobenzylamine (2.03 g, 20 mmol) and 5-fluoroindole-2-carboxylic acid (3.58 g, 20 mmol) in DMF (50 mL), was added a solution of DIEA (6.98 mL, 40 mmol) in 15 mL $CH_2Cl_2$. The mixture was cooled to 0° C. and PyBOP (10.41 g, 20 mmol) was added portion wise. The reaction mixture was stirred at 0° C. for 30 minutes, then at room temperature for 4 hours. EtOAc (400 mL) was added to the mixture and the organic solution was washed with 2M HCl (4×200 mL), brine (200 mL), $NaHCO_3$ (4×200 mL), and brine (2×200 mL). The organic layer was dried ($MgSO_4$) and concentrated in vacuo to furnish the crude product as off-white solid. Recrystallization from MeOH and $CH_2Cl_2$ provided 5.36 g (93%) of 1z as white crystals: MP 239-241° C.; $^1H$ NMR (DMSO-$d_6$, 500 MHz) δ 11.73 (s, 1H), 9.12 (t, 1H, J=6.1 Hz), 7.39 (complex, 3H), 7.17 (complex, 2H), 7.07 (dd, 1H, J=2.2 and 9.5 Hz), 7.07 (dd, 1H, J=2.2 and 9.0 Hz), 7.03 (ddd, 1H, J=2.4, 9.1 and 9.2 Hz), 4.52 (d, 2H, J=6.1 Hz); Anal. ($C_{16}H_{12}F_2N_2O$) C, 67.13; H, 4.23; N, 9.79; Found; C, 66.91; H, 4.31; N, 9.81.

Synthesis of Compound 1a

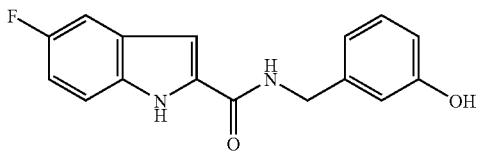

(a) Preparation of Methoxy Intermediate

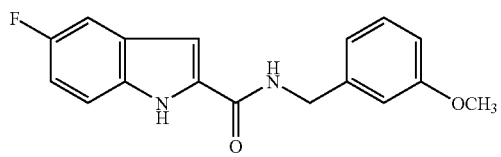

Following same procedure mentioned above for the synthesis of 1z, this compound was prepared starting from 20 mmol of amine and acid. Purification with flash column chromatography afforded 5.43 g (91%) of the methoxy intermediate as off-white crystalline solid: MP 192° C.

(b) Demethylation

A mixture of the methoxy intermediate (5 g, 16.7 mmol) and $CH_2Cl_2$ (80 mL) was placed in a multi neck flask equipped with a dropping funnel and a thermometer. The flask was cooled to 0° C. in an ice/salt bath. A solution of $BBr_3$ in $CH_2Cl_2$ (80 mL) was added dropwise while keeping the temperature less than 5° C. The mixture was stirred at room temperature for 3 hours. After addition of ice and 3M HCl (200 mL), the mixture was left to stir overnight. The precipitated solid product was collected by filtration, washed with water, and dried. Crystallization from $CH_2Cl_2$ and MeOH furnished 4.2 g (88%) of compound 1a: MP 213° C.; $^1$H NMR (DMSO-$d_6$, 400 MHz) δ 11.68 (br, 1H), 9.31 (br, 1H), 9.01 (t, 1H, J=6.0 Hz), 7.39 (complex, 2H), 7.14 (s, 1H), 7.09 (dd, 1H, J=8.0 and 7.7 Hz), 7.02 (ddd, 1H, J=9.2, 8.9 and 2.5 Hz), 6.72 (d, 2H, J=7.3 Hz), 6.61 (d, 1H, J=8.4 Hz), 4.41 (d, 2H, J=5.9 Hz), HRMS (EI): Required $M^+$ for $C_{16}H_{13}FN_2O_2$, 284.0956; Found, 284.0960; Anal. ($C_{16}H_{13}FN_2O_2$) C, 67.60; H, 4.61; F, N, 9.85; Found C, 67.50; H, 4.65; F, N, 9.76.

f. Other Representative Compounds Obtained and Relative Purity Data

The following are examples of compounds obtained using the above methods and their relative purity data. Table VI, below, lists all compounds obtained.

Compound 1bb

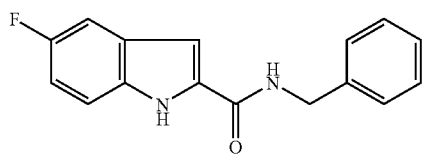

$^1$H NMR (acetone-$d_6$, 400 MHz) δ 10.85 (br, 1H), 8.29 (br, 1H), 7.53 (dd, 1H, J=9.9 and 4.6 Hz), 7.36 (d, 1H, J=7.4), 7.30 (complex, 3H), 7.22 (dd, 1H, J=7.3 and 7.0 Hz), 7.12 (s, 1H) 7.02 (ddd, 1H, J=2.6 and 9.2 and 9.1), 4.60 (d, 2H, J=6.3 Hz).

Compound 1cc

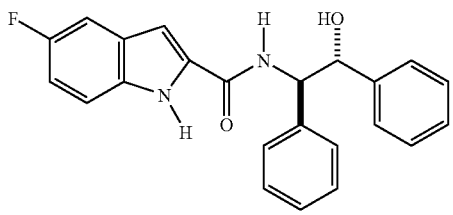

$^1$H NMR (Acetone-$d_6$, 500 MHz) δ 10.74 (br, 2H) 8.01 (d, br, 1H, J=9.0 Hz), 7.45 (dd, 1H, J=9.0 and 4.6 Hz), 7.37 (d, 2H, J=7.4 Hz), 7.34 (d, 2H, J=7.4 Hz), 7.28 (dd, 1H, J=9.5 and 2.5 Hz), 7.24 to 7.10 (complex. m, 7H), 6.99 (ddd, 1H, J=9.3, 9.2 and 2.6 Hz), 5.40 (dd, 1H, J=9.0 and 6.4 Hz), 5.20 (dd, 1H, J=6.2 and 4.6 Hz), 4.71 (d, 1H, J=4.6 Hz); LRMS (EI), m/z 356.1 ($M^+$-$H_2O$).

Compound 1dd

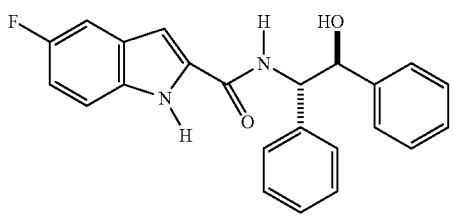

$^1$H NMR (Acetone-$d_6$, 500 MHz) δ 10.80 (br, 2H) 8.04 (d, br, 1H, J=8.7 Hz), 7.43 (dd, 1H, J=9.0 and 4.8 Hz), 7.38 (dd, 2H, J=8.0 and 1.4 Hz), 7.34 (dd, 2H, J=8.0 and 1.4 Hz), 7.28 (dd, 1H, J=9.6 and 2.4 Hz), 7.25 to 7.11 (complex. m, 7H), 6.98 (ddd, 1H, J=9.2, 9.1 and 2.5 Hz), 5.41 (dd, 1H, J=8.8d 6.6 Hz), 5.21 (dd, 1H, J=6.2 and 4.8 Hz), 4.71 (d, 1H, J=4.6 Hz).

Compound 1bbb

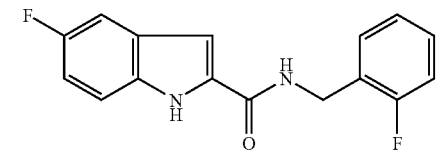

$^1$H NMR (acetone-$d_6$, 500 MHz) δ 10.89 (br, 1H), 8.31 (br, 1H), 7.54 (dd, 1H, J=9.1 and 4.6 Hz), 7.45 (dd, 1H, J=7.7 and 7.7 Hz), 7.29 (complex, 2H), 7.17-7.08 (complex, 3H), 7.03 (ddd, 1H, J=9.2, 9.1 and 2.6 Hz), 4.66 (d, 2H, J=5.8 Hz).

Compound 1yyy

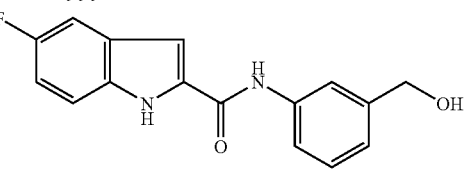

$^1$H NMR (Acetone-$d_6$, 500 MHz) δ 10.99 (br, 1H), 9.57 (br, 1H), 7.80 (s, 1H), 7.76 (d, 1H, J=8.3 MHz), 7.57 (dd, 1H, J=9.0 and 4.4 Hz), 7.35 (dd, 1H, 9.2 and 2.4 Hz), 3.34 (s, 1H), 7.29 (dd, 1H, J=7.7 and 7.8 Hz), 7.09 (d, 1H, J=8.8 Hz), 7.06 (ddd, 1H, J=9.2, 8.9 and 2.4 Hz), 4.63 (d, 2H, J=5.8 Hz), 4.24 (t, 1H, J=5.8 Hz); LRMS (EI) m/z 284.1 (74%, $M^+$).

Compound 1ccc

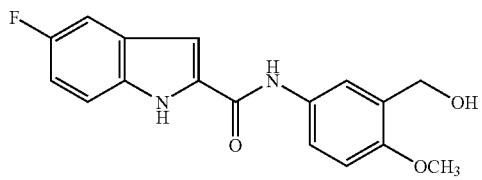

¹H NMR (acetone-d₆, 500 MHz) δ 10.96 (br, 1H), 9.49 (br, 1H), 7.79 (complex, 2H), 7.56 (dd, 1H, J=8.9 and 4.5 Hz), 7.34 (complex, 2H), 7.05 (ddd, 1H, J=9.2, 9.1 and 2.4 Hz), 6.92 (d, 1H, J=8.6 Hz), 4.65 (d, 1H, J=7.0 Hz), 4.06 (t, 1H, J=5.8), 3.81 (s, 1H); LRMS (EI) m/z 314.12 (51%, M⁺).

Compound 1oooo

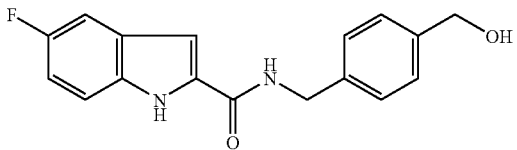

¹H NMR (acetone-d₆, 500 MHz) δ 10.94 (br, 1H), 8.31 (br, 1H), 7.52 (dd, 1H, J=8.9 and 4.6), 7.33 (d, 2H, J=8.9), 7.30 (d, 2H, J=8.5), 7.29 (dd, 1H, J=9.6 and 2.6 Hz), 7.13 (s, 1H), 7.02 (ddd, 1H, J=9.3, 9.1 and 2.4 Hz), 4.60 (d, 4H, J=5.8 Hz), 4.15 (t, 1H, J=5.8 Hz); LRMS (EI) m/z 298.12 (100%, M⁺).

Compound 2f

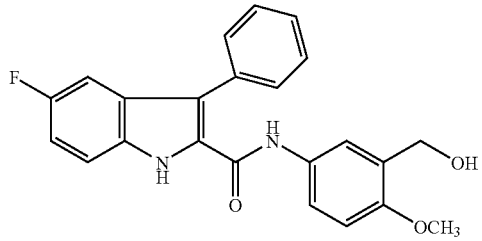

¹H NMR (acetone-d₆, 500 MHz) δ 11.12 (br, 1H), 8.07 (br, 1H), 7.66-77.60 (m, complex, 5H), 7.52 (m, 1H), 7.36 (d, 1H, J=2.2 Hz), 7.30 (dd, 1H, J=8.7 and 2.6), 7.15-7.09 (m, complex, 2H), 6.84 (d, 1H, J=8.8 Hz), 4.56 (d, 2H, J=6.1 Hz), 4.04 (t, 1 h, J=5.8 Hz), 3.77 (s, 3H).

Compound 2g

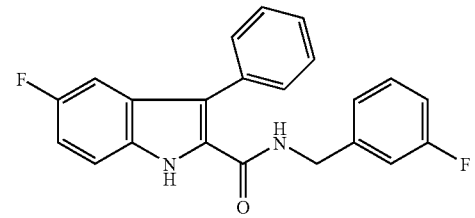

¹H NMR (Acetone-d₆, 500 MHz) δ 11.02 (br, 1H), 7.59 (dd, 1H, J=9.7 and 4.6 Hz), 7.53 (d, 1H, J=9.8 Hz), 7.47 (dd, 2H, J=7.9 and 7.4 Hz), 7.40 (m, 1H), 7.31 (dd, 1H. J=7.0 and 6.5 Hz), 7.08 (complex, 2H), 7.03 (d, 1H, J=7.7 Hz), 6.99 (complex, 2H), 6.91 (br, 1H), 4.48 (d, 2H, J=5.8 Hz); LRMS (EI) m/z 362.14 (85%, M⁺).

Compound 2s

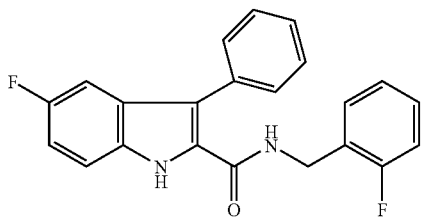

¹H NMR (Acetone-d₆, 500 MHz) δ 11.03 (br, 1H), 7.57-7.45 (complex, 4H), 7.544 (m, 1H), 7.31-7.24 (complex, 2H), 7.13-7.055 (complex, 4H), 6.76 (br, 1H), 4.50 (d, 2H, J=5.2 Hz); LRMS (EI) m/z 362.1 (95%, M⁺).

Compound 3q

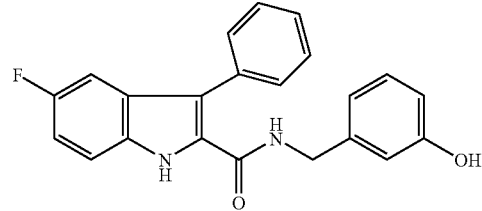

¹H NMR (Acetone-d₆, 500 MHz) δ 10.99 (br, 1H), 8.26 (s, 1H), 7.58 (dd, 1H, J=9.5 and 4.6 Hz), 7.51 (dd, 2H, J=8.2 and 1.4 Hz), 7.46 (dd, 2H, J=7.7 and 7.3 Hz), 7.38 (m, 1H), 7.10-7.05 (complex, 3H), 6.72 (br, 1H), 6.67 (complex, 2H), 6.62 (d, 1H, J=7.6 Hz), 4.38 (d, 2H, J=6.2 Hz); LRMS (EI) m/z 360.12 (100%, M⁺).

2. General Procedure for Oxidation of Benzyl Alcohol Amide Derivatives to Benzaldehyde: Preparation of Compounds 3b, 3d, 3e, 3f, 3g, and 3h The starting benzyl alcohol amide derivative was dissolved in a 1:1 mixture of $CH_2Cl_2$ and THF (5 mL/mmol), pyridinium chlorochromate (2 molar equivalent) was added, and the mixture was stirred at room temperature for 3.5 hours. EtOAc and water were added. The brown solid was removed by filtration. The organic phase was washed several times with $NaHCO_3$, brine, dried, and concentrated. Product aldehyde was purified by crystallization and confirmed by ¹H NMR (disappearance of the methylene of benzyl alcohol and appearance of aldehyde peak).

The following table sets forth the structures made by the above methods:

TABLE VI
LIBRARY OF 5-FLUOROINDOLE-2-CARBAXAMIDE COMPOUNDS AND METHOD OF PREPARATION
| Cmpd Code | Structure | M.Wt. | Method of Preparation |
|---|---|---|---|
| 1a | 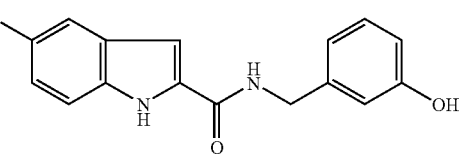 | 284.29 | See Example 1 |
| 1b | 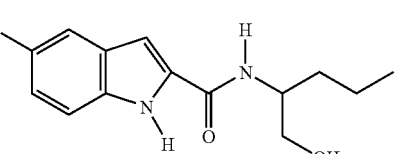 | 264.3 | Amide Coupling Method A |
| 1c | 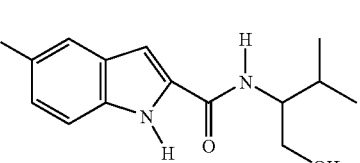 | 264.3 | Amide Coupling Method A |
| 1d | 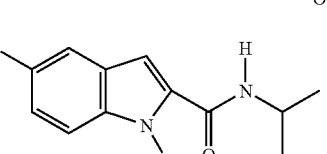 | 236.24 | Amide Coupling Method A |
| 1e | 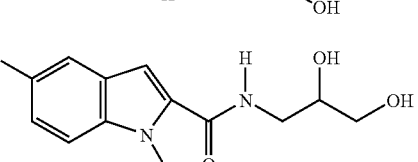 | 252.24 | Amide Coupling Method A |
| 1f | 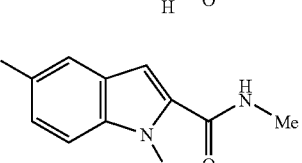 | 192.19 | Amide Coupling Method A |
| 1g | 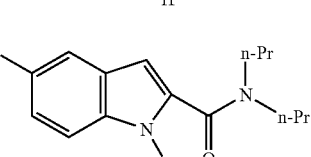 | 262.32 | Amide Coupling Method A |
| 1h | 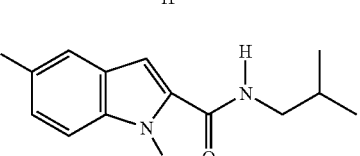 | 234.27 | Amide Coupling Method A |
| 1i | 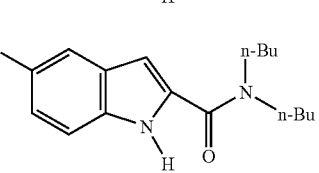 | 290.38 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 1j | 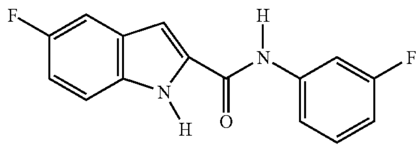 | 272.25 | Amide Coupling Method A |
| 1k | 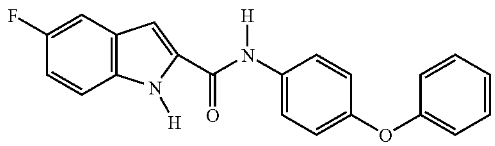 | 346.35 | Amide Coupling Method A |
| 1l | 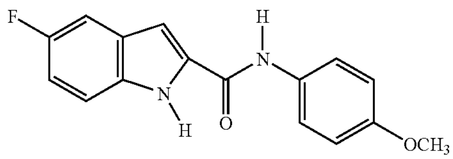 | 284.29 | Amide Coupling Method A |
| 1m | 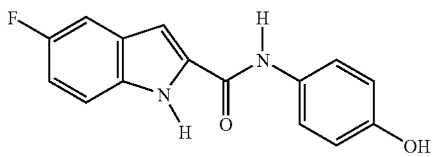 | 270.26 | Amide Coupling Method A |
| 1n | 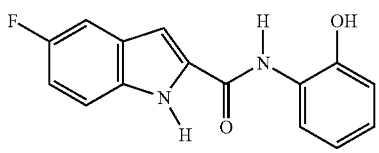 | 270.26 | Amide Coupling Method A |
| 1o | 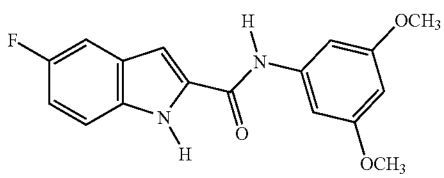 | 314.31 | Amide Coupling Method A |
| 1p | 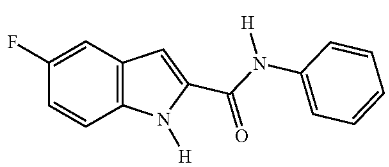 | 254.26 | Amide Coupling Method A |
| 1q | 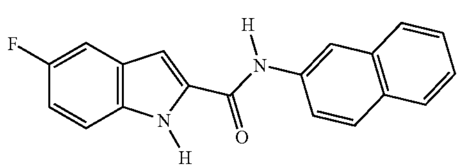 | 304.32 | Amide Coupling Method A |
| 1r | 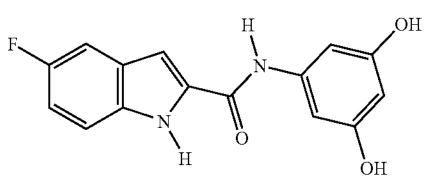 | 286.26 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 1s | 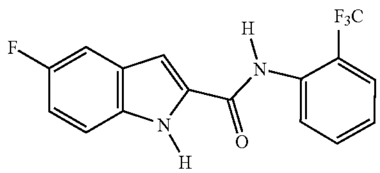 | 322.26 | Amide Coupling Method A |
| 1t | 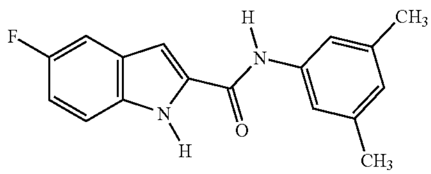 | 282.31 | Amide Coupling Method A |
| 1u | 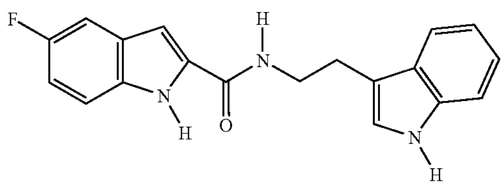 | 321.35 | Amide Coupling Method A |
| 1v | 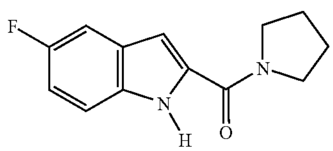 | 232.25 | Amide Coupling Method A |
| 1w | 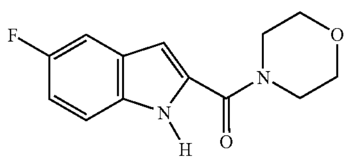 | 248.25 | Amide Coupling Method A |
| 1x | 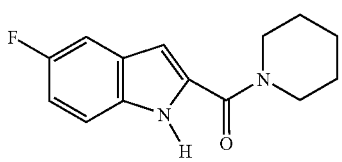 | 246.28 | Amide Coupling Method A |
| 1y | 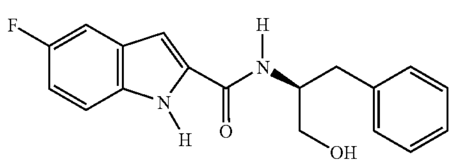 | 312.34 | Amide Coupling Method A |
| 1z | 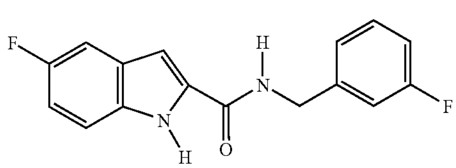 | 286.28 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 1aa | 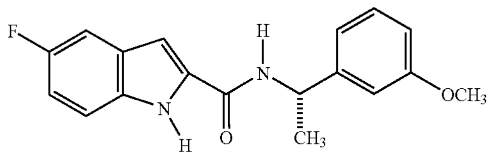 | 312.34 | Amide Coupling Method A |
| 1bb | 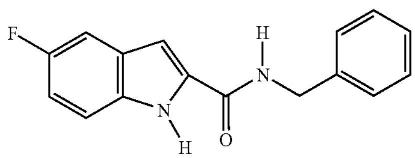 | 286.29 | Amide Coupling Method A |
| 1cc | 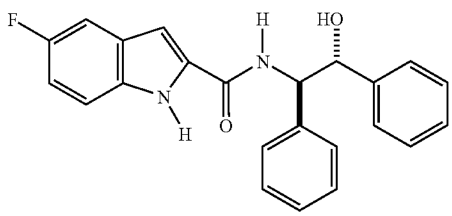 | 374.41 | Amide Coupling Method A |
| 1dd | 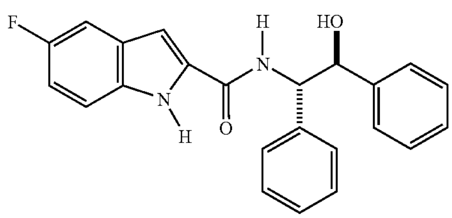 | 374.41 | Amide Coupling Method A |
| 1ee | 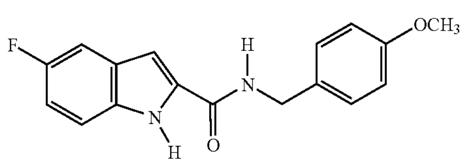 | 298.31 | Amide Coupling Method A |
| 1ff | 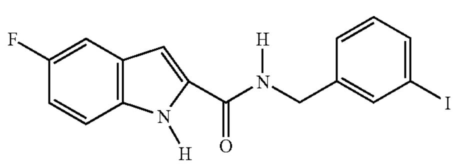 | 394.18 | Amide Coupling Method A |
| 1gg | 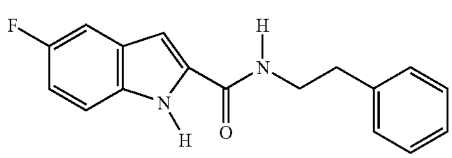 | 282.31 | Amide Coupling Method A |
| 1hh | 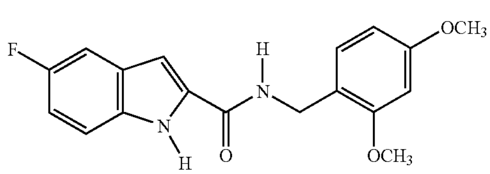 | 328.34 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 1ii | 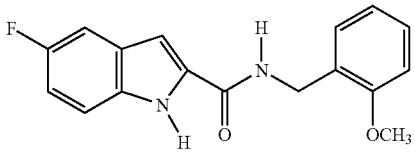 | 298.31 | Amide Coupling Method A |
| 1jj | 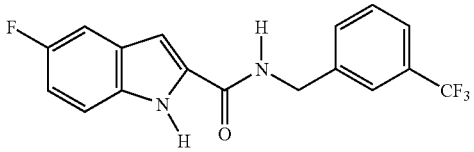 | 336.28 | Amide Coupling Method A |
| 1kk | 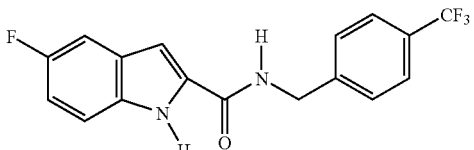 | 336.28 | Amide Coupling Method A |
| 1ll | 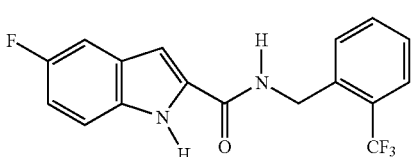 | 336.28 | Amide Coupling Method A |
| 1mm | 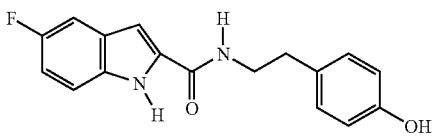 | 298.31 | Amide Coupling Method A |
| 1nn | 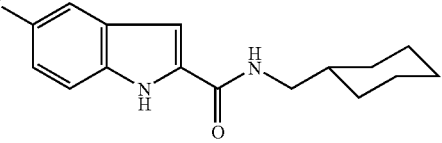 | 274.33 | Amide Coupling Method A |
| 1oo | 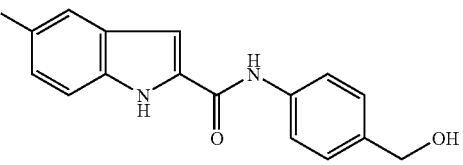 | 284.29 | Amide Coupling Method A |
| 1pp | 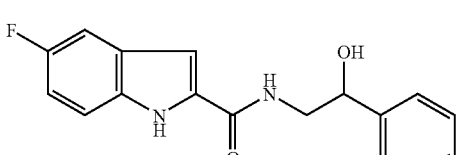 | 298.31 | Amide Coupling Method A |
| 1qq | 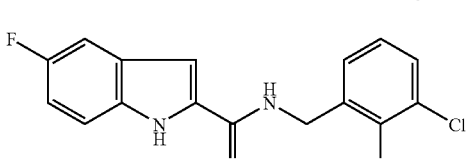 | 337.18 | Amide Coupling Method A |

TABLE VI-continued
LIBRARY OF 5-FLUOROINDOLE-2-CARBAXAMIDE
COMPOUNDS AND METHOD OF PREPARATION
| Cmpd Code | Structure | M.Wt. | Method of Preparation |
|---|---|---|---|
| 1rr | 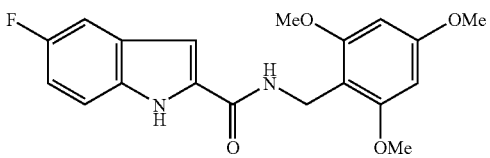 | 358.36 | Amide Coupling Method A |
| 1ss | 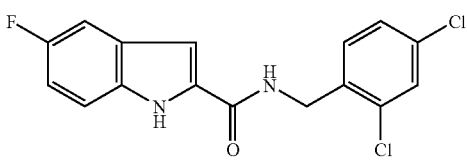 | 337.18 | Amide Coupling Method A |
| 1tt | 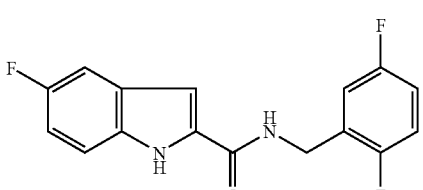 | 304.27 | Amide Coupling Method A |
| 1uu | 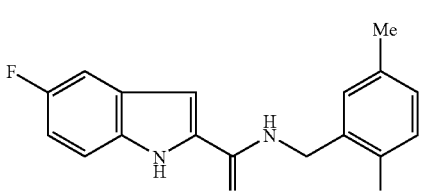 | 296.34 | Amide Coupling Method A |
| 1vv | 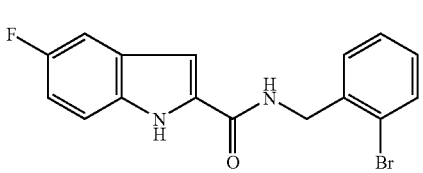 | 347.18 | Amide Coupling Method A |
| 1ww | 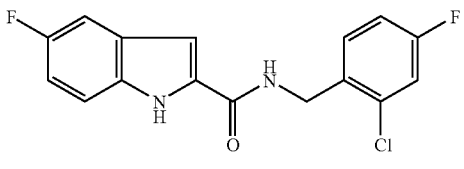 | 320.72 | Amide Coupling Method A |
| 1xx | 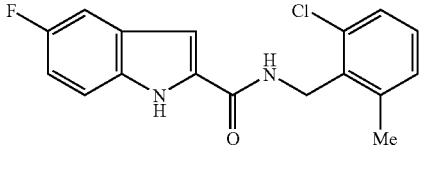 | 316.76 | Amide Coupling Method A |
| 1yy | 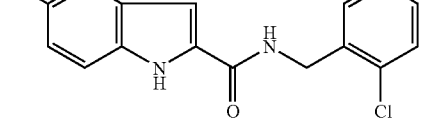 | 302.73 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 1zz | 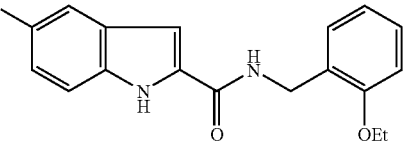 | 312.34 | Amide Coupling Method A |
| 1aaa | 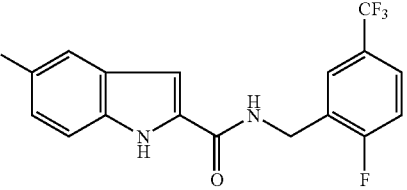 | 354.27 | Amide Coupling Method A |
| 1bbb | 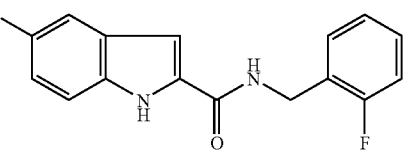 | 286.28 | Amide Coupling Method A |
| 1ccc | 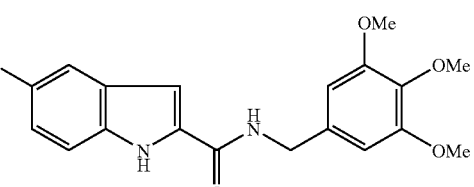 | 358.36 | Amide Coupling Method A |
| 1ddd | 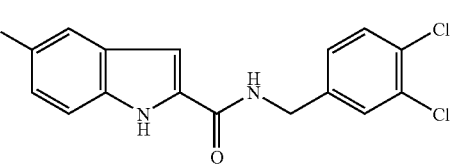 | 337.18 | Amide Coupling Method A |
| 1eee | 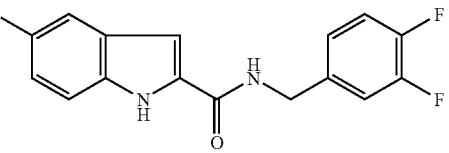 | 304.27 | Amide Coupling Method A |
| 1fff | 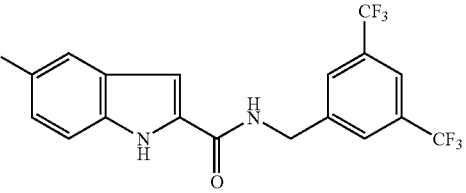 | 404.28 | Amide Coupling Method A |
| 1ggg | 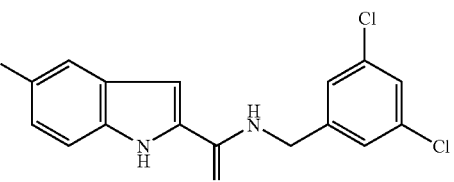 | 337.18 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 1hhh | 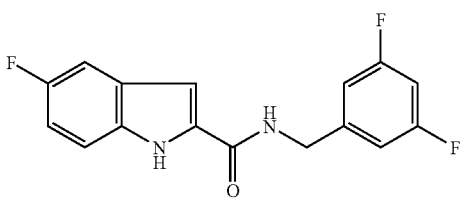 | 304.27 | Amide Coupling Method A |
| 1iii | 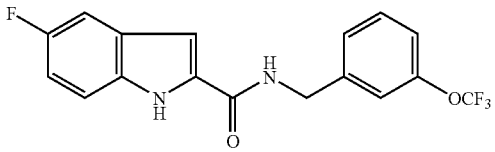 | 352.28 | Amide Coupling Method A |
| 1jjj | 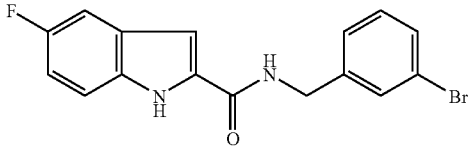 | 347.18 | Amide Coupling Method A |
| 1kkk | 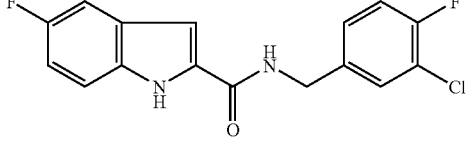 | 320.72 | Amide Coupling Method A |
| 1lll | 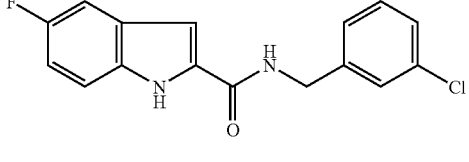 | 302.73 | Amide Coupling Method A |
| 1mmm | 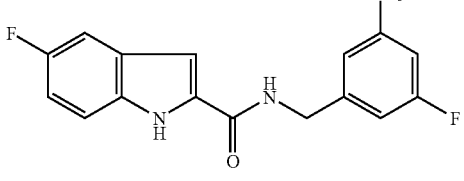 | 354.27 | Amide Coupling Method A |
| 1nnn | 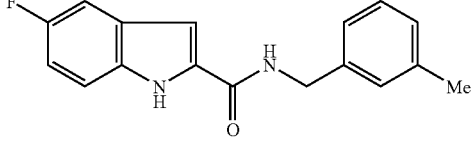 | 282.31 | Amide Coupling Method A |
| 1ooo | 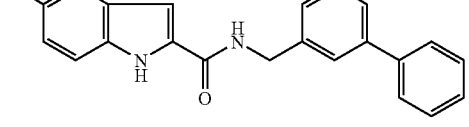 | 344.38 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 1ppp | 5-F-indole-2-C(O)NH-CH2-C6H4-4-OCF3 | 352.28 | Amide Coupling Method A |
| 1qqq | 5-F-indole-2-C(O)NH-CH2-C6H3-3-OMe-4-OBn | 404.43 | Amide Coupling Method A |
| 1rrr | 5-F-indole-2-C(O)NH-CH2-C6H4-4-Cl | 302.73 | Amide Coupling Method A |
| 1sss | 5-F-indole-2-C(O)NH-CH2-C6H3-4-F-2-CF3 | 354.27 | Amide Coupling Method A |
| 1ttt | 5-F-indole-2-C(O)NH-CH2-C6H3-4-F-3-CF3 | 354.27 | Amide Coupling Method A |
| 1uuu | 5-F-indole-2-C(O)NH-CH2-C6H4-4-F | 286.28 | Amide Coupling Method A |
| 1vvv | 5-F-indole-2-C(O)NH-CH2-C6H4-4-Me | 282.31 | Amide Coupling Method A |
| 1www | 5-F-indole-2-C(O)NH-CH2-C6H3-5-Br-2-F | 365.17 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 1xxx | 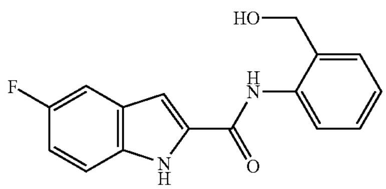 | 284.29 | Amide Coupling Method C |
| 1yyy | 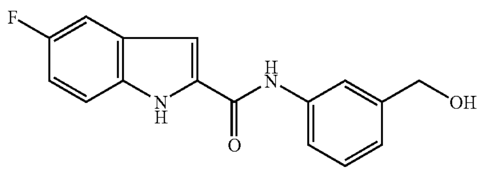 | 284.29 | Amide Coupling Method B |
| 1zzz | 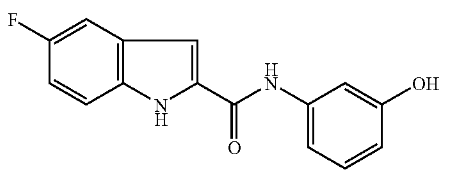 | 270.26 | Amide Coupling Method C |
| 1aaaa | 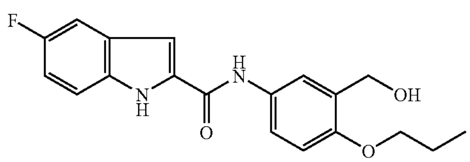 | 342.36 | Amide Coupling Method C |
| 1bbbb | 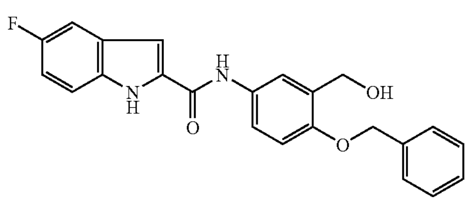 | 390.41 | Amide Coupling Method C |
| 1cccc | 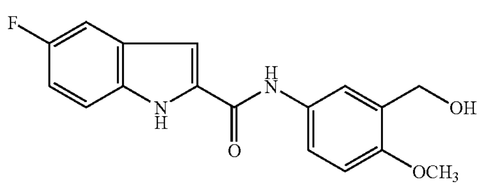 | 314.31 | Amide Coupling Method C |
| 1dddd | 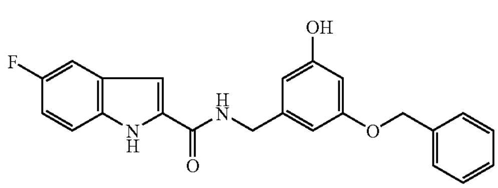 | 390.41 | Amide Coupling Method B |
| 1eeee | 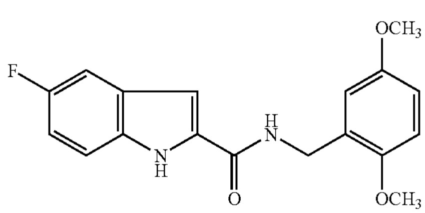 | 328.34 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 1ffff | 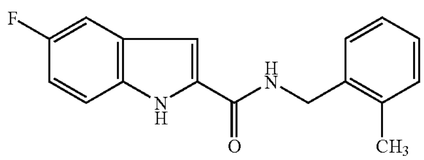 | 282.31 | Amide Coupling Method B |
| 1gggg | 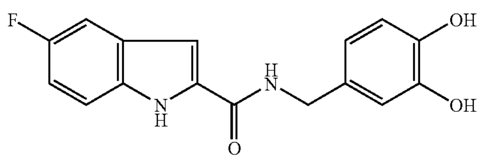 | 300.28 | Amide Coupling Method B |
| 1hhhh | 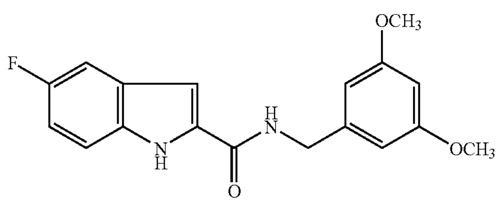 | 328.34 | Amide Coupling Method B |
| 1iiii | 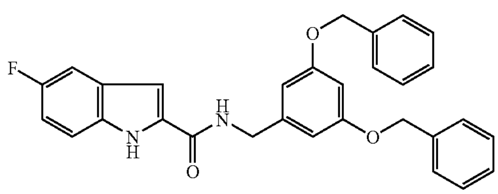 | 480.53 | Amide Coupling Method B |
| 1jjjj | 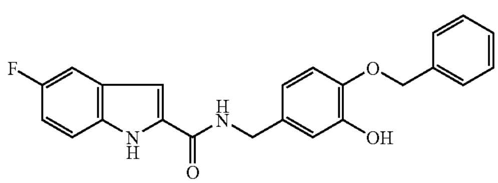 | 390.41 | Amide Coupling Method B |
| 1kkkk | 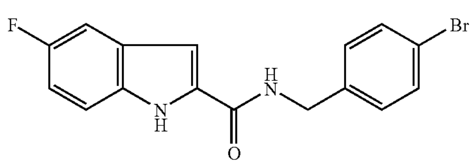 | 347.18 | Amide Coupling Method B |
| 1llll | 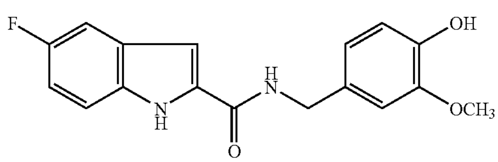 | 314.31 | Amide Coupling Method B |
| 1mmmm | 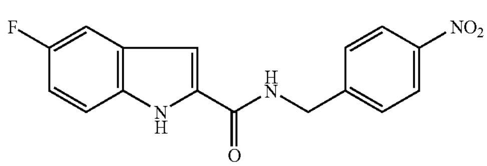 | 313.28 | Amide Coupling Method B |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 1nnnn | 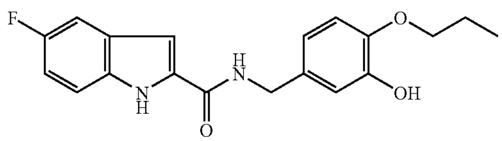 | 342.36 | Amide Coupling Method B |
| 1oooo | 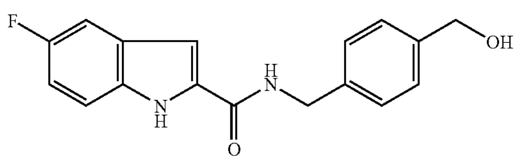 | 298.31 | Amide Coupling Method B |
| 1pppp | 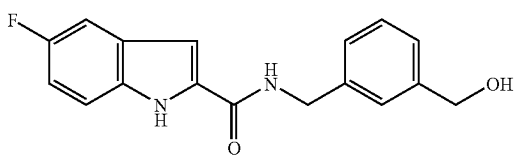 | 298.31 | Amide Coupling Method B |
| 1qqqq | 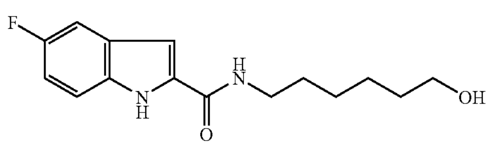 | 278.32 | Amide Coupling Method B |
| 2a | 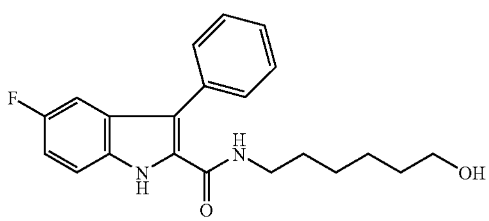 | 354.42 | Amide Coupling Method B |
| 2b | 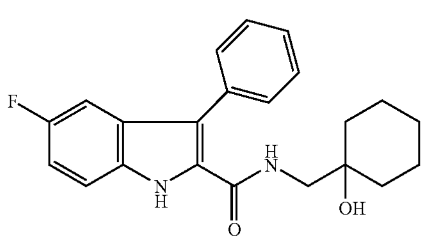 | 366.43 | Amide Coupling Method B |
| 2c | 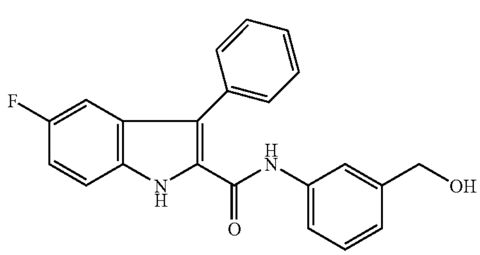 | 360.38 | Amide Coupling Method B |

TABLE VI-continued
LIBRARY OF 5-FLUOROINDOLE-2-CARBAXAMIDE COMPOUNDS AND METHOD OF PREPARATION
| Cmpd Code | Structure | M.Wt. | Method of Preparation |
|---|---|---|---|
| 2d | 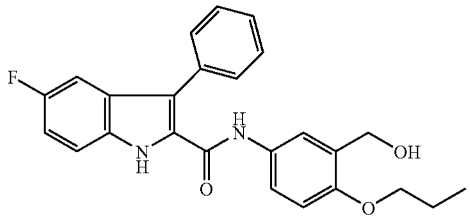 | 418.46 | Amide Coupling Method B |
| 2e | 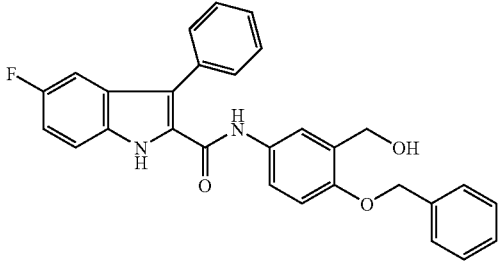 | 466.5 | Amide Coupling Method B |
| 2f | 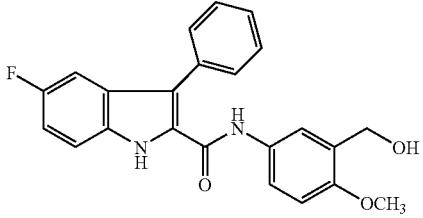 | 390.41 | Amide Coupling Method B |
| 2g | 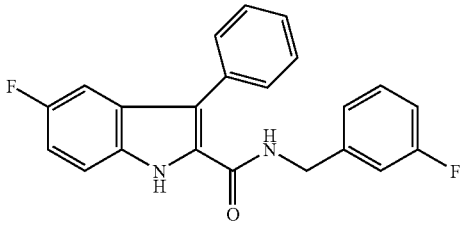 | 362.37 | Amide Coupling Method B |
| 2h | 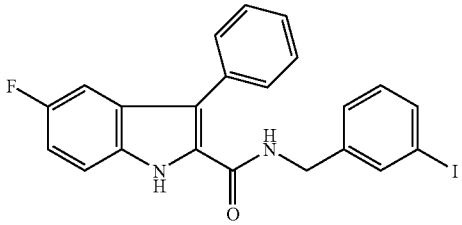 | 470.28 | Amide Coupling Method B |
| 2i | 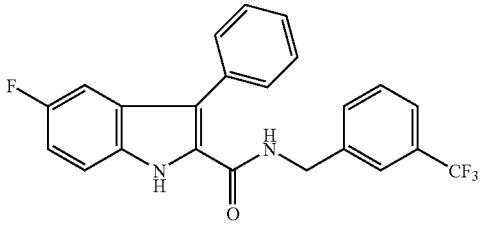 | 412.38 | Amide Coupling Method B |

TABLE VI-continued
LIBRARY OF 5-FLUOROINDOLE-2-CARBAXAMIDE COMPOUNDS AND METHOD OF PREPARATION
| Cmpd Code | Structure | M.Wt. | Method of Preparation |
|---|---|---|---|
| 2j | 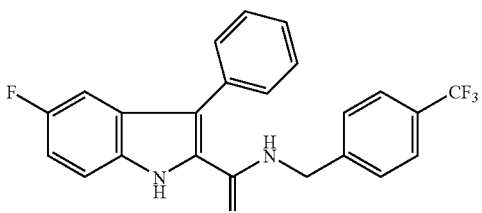 | 412.38 | Amide Coupling Method B |
| 2k | 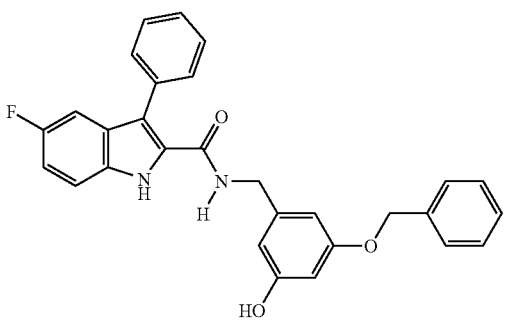 | 466.5 | Amide Coupling Method B |
| 2l | 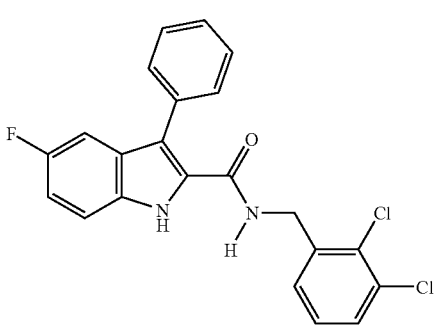 | 413.27 | Amide Coupling Method B |
| 2m | 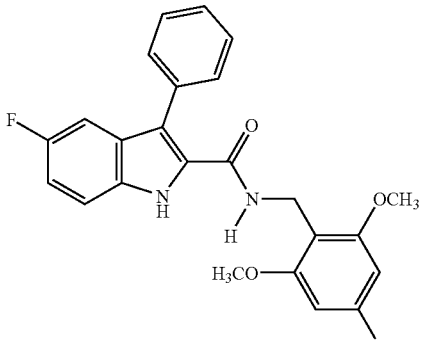 | 434.46 | Amide Coupling Method B |

TABLE VI-continued
LIBRARY OF 5-FLUOROINDOLE-2-CARBAXAMIDE COMPOUNDS AND METHOD OF PREPARATION
| Cmpd Code | Structure | M.Wt. | Method of Preparation |
|---|---|---|---|
| 2n | 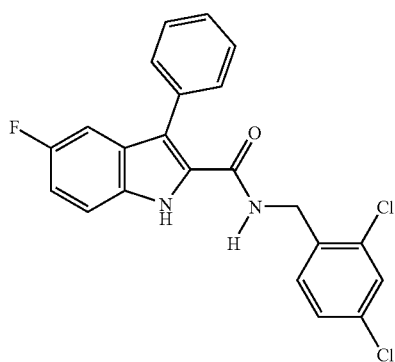 | 413.27 | Amide Coupling Method B |
| 2o | 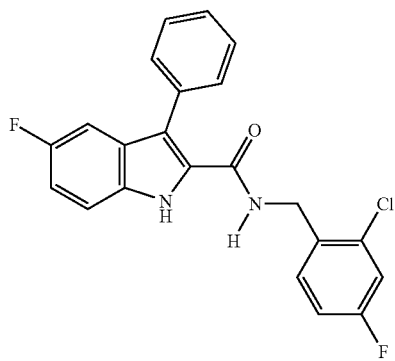 | 396.82 | Amide Coupling Method B |
| 2p | 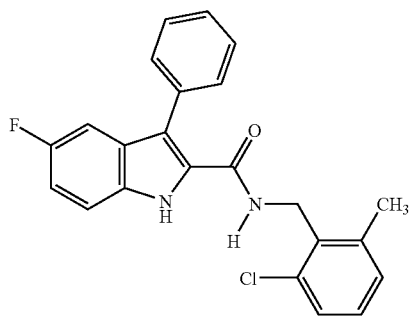 | 392.85 | Amide Coupling Method B |
| 2q | 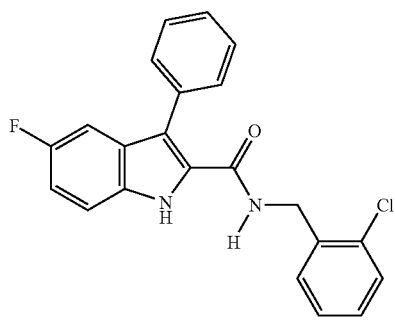 | 378.83 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 2r | 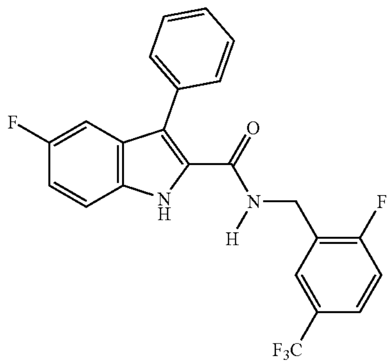 | 430.37 | Amide Coupling Method B |
| 2s | 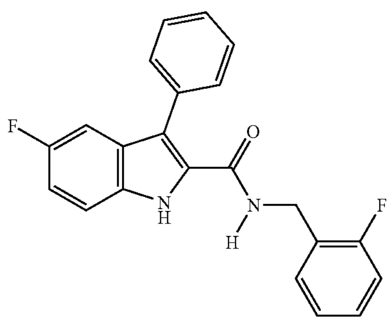 | 362.37 | Amide Coupling Method B |
| 2t | 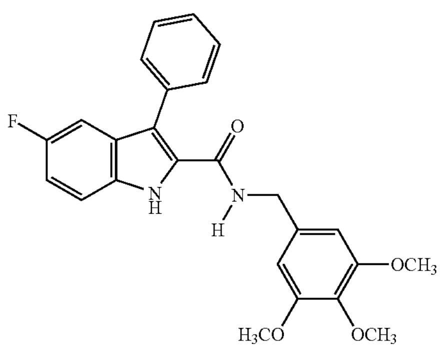 | 434.46 | Amide Coupling Method B |
| 2u | 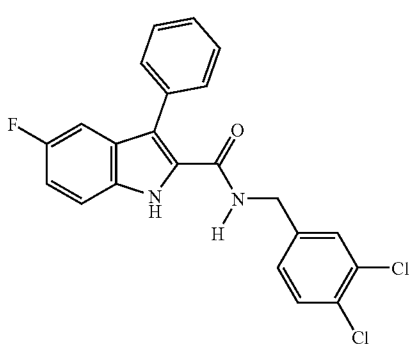 | 413.27 | Amide Coupling Method B |

TABLE VI-continued
LIBRARY OF 5-FLUOROINDOLE-2-CARBAXAMIDE
COMPOUNDS AND METHOD OF PREPARATION
| Cmpd Code | Structure | M.Wt. | Method of Preparation |
|---|---|---|---|
| 2v | 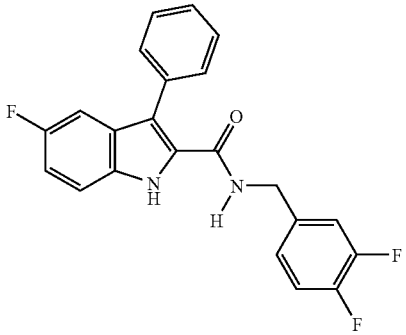 | 380.36 | Amide Coupling Method B |
| 2w | 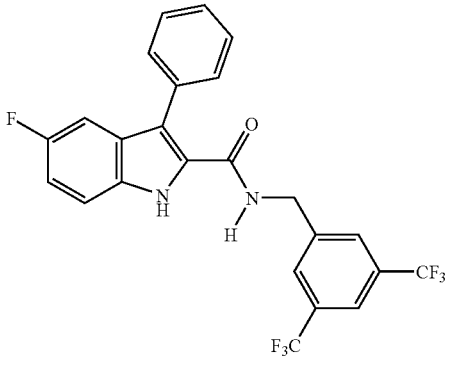 | 480.38 | Amide Coupling Method B |
| 2x | 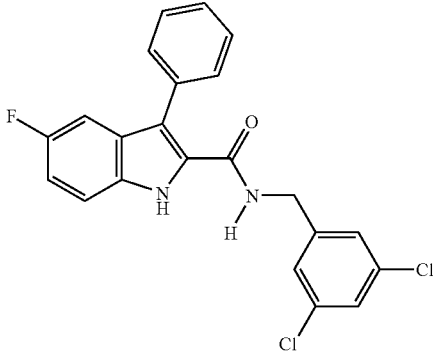 | 413.27 | Amide Coupling Method B |
| 2y | 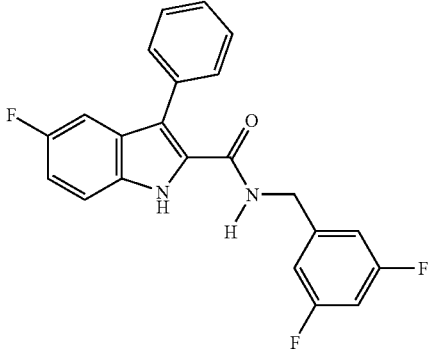 | 380.36 | Amide Coupling Method B |

TABLE VI-continued
LIBRARY OF 5-FLUOROINDOLE-2-CARBAXAMIDE
COMPOUNDS AND METHOD OF PREPARATION
| Cmpd Code | Structure | M.Wt. | Method of Preparation |
|---|---|---|---|
| 2z | 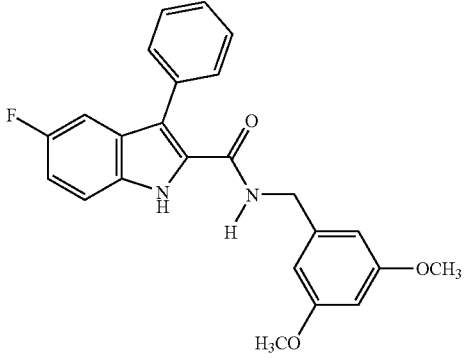 | 404.43 | Amide Coupling Method B |
| 2aa | 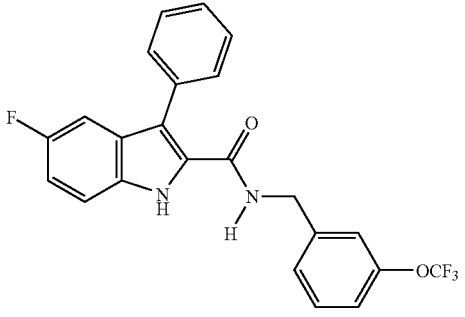 | 428.38 | Amide Coupling Method B |
| 2bb | 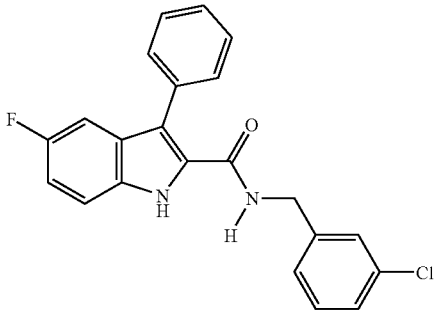 | 378.83 | Amide Coupling Method B |
| 2cc | 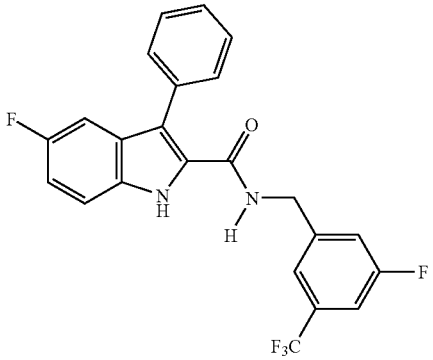 | 430.37 | Amide Coupling Method B |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 2dd | 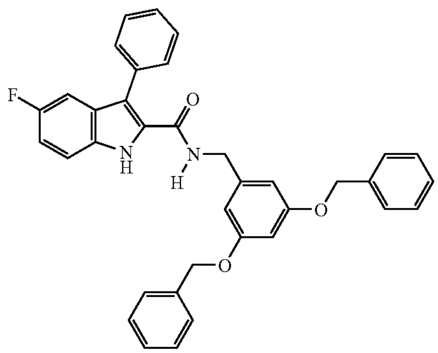 | 556.63 | Amide Coupling Method B |
| 2ee | 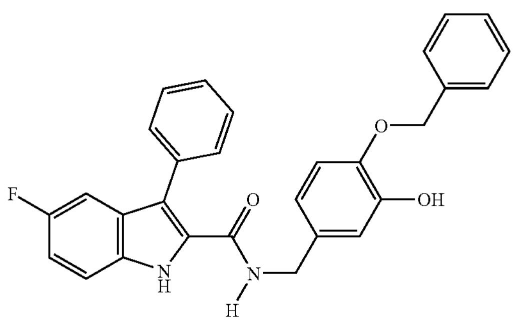 | 466.5 | Amide Coupling Method B |
| 2ff | 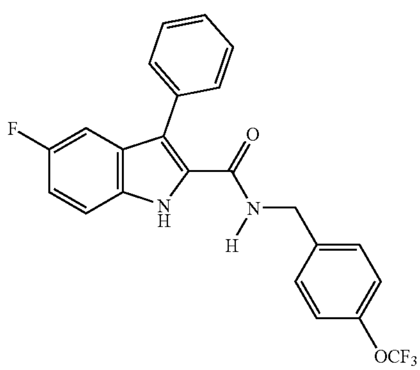 | 428.38 | Amide Coupling Method B |
| 2gg | 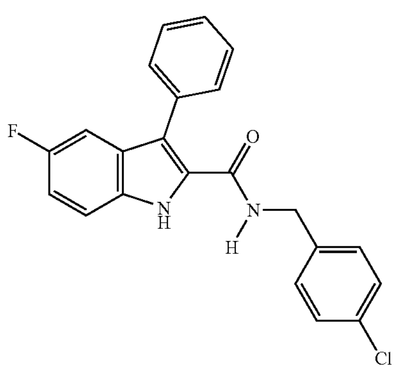 | 378.83 | Amide Coupling Method B |

185 186

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 2hh | 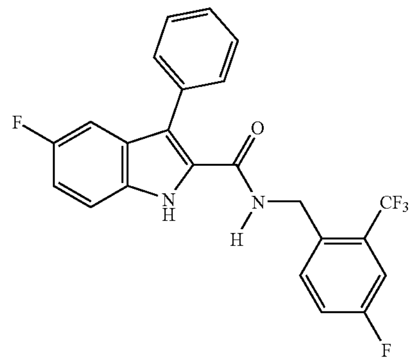 | 430.37 | Amide Coupling Method B |
| 2ii | 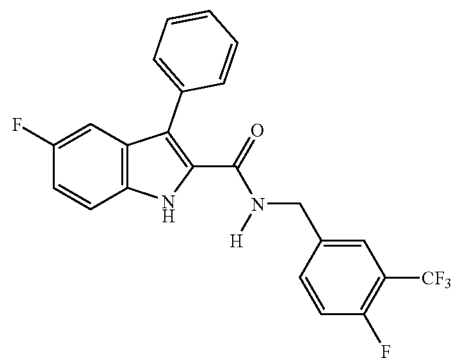 | 431.37 | Amide Coupling Method B |
| 2jj | 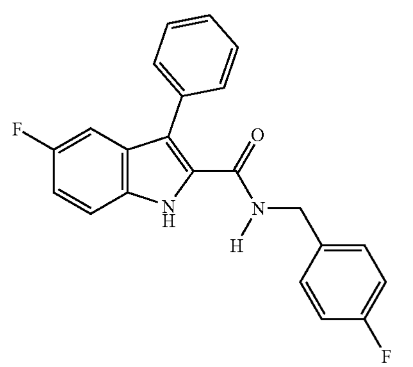 | 362.37 | Amide Coupling Method B |
| 2kk | 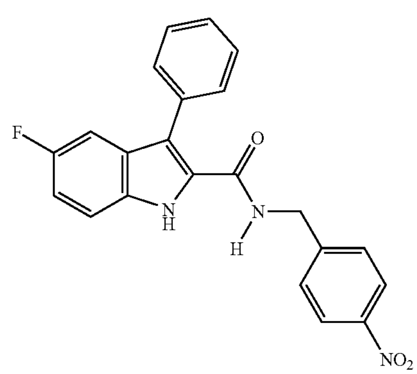 | 389.38 | Amide Coupling Method B |

TABLE VI-continued
LIBRARY OF 5-FLUOROINDOLE-2-CARBAXAMIDE COMPOUNDS AND METHOD OF PREPARATION
| Cmpd Code | Structure | M.Wt. | Method of Preparation |
|---|---|---|---|
| 2ll | 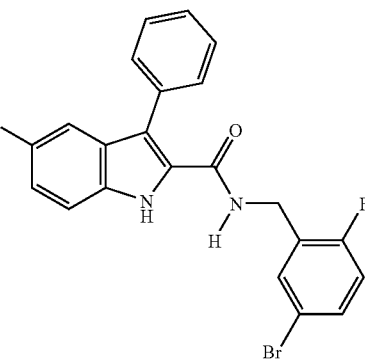 | 441.27 | Amide Coupling Method B |
| 2mm | 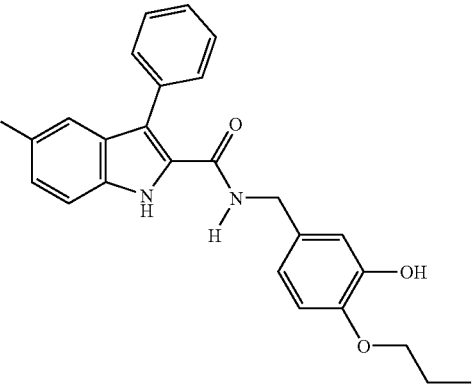 | 418.46 | Amide Coupling Method B |
| 2nn | 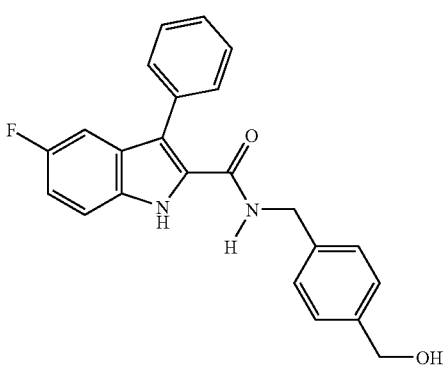 | 374.41 | Amide Coupling Method B |
| 2oo | 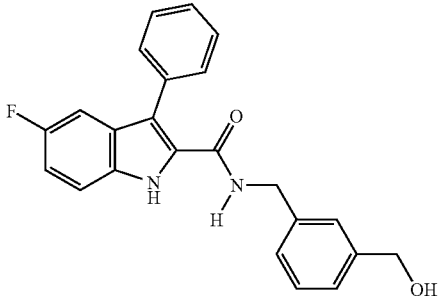 | 375.41 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 3a | 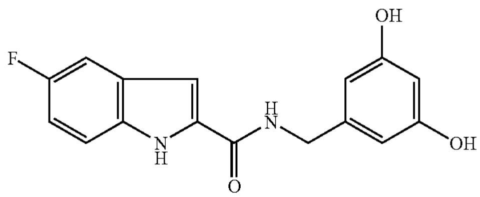 | 300.28 | Demethylation of compound 1hh using BBr$_3$ method in Example 1. |
| 3b | 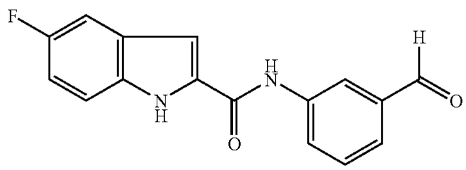 | 282.27 | Oxidation of 1yyy |
| 3c | 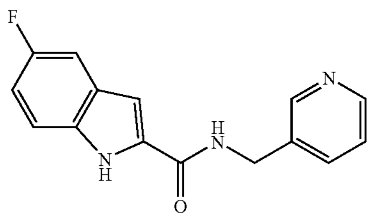 | 269.29 | Amide Coupling Method C |
| 3d | 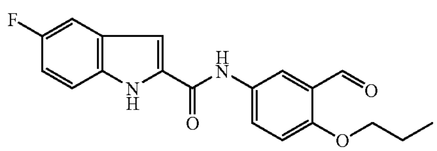 | 340.35 | Oxidation of 1aaaa |
| 3e | 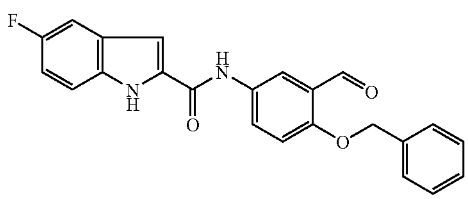 | 388.39 | Oxidation of 1bbbb |
| 3f | 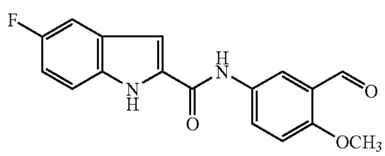 | 312.3 | Oxidation of 1cccc |
| 3g | 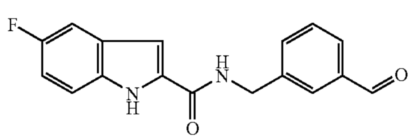 | 296.3 | Oxidation of 1pppp |
| 3h | 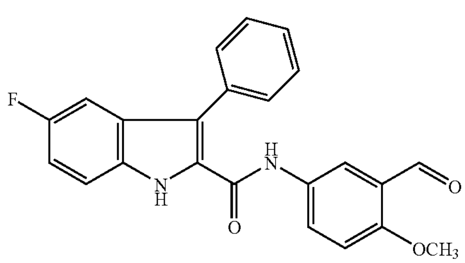 | 388.39 | Oxidation of 2f |

TABLE VI-continued
LIBRARY OF 5-FLUOROINDOLE-2-CARBAXAMIDE
COMPOUNDS AND METHOD OF PREPARATION
| Cmpd Code | Structure | M.Wt. | Method of Preparation |
|---|---|---|---|
| 3i | 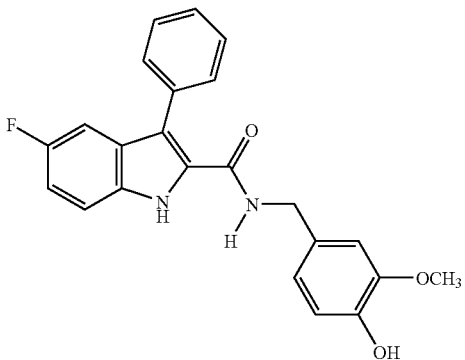 | 390.41 | Amide Coupling Method B |
| 3j | 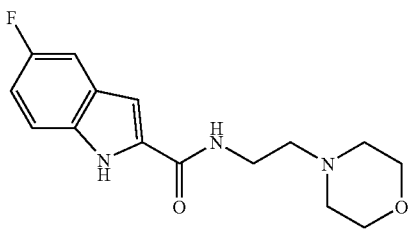 | 291.31 | Amide Coupling Method C |
| 3k | 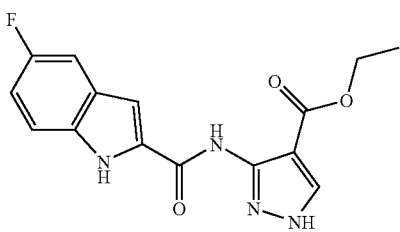 | 316.28 | Amide Coupling Method C |
| 3l | 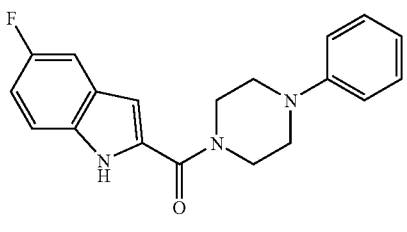 | 323.35 | Amide Coupling Method C |
| 3m | 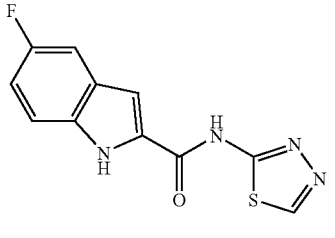 | 262.26 | Amide Coupling Method C |
| 3n | 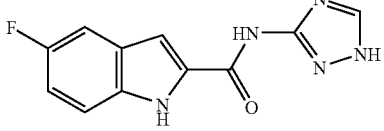 | 245.21 | Amide Coupling Method C |

TABLE VI-continued

LIBRARY OF 5-FLUOROINDOLE-2-CARBAXAMIDE
COMPOUNDS AND METHOD OF PREPARATION

| Cmpd Code | Structure | M.Wt. | Method of Preparation |
|---|---|---|---|
| 3o | 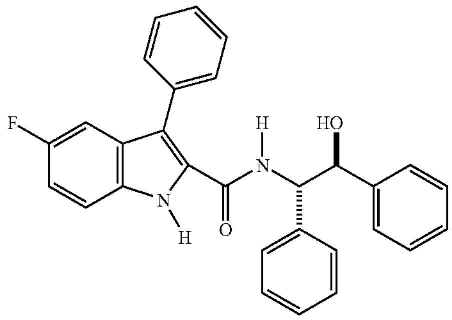 | 450.5 | Amide Coupling Method B |
| 3p | 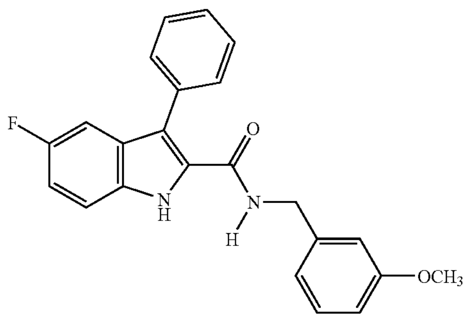 | 374.41 | Amide Coupling Method B |
| 3q | 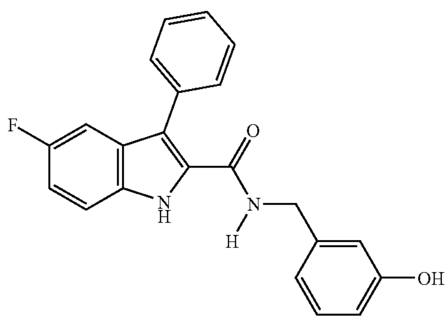 | 360.38 | See synthesis of 1a in Example 1 |
| 3r | 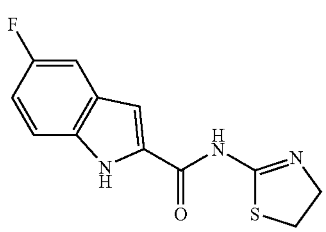 | 263.3 | Amide Coupling Method D |
| 3s | 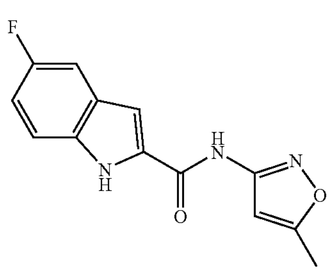 | 259.24 | Amide Coupling Method D |

TABLE VI-continued
LIBRARY OF 5-FLUOROINDOLE-2-CARBAXAMIDE
COMPOUNDS AND METHOD OF PREPARATION
| Cmpd Code | Structure | M.Wt. | Method of Preparation |
|---|---|---|---|
| 3t | 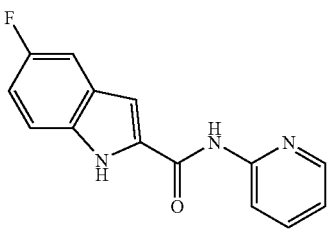 | 255.25 | Amide Coupling Method D |
| 3u | 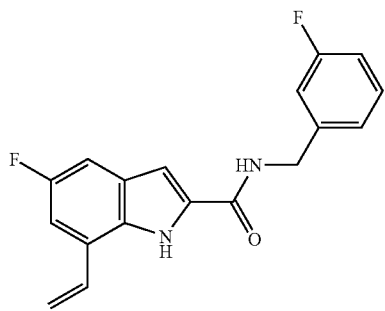 | | |
| 3v | 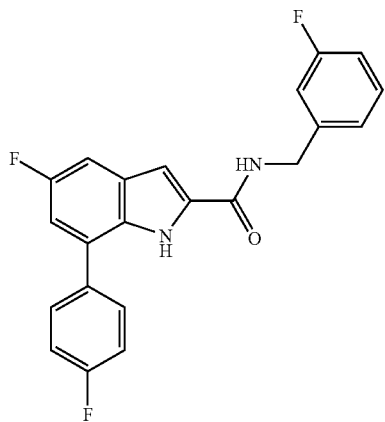 | | |
| 3w | 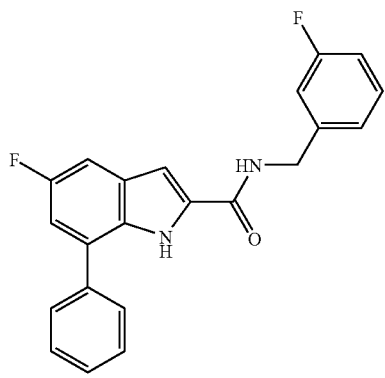 | | |

TABLE VI-continued
LIBRARY OF 5-FLUOROINDOLE-2-CARBAXAMIDE
COMPOUNDS AND METHOD OF PREPARATION
| Cmpd Code | Structure | M.Wt. | Method of Preparation |
|---|---|---|---|
| 3x | 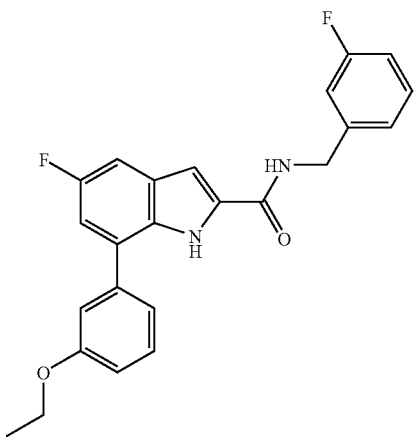 | | |
| 3y | 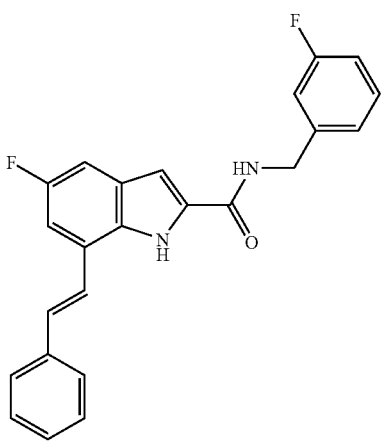 | | |
| 3z | 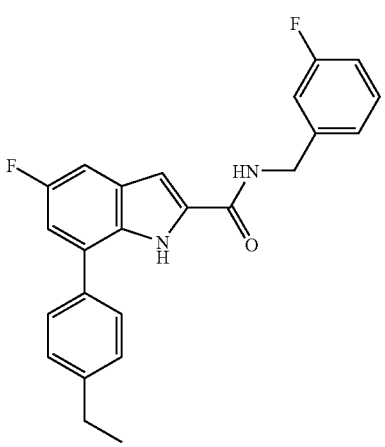 | | |

TABLE VI-continued

LIBRARY OF 5-FLUOROINDOLE-2-CARBAXAMIDE COMPOUNDS AND METHOD OF PREPARATION

| Cmpd Code | Structure | M.Wt. | Method of Preparation |
|---|---|---|---|
| 3aa | 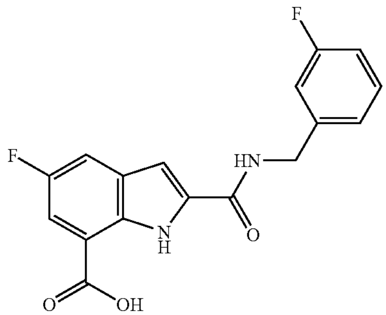 | | |
| 3bb | 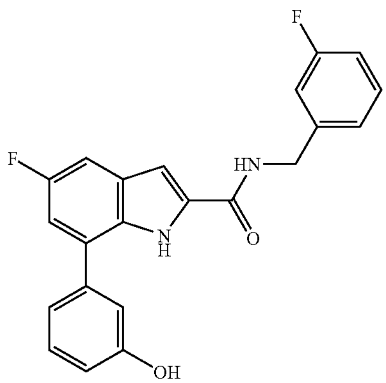 | | |
| 3cc | 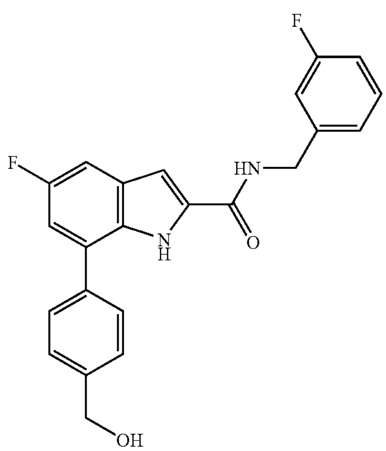 | | |
| 3dd | 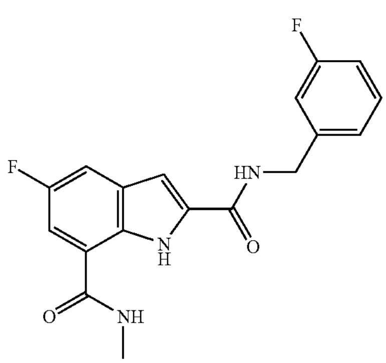 | | |

C. Inhibition of Human Cancer Cell Line H460 and Isolated Src.

Subsequent to synthesis, several of the above compounds were tested for the inhibition of the growth of human lung cancer cell line H460 and the inhibition of isolated Src. To test for inhibition of H460, the cells were seeded at 600 cells/well in 96 well plates in complete medium-RPMI-1640 containing 5% FCS, 5% NuSerum IV, 2 mM L-glutamine, and 10 mM HEPES. Following an overnight incubation, compounds which were solubilized in DMSO and diluted in RPMI-1640, were added to cells plates. After 72 hours, cells were fixed, stained, and total protein/well was determined. Compound concentration which inhibited growth by 50% ($IC_{50}$) was determined and is reported below. To test for inhibition of isolated Src, the compounds were tested using the assay procedure described in Lai et al., 1998, with the following assay components, final concentrations, and conditions: 50.0 mM MOPS, 4.02 mM $MgCl_2$, 6.00 mM $K_3$ citrate (used as a $Mg^{2+}$ buffer to stabilize the free $Mg^{2+}$ at 0.5 mM), 99.0 mM KCl, 10.0 mM 2-mercaptoethanol, 198 µM ADP, 10 U full length human purified recombinant $pp60^{c\text{-}src}$ (Upstate Biotechnology Inc., Lake Placid, N.Y.), 2.00 mM RR-SRC, 4.0% DMSO, pH 7.2, 37° C. These overall assay conditions have been shown to reproduce the intracellular conditions of pH, temperature, free $M^{2+}$ (0.5 mM), ionic strength, osmolality, ATP/ADP, and reduction potential. The results are in Table VII, below.

TABLE VII

INHIBITION OF THE GROWTH OF HUMAN LUNG CANCER CELL LINE H460 AND THE INHIBITION OF ISOLATED SRC

| Compound | $H460^a$ $IC_{50}$ $(\mu M)^b$ | Src $IC_{50}$ (µM) |
|---|---|---|
| 1a | 35 ± 0.59 | $IC_{50}$ = 40 |
| 1z | 15 ± 1.6 | $NT^c$ |
| 1bb | 82 ± 3.5 | NT |
| 1dd | 33 ± 0.78 | NT |
| 1yyy | 104 ± 10 | NT |
| 1cc | 30 ± 0.66 | NT |
| 1cccc | >100 | NT |
| 1oooo | 74 ± 2.7 | NT |
| 2f | 13 ± 0.46 | NT |
| 2s | 26 ± 0.34 | NT |
| 1bbb | >100 | NT |
| 2g | 13 ± 0.56 | NT |
| 3q | 30 ± 0.34 | NT |

$^a$H460 - NSCLC cells.
$^b$All compounds were solubilized in DMSO and further diluted in RPMI 1640 containing 5% FCS, 5% NuSerum IV, 2 mM L-glutamine, and 20 mM HEPES.
$^c$NT = not tested.

These results show that the use of a phenyl group attached to the 3 position of the indole ring can significantly improve the activity of the inhibitor.

D. Inhibition of Epidermal Growth Factor Receptor Tyrosine Kinase (EGFRTK), p56 lck, p55 fyn, and PTP-1B The compounds listed in Table VIII below were tested for inhibition of EGFRTK, a transmembrane receptor tyrosine kinase, p56 lck, a member of the Src family of non-receptor tyrosine kinases, p55 fyn, another member of the Src family of non-receptor tyrosine kinases, and PTP-1B, a phosphotyrosine phosphatase, the opposite of a kinase and a target for type II diabetes and/or obesity. The data in the table are the % inhibition of the indicated enzyme by the compound at a concentration of 10 micromolar. Blanks for a particular enzyme indicate that inhibition was not found.

TABLE VIII

INHIBITION OF EGFRPTK, p56 lck, p55 fyn, and PTP-1B

| Structure | MW | Compound Code | PTP-1B @ 10 µm | EGFRTK @ 10 µm | p 56 Lck @ 10 µm | p55 fyn @ 10 µm |
|---|---|---|---|---|---|---|
| [5-F-indole-2-carboxamide with N-CH(CH₂CH₂CH₃)CH₂OH] | 264.3 | 1b | | | | |
| [5-F-indole-2-carboxamide with N-CH(CH(CH₃)₂)CH₂OH] | 264.3 | 1c | | | | |
| [5-F-indole-2-carboxamide with N-CH(CH₃)CH₂OH] | 236.2 | 1d | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 5-F-indole-2-C(O)NH-CH2-CH(OH)-CH2OH | 252.2 | 1e | | | | |
| 5-F-indole-2-C(O)NH-Me | 192.2 | 1f | | | | |
| 5-F-indole-2-C(O)N(n-Pr)2 | 262.3 | 1g | | | | 19 |
| 5-F-indole-2-C(O)NH-iBu | 234.3 | 1h | | | | |
| 5-F-indole-2-C(O)N(n-Bu)2 | 290.4 | 1i | | | | |
| 5-F-indole-2-C(O)NH-(3-F-phenyl) | 272.3 | 1j | | | | |
| 5-F-indole-2-C(O)NH-(4-phenoxy-phenyl) | 346.4 | 1k | | | | 13 |
| 5-F-indole-2-C(O)NH-(4-OCH3-phenyl) | 284.3 | 1l | | | | |
| 5-F-indole-2-C(O)NH-(4-OH-phenyl) | 270.3 | 1m | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 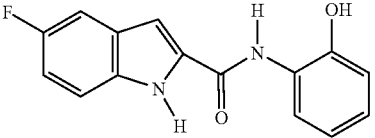 | 270.3 | 1n | | | 12 | |
| 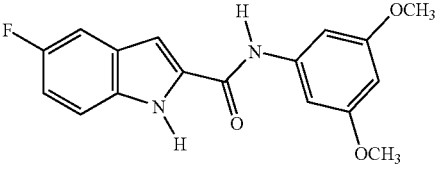 | 314.3 | 1o | | | | |
| 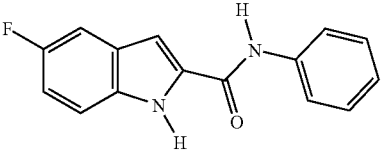 | 254.3 | 1p | | | | |
| 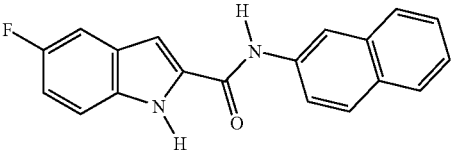 | 304.3 | 1q | | | | |
| 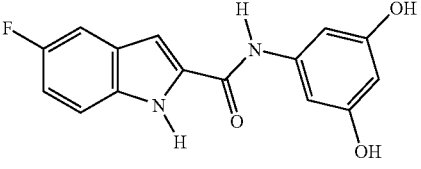 | 286.3 | 1r | | | 11 | |
| 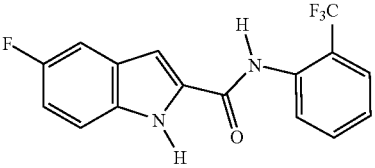 | 322.3 | 1s | | | | |
| 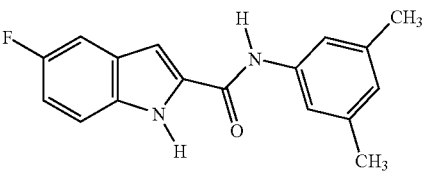 | 282.3 | 1t | | | | 11 |
| 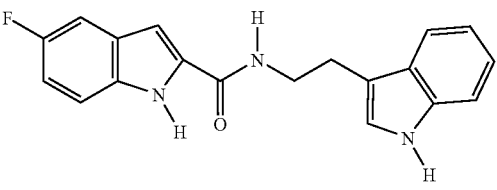 | 321.4 | 1u | | | | 10 |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 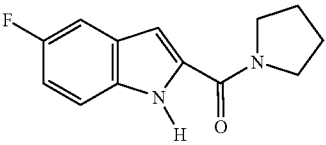 | 232.3 | 1v | | | | |
| 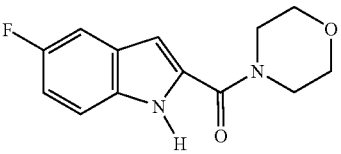 | 248.3 | 1w | | | | 10 |
| 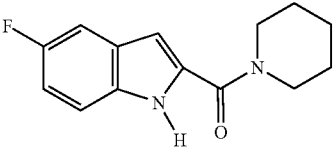 | 246.3 | 1x | | | | |
| 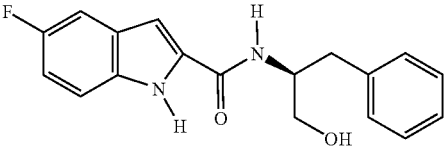 | 312.3 | 1y | | | | |
| 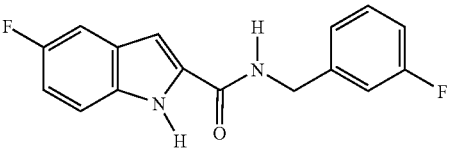 | 286.3 | 1z | | 26 | | |
| 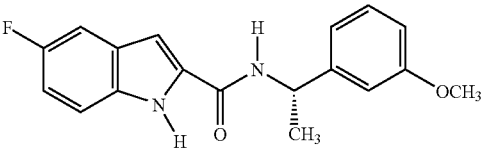 | 312.3 | 1aa | | 12 | | 10 |
| 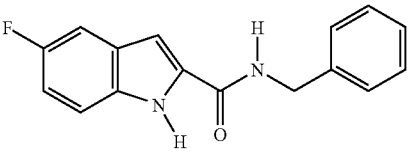 | 268.3 | 1bb | | 19 | | |
| 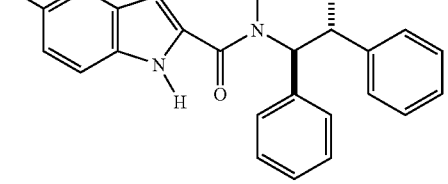 | 374.4 | 1cc | | 19 | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 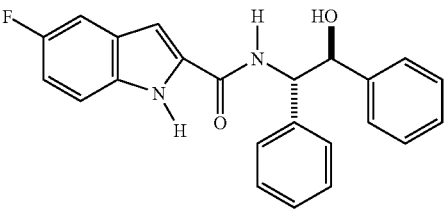 | 374.4 | 1dd | | 41 | | |
| 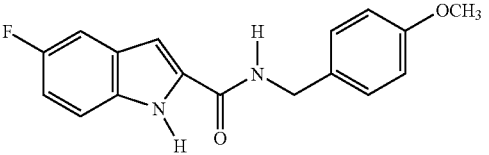 | 298.3 | 1ee | | 16 | | |
| 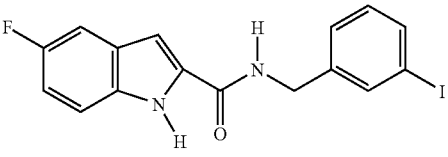 | 394.2 | 1ff | | 24 | | |
| 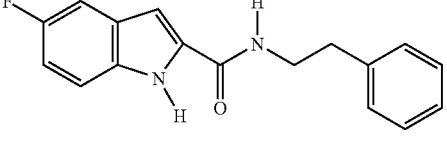 | 282.3 | 1gg | | | | |
| 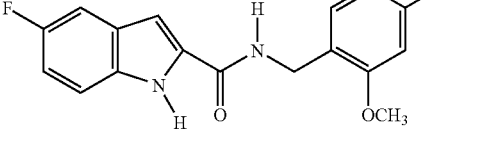 | 328.3 | 1hh | | | | |
| 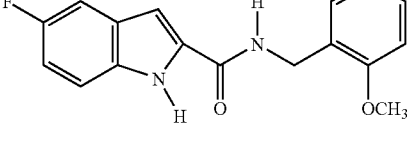 | 298.3 | 1ii | | | | |
| 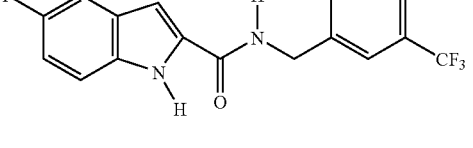 | 336.3 | 1jj | | | | 18 |
| 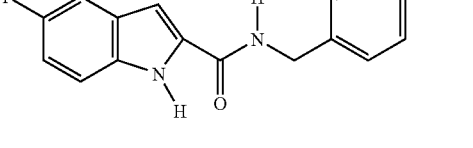 | 336.3 | 1kk | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 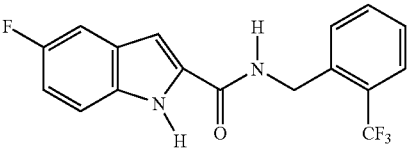 | 336.3 | 1ll | | | | |
| 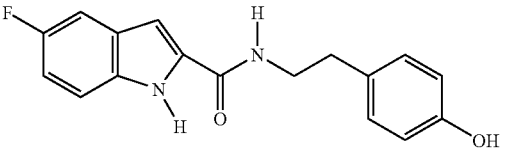 | 298.3 | 1mm | | | | |
| 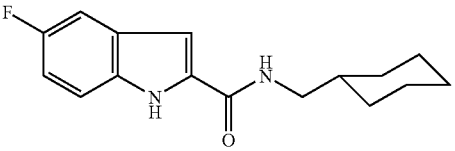 | 274.3 | 1nn | | | | |
| 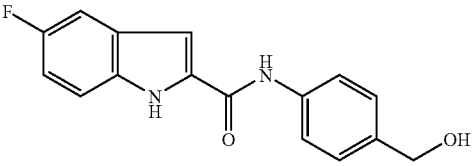 | 284.3 | 1oo | | | | 17 |
| 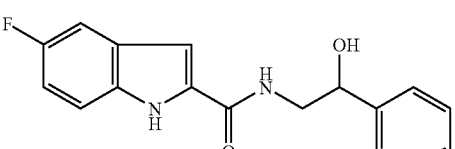 | 298.3 | 1pp | | | | |
| 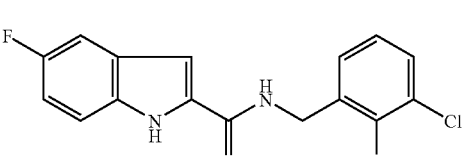 | 337.2 | 1qq | | | | |
| 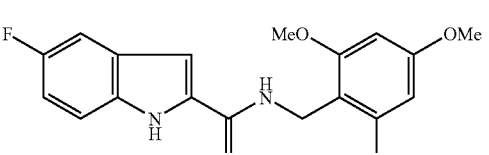 | 358.4 | 1rr | | | 12 | |
| 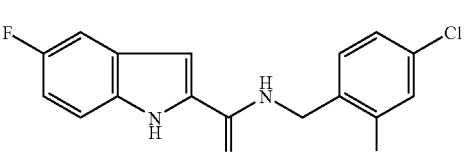 | 337.2 | 1ss | 12 | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| (5-fluoro-1H-indol-2-yl)-N-(2,5-difluorobenzyl)carboxamide | 304.3 | 1tt | | | | |
| (5-fluoro-1H-indol-2-yl)-N-(2,5-dimethylbenzyl)carboxamide | 296.3 | 1uu | | | | |
| (5-fluoro-1H-indol-2-yl)-N-(2-bromobenzyl)carboxamide | 347.2 | 1vv | | | | |
| (5-fluoro-1H-indol-2-yl)-N-(2-chloro-4-fluorobenzyl)carboxamide | 320.7 | 1ww | | | | |
| (5-fluoro-1H-indol-2-yl)-N-(2-chloro-6-methylbenzyl)carboxamide | 316.8 | 1xx | | | | 14 |
| (5-fluoro-1H-indol-2-yl)-N-(2-chlorobenzyl)carboxamide | 302.7 | 1yy | 10 | | | 12 |
| (5-fluoro-1H-indol-2-yl)-N-(2-ethoxybenzyl)carboxamide | 312.3 | 1zz | | | | |
| (5-fluoro-1H-indol-2-yl)-N-(2-fluoro-5-trifluoromethylbenzyl)carboxamide | 354.3 | 1aaa | 12 | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 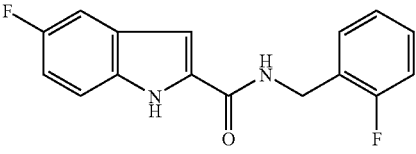 | 286.3 | 1bbb | | | | |
| 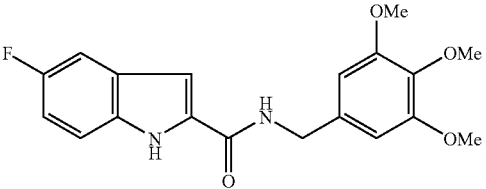 | 358.4 | 1ccc | | | | |
| 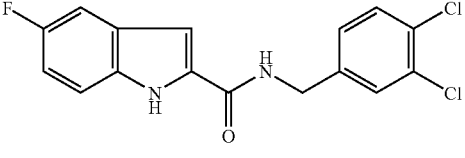 | 337.2 | 1ddd | | | | |
| 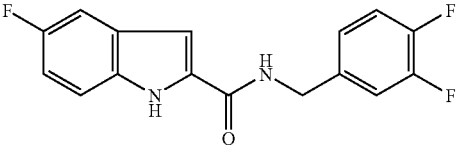 | 304.3 | 1eee | | | | |
| 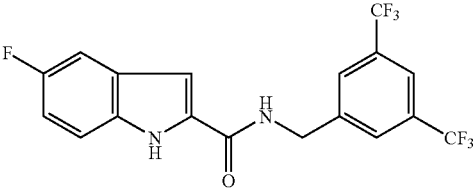 | 404.3 | 1fff | | | | |
| 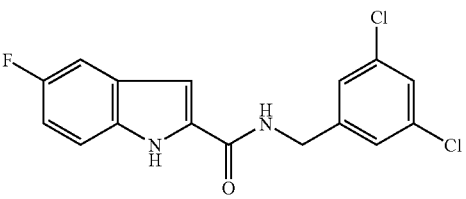 | 337.2 | 1ggg | | | | |
| 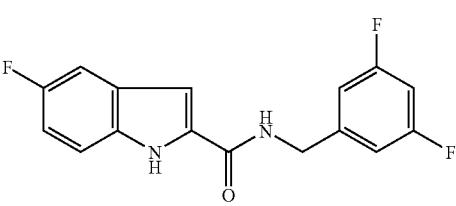 | 304.3 | 1hhh | | | | |
| 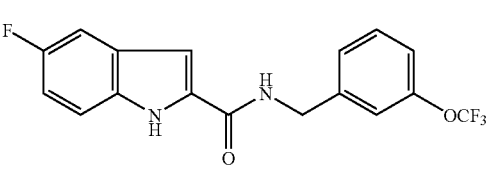 | 352.3 | 1iii | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 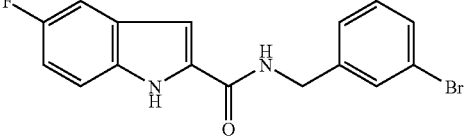 | 347.2 | 1jjj | | | | |
| 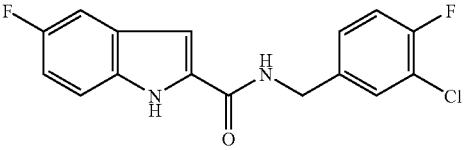 | 320.7 | 1kkk | | | | |
| 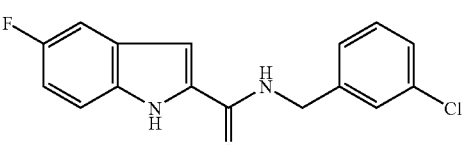 | 302.7 | 1lll | | | | |
| 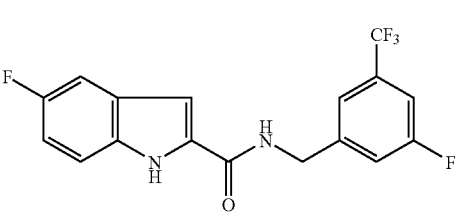 | 354.3 | 1mmm | | | | 14 |
| 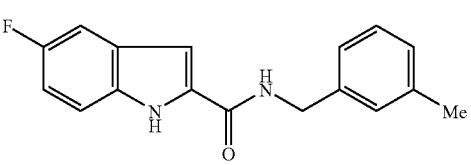 | 282.3 | 1nnn | | | | |
| 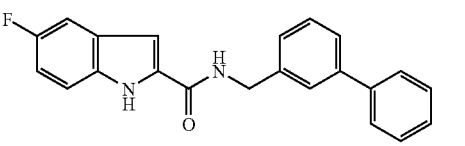 | 344.4 | 1ooo | | | | |
| 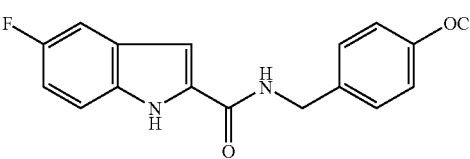 | 352.3 | 1ppp | | | | |
| 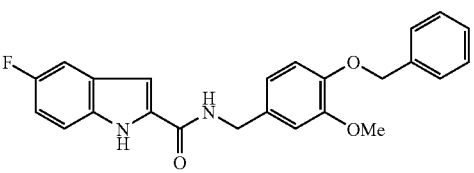 | 404.4 | 1qqq | | | | 11 |
| 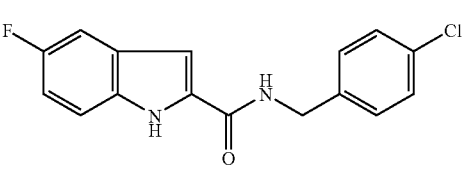 | 302.7 | 1rrr | | | | 15 |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 5-F-indole-2-C(O)NH-CH2-(2-CF3,4-F-phenyl) | 354.3 | 1sss | | | | |
| 5-F-indole-2-C(O)NH-CH2-(3-CF3,4-F-phenyl) | 354.3 | 1ttt | | | | |
| 5-F-indole-2-C(O)NH-CH2-(4-F-phenyl) | 286.3 | 1uuu | 13 | | | 16 |
| 5-F-indole-2-C(O)NH-CH2-(4-Me-phenyl) | 282.3 | 1vvv | | | | |
| 5-F-indole-2-C(O)NH-CH2-(2-F,5-Br-phenyl) | 365.2 | 1www | | | | |
| 5-F-indole-2-C(O)NH-(2-CH2OH-phenyl) | 284.3 | 1xxx | 12 | | | |
| 5-F-indole-2-C(O)NH-(3-CH2OH-phenyl) | 284.3 | 1yyy | | | 11 | |
| 5-F-indole-2-C(O)NH-(3-OH-phenyl) | 270.3 | 1zzz | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| F-indole-C(O)NH-C6H3(CH2OH)(O-propyl) | 342.4 | 1aaaa | | | | |
| F-indole-C(O)NH-C6H3(CH2OH)(O-benzyl) | 390.4 | 1bbbb | | | | |
| F-indole-C(O)NH-C6H3(CH2OH)(OCH3) | 314.3 | 1cccc | 20 | 19 | | |
| F-indole-C(O)NH-CH2-C6H3(OH)(O-benzyl) | 390.4 | 1dddd | 16 | | | |
| F-indole-C(O)NH-CH2-C6H3(OCH3)2 | 328.3 | 1eeee | | | | |
| F-indole-C(O)NH-CH2-C6H4-CH3 | 282.3 | 1ffff | | 12 | | |
| F-indole-C(O)NH-CH2-C6H3(OH)2 | 300.3 | 1gggg | | 25 | | |
| F-indole-C(O)NH-CH2-C6H3(OCH3)2 | 328.3 | 1hhhh | 17 | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| (5-fluoro-1H-indole-2-carboxamide with N-benzyl-3,5-bis(benzyloxy)phenyl) | 480.5 | 1iiii | | 12 | | |
| (5-fluoro-1H-indole-2-carboxamide with N-benzyl-4-benzyloxy-3-hydroxyphenyl) | 390.4 | 1jjjj | 15 | | | |
| (5-fluoro-1H-indole-2-carboxamide with N-(4-bromobenzyl)) | 347.2 | 1kkkk | | 30 | | |
| (5-fluoro-1H-indole-2-carboxamide with N-benzyl-4-hydroxy-3-methoxyphenyl) | 314.3 | 1llll | | | | |
| (5-fluoro-1H-indole-2-carboxamide with N-(4-nitrobenzyl)) | 313.3 | 1mmmm | | | | 29 |
| (5-fluoro-1H-indole-2-carboxamide with N-benzyl-4-propoxy-3-hydroxyphenyl) | 342.4 | 1nnnn | | 17 | | 11 |
| (5-fluoro-1H-indole-2-carboxamide with N-(4-hydroxymethylbenzyl)) | 298.3 | 1oooo | | 33 | 10 | |
| (5-fluoro-1H-indole-2-carboxamide with N-(3-hydroxymethylbenzyl)) | 298.3 | 1pppp | | | | |
| (5-fluoro-1H-indole-2-carboxamide with N-(6-hydroxyhexyl)) | 278.3 | 1qqqq | | 18 | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 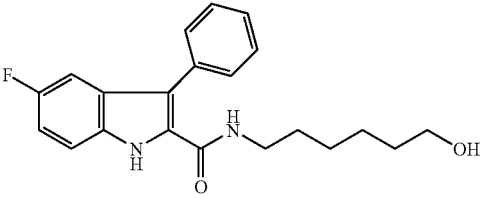 | 354.4 | 2a | | | | |
| 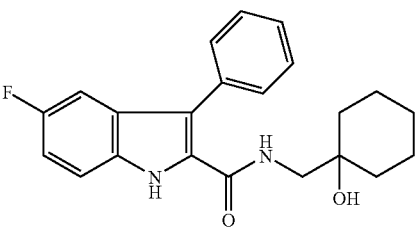 | 366.4 | 2b | | 19 | | 13 |
| 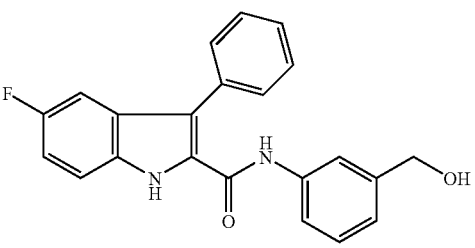 | 360.4 | 2c | | | | |
| 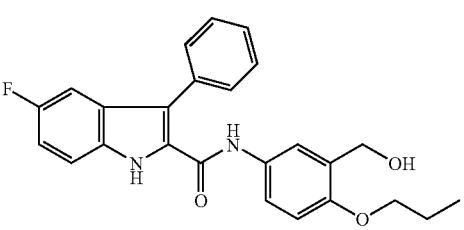 | 418.5 | 2d | | 23 | | |
| 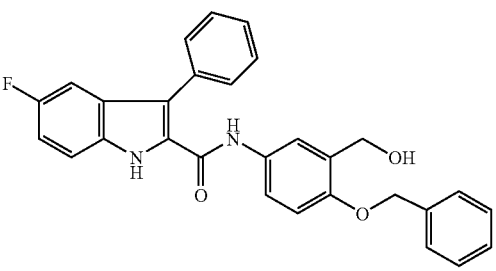 | 466.5 | 2e | | 10 | | |
| 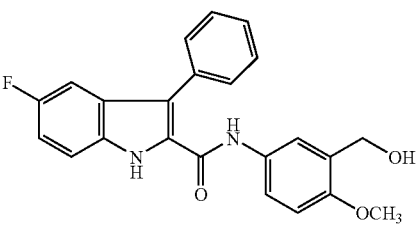 | 390.4 | 2f | | 18 | | 11 |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 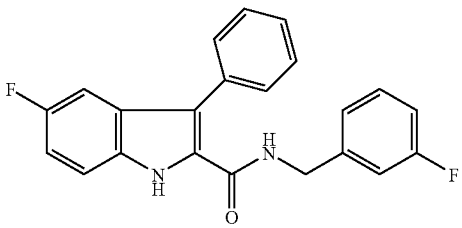 | 362.4 | 2g | | | | |
| 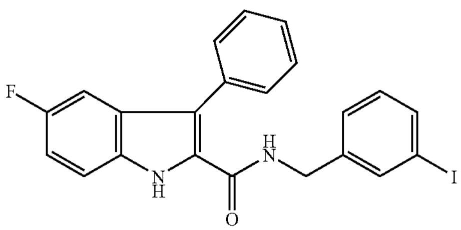 | 470.3 | 2h | | | | |
| | 412.4 | 2i | | | | |
| | 412.4 | 2j | | | 20 | |
| 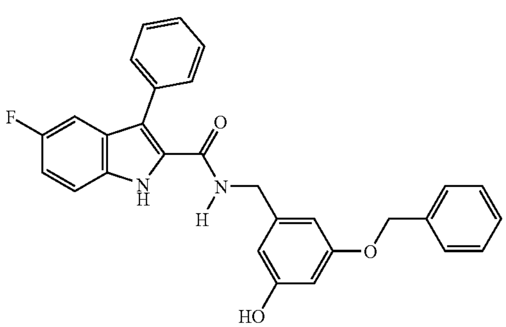 | 466.5 | 2k | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 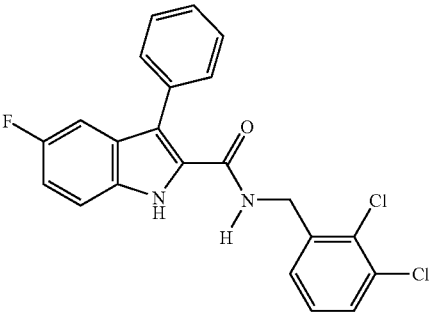 | 413.3 | 2l | | | | |
| 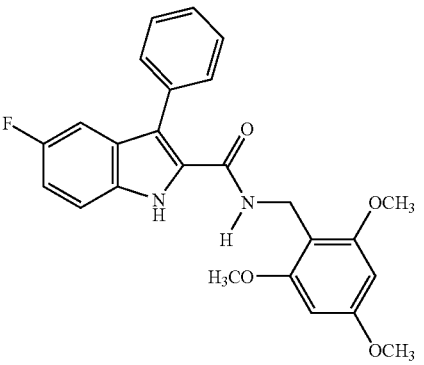 | 434.5 | 2m | | | | |
| 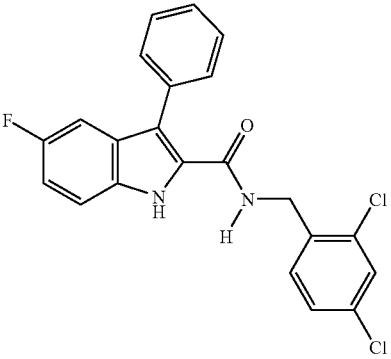 | 413.3 | 2n | | | | |
| 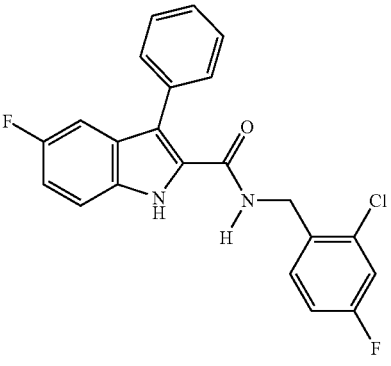 | 396.8 | 2o | | | | 12 |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| (5-fluoro-3-phenyl-1H-indole-2-carboxylic acid (2-chloro-6-methyl-benzyl)amide) | 392.9 | 2p | | | | |
| (5-fluoro-3-phenyl-1H-indole-2-carboxylic acid (2-chloro-benzyl)amide) | 378.8 | 2q | | | | |
| (5-fluoro-3-phenyl-1H-indole-2-carboxylic acid (2-fluoro-5-trifluoromethyl-benzyl)amide) | 430.4 | 2r | | | | |
| (5-fluoro-3-phenyl-1H-indole-2-carboxylic acid (2-fluoro-benzyl)amide) | 362.4 | 2s | | 33 | 10 | 11 |

TABLE VIII-continued
| INHIBITION OF EGFRPTK, p56 lck, p55 fyn, and PTP-1B ||||||||
| Structure | MW | Compound Code | PTP-1B @ 10 μm | EGFRTK @ 10 μm | p 56 Lck @ 10 μm | p55 fyn @ 10 μm |
| --- | --- | --- | --- | --- | --- | --- |
| 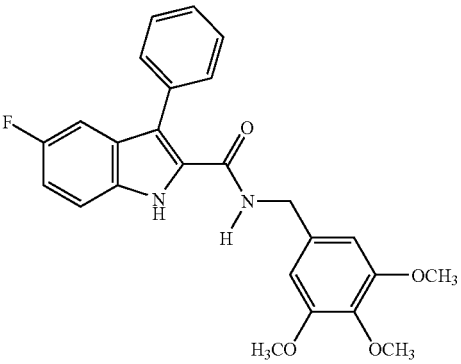 | 434.5 | 2t | | | | |
| 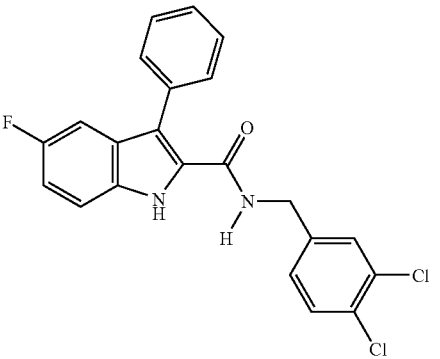 | 413.3 | 2u | | | | |
| 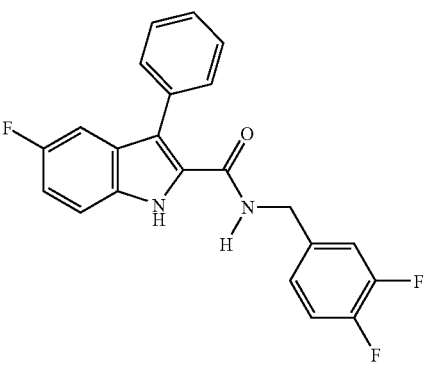 | 380.4 | 2v | | | | |
| 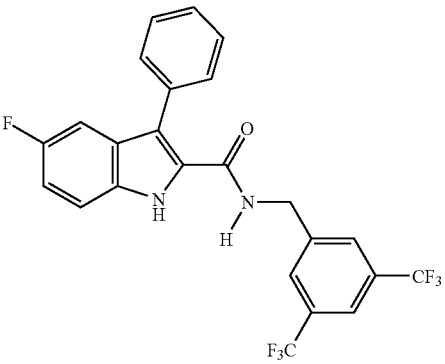 | 480.4 | 2w | 12 | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 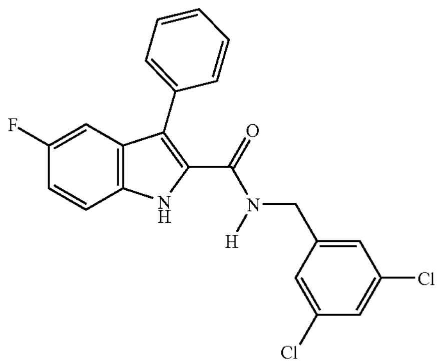 | 413.3 | 2x | | | | |
| 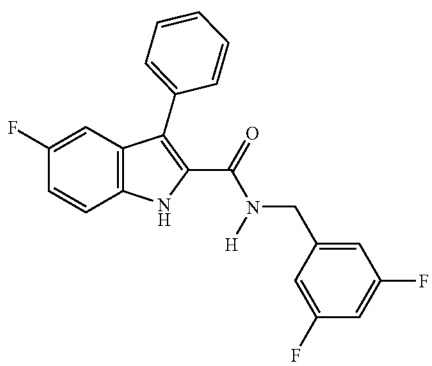 | 380.4 | 2y | | 20 | | |
| 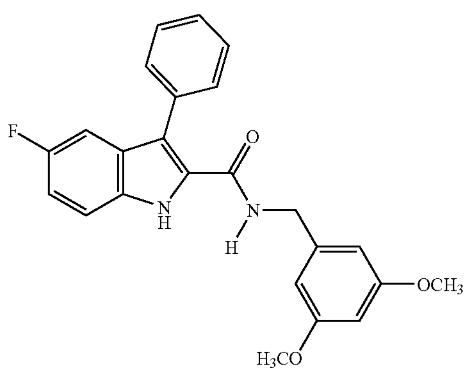 | 404.4 | 2z | | | | |
| 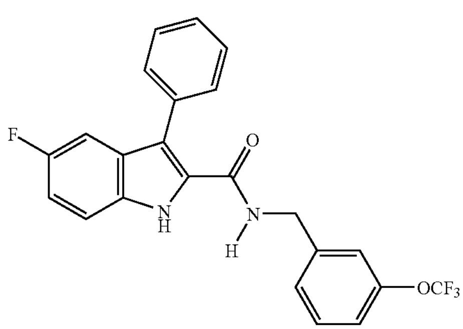 | 428.4 | 2aa | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 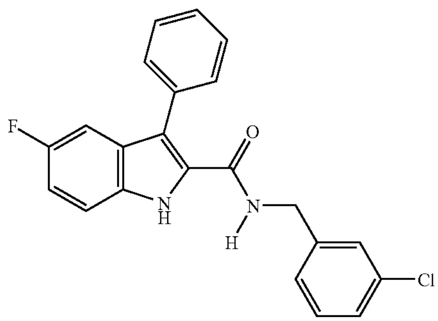 | 378.8 | 2bb | | | | |
| 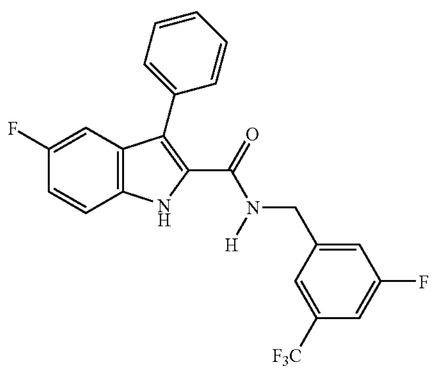 | 430.4 | 2cc | | | | |
| 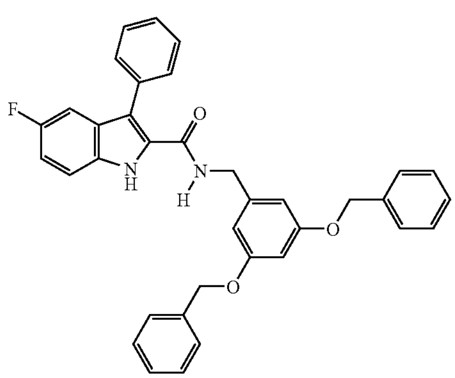 | 556.6 | 2dd | | | | |

TABLE VIII-continued

| | | | INHIBITION OF EGFRPTK, p56 lck, p55 fyn, and PTP-1B | | | |
|---|---|---|---|---|---|---|
| Structure | MW | Compound Code | PTP-1B @ 10 μm | EGFRTK @ 10 μm | p 56 Lck @ 10 μm | p55 fyn @ 10 μm |
| | 466.5 | 2ee | | | | |
| | 428.4 | 2ff | | | | |
| | 378.8 | 2gg | 12 | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 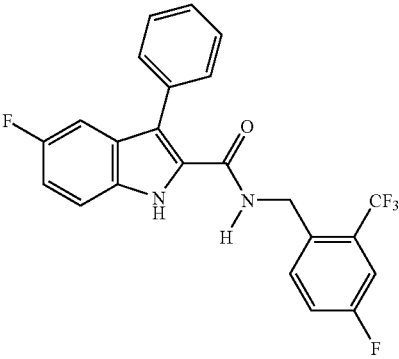 | 430.4 | 2hh | | 12 | | |
| 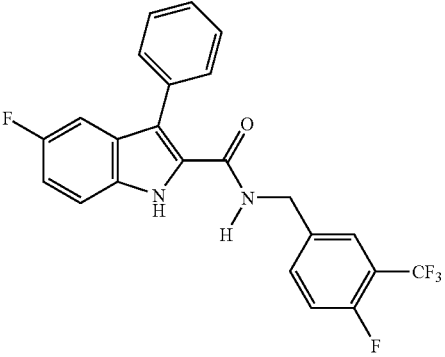 | 430.4 | 2ii | | | | |
| 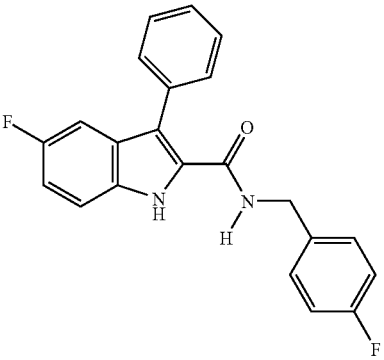 | 362.4 | 2jj | | | | |
| 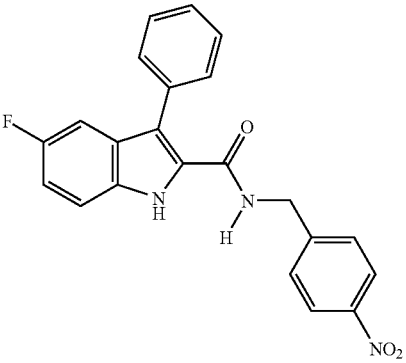 | 389.4 | 2kk | | 24 | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p 56 Lck @ 10 μm | p55 fyn @ 10 μm |
|---|---|---|---|---|---|---|
| 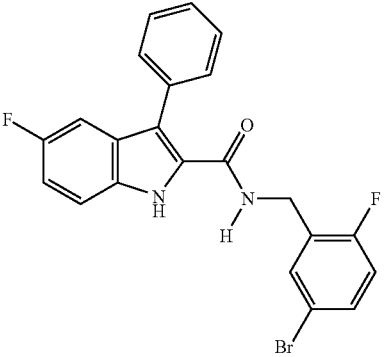 | 441.3 | 2ll | | 10 | | |
| 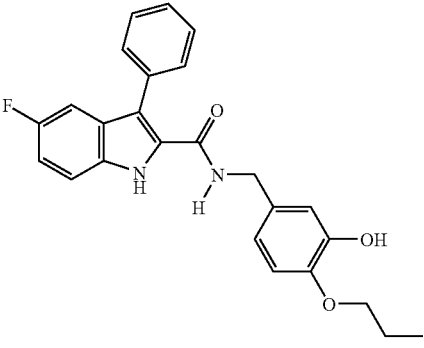 | 418.5 | 2mm | | | | |
| 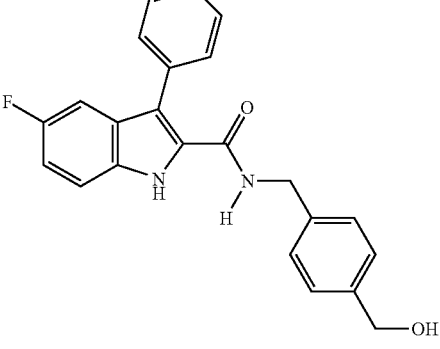 | 374.4 | 2nn | | | | |
| 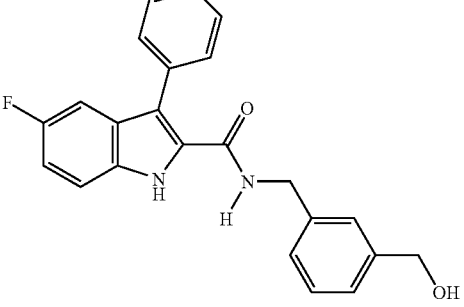 | 374.4 | 2oo | | | | |
E. Mice Toxicity Study
FIG. 15 shows the results of a maximum tolerated dose (MTD) study with two indole inhibitors:

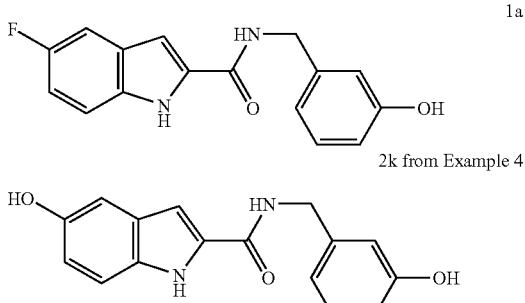

Figure 17:
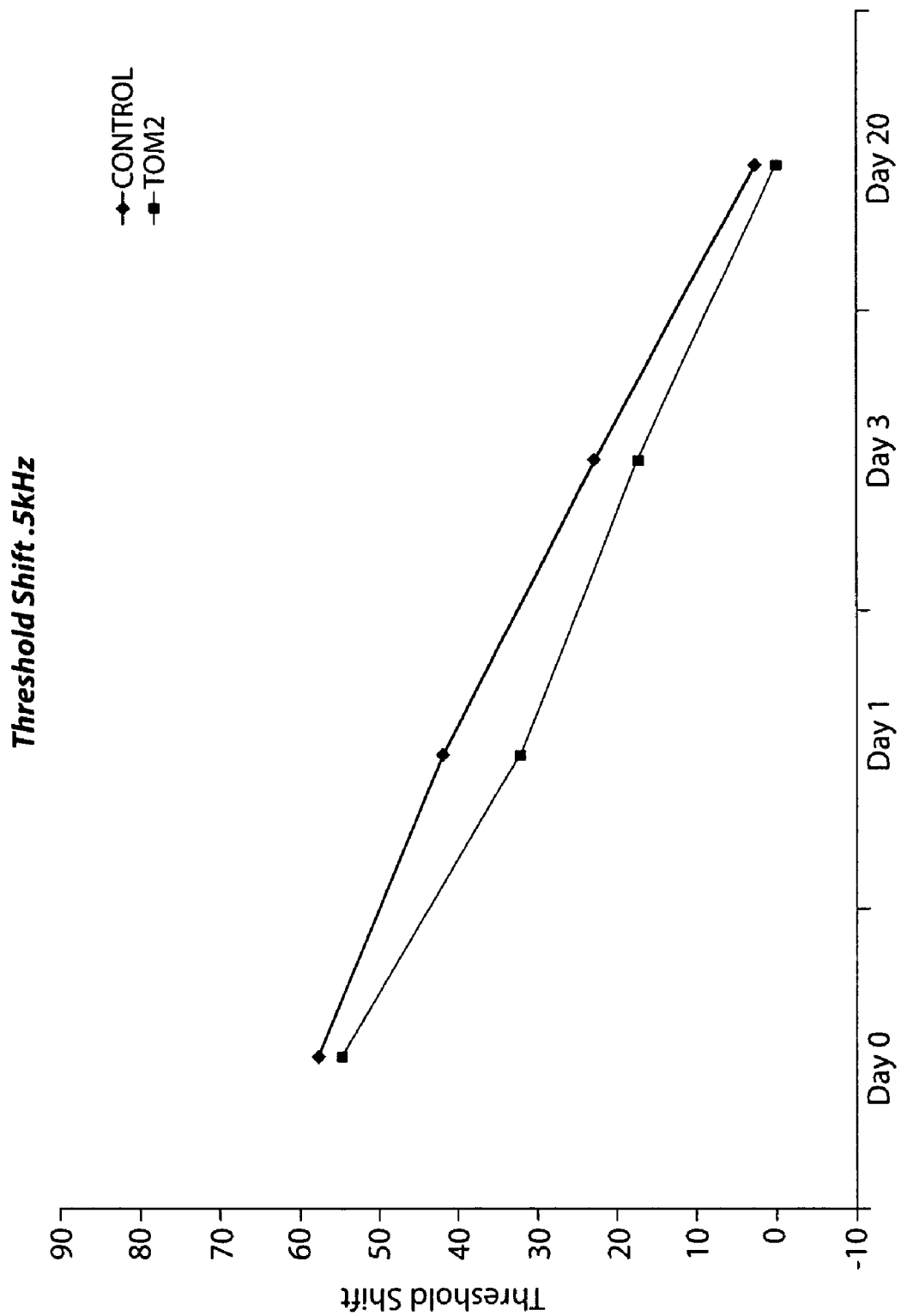
FIG. 17 is a graph showing average threshold shifts (dB) in chinchilla cochleas after exposure to 0.5 kHz band noise at day 0, day 1, day 3, and day 20 after experimental manipulation.

These compounds were administered to SCID mice by intraperitoneal administration in tween80:EtOH. The results in FIG. 17 show that compound 1a is less toxic in mice than compound 2k from Example 4, since the mice exhibited less weight loss when compound 1a was administered.

Example 2

Synthesis and Activity of 7-Substituted Indole Derivative Protein Kinase Inhibitors 7-substituted indole derivative protein kinase inhibitors were synthesized as set forth in Scheme 1, below:

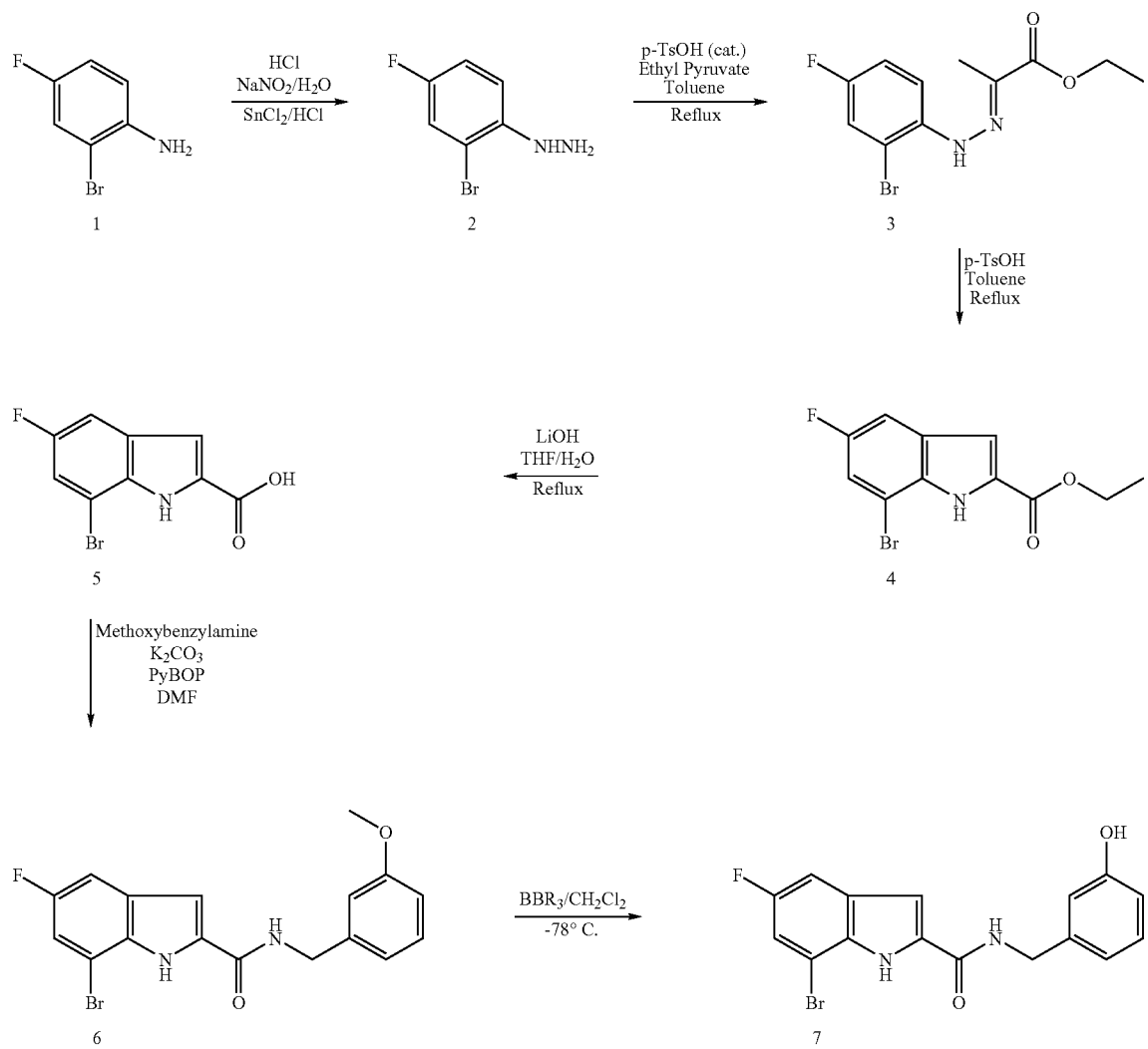

(2-bromo-4-fluoro-phenyl)-hydrazine (2)

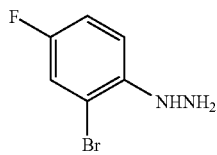

Commercially available 2-bromo-4-fluoroaniline 1 (2.36 ml, 20.75 mmol) was added to a stirring solution of concentrated hydrochloric acid (40 ml) that was cooled to −5° C. This solution was allowed to age while stirring for 10 minutes. An aqueous solution of $NaNO_2$ was added over 15 minutes. $SnCl_2$/HCl (10.40 g, 46.1 mmol, 10 ml HCl) was added over 15 minutes and aged for an additional 30 minutes to 1 hour. The mixture was filtered and washed with dichloromethane. The resulting solid was dissolved in 11.0M HCl and extracted 3 times with dichloromethane. The organic layer was vacuum dried overnight to give 3.53 g (83% yield). $^1H$ NMR (400 MHz, $CDCl_3$): δ7.169 (dd, J=8 Hz, J=2.8 Hz 1H), δ 7.076 (dd, J=5.2 Hz, J=9.2 Hz, 1H), δ6.982 (td, J=8.4 Hz, J=2 Hz 1H), δ5.540 (bs, 1H), δ 3.590 (bs, 1H).

2-[(2-bromo-4-fluoro-phenyl)-hydrazono]-propionic acid ethyl ester (3)

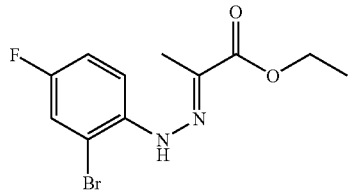

Commercially available p-toluensulfonic acid (38.37 mg, 0.217 mmol) was added to 60 ml of toluene in a round bottom flask and magnetic stir bean. The flask was then fitted with a Dean Stark trap and reflux condenser. The solution was then allowed to stir for 2 hours. After 2 hours, the solution was cooled and 2-(bromo-4-phenyl)hydrazine (4.135 g, 20.17 mmol) was added. The solution was then refluxed for an additional 1.5 hours using the same apparatus. After 1.5 hours, the solution was placed on the rotary evaporator to remove the toluene. A dark brown tar-like substance was left in the flask. An appropriate amount of hexanes were added to the flask and refluxed to dissolve the pure hydrazine. The hexanes took on a yellow color and were then decanted hot into another flask leaving the tar-like side product behind. This was repeated. The flask containing the hexane solution was refluxed so as to dissolve the precipitating hydrazine and placed in the freezer to form crystals. 3.6 g (11.9 mmol, 87% yield) of 3. $^1H$ NMR (Acetone-$d_6$): δ 12.369 (bs, 1H), δ 7.646 (dd, J=9.2 Hz, J=5.6 Hz 1H), δ 7.449 (dd, J=8.2 Hz, J=2.8 Hz 1H), δ 7.22 (td, J=8.6 Hz, J=2.8 Hz, 1H), δ 4.37 (q, J=7.2 Hz, 2H), δ 2.203 (s, 3H), δ 1.402 (t, J=7.2 Hz, 3H).

7-bromo-5-fluoro-1H-indole-2-carboxylic acid ethyl ester (4)

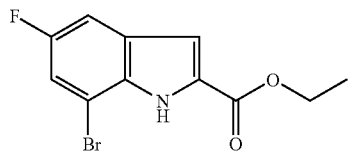

Commercially available p-toluensulfonic acid dihydrate (2.26 g, 11.9 mmol) was added to 120 ml of toluene and dried under reflux using a Dean Stark apparatus for 2 hours. 2-[(2-bromo-4-fluoro-phenyl)-hydrazono]-propionic acid ethyl ester (3.6 g, 11.9 mmol), was added to the cooled solution, and refluxed for an additional 1.5 hours. After 1.5 hours the solution was cooled. The toluene was removed under reduced pressure. Then the solid was refluxed with hexane to isolate the indole ester. The resulting hexane solution was refluxed to dissolve the precipitating indole, and placed in the freezer for crystallization. After removal of supernatant and drying of crystals gave 3.30 g, 11.543 mmol of 4 (97% yield). $^1H$ NMR (400 MHz, Acetone-$d_6$): δ 10.85 (bs, 1H), δ 7.45 (dd, J=9.2 Hz, J=2.4 Hz, 1H), δ 7.39 (dd, J=9.2 Hz, J=2.0 Hz, 1H), δ 7.28 (d, J=2.0 Hz, 1H), δ 4.36 (q, J=6.8 Hz, 2H), δ 1.345 (t, J=6.8 Hz, 1H).

7-bromo-5-fluoro-1H-indole-2-carboxylic acid (5)

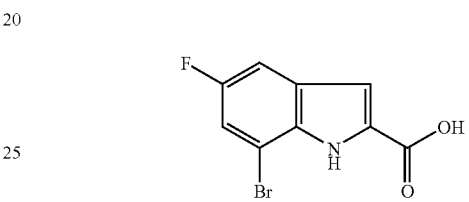

Tetrahydrofuran (35.2 ml), water (23.5 ml), lithium hydroxide (2.61 g, 10.9 mmol), and 7-bromo-5-fluoro-1H-indole-2-carboxylic acid ethyl ester (3.11 g, 10.9 mmol) were added to a round bottom flask and mixed with a magnetic stirrer. This mixture was refluxed for 1 hour. The THF was removed via rotary evaporator, and the aqueous solution was acidified with 1M HCL, and extracted with ethyl acetate. $^1H$ NMR (DMSO-$d_6$): δ 13.206 (bs, 1H), δ 11.876 (s, 1H), δ 7.498-7.445 (m, 2H), δ 7.19 (d, J=2.0 Hz, 1.0H).

7-bromo-5-fluoro-1H-indole-2-carboxylic acid 3-methoxy-benzylamide (6)

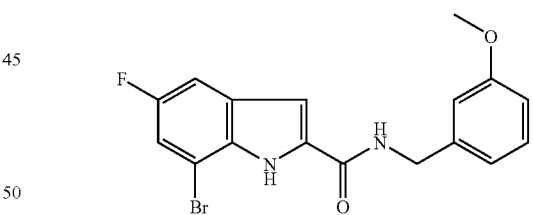

To a round bottom flask that has been fire dried, flushed with a continuous stream of argon, and equipped with a stir bean, DMF (4.8 ml) was added. To this stirring solution 5 (600 mg, 2.33 mmol), was combined with methoxybenzylamine (328 µL, 2.56 mmol), and PyBOP (1.33 g, 2.56 mmol). This solution was then cooled to a temperature of 0 degrees C. After 2 minutes diisopropylamine (1.7 ml, 9.67 mmol) was added and the entire solution was allowed to stir at room temperature overnight. The reaction was then diluted with roughly 60 ml of ethyl acetate and extracted 3× with saturated sodium bicarbonate, and 3× with 1M HCl in appropriate volumes to remove any unreacted starting materials. The ethyl acetate layer was isolated and dried over sodium sulfate. The ethyl acetate was removed using a rotary evaporator to yield a brownish film on the sides of the flask. Hexanes were added to the flask and refluxed. A solid then formed on the sides of the flask, and the hexanes were removed via rotary evaporator to give 709.0 mg of 6 (81% yield). $^1$H NMR (400 MHz, DMSO-d$_6$) δ 11.537 (bs, 1H), δ 9.092 (t, J=5.6 Hz, 1H), δ 7.49 (dd, J=9.4 Hz, J=2.4 Hz 1H), 6 (dd, J=8.8 Hz, J=2 Hz 1H), δ 7.268-7.228 (m, 2H), δ 6.91 (d, J=6.8 Hz, 2H), δ 6.82 (d, J=8.2 Hz, 1H), δ 4.48 (d, J=6 Hz, 2H), δ 3.729 (s, 3H).

7-bromo-5-fluoro-1H-indole-2-carboxylic acid 3-hydroxy-benzylamide (7)

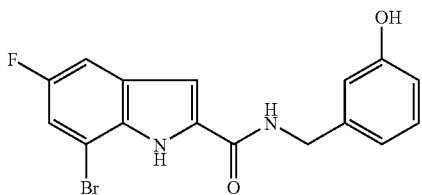

A stirring solution of methylene chloride (1 ml) was cooled to −78 degrees in a dry ice acetone bath and flushed with a stream of argon. To this cold stirring solution 6 (50 mg, 0.133 mmol) was added. 7 equivalents of BBr$_3$ was added and allowed to stir at −78 degrees for 1 hour, and then the solution was allowed to stir at room temperature overnight. The reaction was then quenched with excess water, then neutralized with saturated sodium bicarbonate, and extracted with methylene chloride. The methylene chloride layer was dried over sodium sulfate and removed under reduced pressure to yield 35.0 mg of 2 (70% yield). $^1$H NMR (400 MHz, Acetone-d$_6$) δ 10.633 (bs, 1H), δ 8.42 (d, J=15.6, 2H), 7.48 (dd, J=9.2 Hz, J=2.4 Hz, 1H), δ 7.42 (dd, J=9 Hz, J=2.4 Hz, 1H), δ 7.373 (d, J=2.4 Hz, 1H), δ 7.217 (t, J=7.6 Hz, 1H), δ 6.932-6.898 (m, 2H), δ 6.80 (dd, J=2 Hz, J=8 Hz, 1H), δ 4.634 (d, J=5.6 Hz, 2H). Disappearance of the characteristic methoxy peak at 3.7 ppm indicates a successful deprotection.

Example 3

Design, Synthesis and Activity of Non-ATP Competitive Hydroxynaphthalene Derivative Inhibitors of pp60$^{c\text{-}Src}$ Tyrosine Kinase The crystal structure of the autoinhibited human IRTK catalytic domain (Hubbard et al., 1994) was used to carry out qualitative molecular modeling studies (SYBYL™, 6.4, Tripos Inc., St. Louis) wherein a naphthalene ring was superimposed upon the IRTK Tyr 1,162. The IRTK region containing Tyr 1,162 folds back into the active site, with Tyr 1,162 positioned analogous to a phosphorylatable Tyr in a peptide substrate, thereby autoinhibiting the tyrosine kinase. This superimposition indicated that an amide carbonyl should be placed at the 2-position (Scheme 1) of the

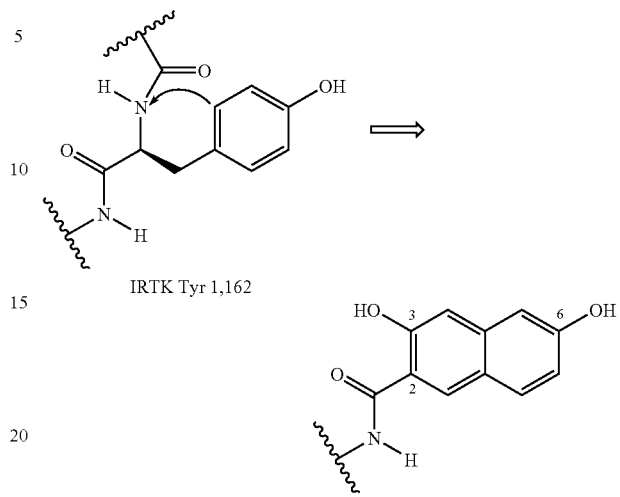

Scheme 1 naphthalene ring to mimic the Tyr 1,162 carbonyl and a hydroxyl group should be positioned at the 6-position to mimic the Tyr 1,162 hydroxyl group. These modeling studies also indicated that a hydroxyl group at the 3-position could mimic the Tyr 1,162 NH.

In order to test these design concepts experimentally, the 2-position carbonyl group was appended as either a methyl ester or as a series of amides (Table IX). The hydroxy N-phenyl (X=0) and N-benzyl (X=1) amides were chosen based upon the increase in pp60$^{c\text{-}src}$ inhibitor potency observed with iminochromene analogs containing appended hydroxy N-phenyl amide side-chains (Huang et al., 1995). Analogs wherein the 6-hydroxyl group was either deleted or moved were also prepared to determine if a drop in potency occurs as predicted from the modeling studies.

The series of 2-carbonyl-3,5-dihydroxy naphthalene inhibitors (1a, 2a-2d, 2i-2l, 2o-2p) and 2-carbonyl-3,7-dihydroxy naphthalene inhibitors (1c, 2t-2u) were synthesized from commercially available (Aldrich) 3,5-dihydroxy-2-naphthoic acid and 3,7-dihydroxy-2-naphthoic acid, respectively. The methyl esters 1a and 1c were obtained by refluxing the respective acid starting materials for 48 h in methanol pre-saturated with HCl gas. The amides (2a-2d, 2i-2l, 2o-2p, 2t-2u) were synthesized by coupling the respective carboxylic acid with commercially available (Aldrich or Lancaster) amines using one of two methods. The first method utilized the NBS/PPh$_3$ methodology as described by Froyen (Froyen, 1997). The second method utilized IIDQ (Aldrich) as the coupling reagent. The carboxylic acid was first reacted with 1.0 eq. IIDQ in anhydrous DMF at room temperature for 24 hours. The respective amine (2.0 eq.) was then added neat and the reaction was heated to 80° C. for 2-6 hours. After aqueous workup, purification was achieved by silica gel chromatography and precipitation from CH$_2$Cl$_2$/hexane, followed by preparative C-18 RP-HPLC (CH$_3$CN/H$_2$O), if necessary. The benzyl amines were commercially available only as their corresponding hydroxyl protected methyl ethers. Consequently, after amide formation, the hydroxyl groups were deprotected by treatment with 6 eq. BBr$_3$ in DCM for 1 minute at −78° C. followed by 1 hour at room temperature.

TABLE IX pp60[c-src] INHIBITORY ACTIVITY OF HYDROXYNAPHTHALENE DERIVATIVES AND SELECT PUBLISHED INHIBITORS.[a,b,c]

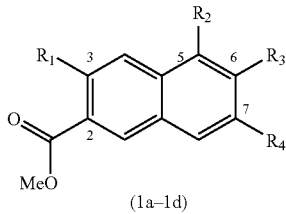

(1a–1d)

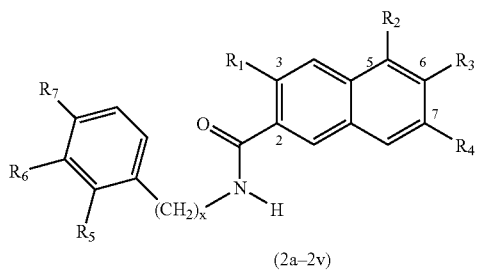

(2a–2v)

| Cmpd | $R_1$ | $R_2$ | $R_3$ | $R_4$ | $R_5$ | $R_6$ | $R_7$ | $R_8$ | % Inhibition at 100 μM (std. dev.) | $IC_{50}$ (μM) |
|---|---|---|---|---|---|---|---|---|---|---|
| 1a | OH | OH | H | H | N/A | N/A | N/A | N/A | 5 (+/−2) | n.t. |
| 1b | OH | H | OH | H | N/A | N/A | N/A | N/A | 47 (+/−3) | n.t. |
| 1c | OH | H | H | OH | N/A | N/A | N/A | N/A | 19 (+/−6) | n.t. |
| 1d | $NH_2$ | H | H | H | N/A | N/A | N/A | N/A | Inactive | n.t. |
| 2a | OH | OH | H | H | OH | H | H | 0 | 12 (+/−4) | n.t. |
| 2b | OH | OH | H | H | H | OH | H | 0 | 51 (+/−1) | 150 |
| 2c | OH | OH | H | H | H | H | OH | 0 | 60 (+/−7) | n.t. |
| 2d | OH | OH | H | H | OH | H | OH | 0 | 14 (+/−2) | n.t. |
| 2e | OH | H | OH | H | OH | H | H | 0 | 39 (+/−5) | n.t. |
| 2f | OH | H | OH | H | H | OH | H | 0 | 89 (+/−1) | 16 |
| 2g | OH | H | OH | H | H | H | OH | 0 | 23 (+/−5) | n.t. |
| 2h | OH | H | OH | H | OH | H | OH | 0 | 56 (+/−1) | n.t. |
| 2i | OH | OH | H | H | H | OMe | H | 0 | 33 (+/−5) | n.t. |
| 2j | OH | OH | H | H | H | H | OMe | 0 | 35 (+/−8) | n.t. |
| 2k | OH | OH | H | H | OMe | H | H | 1 | 13 (+/−3) | n.t. |
| 2l | OH | OH | H | H | H | H | OMe | 1 | 14 (+/−2) | n.t. |
| 2m | OH | H | OH | H | OMe | H | H | 1 | inactive | n.t. |
| 2n | OH | H | OH | H | H | H | OMe | 1 | 4 (+/−7) | n.t. |
| 2o | OH | OH | H | H | OH | H | H | 1 | 41 (+/−2) | n.t. |
| 2p | OH | OH | H | H | H | H | OH | 1 | 49 (+/−4) | n.t. |
| 2q | OH | H | OH | H | OH | H | H | 1 | 42 (+/−2) | n.t. |
| 2r | OH | H | OH | H | H | OH | H | 1 | 55 (+/−3) | nt. |
| 2s | OH | H | OH | H | H | H | OH | 1 | 42 (+/−3) | nt. |
| 2t | OH | H | H | OH | H | OH | H | 0 | 68 (+/−5) | n.t. |
| 2u | OH | H | H | OH | H | OH | H | 1 | 40 (+/−3) | n.t. |
| 2v | H | H | OH | H | H | OH | H | 0 | 45 (+/−5) | n.t. |
| Iminochrome 9TA | | | | | | | | | 30 (+/−15) | Lit[8]: 0.118 |
| Piceatannol | | | | | | | | | 41 (+/−2) | Lit[13]: 66 (lck) |
| ST-638 | | | | | | | | | 37 (+/−5) | Lit[14]: 18 |
| Emodin[d] | | | | | | | | | 22 (+/−3) | Lit[15]: 38 |
| Tyrophostin A47 | | | | | | | | | 43 (+/−3) | |

Table IX Footnotes:
[a]The previously described assay procedure (Lai et al., 1998) was used with the following assay components, final concentrations and conditions: 50.0 mM MOPS, 4.02 mM $MgCl_2$, 6.00 mM $K_3$citrate (used as a $Mg^{2+}$ buffer to stabilize the free $Mg^{2+}$ at 0.5 mM), 99.0 mM KCl, 10.0 mM 2-mercaptoethanol, 198 μM ATP, 19.8 μM ADP, 10 U full length human purified recombinant pp60[c-src] (Upstate Biotechnology Inc.), 2.00 mM RR-SRC, 4.0% DMSO, pH 7.2, 37° C. These overall assay conditions have been shown (Choi, 1999) to reproduce the intracellular conditions of pH, temp., free $Mg^{2+}$ (0.5 mM), ionic strength, osmolality, ATP/ADP and reduction potential.
[b]All new compounds were characterized by proton NMR, EI or FAB(+) MS and are pure by TLC.
[c]N/A = Not applicable, n.t. = Not tested.
[d]ATP-competitive.

The series of 2-carbonyl, 3,6-dihydroxy naphthalene inhibitors (1b, 2e-2h, 2m-2n, 2q-2s) were synthesized from 3,6-dihydroxy-2-naphthoic acid 6 using the methods described above. The synthesis of intermediate 6 that was developed is shown in Scheme 2 beginning with commercially available 2,7-dihydroxynaphthalene 3 (Aldrich).

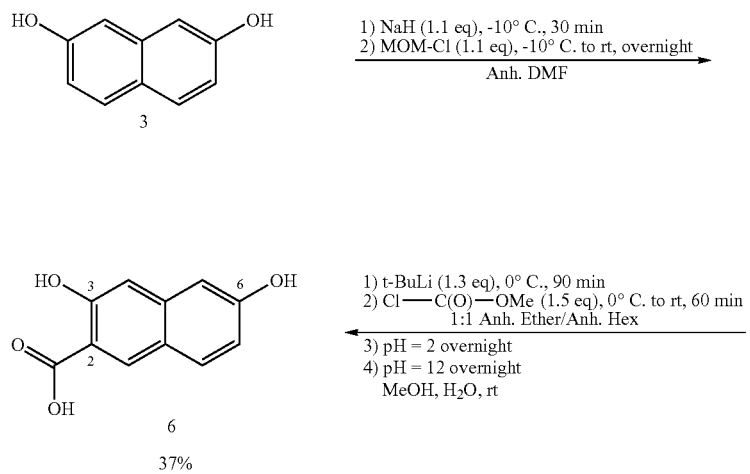

Compound 1d was synthesized from 3-amino-2-naphthoic acid (Aldrich) by reaction with TMS-diazomethane in DCM at room temperature. Compound 2v was synthesized from 6-hydroxy-2-naphthoic acid (Aldrich) using the amidation method described by Froyen (Froyen, 1997).

Kinase assay conditions have been shown to influence the measured inhibitory activity (Lawrence et al., 1998). Consequently, in order to accurately determine the relative potency of the newly designed class of pp60$^{c\text{-}src}$ inhibitors, the inhibitory activity of four previously published, non-ATP competitive PTK inhibitors, was also tested. Piceatannol, ST-638, and Tyrphostin A47 were chosen because they are commercially available (Sigma or Calbiochem), and are representative of the spectrum of known non-ATP competitive PTK inhibitors. Emodin (Calbiochem) is ATP-competitive when analyzed with the tyrosine kinase p56$^{lck}$. Previously, iminochromene 9TA was the most potent non-ATP competitive pp60$^{c\text{-}src}$ inhibitor reported (Huang et al., 1995). Since iminochromene 9TA was not commercially available, it was synthesized using a novel route by converting 3-Aminophenol to the corresponding TBDMS ether (1.1 eq. TBDMS-Cl, 1.1 eq. DIEA, 5 mol % DMAP, DMF, 24 h, rt, 71%). The resulting aniline was coupled using 2.0 eq. of cyanoacetic acid (1.1 eq. EDCI, 1.1 eq. TEA, DMF, 18 h, 75° C., 70%). Condensation of the resulting amide with 1.2 eq. of 2,3-dihydroxybenzaldehyde (cat. piperidine, abs. EtOH, 2 h, 60° C.) followed by deprotection (1.1 eq. TBAF, THF, 15 m, 43% overall) gave iminochromene 9TA with satisfactory elemental, FAB(+)MS and $^1$H NMR analysis after purification by flash chromatography (10:1, DCM:MeOH).

The inhibitory activities shown in Table IX for compounds 1a-d and 2a-2v were determined using purified, full length, human recombinant pp60$^{c\text{-}src}$. Due to the number of compounds tested, and the associated cost, their rank order potencies were first determined at a constant inhibitor concentration (100 µM). As predicted by the modeling studies, based upon analogy to the IRTK Tyr 1,162 hydroxyl group, a preference for positioning the naphthalene hydroxyl group on carbon 6 vs. 5 or 7 was observed in both the ester (1b, 47% vs. 1a, 5% & 1c, 19%) and amide (e.g. 2f, 89% vs. 2b, 51% & 2t, 68%) series. The prediction that attaching a hydroxyl group at naphthalene carbon 3 (mimicking the Tyr 1,162 NH) would improve potency was also confirmed (2f, 89% vs. 2v, 45%). Finally, the prediction that extending the inhibitor as an amide at the 2 position (mimicking the peptide bond) could further improve potency was confirmed as well (e.g. 2f, 89% vs. 1b, 47%).

The data provided in Table IX demonstrate that moving the hydroxyl group from the optimal 6 position to the adjacent naphthalene carbon 5 results in a different structure activity profile with regard to the optimal concurrent positioning of the hydroxyl group(s) in the amide side chain (e.g. 2f/2g vs. 2b/2c). Also of note is the replacement of the amide side chain hydroxyl group with a corresponding methoxy group in compounds 2i-2n. In the case of the N-phenyl amides (2i-2j), their activity, relative to the corresponding hydroxy amides (2b-2c), was not reduced as significantly as in the case of the N-benzyl amides (2k-2n vs. 2o-2q, 2s). This suggests that in the benzyl derivatives, the amide side chain hydroxyl groups either interact with the enzyme as hydrogen bond donors, or the methoxy groups are too large to fit in the binding site.

A more quantitative analysis of the selectivity for positioning a hydroxyl group on carbon 6 vs. 5 is provided by comparing the IC$_{50}$'s of 2f (16 µM) vs. 2b (150 µM), respectively. These results also confirm that a drop in % inhibition from ca. 90% to ca. 50% represents an order of magnitude difference in potency, as expected. Similarly, a drop in % inhibition from ca. 50% to 10% would represent another order of magnitude difference in potency.

A direct comparison of the most potent inhibitor from this series, compound 2f, with the five previously reported PTK inhibitors shown in Table IX demonstrates that, under these assay conditions, 2f is more potent by one to two orders of magnitude. Interestingly, iminochromene 9TA was previously reported (Huang et al., 1995) to have an IC$_{50}$ of 118 nM against pp60$^{c\text{-}src}$, and was the most potent known non-ATP competitive pp60$^{c\text{-}src}$ inhibitor, but under the current assay conditions only a 30% inhibition at 100 µM was observed. These results re-emphasize (Lawrence et al., 1998) the importance of comparing protein kinase inhibitors under identical assay conditions.

A goal of these studies was to obtain non-peptide pp60$^{c\text{-}src}$ inhibitors which do not compete with ATP. Consequently the % inhibition of pp60$^{c\text{-}src}$ by 2f and 2b at constant inhibitor concentrations was monitored as a function of increasing [ATP] up to a cellular mimetic 1 mM level. Since the [ATP] had little effect on the % inhibition, both 2f and 2b are non-competitive inhibitors with respect to ATP. The % inhibition was measured using ATP concentrations of 200, 500 & 1,000

μM while holding the inhibitor concentration constant. If the inhibitor is directly competing with ATP, then this 5-fold overall increase in [ATP] is equivalent to decreasing the inhibitor concentration 5-fold in terms of the effect on % inhibition. Consequently the % inhibition should decrease to the value observed in the $IC_{50}$ dose-response curve (obtained with 200 μM ATP) for ⅕ of the set inhibitor concentration used in this experiment if direct competition with ATP is occurring. For inhibitor 2f (set at 25 μM) a 62% (+/−5), 54% (+/−3) and 50% (+/−1) inhibition at 200 μM, 500 μM and 1,000 μM ATP, respectively, was obtained whereas the level of inhibition should have dropped to ca. 20% at 1,000 μM ATP if direct competition with ATP were occurring. Similarly, for inhibitor 2b (set at 300 μM) an 84% (+/−1), 81% (+/−1) and 77% (+/−2) inhibition at 200 μM, 500 μM and 1,000 μM ATP, respectively, was obtained. The high cost of many kinases has stimulated other researchers to monitor inhibitor potency as a function of increasing [ATP] for the same purpose (Saperstein et al., 1989; Burke et al., 1993; Davis et al., 1989; Davis et al., 1992; Faltynek et al., 1995; and Sawutz et al., 1996).

In summary, structure-based design has produced a series of hydroxynaphthalene pp60$^{c-src}$ non-peptide inhibitors that do not compete with ATP. Results with compounds from this series in cell-based assays, as well as detailed kinetic studies under various assay conditions, will be reported in due course. An extension of these design concepts from the naphthalene scaffold to an indole scaffold is reported in the following Example.

Example 4

Design, Synthesis and Activity of Non-ATP Competitive Hydroxyindole Derivative Inhibitors of pp60$^{c-src}$ Tyrosine Kinase In the preceding example, the structure-based design of a series of pp60$^{c-src}$ inhibitors utilizing a naphthalene scaffold is described. These compounds were designed to bind in the peptide substrate site because of the potential for greater selectivity and efficacy in a cellular environment relative to the alternative ATP substrate site. This example presents an extension of these design concepts to a series of pp60$^{c-src}$ inhibitors based upon an indole scaffold. Once again the crystal structure of the autoinhibited insulin receptor PTK (IRTK) was used to carry out qualitative molecular modeling studies, except in this case an indole ring was superimposed upon the IRTK Tyr 1,162. This superimposition indicated that the indole NH can mimic the Tyr 1,162 NH, that a carbonyl should be placed at the 2-position, and a hydroxyl group at the 5 position to mimic the Tyr 1,162 carbonyl and OH, respectively (Scheme 1).

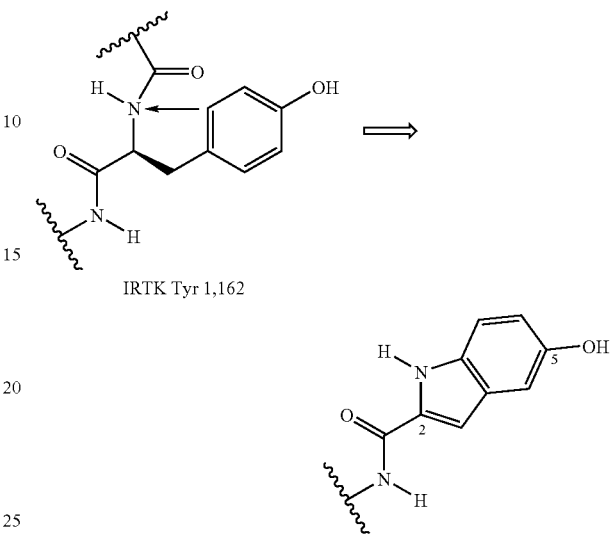

Scheme 1

The conceptual cyclization of Tyr 1,162 to the smaller 5-membered ring of an indole illustrated in Scheme 1, relative to a 6-membered ring in the case of the naphthalene scaffold (Karni et al., 1999), results in a movement of the optimal positioning of the OH from carbon 6 in the naphthalene scaffold to carbon 5 in the indole scaffold.

The indole amide derivatives containing hydroxy phenyl/benzyl side chains 2d-f, 2j-l (Table X), respectively, were selected based upon the increase in pp60$^{c-src}$ inhibitor potency observed for the analogous naphthalene-based hydroxy phenyl amides reported in the previous example. The corresponding methyl ethers 2a-c,g-i,v are precursors in the synthesis. The additional analogs shown in Table X were prepared to begin expanding the range of side chains beyond the hydroxy/methoxy groups that have now been extensively probed with both the indole and naphthalene scaffolds.

The indole amides containing only hydroxy or methoxy side chains were synthesized as illustrated:

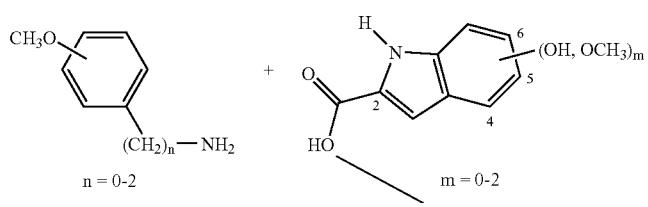

Scheme 2

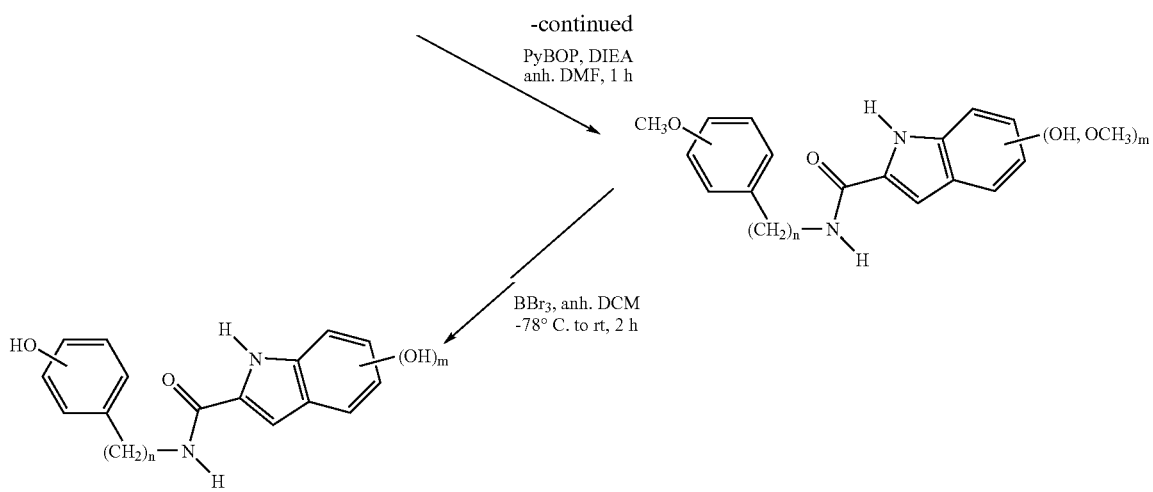

The 2-indolecarboxylic acid derivative, the methoxyphenyl amine (1.1 eq, Aldrich, Lancaster or Fluka), and the coupling reagent PyBOP (benzotriazol-1-yloxy)tripyrrolidino-phosphonium-hexafluorophosphate) (1 eq, Fluka) were dissolved in anhydrous DMF. The solution was cooled to 0° C. under argon and then diisopropylethylamine (DIEA, 3 eq) was added. The reaction was stirred at 0° C. for 1 m followed by 1 hour at room temperature. After workup the residue was purified by silica gel chromatography.

The methyl ethers were cleaved with boron tribromide (1 M in DCM, Aldrich) when desired. The indole amide methyl ether was suspended in dry DCM and cooled to −78° C. under argon. One equivalent of $BBr_3$ was added for each heteroatom in the starting material plus one excess equivalent. The resulting dark red solution was stirred at −78° for 30 m and then at room temperature for 1-2 hours. The reaction was quenched with water (10 minutes) before workup.

TABLE X pp60$^{c-src}$ INHIBITORY ACTIVITY OF HYDROXYINDOLE DERIVATIVES.[a,b,c]

| Cmpd | $R_1$ | $R_2$ | $R_3$ | $R_4$ | $R_5$ | $R_6$ | $R_7$ | % Inhibition at 100 μM (std. dev.) |
|---|---|---|---|---|---|---|---|---|
| 1a | H | OH | H | $CH_3$ | N/A | N/A | N/A | 40 (+/−5) [at 500 μM] |
| 1b | H | OH | OH | $CH_2CH_2$ | N/A | N/A | N/A | 28 (+/−3) |
| 2a | H | OH | H | — | $OCH_3$ | H | H | 3 (+/−1) |
| 2b | H | OH | H | — | H | $OCH_3$ | H | 21 (+/−2) |
| 2c | H | OH | H | — | H | H | $OCH_3$ | 39 (+/−9) |
| 2d | H | OH | H | — | OH | H | H | 43 (+/−1) |
| 2e | H | OH | H | — | H | OH | H | 30 (+/−6) |
| 2f | H | OH | H | — | H | H | OH | 45 (+/−3) |
| 2g | H | OH | H | $CH_2$ | $OCH_3$ | H | H | 21 (+/−5) |
| 2h | H | OH | H | $CH_2$ | H | $OCH_3$ | H | 7 (+/−6) |

TABLE X-continued pp60$^{c-src}$ INHIBITORY ACTIVITY OF HYDROXYINDOLE DERIVATIVES.[a,b,c]

| | | | | | | | | |
|---|---|---|---|---|---|---|---|---|
| 2i | H | OH | H | CH$_2$ | H | H | OCH$_3$ | 18 (+/−4) |
| 2j | H | OH | H | CH$_2$ | OH | H | H | 24 (+/−3) |
| 2k | H | OH | H | CH$_2$ | H | OH | H | 74 (+/−2) [IC$_{50}$ = 38 μM] |
| 2l | H | OH | H | CH$_2$ | H | H | OH | 54 (+/−2) |
| 2m | H | OH | H | CH$_2$CH$_2$ | H | H | OH | 21 (+/−7) |
| 2n | H | OH | H | CH$_2$ | H | H | CO$_2$H | not active |
| 2o | H | OH | H | CH$_2$ | H | H | CO$_2$CH$_3$ | 11 (+/−4) |
| 2p | H | OH | H | — | H | H | CH$_2$CO$_2$H | 7 (+/−6) |
| 2q | H | OH | H | — | H | H | CH$_2$CO$_2$CH$_3$ | 32 (+/−7) |
| 2r | H | OH | H | — | H | F | H | 21 (+/−7) |
| 2s | H | OH | H | CH$_2$ | H | F | H | 57 (+/−6) |
| 2t | H | OH | OH | CH$_2$ | H | OH | H | 26 (+/−2) |
| 2u | H | H | OH | CH$_2$ | H | OH | H | 56 (+/−6) |
| 2v | H | H | H | CH$_2$ | H | H | OCH$_3$ | 4 (+/−4) |
| 2w | H | H | H | CH$_2$ | H | H | OH | 36 (+/−4) |
| 2x | OH | H | H | CH$_2$ | H | OH | H | 60 (+/−3) |
| 2y | H | OH | H | CH(CH$_3$)R | H | OH | H | 15 (+/−3) |
| 2z | H | OH | H | CH(CH$_3$)S | H | OH | H | 13 (+/−7) |

[a]All compounds were tested as described in the preceding Example.[5]
[b]All compounds were characterized by proton NMR, FAB(+) MS and are pure by TLC.
[c]N/A = Not applicable.

Using this synthetic route, the series of 5-hydroxyindole amide inhibitors 2a-m,y,z were prepared from 5-hydroxy-2-indolecarboxylic acid. The 4- and 6-hydroxyindole amides (2x,u, respectively) were synthesized from methyl 4-methoxy-2-indolecarboxylate and methyl 6-methoxy-2-indolecarboxylate, respectively. The 5,6-dihydroxyindole amide 2t was prepared from ethyl 5,6-dimethoxyindole-2-carboxylate. Sonication of the esters in 1 N NaOH for 1 hour provided the corresponding carboxylic acids for coupling. The des-hydroxy indole amides 2v,w were synthesized from indole-2-carboxylic acid. All of the indole starting materials were commercially available (Aldrich or Lancaster).

The fluoro inhibitors 2r,s were likewise prepared from the corresponding fluorophenyl amines (Aldrich). The inhibitors containing esters or carboxylic acids on the amide side chain, 2n-q, were prepared from the corresponding amino carboxylic acids (Aldrich). The side chain carboxylic acid was first protected as a methyl ester (anh. MeOH pre-saturated with HCl, reflux, 1 d), followed by PyBOP coupling (as above), then saponification back to the carboxylic acid when desired.

The methyl ester 1a was prepared by refluxing a solution of the carboxylic acid overnight in anhydrous methanol pre-saturated with HCl gas. The ethyl ester 1b was prepared by BBr$_3$ deprotection of ethyl 5,6-dimethoxyindole-2-carboxylate as above. All of the inhibitors listed in Table X were purified by silica gel chromatography.

As in Marsilje 2000, the rank order activity of this series of pp60$^{c-src}$ inhibitors was first determined at a constant inhibitor concentration (Table X). The same inhibitor concentration (100 μM) was used for the current indole series of inhibitors, the previous naphthalene series of inhibitors, and five non-ATP competitive literature PTK inhibitors (see preceding example). This allowed an efficient rank order comparison of 59 compounds in total under identical assay conditions.

The modeling studies predicted that a hydroxy group at carbon 5 of the indole scaffold would be optimal. Comparison of the 5-hydroxy indole inhibitor 2k (74%) with the analogous 6-hydroxy indole inhibitor 2u (56%) and 4-hydroxy indole inhibitor 2x (60%) confirms this prediction, although the preference is not strong. The prediction that a hydroxy group at carbon will improve the activity (relative to no hydroxy group) is confirmed by comparing the 5-hydroxy indole inhibitor 2l (54%) with the corresponding des-hydroxy inhibitor 2w (36%).

Extending the indole inhibitors as aryl amides at carbon 2 improved potency, as expected based upon the previous naphthalene inhibitors. For example, the meta-hydroxybenzyl amide indole 2k gives 74% inhibition at 100 μM whereas the analogous methyl ester 1a gives only 40% inhibition at 500 μM. Interestingly, comparing the 5,6-dihydroxy ethyl ester 1b (28%) to the corresponding aryl amide 2t (26%) shows that the simultaneous presence of the second hydroxy at carbon 6 prevents the potency enhancement normally provided by the otherwise preferred meta-hydroxybenzyl amide side chain. This amide side chain was the best of the current series when the 5-hydroxyl group is present alone (2k, 74%) and still gave good inhibition when a 6-hydroxy group was present alone (2u, 56%). Also, the simultaneous presence of two hydroxy groups at carbons 5 and 6 seems well tolerated in the absence of an amide side chain (1b vs. 1a and 2e). This data suggests that a change in the binding orientation of the indole scaffold may have occurred due to the presence of the second hydroxy group and that a different amide side chain may now be preferred. The optimal combination of side chains at carbons 4-7 (including functional group replacements for hydroxy groups (Lai et al., 1999)) and amide side chains is currently under investigation.

In general, the indole scaffold structure-activity-relationships ("SARs") revealed by the data in Table X parallels that reported in the preceding example for the naphthalene scaffold. In both cases positioning a hydroxy group on the scaffold analogous to the Tyr 1,162 OH, as identified by modeling studies, provided the highest potency. Moving this hydroxy group to one of the adjacent carbons reduced the potency, but not dramatically, in both cases. Extending both scaffolds with aryl amides at the position identified by the modeling studies to mimic the Tyr 1,162 peptide bond improved the potency. With both scaffolds, substitution of a methoxy group for the hydroxy groups on the amide side chain usually reduced potency, and did so to a greater extent with the longer benzylamide side chain (e.g. 2k, 74% vs. 2h, 7% compared to 2e, 30% vs. 2b, 21%). The major difference in the SARs for these two scaffolds is that the 5-hydroxyindole scaffold prefers the longer m-hydroxybenzyl amide side chain (2k, 74% vs. 2e, 30%) whereas the analogous 3,6-dihydroxynaphthalene scaffold prefers the shorter amide side chain derived from m-hydroxyaniline. The 5-hydroxyindole scaffold showed essentially no preference for the position of the hydroxyl group on the shorter amide side chain (2d-f) whereas with the longer hydroxybenzyl amide side chain a significant preference for the meta position was observed (2j-l). In the case of the 3,6-dihydroxynaphthalene scaffold the opposite was observed.

Additional molecular modeling studies were carried out to further probe the preference for a longer amide side chain with the indole scaffold. The most active naphthalene inhibitor 3 from the previous report was used as a template upon which the analogous indole inhibitor 2e and the homologated indole inhibitor 2k were superimposed. The three most important side chain functional groups in naphthalene inhibitor 3 are considered to be the 6-hydroxy group (H-bond donor and acceptor), the hydrogen from the 3-hydroxy group (H-bond donor), and the side chain hydroxy group (H-bond acceptor) based upon the rational design and SAR for both series of inhibitors. This three point pharmacophore model is identified in both series by asterisks in Scheme 3.

Scheme 3

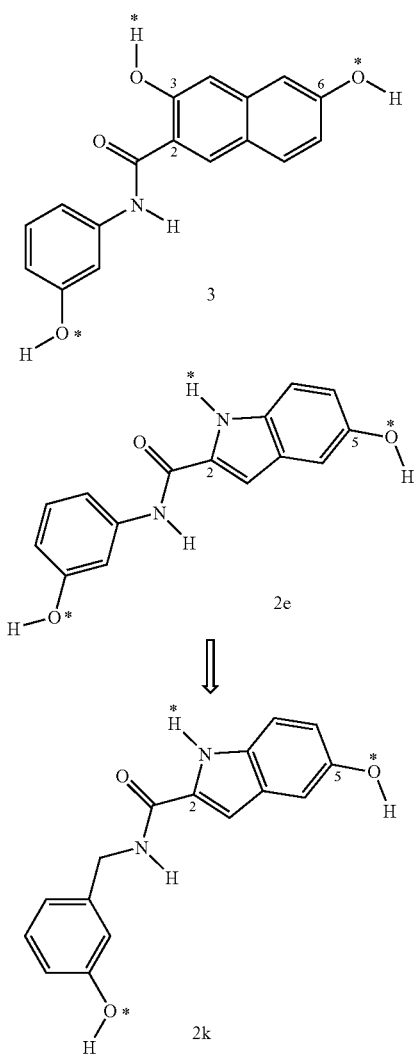

The "multifit" energy minimization and "fit atoms" facilities within SYBYL™ (6.4, Tripos, St. Louis) were used in sequence to superimpose 2e and 2k onto 3. This overall fitting process was carried out with spring constants (multifit) and weights (fit atoms) chosen such that the highest emphasis was on optimally superimposing the scaffold pharmacophore O's and H's (100), followed by the side chain O's (10) and then the intervening amide bond (1). The "multifit" process adjusted the conformations for maximum pharmacophore fit, the subsequent minimization produced the nearest local minimum energy conformations and finally the "fit atoms" process produced the best pharmacophore superimposition of these minimized conformations. As expected, the scaffold pharmacophore O's and H's of both 2e and 2k superimposed closely and similarly upon the corresponding atoms in 3 (all within ca. 0.50 Å). However, the side chain pharmacophore O's of 2e and 2k differed significantly in their superimposition on the corresponding 0 of 3, with displacements of 1.8 Å vs. only 0.08 Å respectively. This close fit of the three key pharmacophore sites between 2k and 3 provides a rationalization for their potency differing by only a factor of 2.4 ($IC_{50}$'s 38 μM vs. 16 μM, respectively).

Extending the amide side chain by another carbon atom reduced the activity (2m, 21% vs. 2l, 54%). Adding a methyl group to the benzylic carbon of 2k, in either stereochemistry, greatly reduced the activity (2y, 15% & 2z, 13% vs. 2k, 74%). Replacing the side chain hydroxy group (in the para position) with a carboxylate anion (2n, 0% vs. 2l, 54% and 2p, 7% vs. 2f, 45%) reduced the activity whereas the corresponding methyl esters (2o, 11% & 2q, 32%, respectively) showed a smaller loss of potency. Importantly, replacing the side chain hydroxy group with a fluorine maintained much of the potency (2s, 57% vs. 2k, 74% and 2r, 21% vs. 2e, 30%). Consequently, the fluoro analog 2s has only one hydroxy group left for potential Phase II metabolism (e.g. glucuronide formation), and this remaining hydroxy group is a current target for replacement (Lai et al., 1998).

Using the same method as in the preceding example (Marsilje, 2000), the most potent inhibitor from the current indole series (2k) was analyzed for ATP competition by monitoring the % inhibition at increasing [ATP] while holding the inhibitor concentration constant. Since the [ATP] had little effect on the % inhibition (The % inhibition was 46% and 41% with 2k at 45 μM and [ATP] at 200 μM or 1,000 μM, respectively.), 2k is non-competitive with respect to ATP under these assay conditions.

In summary, an indole scaffold has been designed, and an initial SAR carried out, for the development of non-ATP competitive $pp60^{c-src}$ inhibitors. The potency of the best indole-based inhibitor from the current series was found to be close to that of the best naphthalene-based inhibitor. The % inhibition was 46% and 41% with 2k at 45 μM and [ATP] at 200 μM or 1,000 μM, respectively.

Example 5

Synthesis of Additional Indole Derivative Protein Kinase Inhibitors

The following results show the synthesis and testing of indole derived protein kinase inhibitors. Four reaction schemes are provided and separately followed by experimental details for the preparation of the final product of each of these reaction schemes. These final products are examples of indole-base tyrosine kinase inhibitors wherein the synthesis with preferred R groups is illustrated (boronic acid, Scheme 1; OH, Scheme 2; an aliphatic amide extension, Scheme 3; and a phosphonic acid Scheme 4).

Scheme 1

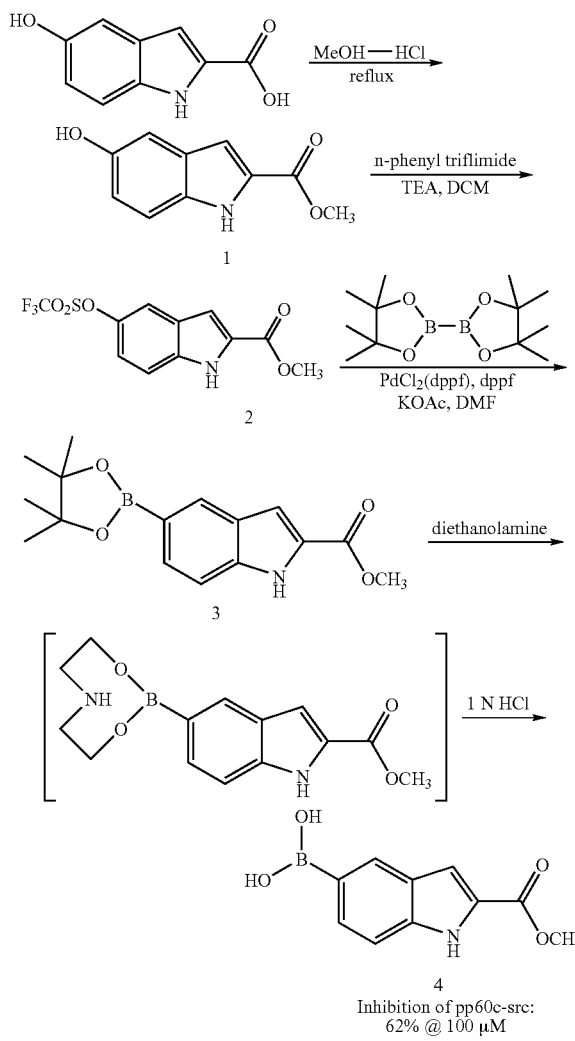

Methyl 5-hydroxy-2-indolecarboxylate (1)

Dissolved 3.50 g 5-hydroxy-2-indolecarboxylic acid in anh. MeOH presaturated with HCl gas. Refluxed for 48 hours. Concentrated in vacuo and triturated with AcCN×3 to remove residual acid. Filtered through silica plug with EtOAc to remove baseline contamination. Recovered 4.32 g (quant. yield) TLC $R_f$=0.78 (EtOAc) 1H NMR (DMSO-$d_6$): 3.82 (s, 3H), 6.78 (d, J=8.8 Hz, 1H), 6.88 (s, 1H), 6.93 (s, 1H), 7.23 (d, J=8.8 Hz, 1H), 8.90 (s, 1H) 11.62 (s, 1H) FAB(+) MS m/e 191.9 (M+1)

Methyl 5-[(trifluoromethyl)sulfonyloxy]indole-2-carboxylate (2)

Added 150 ml anh. DCM to 3.24 g (17 mmol) methyl 5-hydroxy-2-indolecarboxylate (1) and 6.67 g (18.7 mm) n-phenyl trifluoromethane sulfonamide at 0° C. Added 2.6 ml triethylamine dropwise at which point clear yellow solution formed. Stirred at 0° C. for 1 hour. Warmed to room temperature and stirred for 2 hours. Concentrated in vacuo and purified through silica gel column (1/1 EtOAc/hexanes). Recovered 4.69 g (86%). TLC $R_f$=0.63 (1/1 EtOAc/hexanes). HPLC $R_f$=20.879 1H NMR (DMSO-$d_6$): 3.87 (s, 3H), 7.25 (s, 1H), 7.31 (d, J=9.2 Hz, 1H), 7.55 (d, J=9.2 Hz, 1H), 7.80 (s, 1H), 12.34 s, 1H) FAB(+) MS m/e 323.1 (M+1).

Methyl 5-methylindole-2-carboxylate, 4,4,5,5-tetramethyl-1,3,2-dioxaborolanemethyl (3)

500 mg 1.55 mmol methyl 5-[(trifluoromethyl)sulfonyloxy]indole-2-carboxylate (2), 37.9 mg (0.05 mmol) $PdCl_2$ (dppf), 432 mg (1.7 mmol) bispinacolatodiboron, 454.8 mg (4.65 mmol) potassium acetate, and 25.7 mg (0.05 mmol) dppf were added to a flask and vacuum dried at 40° C. for 2 hours. Added 20 ml anh dioxane and heated to 80° C. overnight. Reaction turned black as Pd black precipitated out. Filtered off catalyst and ran silica plug to remove baseline impurities. TLC $R_f$=0.51 (1/4 EtOAc/Hexane) Crude product was taken through to next reaction.

Methyl 5-boronyl indole-2-carboxylate (4)

391.2 mg (1.3 mmol) methyl 5-methylindole-2-carboxylate, 4,4,5,5-tetramethyl-1,3,2-dioxaborolanemethyl (3) was dissolved in EtOAc. 0.25 ml (2.6 mmol) diethanolamine was added, and the reaction was stirred at room temperature overnight. The white ppt which formed was filtered and sonicated in 1 N HCl. The resulting white ppt was filtered, dissolved in MeOH, and concentrated in vacuo. Recovered 36.6 mg (13%). HPLC $R_f$=13.912, 1H NMR (DMSO-$d_6$): 3.85 (s, 3H), 7.15 s, (1H), 7.36 (d, J=8.4 Hz, 1H), 7.67 (d, J=8.4 Hz, 1H), 7.87 (s, 1H), 8.14 (s, 1H), 11.91 (s, 1H).

Scheme 2

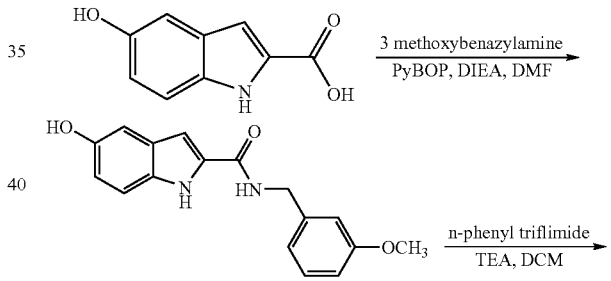

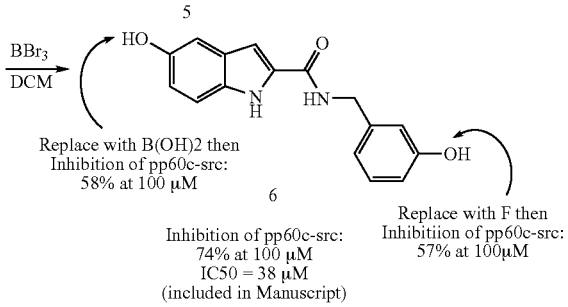

(5-hydroxyindol-2-yl)-N-[(3-methoxyphenyl)methyl]carboxyamide (5)

Dissolved 2.00 g (11.3 mmol) 5-hydroxy-2-indolecarboxylic acid, 1.6 ml (12.4 mmol) 3 methoxybenzylamine, and 5.87 g (11.3 mmol) PyBOP in 10 ml anh. DMF. Cooled to 0° C. and added 5.9 ml (33.9 mmol) DIEA. Stirred for 5 minutes at 0° C. and allowed to warm to room temperature for 1 hour. Recovered 2.83 g (85% yield) TLC $R_f$=0.34 (1/1 EtOAc/ hexanes) $^1$H NMR (DMSO-d$_6$): 3.70 (s, 3H), 4.43 (d, J=4.4 Hz, 2H) 6.69 (d, J=8.8 Hz, 1H), 6.78 (d, J=7.7 Hz, 1H), 6.83 (s, 1H), 6.86 (s, 1H), 6.94 (s, 1H), 7.20 (m, 3H), 8.92 (t, J=4.4 Hz, 1H), 11.36 (s, 1H) FAB(+) MS m/e 297.3 (M+1)

(5-hydroxyindol-2-yl)-N-[(3-hydroxyphenyl)methyl]carboxyamide (6)

Added 20 ml anh. DCM to 200 mg (0.67 mmol) (5-hydroxyindol-2-yl)-N-[(3-methoxyphenyl)methyl]carboxyamide (5) and cooled to −78° C. under argon. Added 4.0 ml (4.0 mmol, 6 eq) BBr$_3$. Held at −78° C. for 5 minutes and warmed to rt. After 90 minutes at room temperature, quenched with H$_2$O and stirred for 10 minutes. Diluted reaction mix with EtOAc and washed with NaHCO$_3$ and brine. Dried organic layer over MgSO$_4$ and concentrated in vacuo. Ran through silica plug to remove baseline contamination. Recovered X mg. (80% yield.) TLC R$_f$=0.21 (1/1 EtOAc/hexanes). $^1$H NMR (DMSO-d$_6$): 4.38 (d, J=4.8 Hz, 2H), 6.59 (d, J=8.8 Hz, 1H), 6.71 (m, 3H) 6.83 (d, J=1.8 Hz, 1H), 6.94 (s, 1H), 7.08 (dd, J=7.7 Hz, 1H), 7.19 (d, J=8.8 Hz, 1H), 8.84 (t, J=5.9 Hz), 11.28, (s, 1H). FAB(+) MS m/e 283.2 (M+1)

Scheme 3

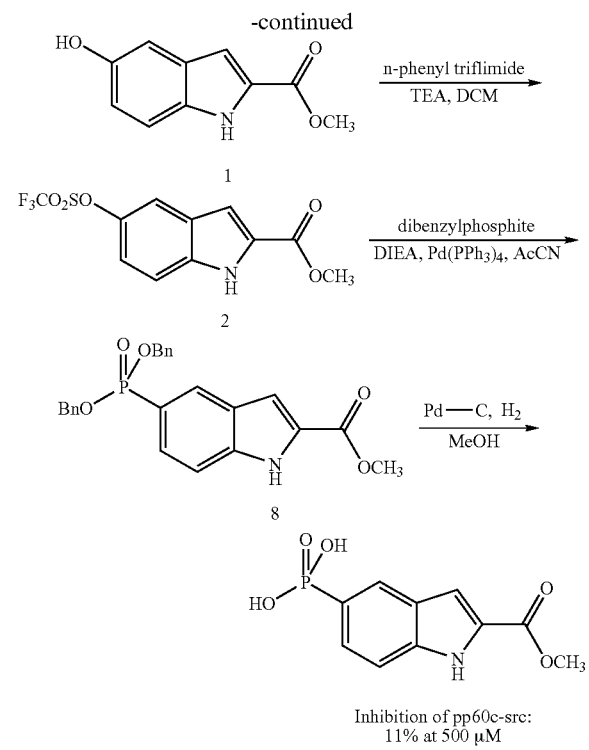

N-(1-carbamoyl-2-methylbutyl)(5-hydroxyindol-2-yl)carboxyamide (7)

100 mg (0.56 mmol) 5-hydroxy-2-indolecarboxylic acid, 103.4 mg (0.62 mmol, 1.1 eq) L-isoleucinamide, and 291 mg (0.56 mmol, 1 eq) PyBOP were all dissolved in 1 ml anh DMF. The solution was cooled to 0° C. and 0.3 ml (1.68 mmol, 3 eq) DIEA was added. The reaction mixture was stirred for 1 minute at 0° C. and at room temperature for 1 hour. The reaction was then diluted with EtOAc and washed with 1 N HClx3 and sated NaHCO3x3. The organic layer was dried over MgSO4, and concentrated in vacuo to give 166.7 mg (91% yield.) TLC R$_f$=0.08 (1/1 EtOAc/hexanes). $^1$H NMR (DMSO-d$_6$): 0.83 (m, 6H), 1.15 (m, 2H), 1.68 (m, 1H), 1.83 (m, 1H), 4.29 (t, J=8.8 Hz, 1H), 6.69 (d, J=8.5 Hz, 1H), 6.83 (s, 1H), 7.01, (s, 1H), 7.06 (s, 1H), 7.19 (d, J=8.4 Hz, 1H), 7.48, (s, 1H), 8.00 (d, 9.2 Hz, 1H), 8.76 (s, 1H), 11.3, (s, 1H). FAB(+) MS m/e 290.1 (M+1)

Scheme 4

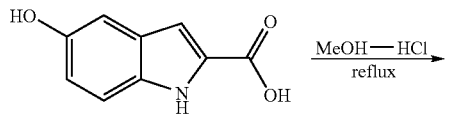

Methyl 5-dibenzylphosphorylindole-2-carboxylate (8)

200 mg (0.62 mmol) methyl 5-[(trifluoromethyl)sulfonyloxy]indole-2-carboxylate (2), 195.8 mg (0.74 mmol, 1.2 eq) dibenzylphosphite, 0.14 ml (0.81 mmol, 1.3 eq) DIEA, and 35.7 mg (0.03 mmol, 5 mol %) Pd(PPh$_3$)$_4$ were all dissolved in anh AcCN under argon. The reaction mix was heated to 80° C. overnight. The solvent was removed under reduced pressure, and the title compound was isolated by silica gel chromatography. 130 mg (50% yield). TLC R$_f$=0.28 (1/1 EtOAc/hexanes) $^1$H NMR (DMSO-d$_6$): 3.85 (s, 3H), 4.98-5.01 (m, 4H), 7.28-7.32 (m, 11H), 7.53-7.55 (m, 2H), 8.17 (d, J=14.6 Hz, 1H) $^{31}$P NMR (DMSO-d$_6$): 23.89.

Methyl 5-phosphonolindole-2-carboxylate

Methyl 5-dibenzylphosphorylindole-2-carboxylate (8) (125 mg) was dissolved in 10 ml MeOH. 20 mg Pd—C was added and the mixture was hydrogenated in a Parr apparatus overnight. Filtered off catalyst and removed solvent under reduced pressure. Obtained 72.5 mg (73% yield). TLC R$_f$=baseline in EtOAc. $^1$H NMR (DMSO-d$_6$): 3.84 (s, 3H), 7.24 (s, 1H), 7.44-7.49 (m, 2H), 8.01 (d, J=14.3 Hz, 1H) 12.11 (s, 1H) $^{31}$P NMR (DMSO-d$_6$): 17.22.

The ester compounds in this example could be increased in potency by converting the ester to an amide and/or adding additional specificity elements.

Example 6

Synthesis of Further Indole Derivative Protein Kinase Inhibitors

The synthesis of some further elaborated indole inhibitors is illustrated in below. These syntheses could result in compounds with greater potency against pp60c-src and other tyrosine kinases. The methyl ester group can be subsequently converted into various amide derivatives to increase potency.
Scheme 1:
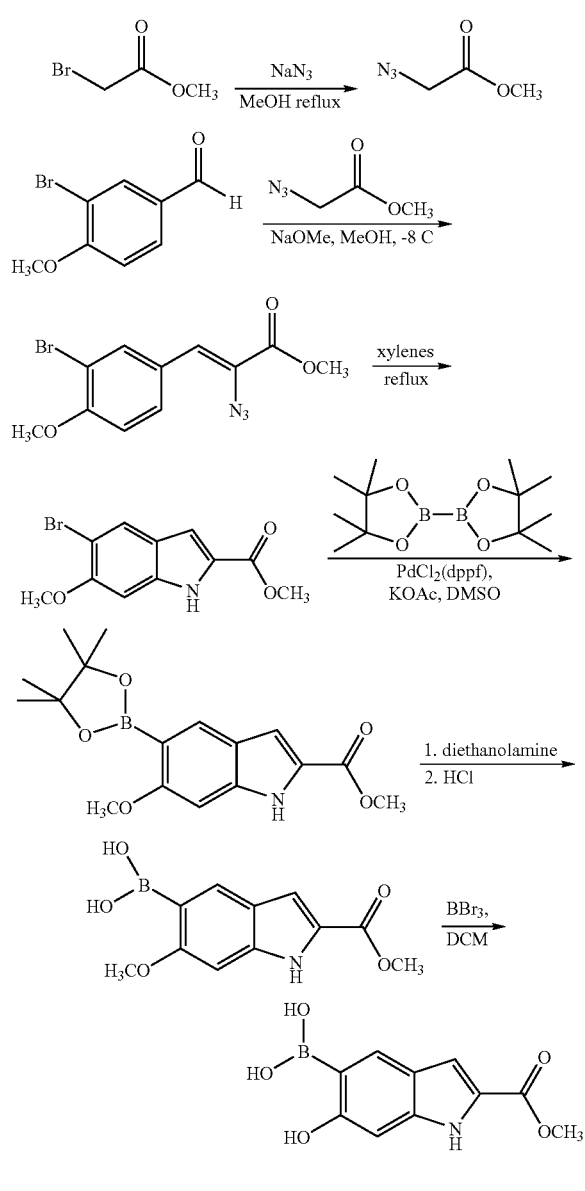
Scheme 2:
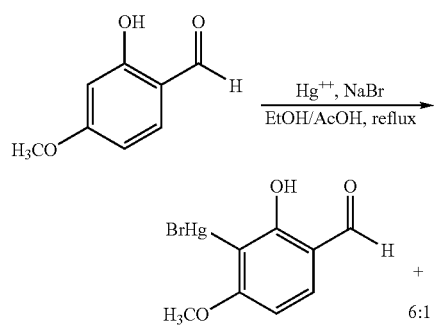
-continued
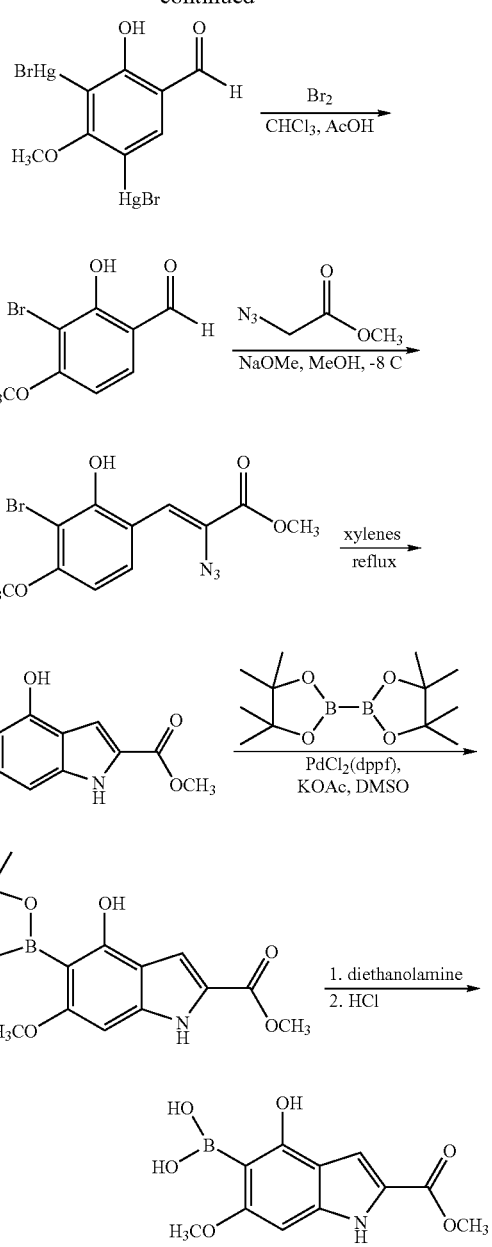

-continued

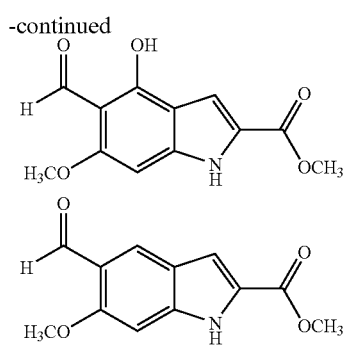

Example 7

Toxicity of Src Inhibitors

There is considerable recent literature support for targeting pp60$^{c\text{-}src}$ (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al., 1999). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano et al., 1997). Additionally, reduced VEGF mRNA expression was noted upon Src inhibition and tumors derived from these Src-inhibited cell lines showed reduced angiogenic development (Ellis et al., 1998).

The issue of potential toxicity of Src inhibition has been addressed with very promising results. For example, a knockout of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., 1997). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be overactivated in a growing number of human tumors, in addition to those noted above (Levitzki, 1996). The potential benefits of Src inhibition for cancer therapy appear to be four-fold based upon the cited, and additional, literature. They are: 1) Inhibition of uncontrolled cell growth caused by autocrine growth factor loop effects, etc. 2) Inhibition of metastasis due to triggering apoptosis upon breaking free from the cell matrix. 3) Inhibition of tumor angiogenesis via reduced VEGF levels. 4) Low toxicity.

The initial non-peptide Src inhibitors have also shown very encouraging results in four different series of cell culture assays. 1) In the NIH 60-tumor cell panel assay, broad activity (as one would expect for a Src inhibitor) was seen against the tumor cell lines, including the prostate lines. For example, three of the inhibitors gave the following growth inhibition IC$_{50}$'s against the NIH prostate cancer cell lines: 45 (PC-3, 15 µM; DU-145, 38 µM), 43-meta (PC-3, 19 µM), 49-meta (PC-3, 39 µM; DU-145, >100 µM). 2) In the v-Src transformed normal rat kidney cell line (LA25) 43-meta and 45 specifically blocked the v-Src induced cell growth without inhibiting the normal growth of the parent non-transformed cells. This result showed that the inhibitors do not affect normal cells but are effective in blocking Src induced cell transformation. 3) The Src inhibitors were compared to the cancer drugs etoposide, taxol, doxorubicin and cisplatin in ovarian tumors from three different patients and an abdominal carcinoma from another patient. In all cases, the Src inhibitors were at least as effective, and typically more effective, than the known cancer drugs, with full efficacy seen at the lowest dose tested (3 µM). 4) The Src inhibitors were also tested for inhibition of normal human fibroblast cell growth and found no inhibition of normal cell growth (both subconfluent and confluent; some enhanced growth was observed instead), indicating that these inhibitors are not toxic to normal cells even at a 10-fold higher concentration. 5) Two of the Src inhibitors were also tested for inhibition of ts v-Src stimulated LA25 cell growth. These results show that the tested compounds inhibit Src stimulated cell growth. 6) Two of the Src inhibitors were also tested for inhibition of normal rat kidney cell growth.

Overall, the cell data obtained thus far shows what one might expect for Src inhibitors, i.e. broad activity against many cancer cell lines with little or no normal cell toxicity.

The preliminary Src inhibitors are lead structures from which it is possible to design more potent and selective inhibitors. In addition to utilizing the tyrosine kinase crystal structures, molecular modeling studies can be carried out with the natural product tyrosine kinase inhibitor damnacanthal (Faltynek et al., 1995) to investigate its peptide-competitive binding mode. These additional modeling studies are enable one to design further analogs of Src inhibitors wherein the key pharmacophore elements of damnacanthal are incorporated into the new inhibitors. Their syntheses will be undertaken and the isolated Src testing done as reported (Marsilje 2000).

Example 8

Protection Against Noise-Induced Hearing Loss Using PTK Inhibitors

Chinchillas (N=8) were used in studies of noise-induced hearing loss. The animals' hearing sensitivity was measured using standard electrophysical techniques before the experimental manipulation. In particular, hearing thresholds were measured through evoked potentials from recording electrodes chronically implanted in the inferior colliculus, following standard laboratory procedures. Animals were anesthetized, the auditory bullae were opened, and the left and right cochleas were visualized. The round window leading to the scala tympani of the cochlea was used as the access point for drug application. Four animals were treated with 30 µl of 3 mM TOM 2-32, emulsified in DMSO, to 1000 mM of saline solution, which was placed on the round window of one ear, and a control solution of 3 mM DMSO to 1000 mM of saline solution, which was placed on the round window of the other ear. Five animals were treated with 30 µl of 3 mM compound 1a, emulsified in DMSO, to 1000 mM of saline solution, which was placed on the round window of one ear, and a control solution of 3 mM DMSO to 1000 mM of saline solution, which was placed on the round window of the other ear (one animal was lost prior to the end of the experiments). In each case, the solution was allowed to set on the round window for 30 minutes, then the auditory bullae were closed. Subsequently, the animals were exposed to 4 kHz band noise at 105 dB SPL for four hours. Following the noise exposure, the animals' hearing was tested at day 1, day 3, day 7, and day 20 to determine evoked potential threshold shifts. Permanent threshold shift was assessed at day 20. The cochleas were harvested at day 20 to allow for morphological examination of the cochleas. Data for TOM 2-32 is shown in Tables XI-XIII and data for compound 1a is shown in Table XIV, below.

TABLE XI

|  | 0.5 kHz | 1 kHz | 2 kHz | 4 kHz | 8 kHz |
| --- | --- | --- | --- | --- | --- |
| Pretest |  |  |  |  |  |
| Control | 20 | 20 | 15 | 15 | 15 |
|  | 25 | 20 | 25 | 20 | 10 |
| Control | 22.5 | 20 | 20 | 17.5 | 12.5 |
| TOM2 | 25 | 25 | 20 | 15 | 10 |
|  | 30 | 30 | 30 | 20 | 10 |
| TOM2 | 27.5 | 27.5 | 25 | 17.5 | 10 |
| TOM2 6778 |  |  |  |  |  |
| Day 0 | 55 | 70 | 75 | 85 | 80 |
| Day 1 | 35 | 30 | 65 | 75 | 75 |
| Day 3 | 15 | 5 | 40 | 45 | 60 |
| Day 20 | 5 | 5 | 25 | 30 | 0 |
| Control 6778 |  |  |  |  |  |
| Day 0 | 60 | 75 | 80 | 80 | 75 |
| Day 1 | 45 | 40 | 75 | 75 | 75 |
| Day 3 | 10 | 10 | 50 | 55 | 55 |
| Day 20 | 5 | 10 | 40 | 35 | 25 |
| TOM 6679 |  |  |  |  |  |
| Day 0 | 55 | 60 | 65 | 75 | 75 |
| Day 1 | 30 | 50 | 60 | 70 | 75 |
| Day 3 | 20 | 25 | 40 | 55 | 45 |
| Day 20 | −5 | 0 | 10 | 23 | −5 |
| Control 6679 |  |  |  |  |  |
| Day 0 | 55 | 70 | 70 | 75 | 80 |
| Day 1 | 40 | 60 | 65 | 70 | 80 |
| Day 3 | 35 | 60 | 65 | 75 | 80 |
| Day 20 | 0 | 10 | 25 | 35 | 10 |
| Control |  |  |  |  |  |
| Day 0 | 55 | 70 | 70 | 75 | 80 |
| Day 0 | 70 | 75 | 80 | 80 | 75 |
| Average Day 0 | 57.5 | 72.5 | 75 | 77.5 | 77.5 |
| Day 1 | 40 | 60 | 65 | 70 | 80 |
| Day 1 | 45 | 40 | 75 | 75 | 75 |
| Average Day 1 | 42.5 | 50 | 70 | 72.5 | 77.5 |
| Day 3 | 35 | 60 | 65 | 75 | 80 |
| Day 3 | 10 | 10 | 50 | 55 | 55 |
| Average Day 3 | 22.5 | 35 | 57.5 | 65 | 67.5 |
| Day 20 | 0 | 10 | 25 | 35 | 10 |
| Day 20 | 5 | 10 | 40 | 35 | 25 |
| Average Day 20 | 2.5 | 10 | 32.5 | 35 | 17.5 |
| TOM2 |  |  |  |  |  |
| Day 0 | 55 | 70 | 75 | 85 | 80 |
| Day 0 | 55 | 60 | 65 | 75 | 75 |
| Average day 0 | 55 | 65 | 70 | 80 | 77.5 |
| Day 1 | 35 | 30 | 65 | 75 | 75 |
| Day 1 | 30 | 50 | 60 | 70 | 75 |
| Average Day 1 | 32.5 | 40 | 62.5 | 72.5 | 75 |
| Day 3 | 15 | 5 | 40 | 45 | 60 |
| Day 3 | 20 | 25 | 40 | 55 | 45 |
| Average Day 3 | 17.5 | 15 | 40 | 50 | 52.5 |
| Day 20 | 5 | 5 | 25 | 30 | 0 |
| Day 20 | −5 | 0 | 10 | 23 | −5 |
| Average Day 20 | 0 | 2.5 | 17.5 | 26.5 | −2.5 |

TABLE XI-continued

|  | 0.5 kHz | 1 kHz | 2 kHz | 4 kHz | 8 kHz |
| --- | --- | --- | --- | --- | --- |
| Control Day 0 | 57.5 | 72.5 | 75 | 77.5 | 77.5 |
| TOM2 Day 0 | 55 | 65 | 70 | 80 | 77.5 |
| Control Day 1 | 42.5 | 50 | 70 | 72.5 | 77.5 |
| TOM2 Day 1 | 32.5 | 40 | 62.5 | 72.5 | 75 |
| Control Day 3 | 22.5 | 35 | 57.5 | 65 | 67.5 |
| TOM2 Day 3 | 17.5 | 15 | 40 | 50 | 52.5 |
| Control Day 20 | 2.5 | 10 | 32.5 | 35 | 17.5 |
| TOM2 Day 20 | 0 | 2.5 | 17.5 | 26.5 | −2.5 |
| Control Day 0 | 57.5 | 72.5 | 75 | 77.5 | 77.5 |
| Control Day 1 | 42.5 | 50 | 70 | 72.5 | 77.5 |
| Control Day 3 | 22.5 | 35 | 57.5 | 65 | 67.5 |
| Control Day 20 | 2.5 | 10 | 32.5 | 35 | 17.5 |
| TOM2 Day 0 | 55 | 65 | 70 | 80 | 77.5 |
| TOM2 Day 1 | 32.5 | 40 | 62.5 | 72.5 | 75 |
| TOM2 Day 3 | 17.5 | 15 | 40 | 50 | 52.5 |
| TOM2 Day 20 | 0 | 2.5 | 17.5 | 26.5 | −2.5 |
| TOM2 Day 20 | 0 | 2.5 | 17.5 | 26.5 | −2.5 |
| Control Day 20 | 2.5 | 10 | 32.5 | 35 | 17.5 |

TABLE XII

|  | 0.5 kHz | 1 kHz | 2 kHz | 4 kHz | 8 kHz |
| --- | --- | --- | --- | --- | --- |
| TOM2 6696 |  |  |  |  |  |
| day 0 | 38 | 50 | 70 | 75 | 80 |
| day 1 | 27 | 20 | 70 | 75 | 65 |
| day 3 | 10 | 15 | 55 | 53 | 55 |
| day 7 | 13 | 10 | 45 | 50 | 50 |
| day 20 |  |  |  |  |  |
| Control 6696 |  |  |  |  |  |
| day 0 | 35 | 45 | 75 | 80 | 90 |
| day 1 | 30 | 40 | 75 | 80 | 80 |
| day 3 | 7 | 15 | 50 | 60 | 70 |
| day 7 | 5 | 15 | 45 | 50 | 60 |
| day 20 |  |  |  |  |  |
| TOM2 6698 |  |  |  |  |  |
| day 0 | 30 | 45 | 65 | 70 | 80 |
| day 1 | 0 | 15 | 45 | 65 | 60 |
| day 3 | −5 | 5 | 25 | 40 | 40 |
| day 7 | −5 | 5 | 25 | 25 | 0 |
| day 20 | −5 | 0 | 0 | 0 | −5 |
| Control 6698 |  |  |  |  |  |
| day 0 | 55 | 40 | 65 | 70 | 80 |
| day 1 | 10 | 15 | 45 | 60 | 70 |
| day 3 | 15 | 15 | 45 | 40 | 55 |
| day 7 | 5 | 5 | 25 | 35 | 10 |
| day 20 | 10 | 10 | 20 | 30 | 5 |
| TOM2 6699 |  |  |  |  |  |
| day 0 | 70 | 65 | 70 | 75 | 85 |
| day 1 | 60 | 65 | 70 | 75 | 85 |
| day 3 | 25 | 20 | 70 | 70 | 75 |
| day 7 | 10 | 5 | 45 | 40 | 45 |
| day 20 | 10 | 10 | 45 | 40 | 45 |
| Control 6699 |  |  |  |  |  |
| day 0 | 70 | 70 | 65 | 70 | 85 |
| day 1 | 60 | 70 | 65 | 70 | 85 |
| day 3 | 50 | 65 | 60 | 65 | 70 |
| day 7 | 38 | 55 | 50 | 45 | 65 |
| day 20 | 28 | 35 | 50 | 45 | 60 |
| Pretest |  |  |  |  |  |
| Controls | 25 | 25 | 30 | 25 | 10 |
|  | 25 | 30 | 30 | 25 | 15 |
| Controls | 25 | 27.5 | 30 | 25 | 12.5 |
| TOM2 | 35 | 30 | 30 | 25 | 15 |
|  | 25 | 30 | 25 | 20 | 10 |
| TOM2 | 30 | 30 | 27.5 | 22.5 | 12.5 |

TABLE XIII

|  | Control | TOM2 |
|---|---|---|
| 0.5 kHz | | |
| day 0 | 62.5 | 50 |
| day 1 | 35 | 30 |
| day 3 | 32.5 | 10 |
| day 7 | 21.5 | 2.5 |
| day 20 | 19 | 2.5 |
| 1 kHz | | |
| day 0 | 55 | 55 |
| day 1 | 42.5 | 40 |
| day 3 | 40 | 12.5 |
| day 7 | 30 | 5 |
| day 20 | 22.5 | 5 |
| 2 kHz | | |
| day 0 | 65 | 67.5 |
| day 1 | 55 | 57.5 |
| day 3 | 52.5 | 47.5 |
| day 7 | 37.5 | 35 |
| day 20 | 35 | 22.5 |
| 4 kHz | | |
| day 0 | 70 | 72.5 |
| day 1 | 65 | 70 |
| day 3 | 52.5 | 55 |
| day 7 | 40 | 32.5 |
| day 20 | 37.5 | 20 |
| 8 kHz | | |
| day 0 | 82.5 | 82.5 |
| day 1 | 77.5 | 72.5 |
| day 3 | 62.5 | 57.5 |
| day 7 | 37.5 | 22.5 |
| day 20 | 32.5 | 20 |

TABLE XIV

|  | 0.5 kHz | 1 kHz | 2 kHz | 4 kHz | 8 kHz |
|---|---|---|---|---|---|
| Pretest | | | | | |
| Control 6821 | 30 | 20 | 25 | 15 | 7.5 |
| Control 6845 | 30 | 25 | 20 | 15 | 10 |
| Control 6850 | 27 | 25 | 15 | 10 | 0 |
| Control 6828 | 20 | 15 | 20 | 5 | 5 |
| Control 6829 | 20 | 20 | 20 | 20 | 5 |
| Control | 25.4 | 21 | 20 | 13 | 5.5 |
| CH65 6821 | 30 | 22.5 | 25 | 20 | 10 |
| CH65 6845 | 35 | 25 | 25 | 10 | 0 |
| CH65 6850 | 25 | 25 | 10 | 12 | 0 |
| CH65 6828 | 20 | 25 | 15 | 5 | 0 |
| CH65 6829 | 23 | 25 | 25 | 15 | 10 |
| CH65 | 26.6 | 24.5 | 20 | 12.4 | 4 |
| Day 1 | | | | | |
| Control 6821 | 5 | 25 | 50 | 60 | 72.5 |
| Control 6845 | 15 | 15 | 40 | 75 | 80 |
| Control 6850 | 8 | 10 | 25 | 65 | 55 |
| Control 6828 | 5 | 20 | 55 | 75 | 80 |
| Control Day 1 | 8.25 | 17.5 | 42.5 | 68.75 | 71.875 |
| ctrlsd | 4.716991 | 6.454972 | 13.22876 | 7.5 | 11.79248 |
| CH65 6821 | 0 | 2.5 | 0 | 10 | 0 |
| CH65 6845 | 5 | 20 | 25 | 35 | 30 |
| CH65 6850 | 10 | 0 | 20 | 68 | 35 |
| CH65 6828 | 0 | 5 | 55 | 55 | 25 |
| CH65 Day 1 | 3.75 | 6.875 | 25 | 42 | 22.5 |
|  | 4.787136 | 8.984941 | 22.7303 | 25.28504 | 15.54563 |
| Day 3 | | | | | |
| Control 6821 | 10 | 25 | 50 | 55 | 67.5 |
| Control 6845 | 10 | 15 | 35 | 55 | 45 |
| Control 6850 | 3 | 5 | 15 | 25 | 15 |
| Control 6828 | 5 | 15 | 40 | 65 | 55 |
| Control 6829 | 20 | 20 | 35 | 45 | 45 |
| Control | 9.6 | 16 | 35 | 49 | 45.5 |
| Day 3 | 6.580274 | 7.416198 | 12.74755 | 15.16575 | 19.39716 |
| CH65 6821 | 5 | 7.5 | 0 | 10 | 0 |
| CH65 6845 | 5 | 5 | 0 | 0 | 15 |
| CH65 6850 | 5 | 2 | 15 | 25 | 15 |
| CH65 6828 | 0 | 0 | 40 | 55 | 0 |
| CH65 6829 | 12 | 20 | 35 | 45 | 45 |
| CH65 Day 3 | 5.4 | 6.9 | 18 | 27 | 15 |
|  | 4.27785 | 7.861298 | 18.90767 | 23.07596 | 18.37117 |
| Day 7 | | | | | |
| Control 6821 | 0 | 10 | 20 | 20 | 45 |
| Control 6845 | 10 | 15 | 25 | 45 | 45 |
| Control 6850 | 6 | 5 | 15 | 30 | 10 |
| Control 6828 | 10 | 20 | 37 | 65 | 60 |
| Control 6829 | 20 | 25 | 45 | 40 | 55 |
| Control | 9.2 | 15 | 28.4 | 40 | 43 |
| Day 7 | 7.293833 | 7.905694 | 12.36123 | 16.95582 | 19.55761 |
| CH65 6821 | 0 | 0 | 0 | 0 | 0 |
| CH65 6845 | 5 | 15 | 0 | 5 | 20 |
| CH65 6850 | 8 | 0 | 15 | 15 | 0 |
| CH65 6828 | 15 | 0 | 40 | 55 | 30 |
| CH65 6829 | 12 | 15 | 20 | 45 | 40 |
| CH65 Day 7 | 8 | 6 | 15 | 24 | 18 |
|  | 5.87367 | 8.215838 | 16.58312 | 24.59675 | 17.888854 |
| Day 20 | | | | | |
| Control 6821 | 0 | 10 | 25 | 35 | 7.5 |
| Control 6845 | 0 | 5 | 25 | 45 | 40 |
| Control 6850 | 8 | 0 | 10 | 20 | 10 |
| Control 6829 | 15 | 20 | 30 | 30 | 18 |
| Control | 5.75 | 8.75 | 22.5 | 32.5 | 18.875 |
| Day 20 | 7.228416 | 8.539126 | 8.660254 | 10.40833 | 14.77822 |
| CH65 6821 | 0 | 0 | 0 | 0 | −5 |
| CH65 6845 | 0 | 0 | 0 | 0 | 5 |
| CH65 6850 | 5 | 0 | 15 | 11 | 0 |
| CH65 6829 | 7 | 5 | 10 | 25 | 15 |
| CH65 | 3 | 1.25 | 6.25 | 9 | 3.75 |
| Day 20 | 3.559026 | 2.5 | 7.5 | 11.80603 | 8.539126 |
| Control Day 1 | 8.25 | 17.5 | 42.5 | 68.75 | 71.875 |
| Control Day 3 | 9.6 | 16 | 35 | 49 | 45.5 |
| Control Day 7 | 9.2 | 15 | 28.4 | 40 | 43 |
| Control Day 20 | 5.75 | 8.75 | 22.5 | 32.5 | 18.875 |
| Ch65 Day 1 | 3.75 | 6.875 | 25 | 42 | 22.5 |
| CH65 Day 3 | 5.4 | 6.9 | 18 | 27 | 15 |
| CH65 Day 7 | 8 | 6 | 15 | 24 | 18 |
| CH65 Day 20 | 3 | 1.25 | 6.25 | 9 | 3.75 |

Figure 16:
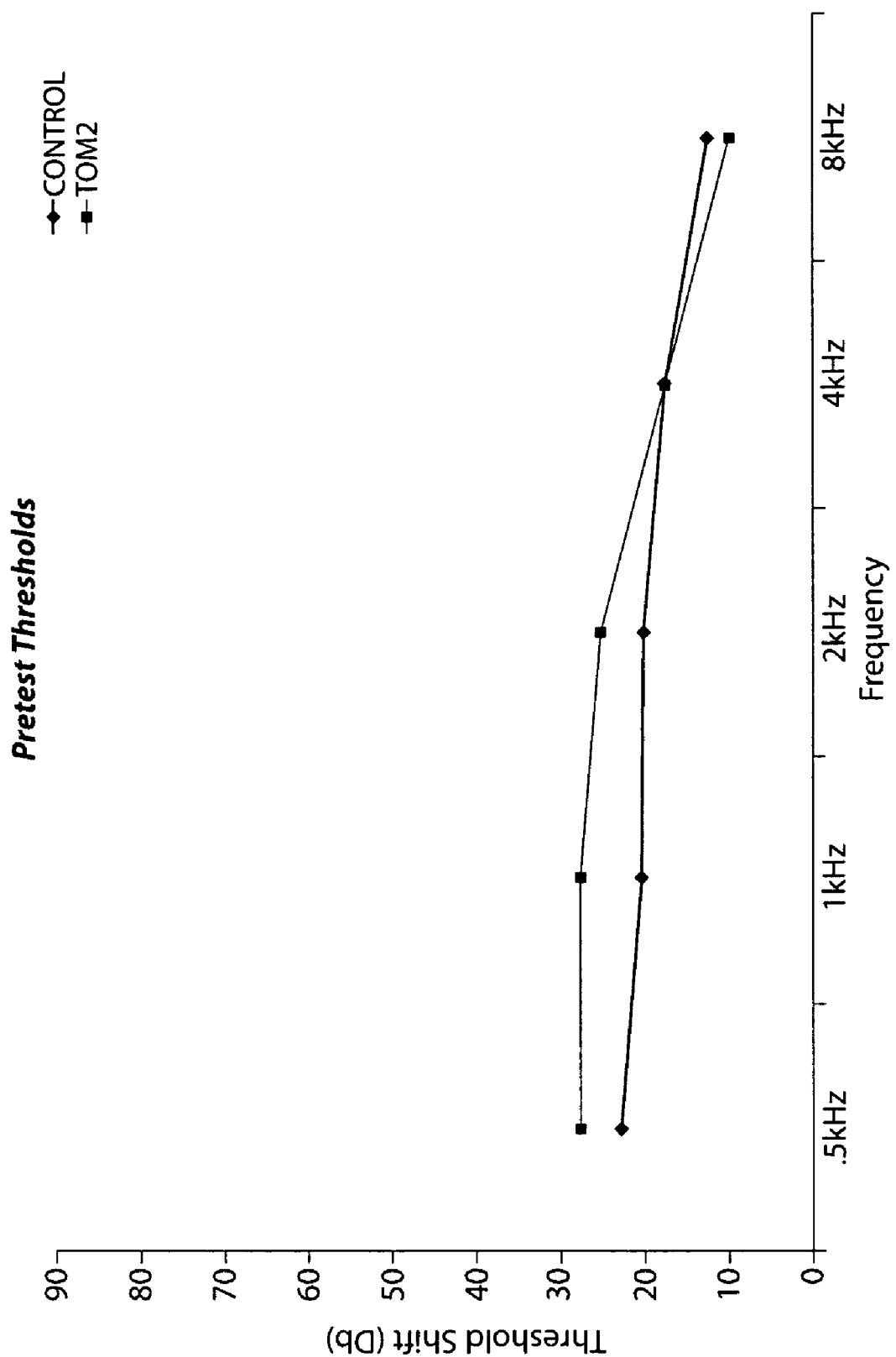
FIG. 16 is a graph showing average threshold shifts (dB) in chinchilla cochleas after exposure to 0.5 kHz, 1 kHz, 2 kHz, 4 kHz, and 8 kHz band noise prior to experimental manipulation.
Figure 18:
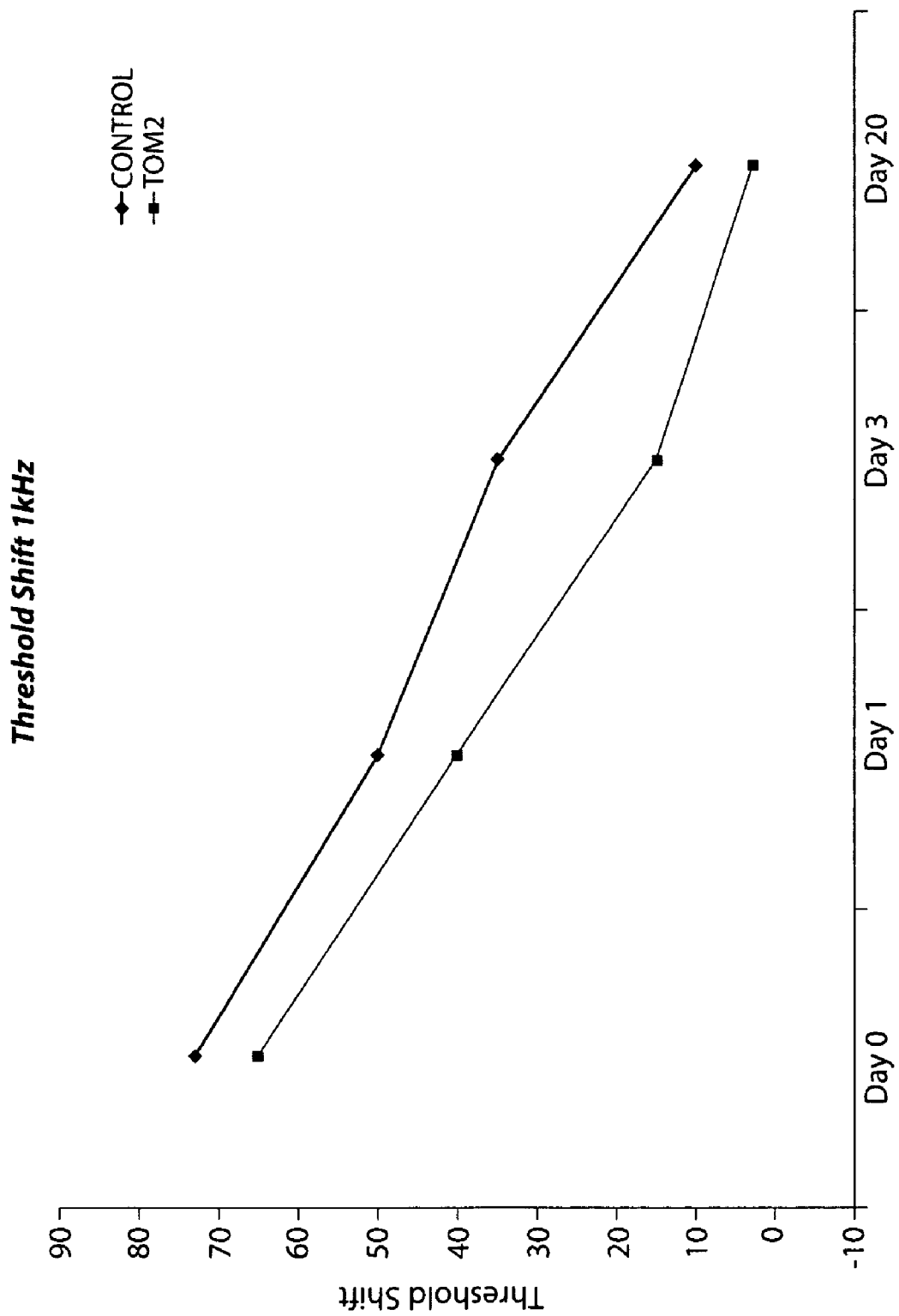
FIG. 18 is a graph showing average threshold shifts (dB) in chinchilla cochleas after exposure to 1 kHz band noise at day 0, day 1, day 3, and day 20 after experimental manipulation.
Figure 19:
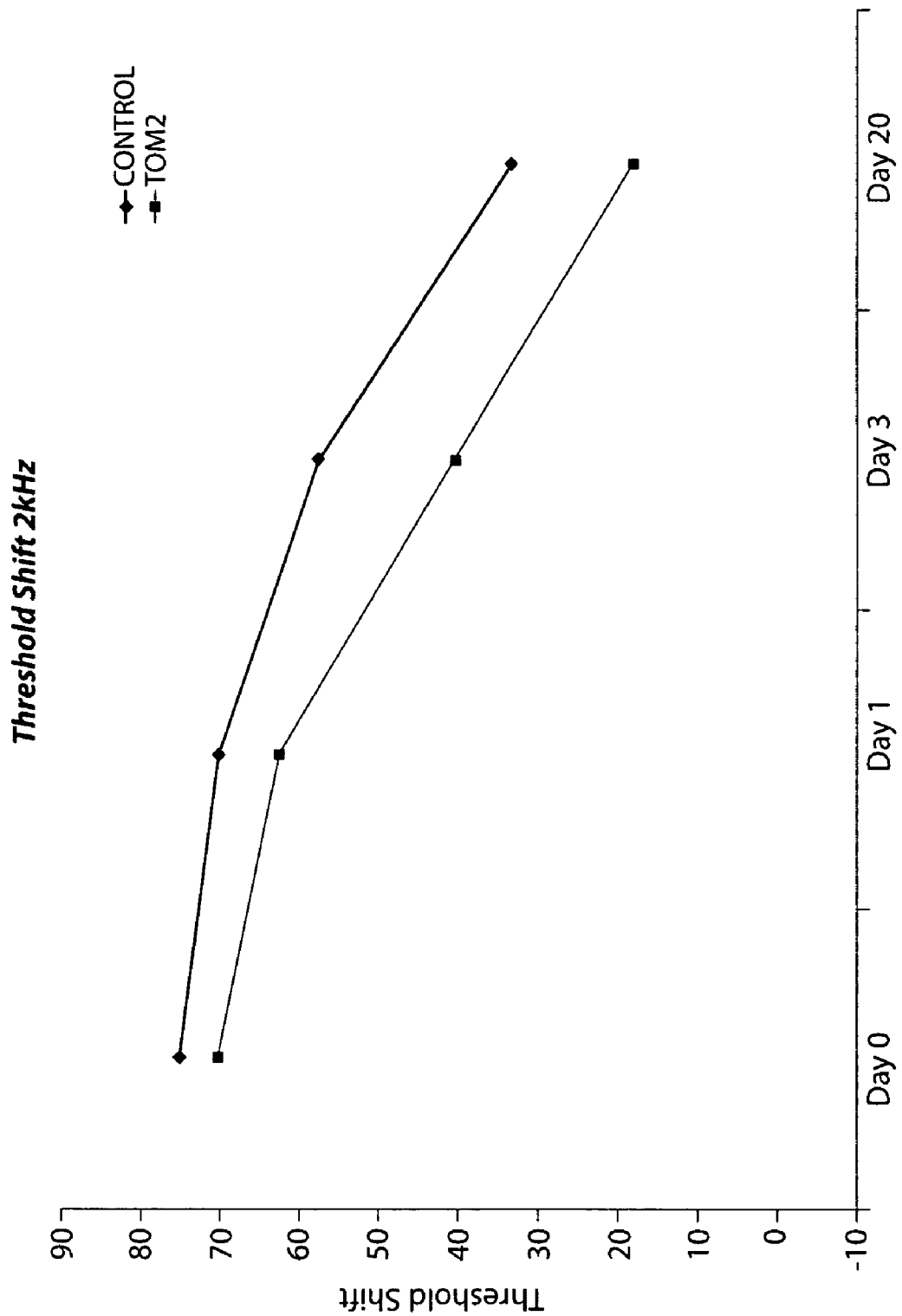
FIG. 19 is a graph showing average threshold shifts (dB) in chinchilla cochleas after exposure to 2 kHz band noise at day 0, day 1, day 3, and day 20 after experimental manipulation.
Figure 20:
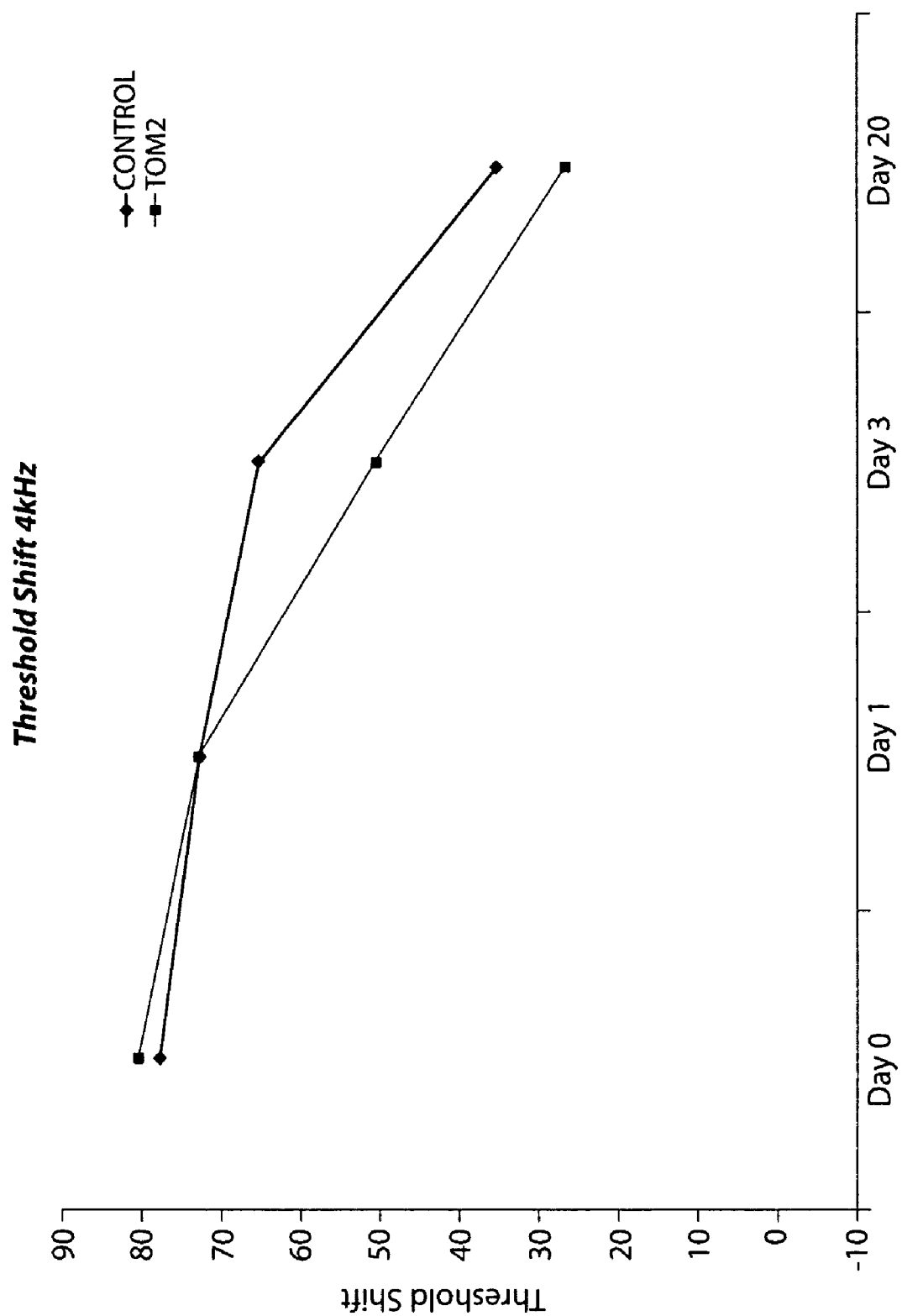
FIG. 20 is a graph showing average threshold shifts (dB) in chinchilla cochleas after exposure to 4 kHz band noise at day 0, day 1, day 3, and day 20 after experimental manipulation.
Figure 21:
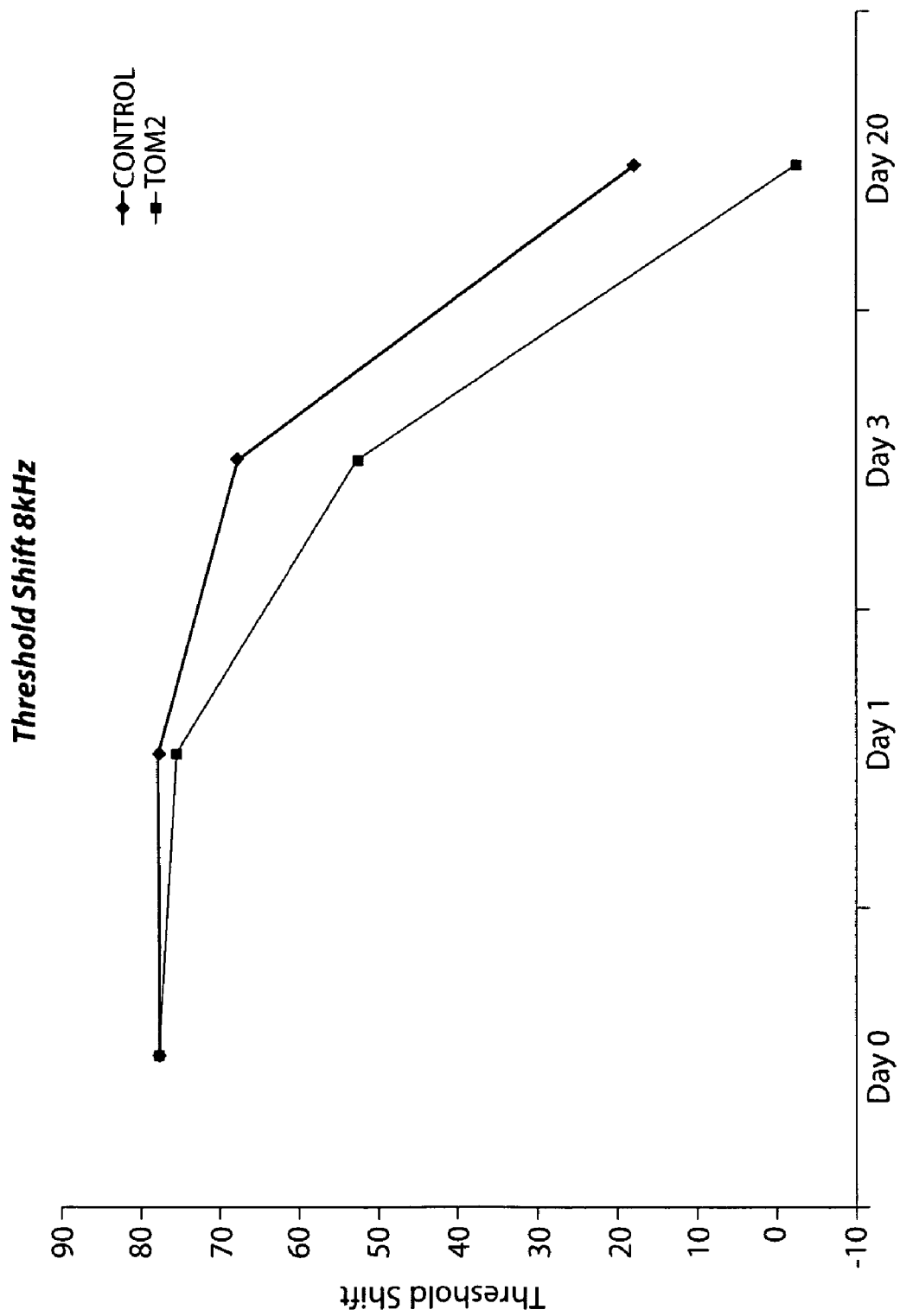
FIG. 21 is a graph showing average threshold shifts (dB) in chinchilla cochleas after exposure to 8 kHz band noise at day 0, day 1, day 3, and day 20 after experimental manipulation.
Figure 22:
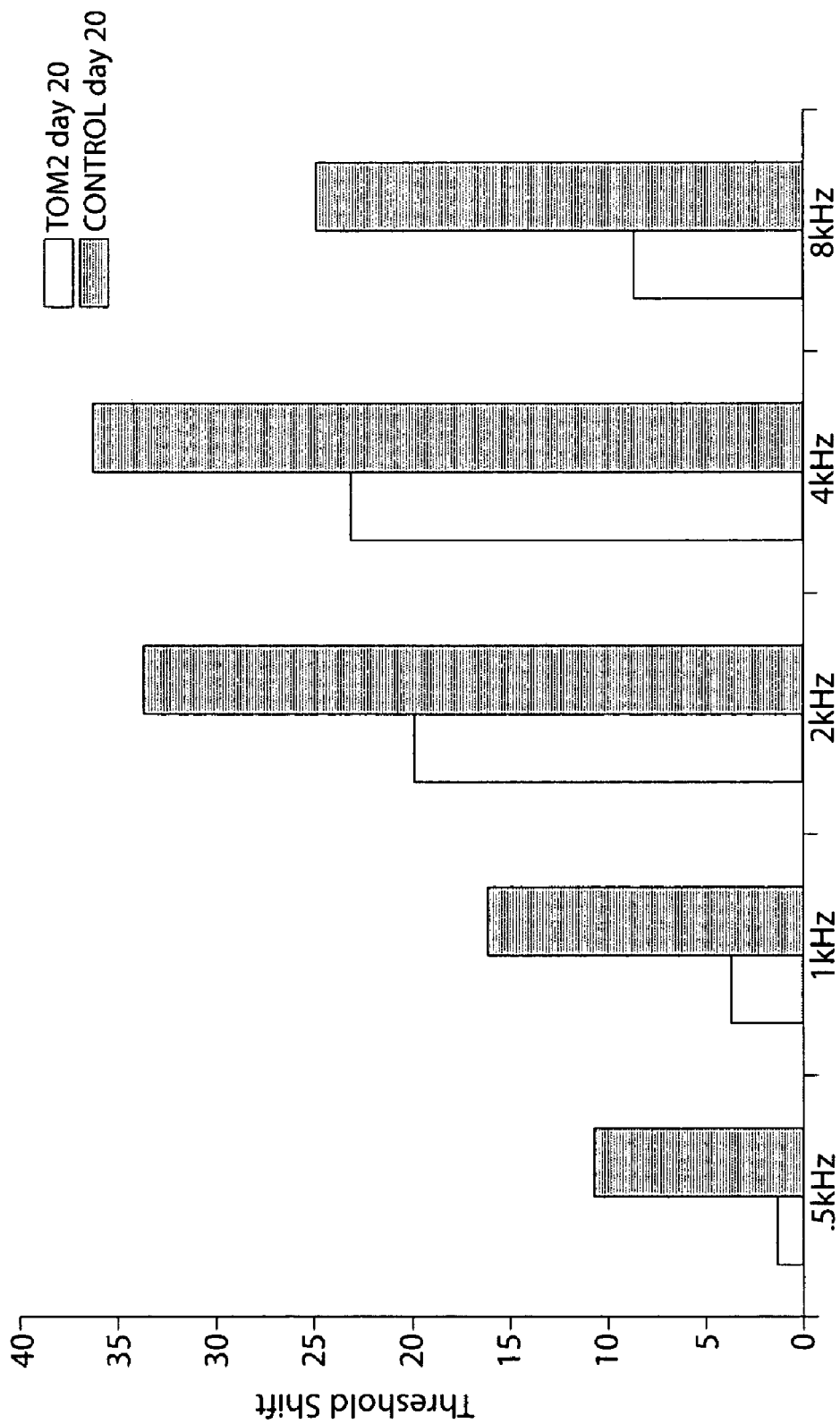
FIG. 22 is a graph showing the average dB threshold shifts in chinchilla cochleas at day 20 for control and treated ears.

FIGS. 16-22 show the average threshold shifts for animals treated with TOM 2-32. In particular, FIG. 16 shows average threshold shifts after exposure to 0.5 kHz, 1 kHz, 2 kHz, 4 kHz, and 8 kHz band noise tested prior to experimental manipulation (i.e., exposure to 4 kHz band noise at 105 dB for four hours). FIG. 17 shows average threshold shifts after exposure to 0.5 kHz band noise at day 0, day 1, day 3, and day 20 after experimental manipulation. FIG. 18 shows average threshold shifts after exposure to 1 kHz band noise at day 0, day 1, day 3, and day 20 after experimental manipulation. FIG. 19 shows average threshold shifts after exposure to 2 kHz band noise at day 0, day 1, day 3, and day 20 after experimental manipulation. FIG. 20 shows average threshold shifts after exposure to 4 kHz band noise at day 0, day 1, day 3, and day 20 after experimental manipulation. FIG. 21 shows average threshold shifts after exposure to 8 kHz band noise at day 0, day 1, day 3, and day 20 after experimental manipulation. FIG. 22 shows the average dB threshold shift at day 20 for control and treated ears. As shown in FIGS. 17-22 the average dB threshold shifts for treated ears were lower, indicating less hearing loss.

Figure 23:
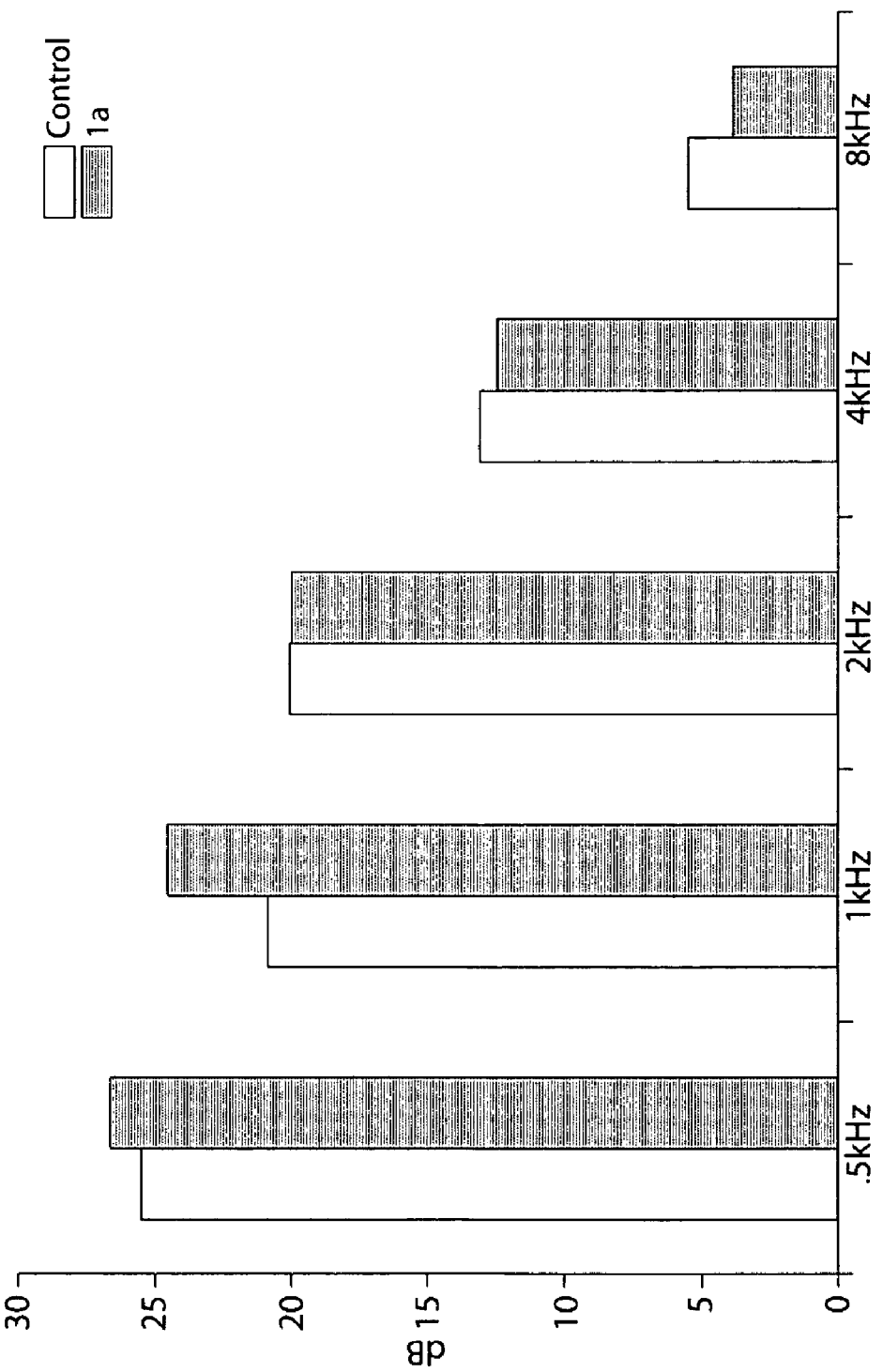
FIG. 23 is a graph showing average threshold shifts (dB) in chinchilla cochleas after exposure to 0.5 kHz, 1 kHz, 2 kHz, 4 kHz, and 8 kHz band noise prior to experimental manipulation.
Figure 24:
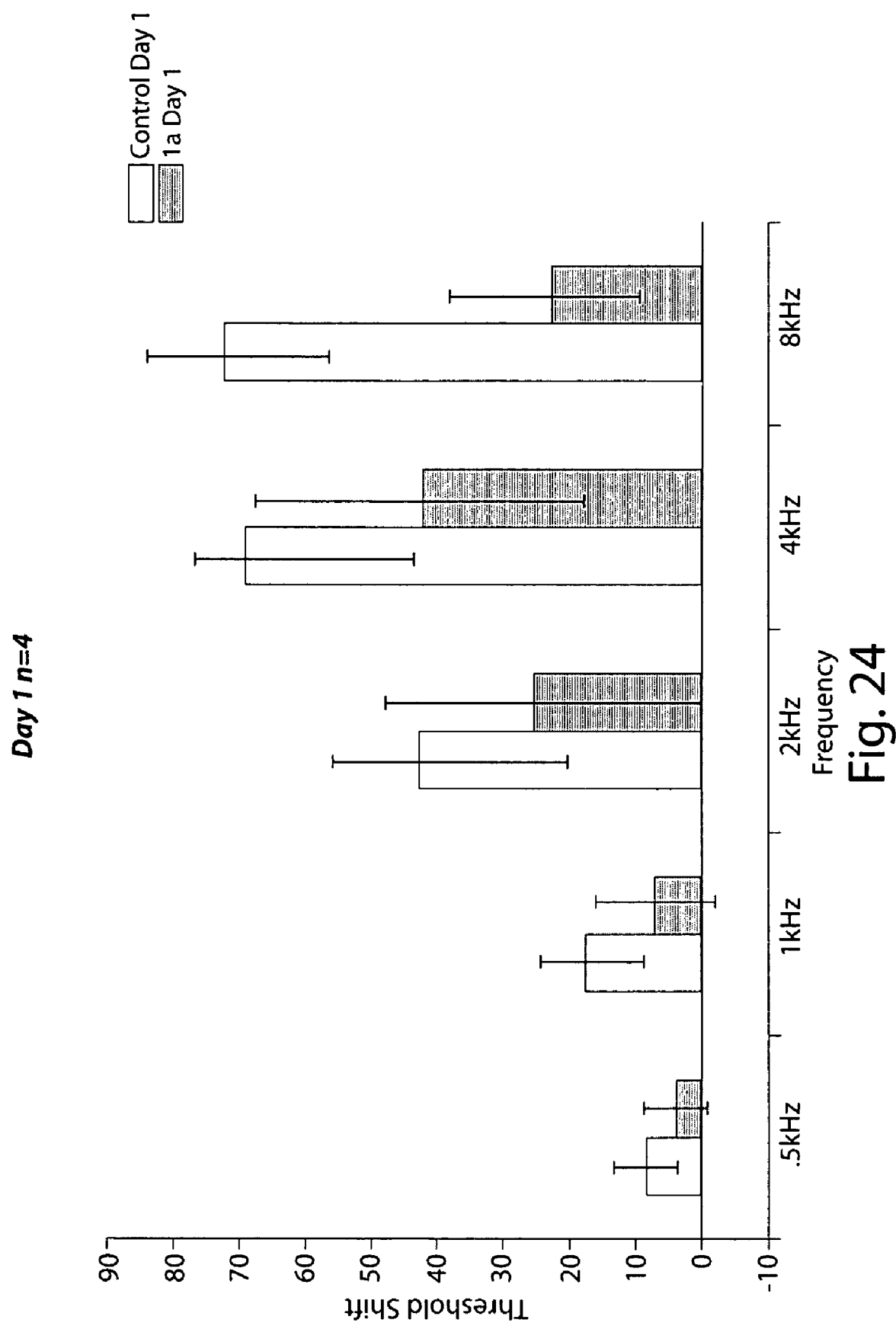
FIG. 24 is a graph showing average threshold shifts (dB) in chinchilla cochleas after exposure to 0.5 kHz, 1 kHz, 2 kHz, 4 kHz, and 8 kHz band noise on day 1 after experimental manipulation.
Figure 25:
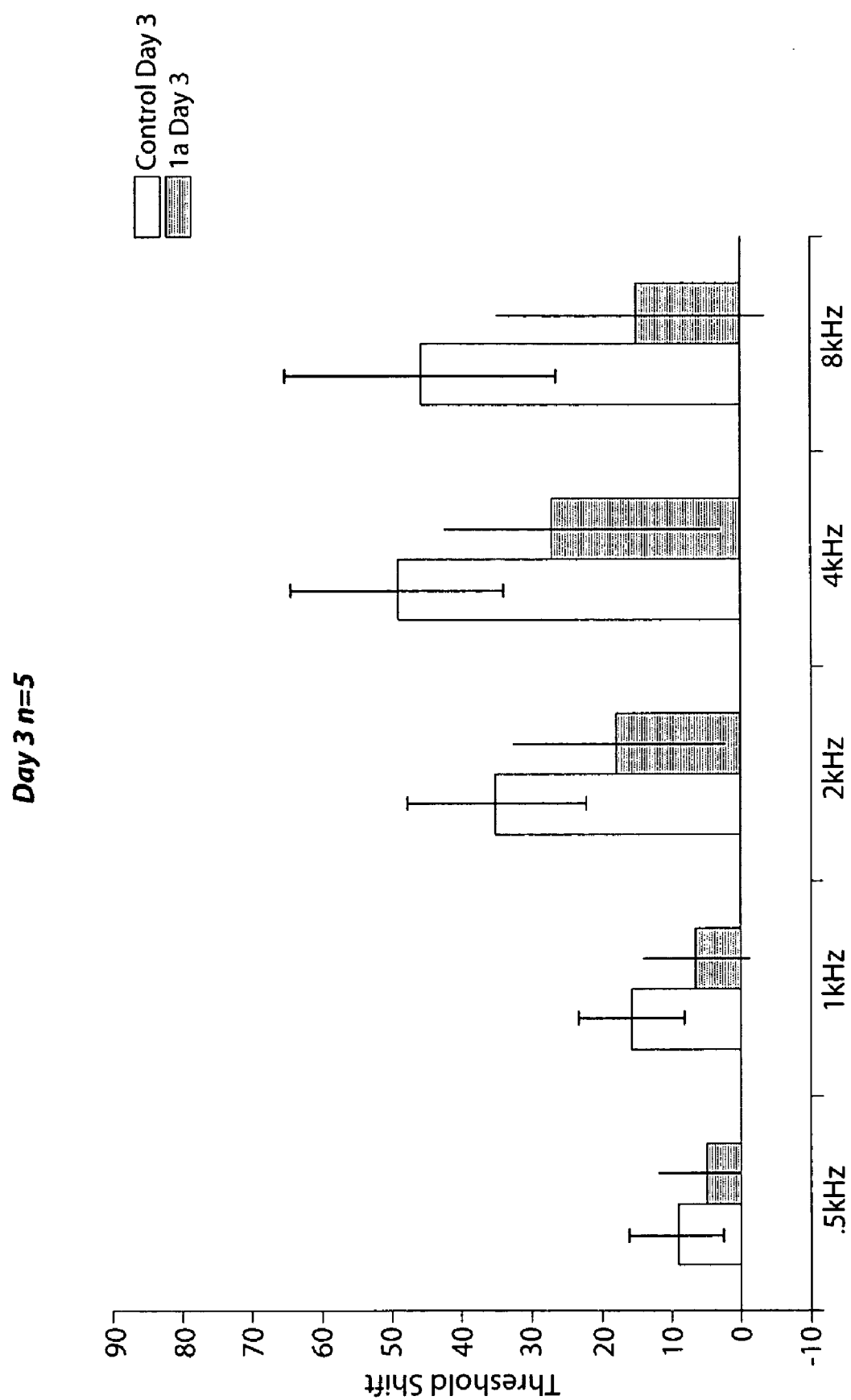
FIG. 25 is a graph showing average threshold shifts (dB) in chinchilla cochleas after exposure to 0.5 kHz, 1 kHz, 2 kHz, 4 kHz, and 8 kHz band noise on day 3 after experimental manipulation.
Figure 26:
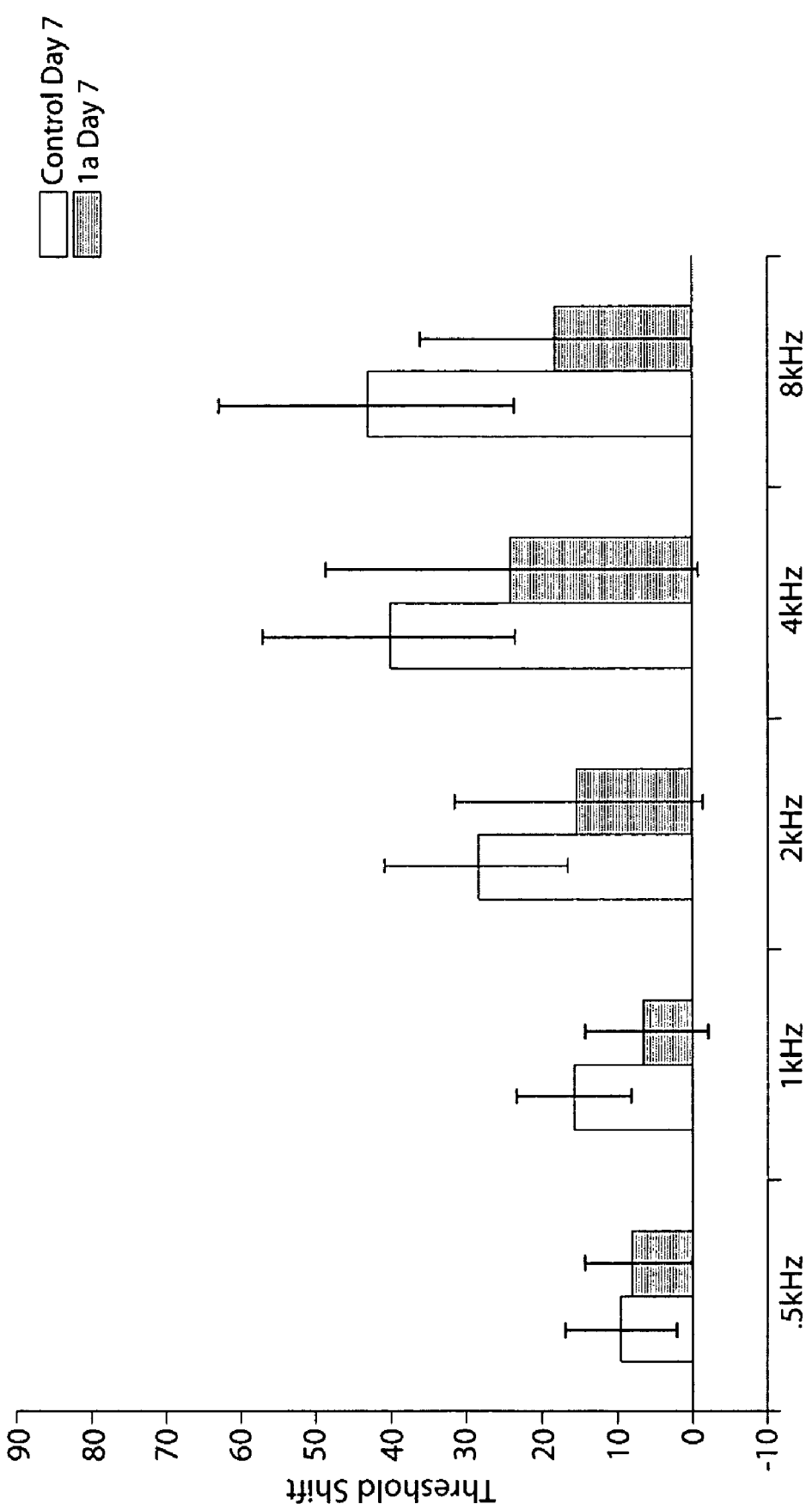
FIG. 26 is a graph showing average threshold shifts (dB) in chinchilla cochleas after exposure to 0.5 kHz, 1 kHz, 2 kHz, 4 kHz, and 8 kHz band noise on day 7 after experimental manipulation.
Figure 27:
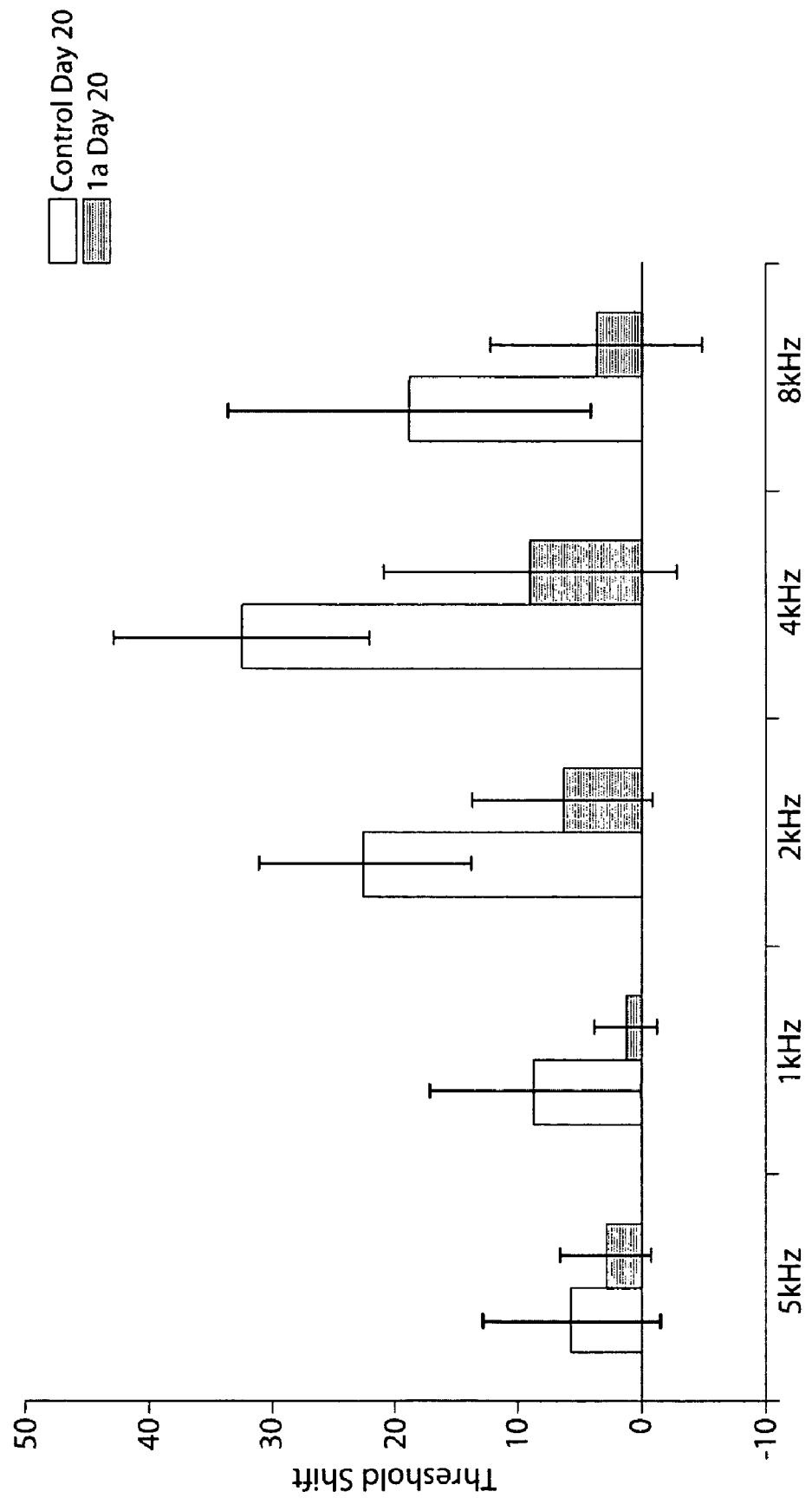
FIG. 27 is a graph showing average threshold shifts (dB) in chinchilla cochleas after exposure to 0.5 kHz, 1 kHz, 2 kHz, 4 kHz, and 8 kHz band noise on day 20 after experimental manipulation.
Figure 28:
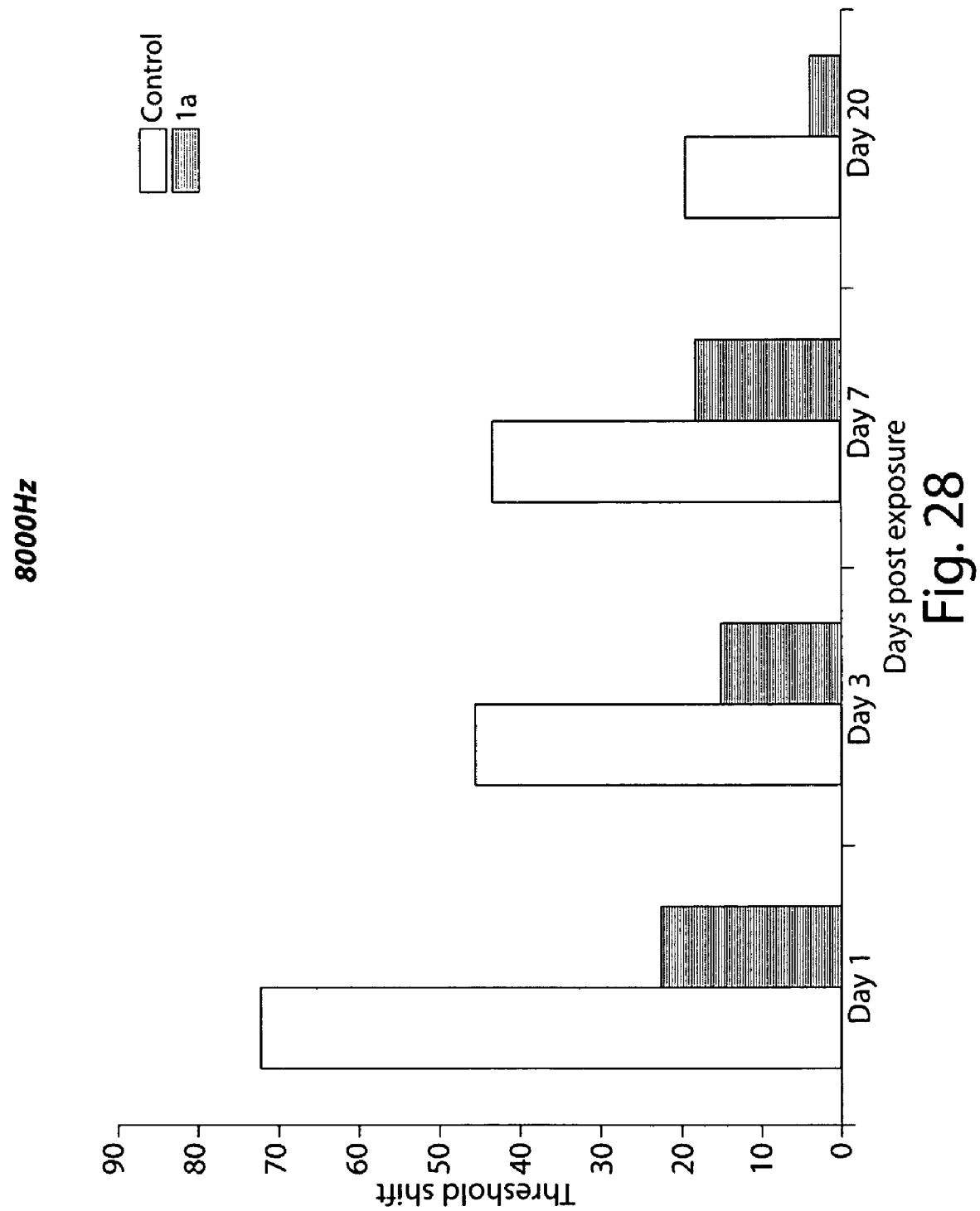
FIG. 28 is a graph showing average threshold shifts (dB) in chinchilla cochleas after exposure to 8000 Hz on day 1, day 3, day 7, and day 20.

FIGS. 23-28 show the average threshold shifts for animals treated with compound 1a. In particular, FIG. 23 shows average threshold shifts after exposure to 0.5 kHz, 1 kHz, 2 kHz, 4 kHz, and 8 kHz band noise tested prior to experimental manipulation. FIG. 24 shows average threshold shifts after exposure to 0.5 kHz, 1 kHz, 2 kHz, 4 kHz, and 8 kHz band noise on day 1 after experimental manipulation. FIG. 25 shows average threshold shifts after exposure to 0.5 kHz, 1 kHz, 2 kHz, 4 kHz, and 8 kHz band noise on day 3 after experimental manipulation. FIG. 26 shows average threshold shifts after exposure to 0.5 kHz, 1 kHz, 2 kHz, 4 kHz, and 8 kHz band noise on day 7 after experimental manipulation. FIG. 27 shows average threshold shifts after exposure to 0.5 kHz, 1 kHz, 2 kHz, 4 kHz, and 8 kHz band noise on day 20 after experimental manipulation. FIG. 18 shows average threshold shifts after exposure to 8000 Hz on day 1, day 3, day 7, and day 20. As shown in FIGS. 24-28, the average dB threshold shifts for treated ears were lower, indicating less hearing loss.

As shown in FIGS. 16-28, both TOM 2-32 and CH-65 provided protection against the noise exposure. However, compound 1a provided the greatest level of protection. In particular, the PTK inhibitor treated ears had, on average, 15 to 25 dB less hearing loss than the control ears and the animals showed no side effects of the experimental manipulation.

Example 9

Inhibition of Noise-Induced Apoptosis in Cochlear Hair Cells Using Inhibitors of the PTKs Chinchillas (N=3) were exposed to 75-pairs of impulse noise at 155 dB pSPL. The animals were sacrificed 5 minutes after the noise exposure. The cochleas were examined for activation of the focal adhesion complex using an antibody against focal adhesion kinase, which is an intrinsic member of the complex.

FIGS. 29A-F show the effect of high level impulse noise on chinhilla cochleas without treatment with a PTK inhibitor. In particular, FIG. 29A is an electron micrograph which shows the cochlear damage following high level impulse noise (155 dB). FIG. 29A shows a spilt at the reticular lamina (S). The split appears to be between the second and third rows of outer hair cells. FIG. 29B depicts a cochlea stained immunohistochemcially for focal adhesion kinase (FAK) following a moderately high level octave band noise (105 dB). The staining observed in FIG. 29B is relatively low level and approximates that observed without noise. The staining appears to be localized primarily at the pharangeal processes of the Deiter cells and not at the hair cells. Upon elevating the noise level to 110 dB OBN, apoptotic cells appeared, as shown in FIG. 29C. These apoptotic cells are located in two regions of the upper left quadrant of the figure and the nuclei appear bright and highly condensed, whereas the normal nuclei are large and more diffuse in color. FIG. 29D is a photo of the same cells stained with focal adhesion kinase (FAK) antibody (as in FIG. 29B; however, here the pharangeal processes appear to surround a lesion where cells are missing). These lesions correspond to the areas in FIG. 29C where the cells underwent apoptosis. FIG. 29E shows the same region but at a lower vertical plane, demonstrating that the lesion extends well below the cuticular plate and into the cell body. FIG. 29F shows cochleas exposed to impulse noise at 155 dB SPL. The cochleas lost their integrity at the cuticular plate and were heavily stained throughout. Many dark areas are seen, which represent areas where hair cells have died.

Figure 30:
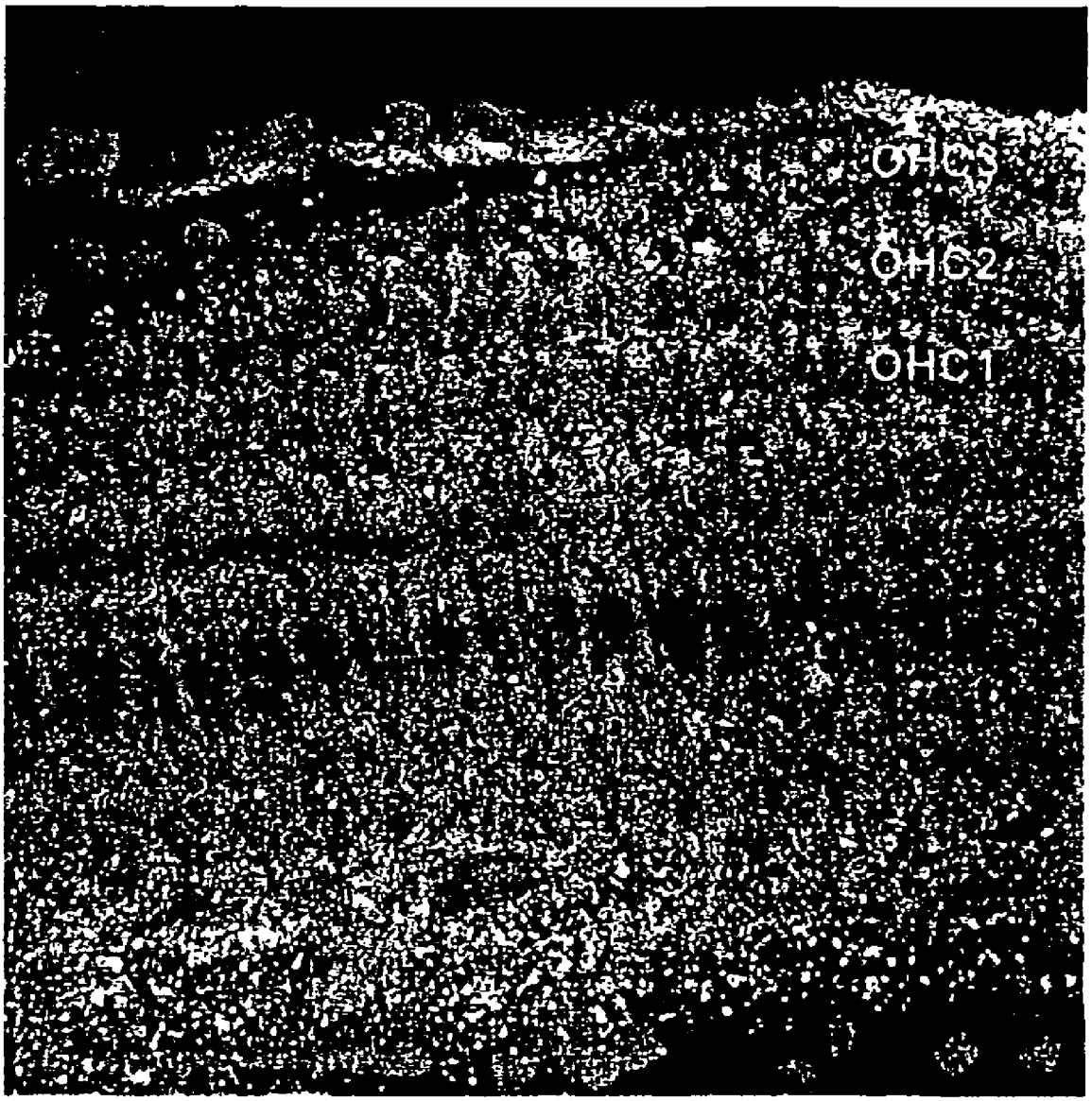
FIGS. 30A-B are confocal images of chinchilla cochleas exposed to high level noise.
Figure 30B:
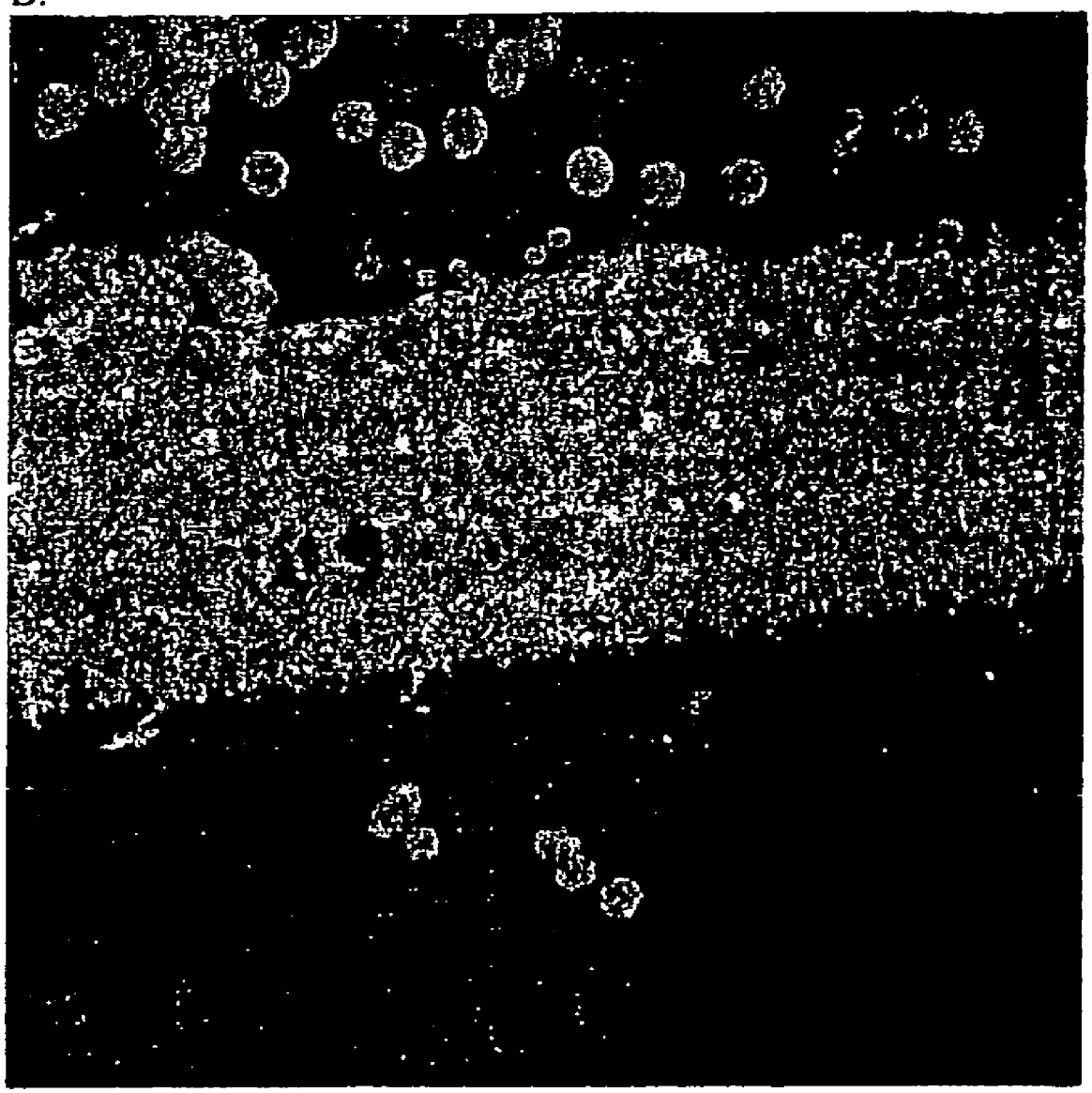

FIG. 30A shows a cochlea pretreated with compound 1a, whereas FIG. 30B shows an untreated cochlea following exposure to high level noise (155 dB). In the treated cochlea (FIG. 30A), there is a high level of FAK staining that extends beyond the pharangeal processes of the Deiter cells and well into the cuticular plate. The punctate nature of the staining is indicative of the formation of focal adhesion complexes of which FAK is an intrinsic member. Furthermore, the three rows of hair cell nuclei (labeled OHC1-3) appear both in order and intact and without any indication of apoptosis taking place. Since FAK is known to be active within focal adhesion complexes, this data strongly suggests that FAK is active following a high noise exposure. It is hypothesized that it is the inhibition of the kinase function that is prevented through the treatment with compound 1a and results in the survival of cochlear hair cells.

In contrast to FIG. 30A, FIG. 30B demonstrates a somewhat lower level of FAK staining, but also shows a remarkably high level of cell death. In this figure, nearly half of the cells have died by apoptosis, as indicated by the number of condensed nuclei. This contrasts with FIG. 30A, where no apoptotic nuclei were observed with treatment. Since compound 1a can inhibit phosphorylation of several FAK substrates, including paxillin and pp130cas, it is believed that FAK kinase function in the cochlea is playing a protective role in response to high level noise exposure.

As described above, the PTK inhibitor treated ears showed less outer hair cell loss than controls. This indicates that anoikis (detachment from the cell's matrix, resulting in apoptosis) may play a significant role in noise-induced hair cell loss, and that blockage of apoptotic signals generated at the cell matrix can prevent hair cell loss.

More specifically, using the above chinchilla animal model, it has been demonstrated that focal adhesion complexes are formed in response to extremely high level noise. FAK is activated upon formation of these complexes and is known to initiate several signaling cascades, first through a series of autophosphorylation events and subsequently through phosphorylation of downstream peptide substrates. It has been demonstrated that apoptotic cells are seen within the lesion surrounded by focal adhesion complexes. Furthermore, addition of the $pp60^{c\text{-}src}$ inhibitor prevents the apoptotic response without preventing the formation of the focal adhesion complex. These data suggest that the downstream signaling through tyrosine phosphorylation by FAK may be an early step in the apoptotic signaling of hair cells. Since FAK is activated by shear stress in other organic systems, these observations may represent the first signaling pathway identified in the ear to be activated by mechanical stress.

Example 10

Inhibition of Isolated Kinases

It is believed that the conformation of Src outside cells vs. inside cells is markedly different, because inside cells, Src is embedded in multiprotein signaling complexes. Thus, because the peptide substrate binding site is not well formed in isolated Src (as shown by Src x-ray structures), it is believed that the activity against isolated Src for a peptide substrate binding inhibitor would be weak. Binding to this site will require the inhibitor to capture the very small percentage of total Src protein in the isolated enzyme assay that is in the same conformation that exists inside cells. This requires a large excess of the inhibitor to drain significant amounts of the enzyme from the catalytic cycle in the assay.

However, inside cells this large inhibitor excess is not needed because the SH2 & SH3 domain binding proteins have already shifted the Src conformation so that the peptide substrate binding site is fully formed. Now, low concentrations of the inhibitor can remove the enzyme from the catalytic cycle since all of the enzyme is in the tight binding conformation.

KX2-328 is AstraZeneca's published ATP-competitive Src inhibitor (AZ28) and is used as a postive control in many of the experiments described herein. Note that KX2-391 has weak activity against isolated kinases because the peptide binding site is not well formed outside of cells (a close analog, KX2-394 is a little more potent against isolated Src), but have very potent activity inside whole cells. Without wishing to be bound by theory, it is thought that the difference in activity is attributed to the fact that the peptide binding site is now fully formed in cells due to the allosteric effects of the binding protein partners in the multi-protein signaling complexes, relative to isolated kinase assays.

Table XV illustrates percent activity of isolated kinases in the presence of the AstraZeneca ATP-competitive inhibitor (KX-328, AZ-28) or KX2-391 relative to control (untreated) isolated kinases.

TABLE XV

| Target | AZ28 @ 10 µM | KX2-391 @ 10 µM |
|---|---|---|
| Abl(h) | 1 | 120 |
| CHK1(h) | NT | 105 |
| EGFR(h) | 3 | 134 |
| FGFR2(h) | 94 | 94 |
| Fyn(h) | 2 | 85 |
| IGF-1R(h) | 110 | 101 |
| IR(h) | 125 | 112 |
| Lck(h) | 1 | 109 |
| Lyn(h) | 0 | 113 |
| MAPK2(h) | 105 | 112 |
| PDGFRβ(h) | 98 | 110 |
| PKCα(h) | 111 | 111 |
| Pyk2(h) | 43 | 97 |
| Yes(h) | 1 | 92 |
| ZAP-70(h) | 97 | 108 |
| PI3 kinase | 99 | 100 |

The AstraZeneca ATP competitive inhibitor shows the typical off target kinase inhibition activity for ATP-competitive inhibitors, poor selectivity as evidenced by strong inhibition of Abl, EGFRTK, Fyn, Lck, Lyn & Yes. In contrast, poor inhibition of these off-target kinases is seen with KX2-391.

However, KX2-391 is a more potent inhibitor of Src-driven cell growth, assayed as described above. In the c-Src/NIH-3T3 engineered cell line, the $GI_{50}$ for AZ28 is 99 nM, vs. 13 nm for KX2-391, and in the NCI human colon cancer cell line HT29, the $GI_{50}$ for AZ28 is 794 nM, vs. 23 nm for KX2-391. Similar to KX2-391, the $GI_{50}$ for KX2-394 in the c-Src/NIH-3T3 engineered cell line is 13 nM, and in the NCI human colon cancer cell line HT29, the $GI_{50}$ for KX2-394 is 794 nM, vs. 33 nm.

In separate examples, titration data indicate that AZ28 is a potent inhibitor of isolated Src (IC50=8 nM). The titration data with FAK shows that AZ28 is at least ca. 100× less potent against isolated FAK (IC50>500 nM). Whereas, titration data indicate that KX2-391 and KX2-394 are less potent inhibitors of isolated Src (IC50=46 µM and 5 µM, respectively). The titration data with FAK shows that KX2-391 and KX2-394 are similarly potent against isolated FAK (IC50>48 µM).

Note that AZ28 is 10-100× less potent against cell growth than against isolated Src. This is typical of ATP competitive inhibitors since the concentration of competing ATP is much higher in whole cells than in the isolated enzyme assays Example 11

Effect of Compounds on Intracellular Phosphorylation Levels

HT29 (colon cancer) and c-Src527F/NIH-3T3 (Src transformed) cell lines were treated with KX2-391 or with AstraZeneca's ATP competitive Src inhibitor AZ28. AZ28 serves as a positive comparator to show what a validated Src inhibitor should do in these assays. After treatment with compound, cells were lysed, subjected to PAGE and probed with a battery of antibodies. The antibodies were selected to determine whether compounds caused changes in phosphorylation of known Src substrates. In addition, off-target protein phosphorylation was also investigated. Further, induction of apoptosis was evaluated via Caspase 3 cleavage. Multiple doses of each compound were tested because the trends in response to increasing drug concentration are the most reliable indicator of activity.

Figure 31A:
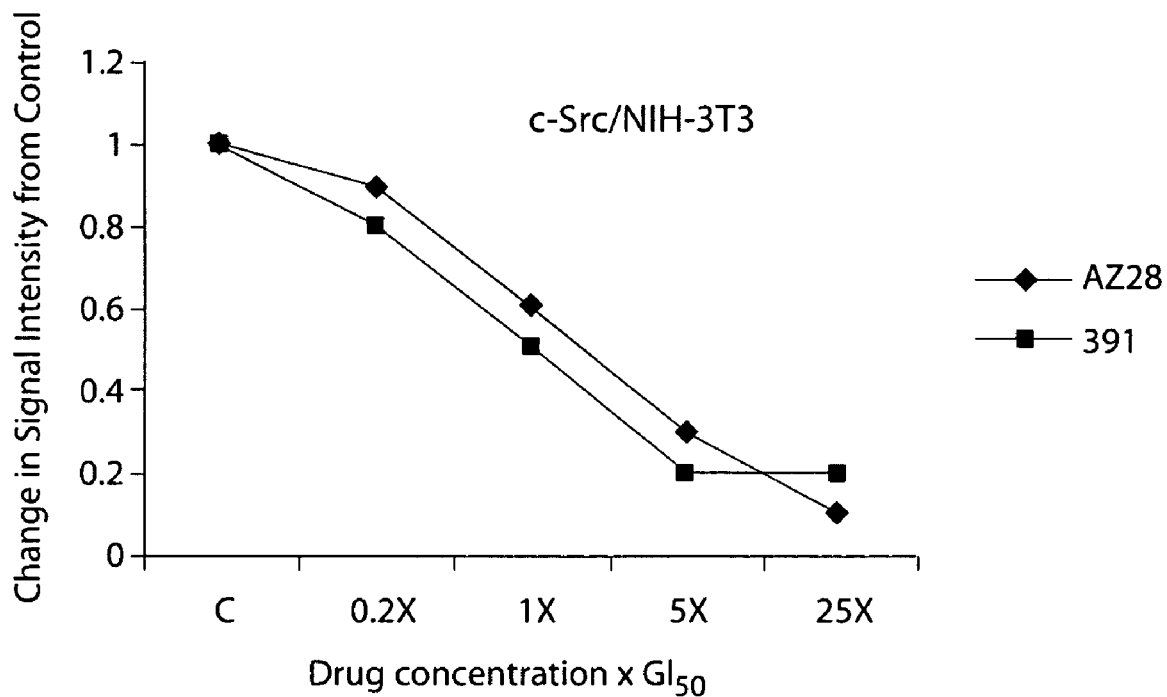
FIG. 31A is a graph indicating the effect of AZ28 and KX2-391 on Src autophosphorylation in c-Src/NIH-3T3 cells.
Figure 31B:
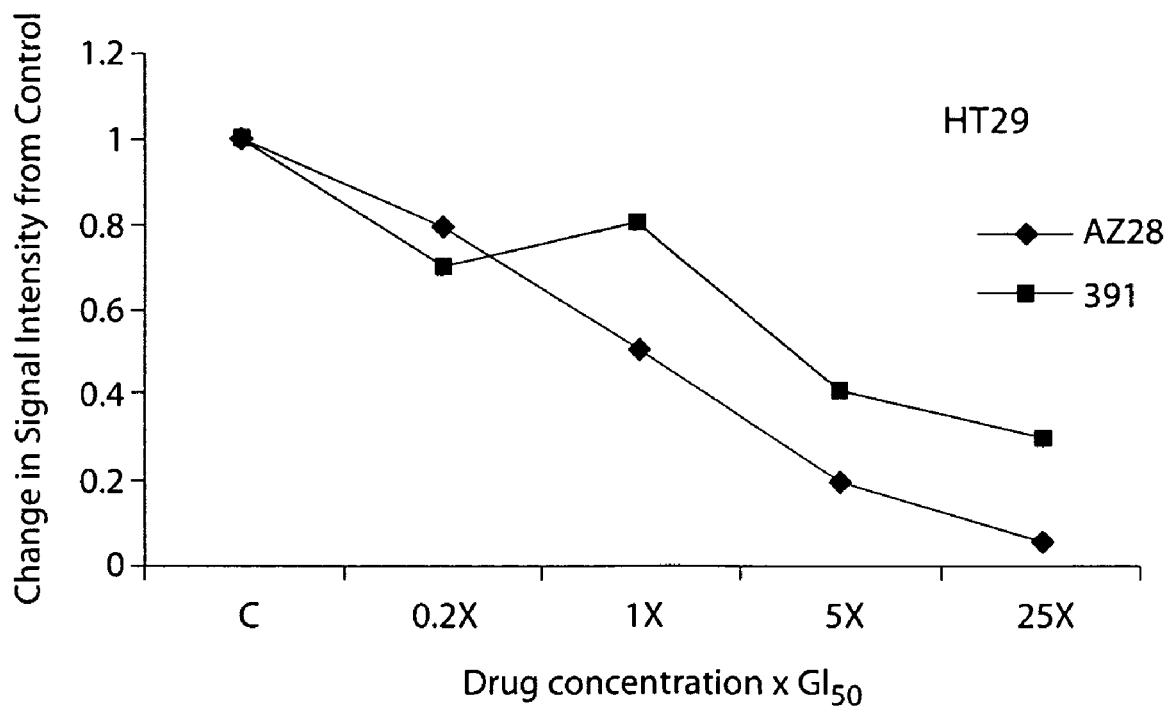
FIG. 31B is a graph indicating the effect of AZ28 and KX2-391 on Src autophosphorylation in HT-29 cells.

A dose response curve for KX2-391 was generated using the GI50 for this compound in each of the two cell lines as the 1× concentration. Three additional doses 0.2×, 5× & 25× multiples the GI50's were also tested in addition to a no drug control "C". The same range of multiples of the GI50 for AZ28 in these two cell lines was run as a comparison. As shown in FIG. 31, the expected dose response for Src-Y416 autophosphorylation was obtained in both cell lines, and for both compounds. This data indicates that KX2-391 is a Src inhibitor inside cells.

Figure 32A:
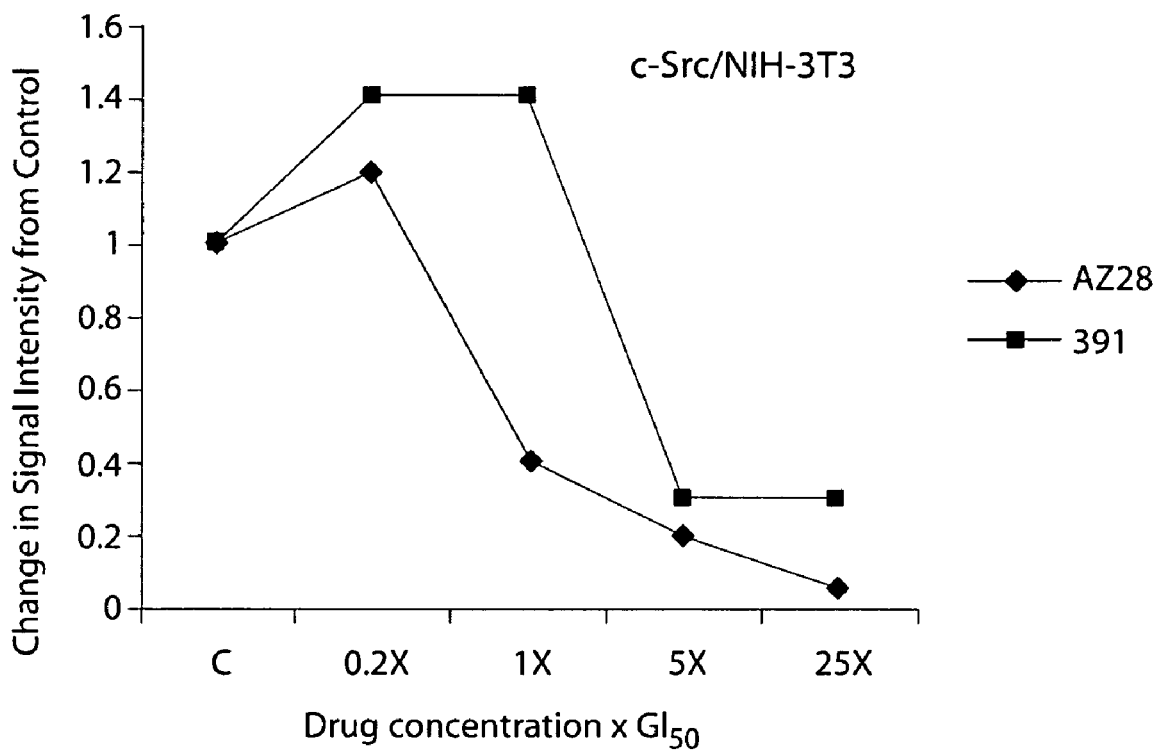
FIG. 32A is a graph indicating the effect of AZ28 and KX2-391 on FAK phosphorylation in c-Src/NIH-3T3 cells.
Figure 32B:
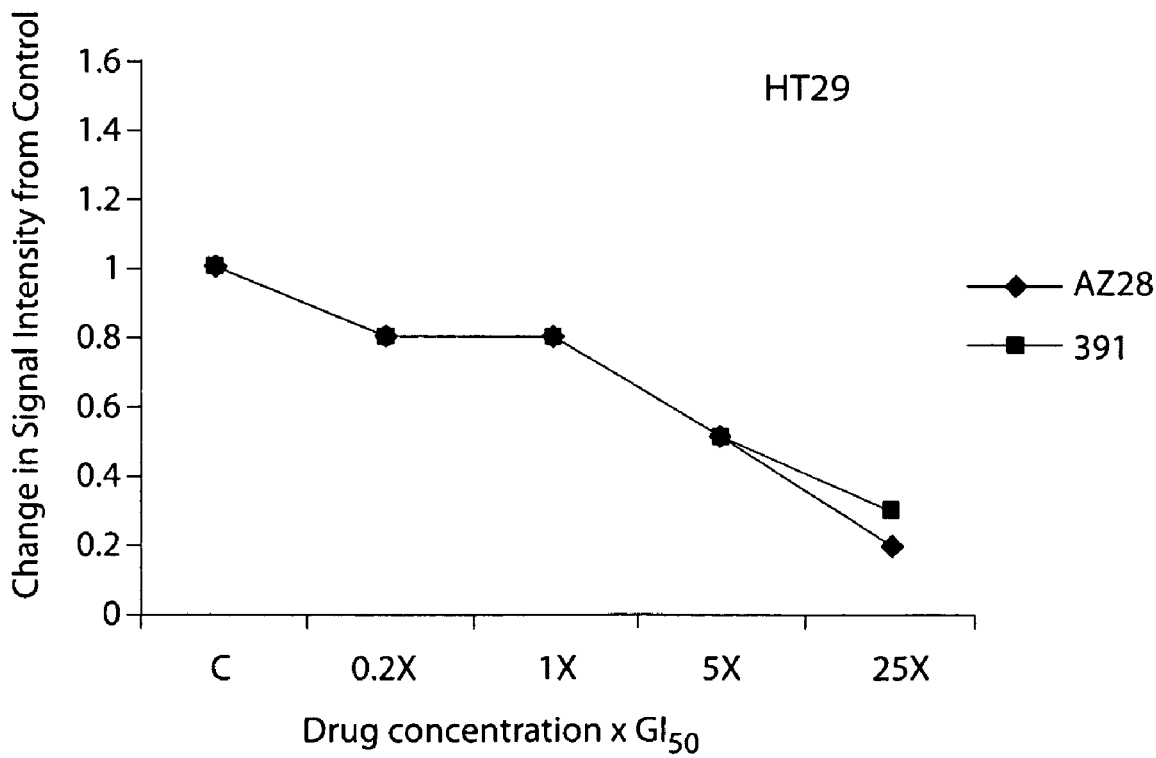
FIG. 32B is a graph indicating the effect of AZ28 and KX2-391 on FAK phosphorylation in HT-29 cells.

FIG. 32 shows phosphorylation of FAK Tyr 925, a known Src transphorylation substrate within cells. KX2-391 and AZ28 inhibited Src trans-phosphorylation. This data indicates that KX2-391 is a Src inhibitor inside cells.

Figure 33A:
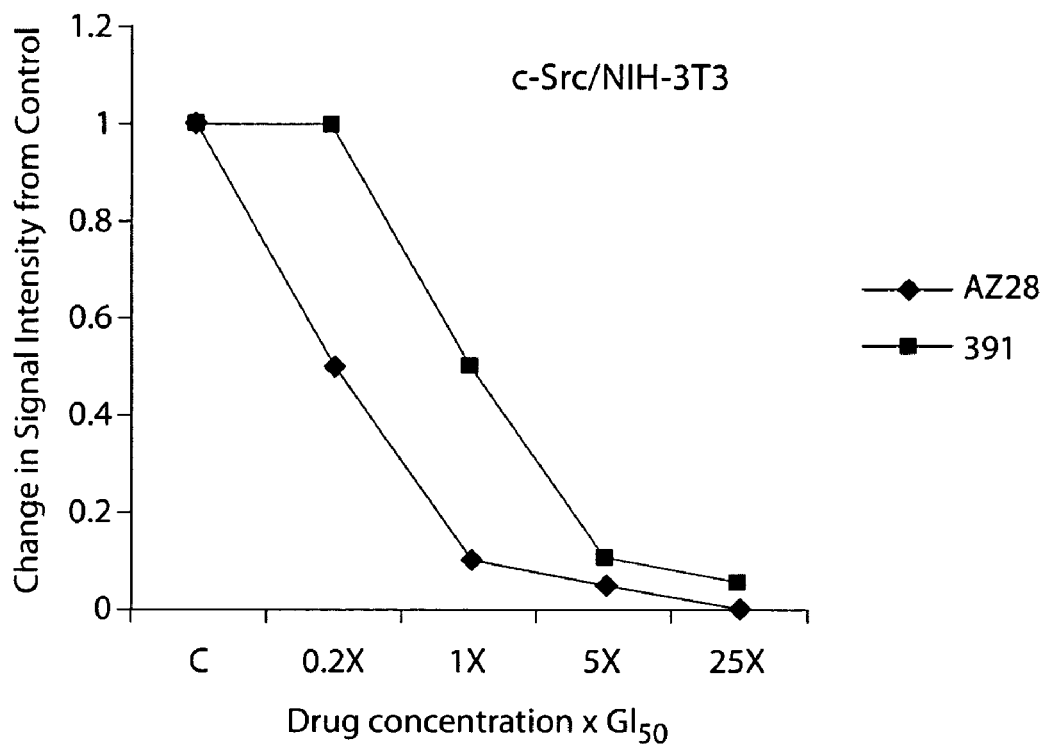
FIG. 33A is a graph indicating the effect of AZ28 and KX2-391 on Shc phosphorylation in c-Src/NIH-3T3 cells.
Figure 33B:
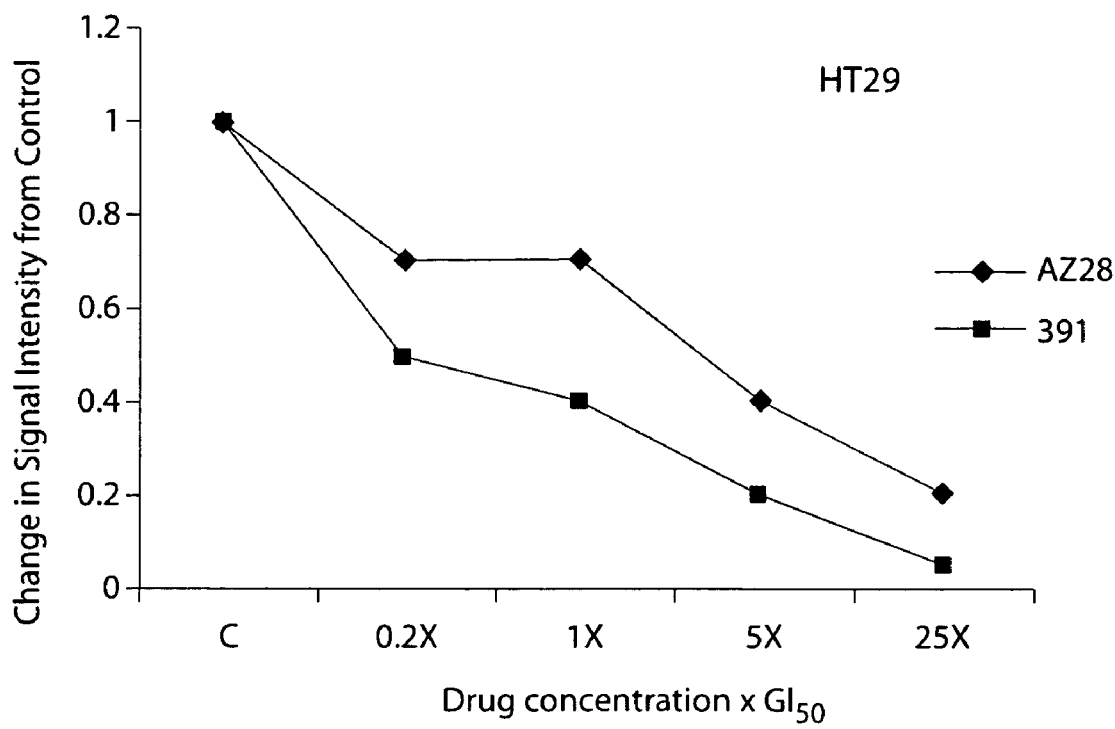
FIG. 33B is a graph indicating the effect of AZ28 and KX2-391 on Shc phosphorylation in HT-29 cells.

FIG. 33 shows phosphorylation of Shc Y239/240, a known Src transphorylation substrate within cells. KX2-391 and AZ28 inhibited Src trans-phosphorylation. This data indicates that KX2-391 is a Src inhibitor inside cells.

Figure 34:
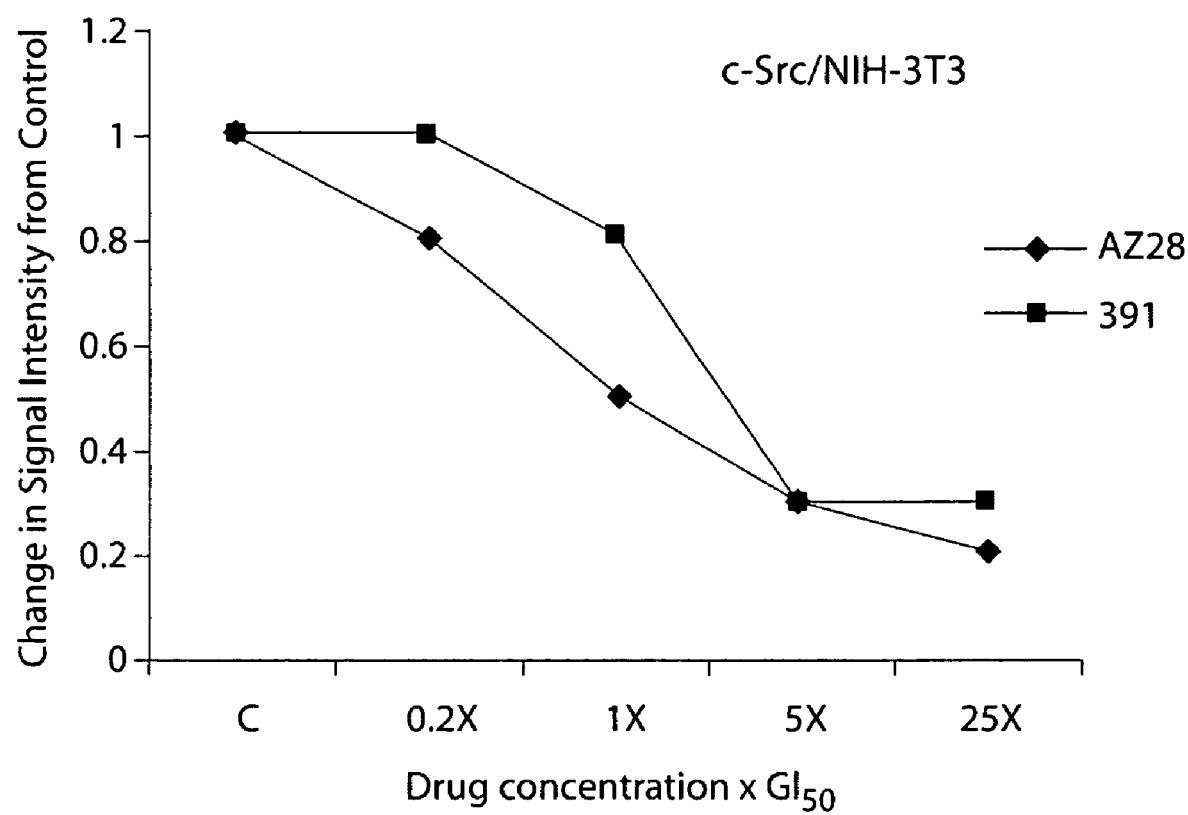
FIG. 34 is a graph indicating the effect of AZ28 and KX2-391 on paxillin phosphorylation in c-Src/NIH-3T3 cells.

FIG. 34 shows phosphorylation of Paxillin Y-31, a known Src transphorylation substrate within cells. KX2-391 and AZ28 inhibited Src trans-phosphorylation. This data indicates that KX2-391 is a Src inhibitor inside cells. Note: paxillin Y-31 was not detected in HT29 cells with or without added drug.

Figure 35A:
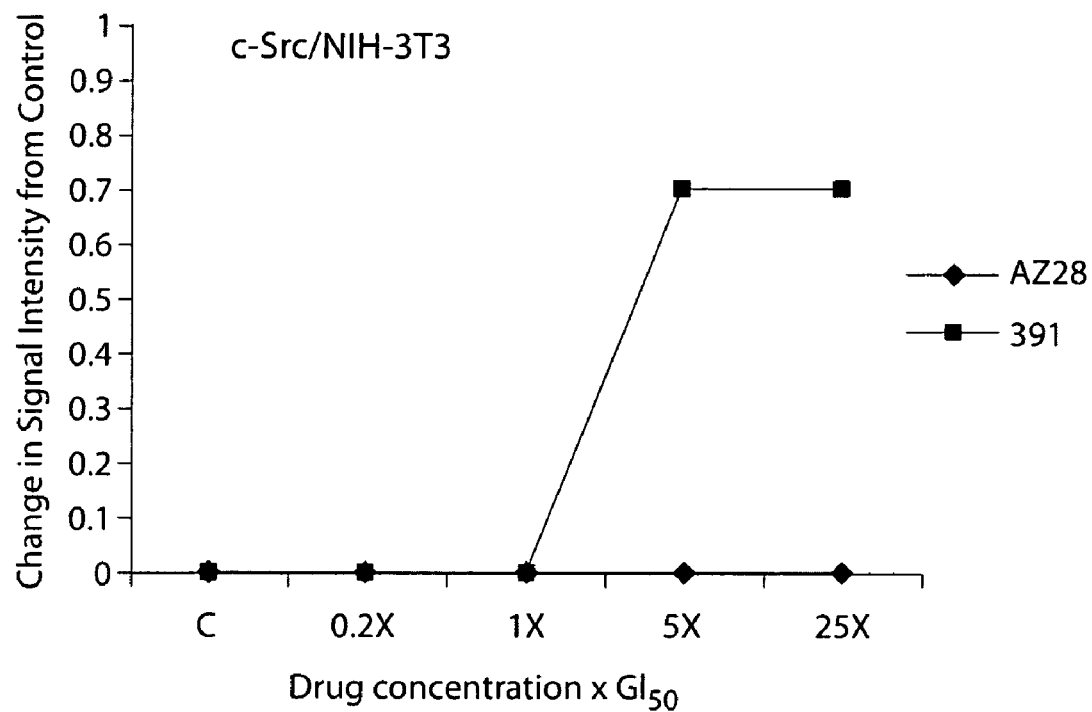
FIG. 35A is a graph indicating the effect of AZ28 and KX2-391 on caspase-3 cleavage in c-Src/NIH-3T3 cells.
Figure 35B:
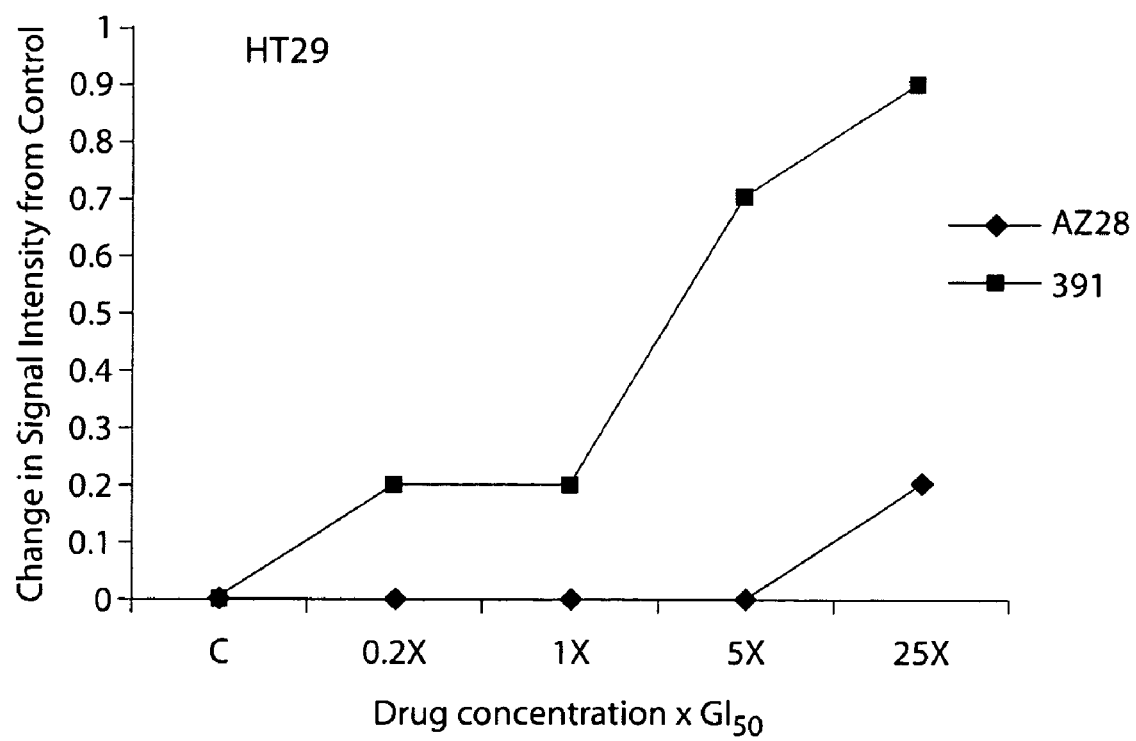
FIG. 35B is a graph indicating the effect of AZ28 and KX2-391 on caspase-3 cleavage in HT-29 cells.

Cleavage of Caspase-3 is a good measure of induction of apoptosis. It is known that AZ28 is not effective in inducing apoptosis in HT29 (colon cancer) and c-Src527F/NIH-3T3 (Src transformed) cell lines. In contrast, as shown in FIG. 35, KX2-391 is very effective in inducing apoptosis.

Figure 36A:
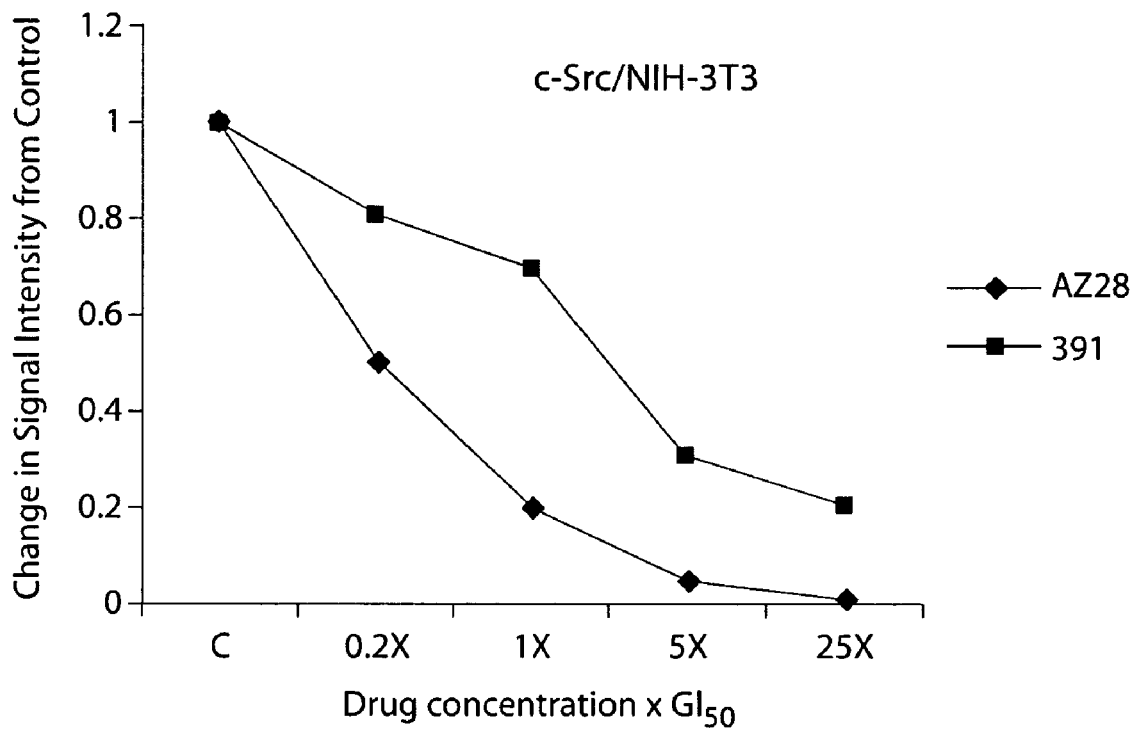
FIG. 36A is a graph indicating the effect of AZ28 and KX2-391 on total phosphotyrosine levels in c-Src/NIH-3T3 cells.
Figure 36B:
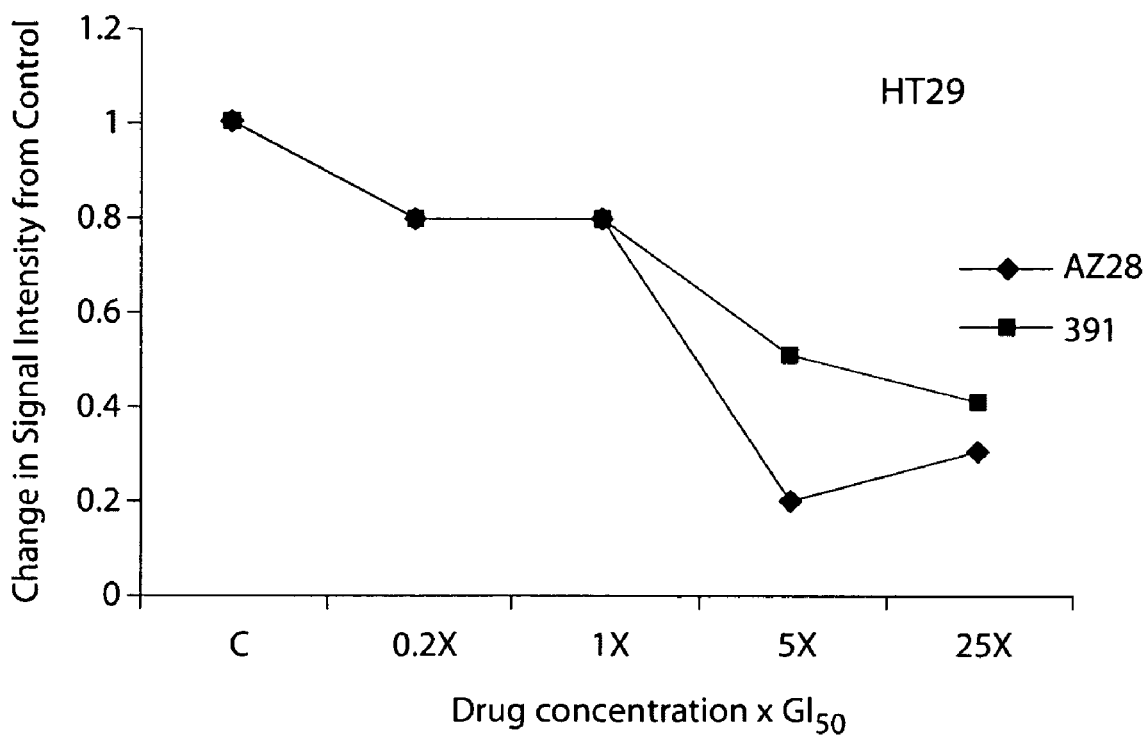
FIG. 36B is a graph indicating the effect of AZ28 and KX2-391 on total phosphotyrosine levels in HT-29 cells.

Since Src activity is very high in both HT29 (colon cancer) and c-Src527F/NIH-3T3 (Src transformed) cell lines, one would expect to see a reduction in the total phosphotyrosine levels when Src activity is inhibited. FIG. 36 indicates that this is true for both AZ28 and KX2-391. This data indicates that KX2-391 is a Src inhibitor inside cells.

Figure 37:
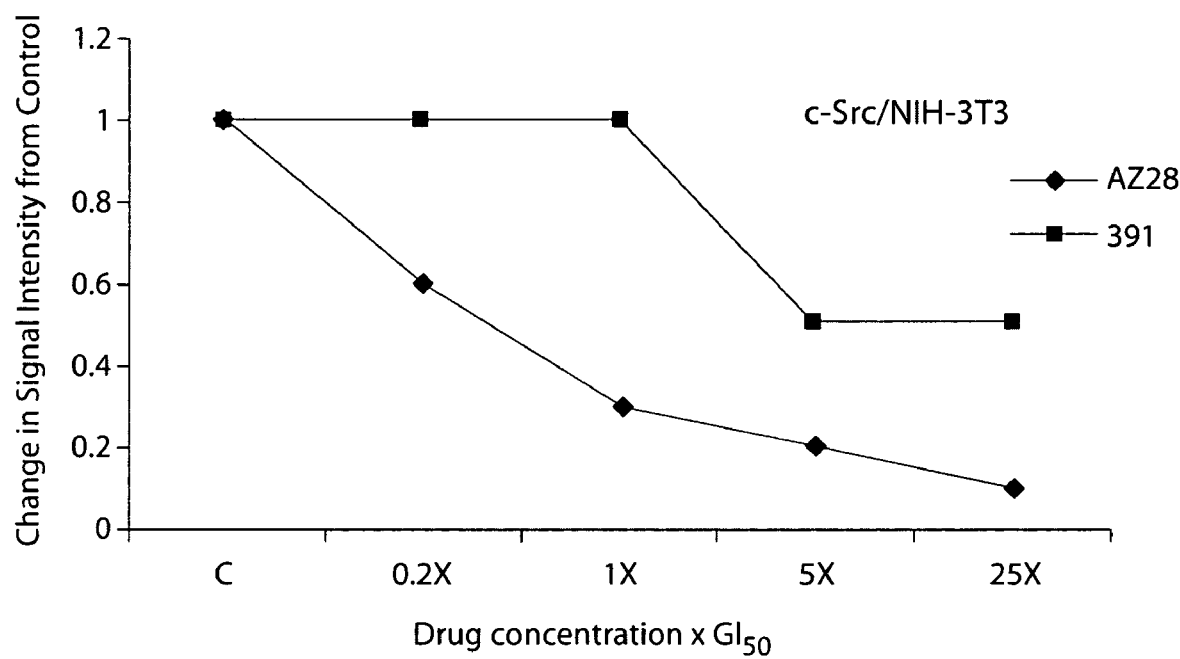
FIG. 37 is a graph indicating the effect of AZ28 and KX2-391 on autophosphorylation of PDGFR in c-Src/NIH-3T3 cells.

PDGF receptor tyrosine kinase autophosphorylates on Y572/574. This is thought not to be a direct Src substrate in cells. It is known that AZ28 is not a potent inhibitor of isolated PDGF receptor tyrosine kinase (see Table XV). Nevertheless, a dose response reduction in PDGF receptor autophosphorylation is seen with AZ28, as shown in FIG. 37. This suggests that this is an indirect effect. Some effect is seen with KX2-391, however it is somewhat less potent. Thus, KX2-391 is less active than AZ28 against indirect PDGF autophoshorylation inhibition. PDGF receptor tyrosine kinase Y572/574 was not detected in HT29 cells with no drug added (as well as with drug added).

Figure 38A:
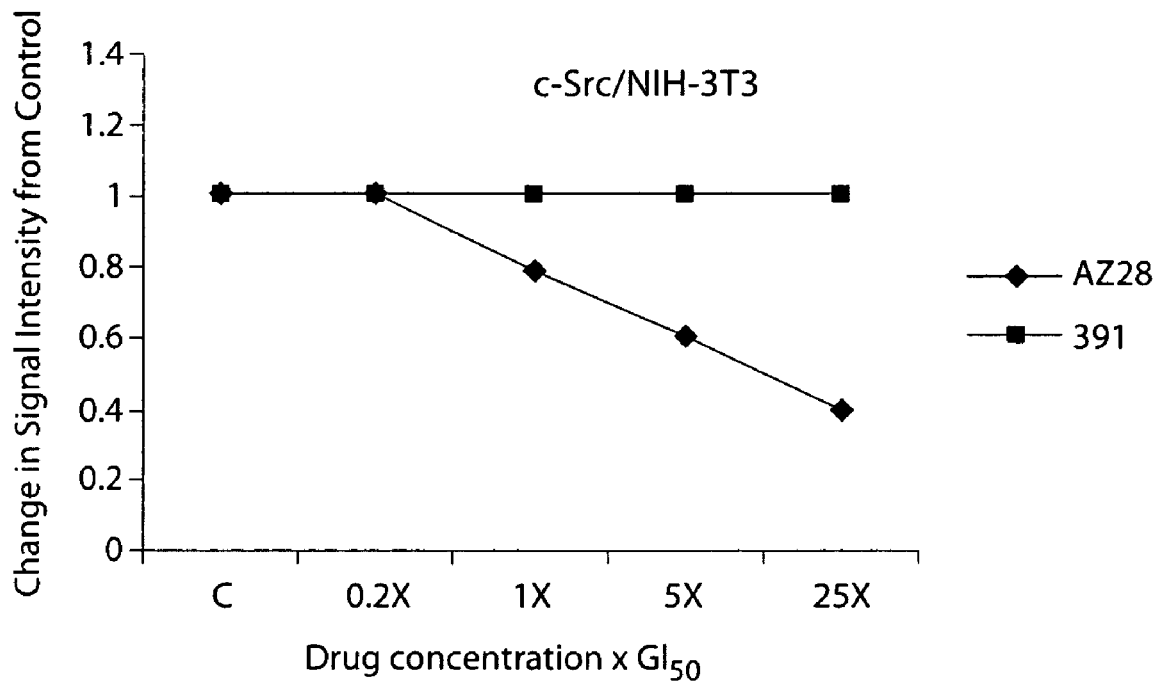
FIG. 38A is a graph indicating the effect of AZ28 and KX2-391 on autophosphorylation of FAK in c-Src/NIH-3T3 cells.
Figure 38B:
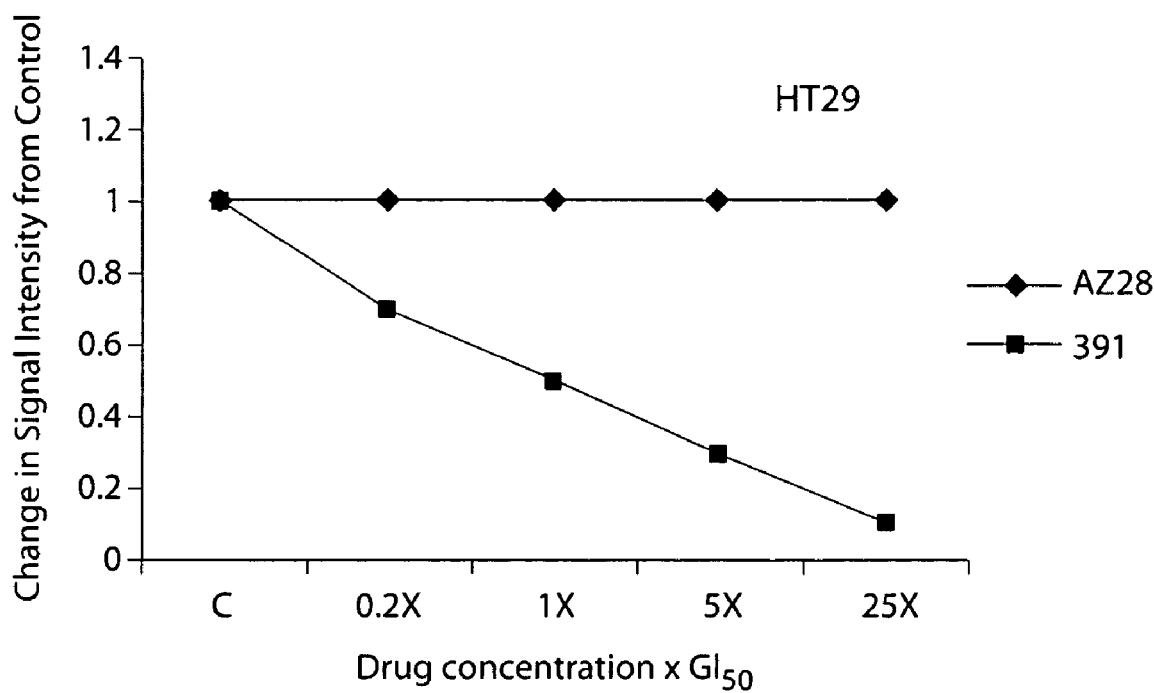
FIG. 38B is a graph indicating the effect of AZ28 and KX2-391 on autophosphorylation of FAK in HT-29 cells.

FAK Y397 is mainly a FAK autophosphorylation site and only a poor Src transphorylation site. AZ28 is not a potent FAK inhibitor (see isolated enzyme data in Table XV). Nevertheless, some inhibition of FAK autophosphorylation in c-Src527F/NIH3T3 cells with AZ28 is shown in FIG. 38. However, no inhibition of FAK autophosphorylation in c-Src527F/NIH3T3 cells is seen with KX-391. The opposite is true in the NCI human colon cancer cell line HT29.

Figure 39A:
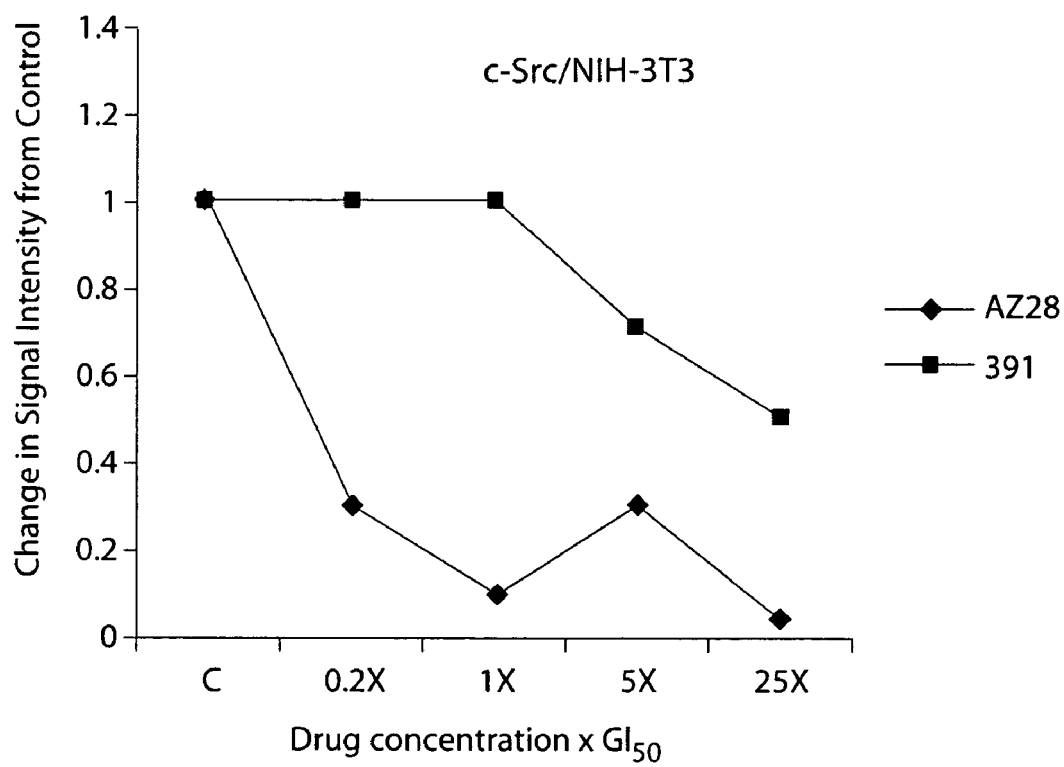
FIG. 39A is a graph indicating the effect of AZ28 and KX2-391 on autophosphorylation of EGFR in c-Src/NIH-3T3 cells.
Figure 39B:
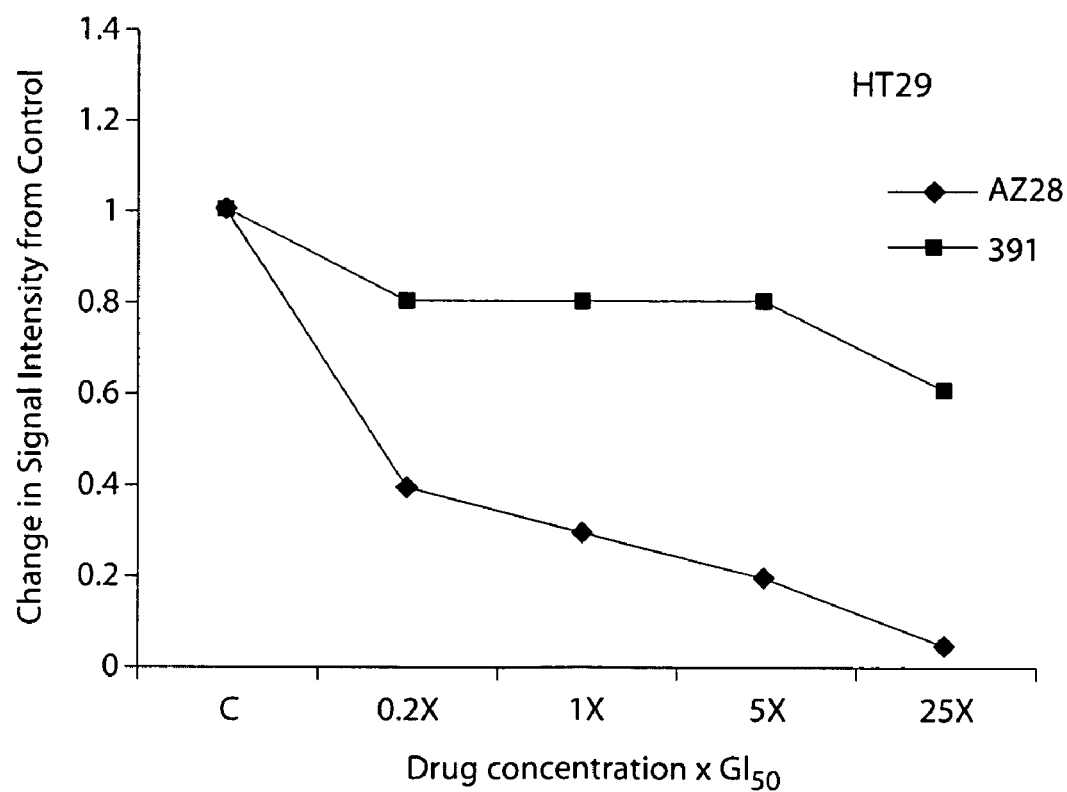
FIG. 39B is a graph indicating the effect of AZ28 and KX2-391 on autophosphorylation of EGFR in HT-29 cells.

The isolated enzyme data shown in Table XV demonstrated that AZ28 is a potent EGFR tyrosine kinase inhibitor. In agreement with this the tumor cell data in FIG. 39 shows that AZ28 potently inhibits EGFR tyrosine kinase autophosphorylation. This site is not a direct Src phosphorylation site. The tumor cell data in FIG. 39 also shows that KX-391 is less active against the off target autophosphorylation of EGFRTK.

Example 12

Protection Against Noise-Induced Hearing Loss Using PTK Inhibitors

Chinchillas (N=6) were used in studies of noise-induced hearing loss. The animals' hearing sensitivity was measured using standard electrophysical techniques before the experimental manipulation. In particular, hearing thresholds were measured through evoked potentials from recording electrodes chronically implanted in the inferior colliculus, following standard laboratory procedures. Animals were anesthetized, the auditory bullae were opened, and the left and right cochleas were visualized. The round window leading to the scala tympani of the cochlea was used as the access point for drug application. Animals were treated with KX1-004, KX1-141, KX1-329 or KX2-328 (a non-ATP competitive inhibitor from Astrazeneca), emulsified in DMSO, in 1000 mM of saline solution, which was placed on the round window of one ear. A control solution of 3 mM DMSO in 1000 mM of saline solution was placed on the round window of the other ear. The solution was allowed to set on the round window for 30 minutes, then the auditory bullae were closed. Subsequently, the animals were exposed to 4 kHz band noise at 105 dB SPL for four hours. Following the noise exposure, the animals' hearing was tested at day 1, day 7, and day 21 to determine evoked potential threshold shifts. Permanent threshold shift was assessed at day 21.

Figure 40:
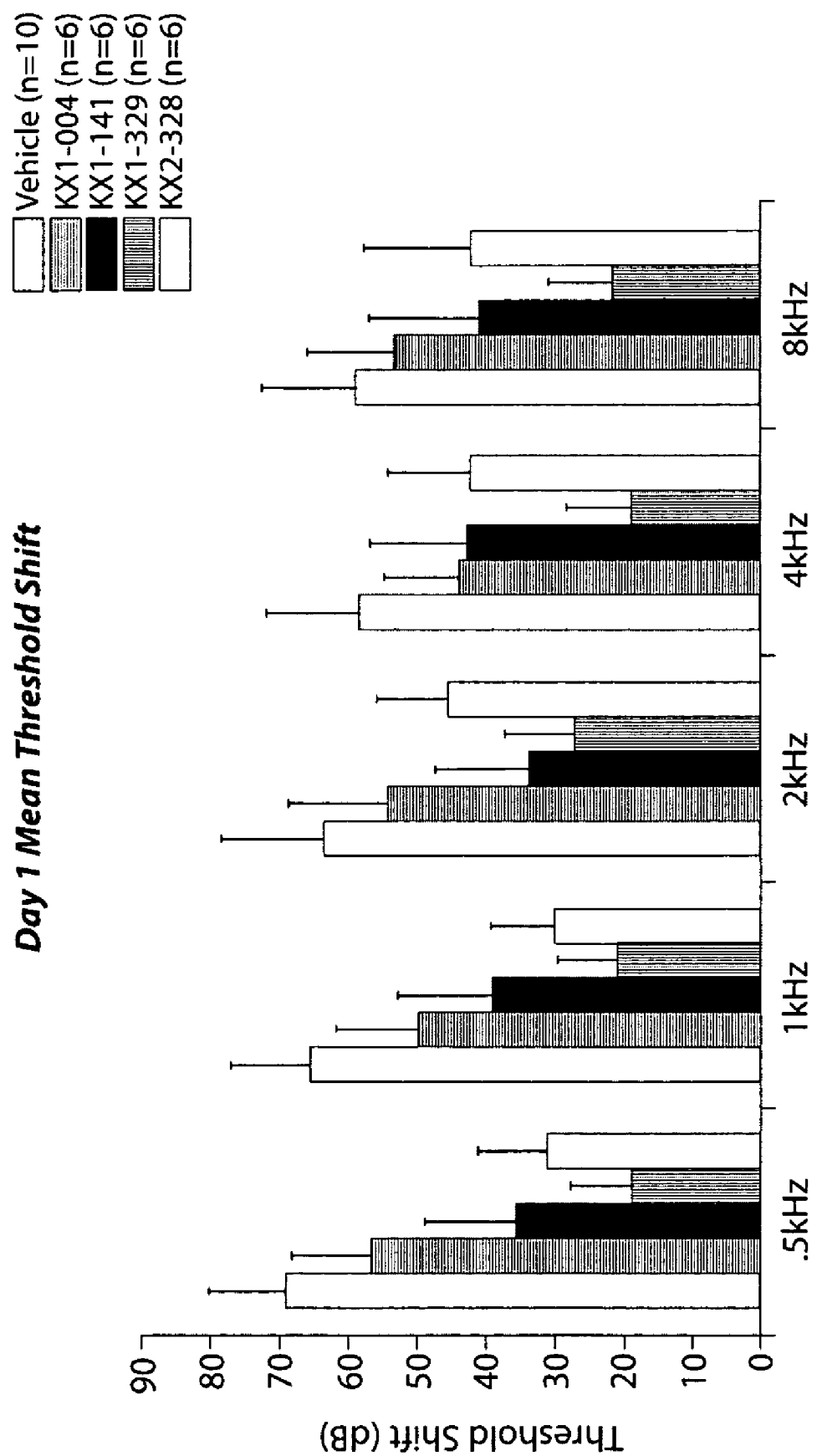
FIG. 40 is a bar chart showing the average threshold shifts (dB) in chinchilla cochleas after exposure to 0.5 kHz, 1 kHz, 2 kHz, 4 kHz, and 8 kHz band noise on day 1 after experimental manipulation.
Figure 41:
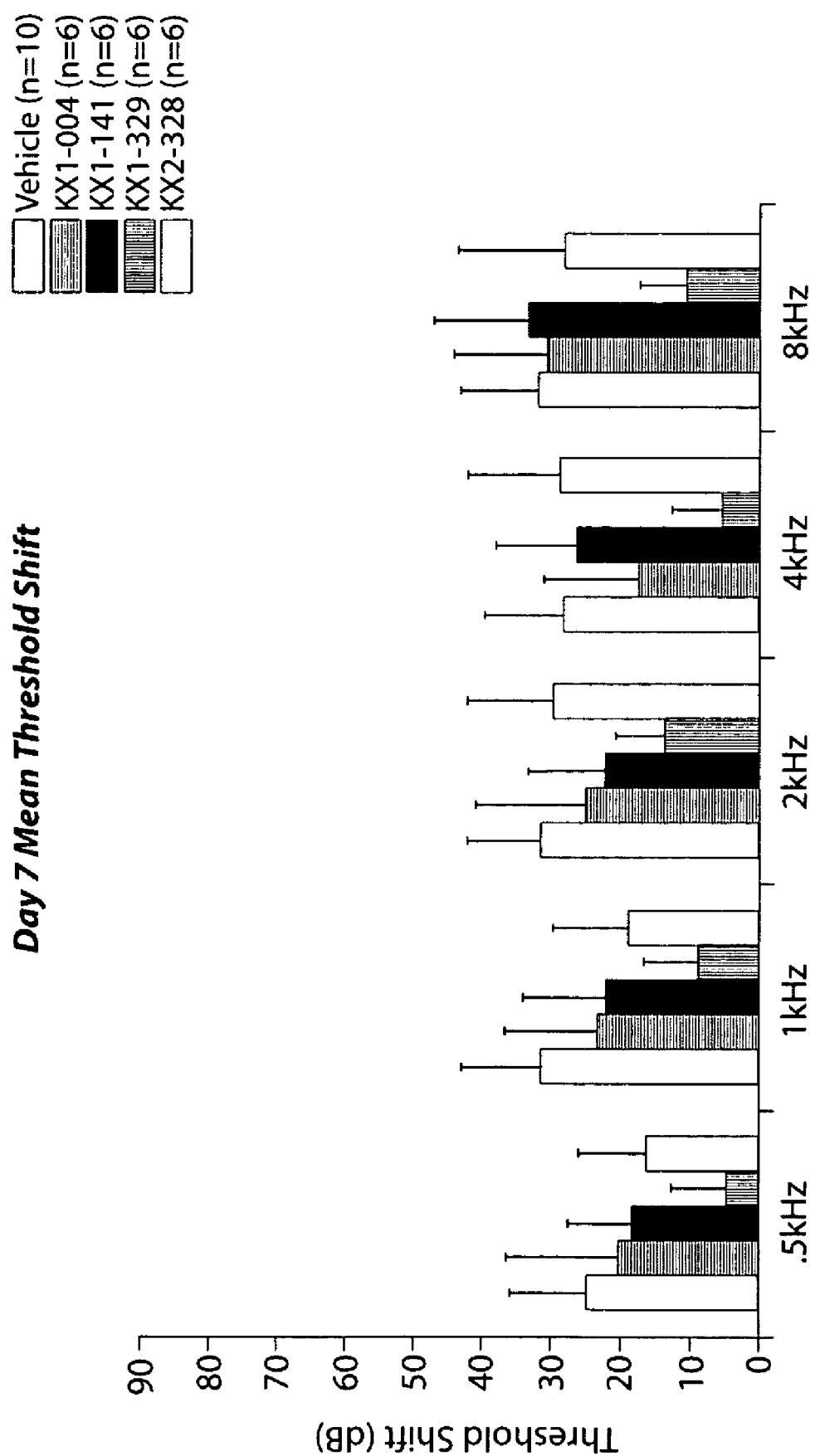
FIG. 41 is a graph showing the average threshold shifts (dB) in chinchilla cochleas after exposure to 0.5 kHz, 1 kHz, 2 kHz, 4 kHz, and 8 kHz band noise on day 7 after experimental manipulation.
Figure 42:
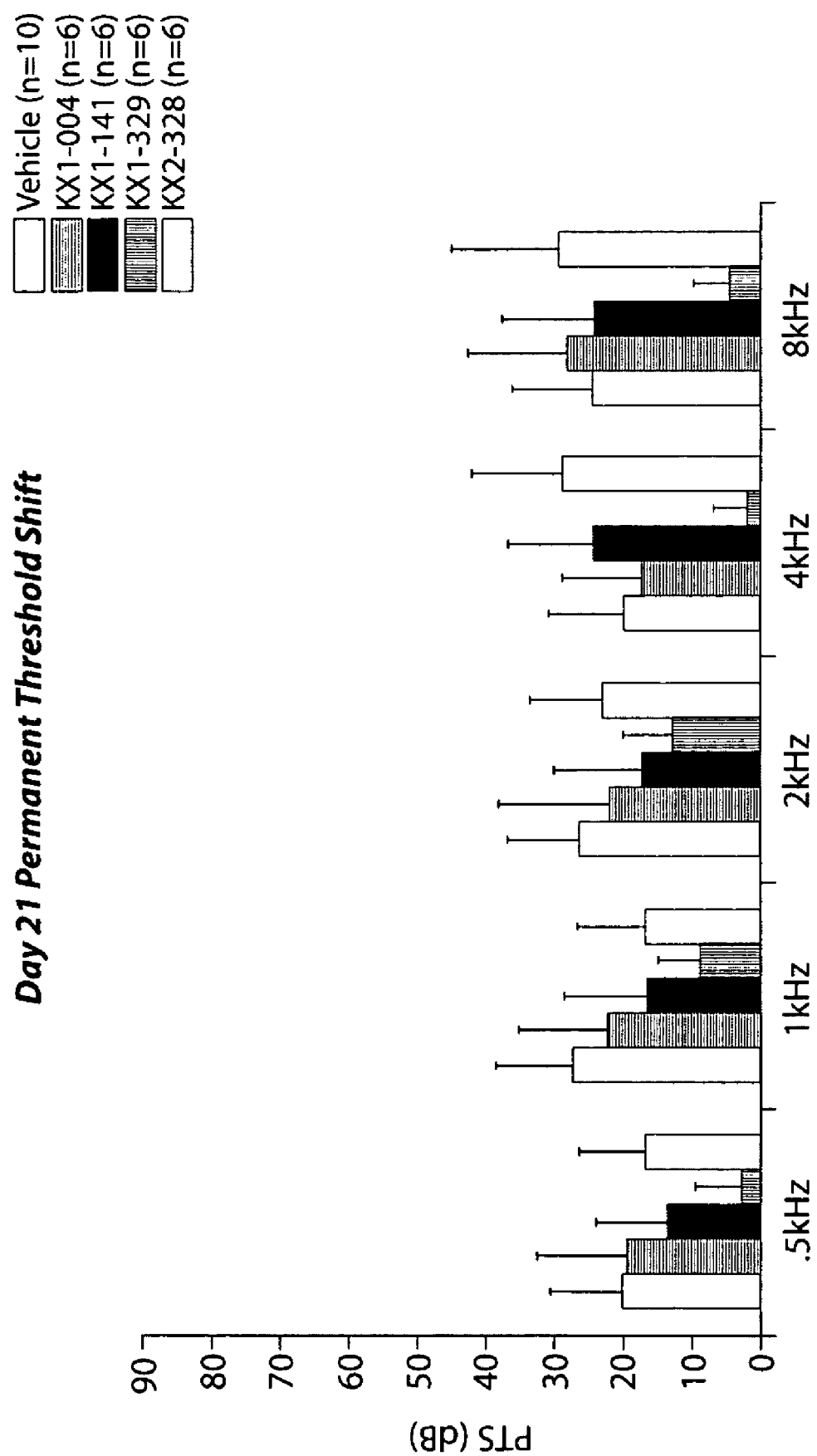
FIG. 42 is a graph showing the average threshold shifts (dB) in chinchilla cochleas after exposure to 0.5 kHz, 1 kHz, 2 kHz, 4 kHz, and 8 kHz band noise on day 21 after experimental manipulation.

FIGS. 40-42 show the average threshold shifts for animals treated with KX1-004, KX1-141, KX1-329 or KX2-328. In particular, FIG. 40 shows average threshold shifts after exposure to 0.5 kHz, 1 kHz, 2 kHz, 4 kHz, and 8 kHz band noise on day 1 after experimental manipulation. FIG. 41 shows average threshold shifts after exposure to 0.5 kHz, 1 kHz, 2 kHz, 4 kHz, and 8 kHz band noise on day 7 after experimental manipulation. FIG. 42 shows average threshold shifts after exposure to 0.5 kHz, 1 kHz, 2 kHz, 4 kHz, and 8 kHz band noise on day 21 after experimental manipulation. As shown in FIGS. 40-42, in most cases, the average dB threshold shifts for ears treated with KX1-004, KX1-141, KX1-329 or KX2-328 were lower, indicating that the compounds reduced the level of hearing loss in treated animals relative to the untreated control animals.

Example 13

Protection Against Cisplatin-Induced Hearing Loss Using PTK Inhibitors

The effects of high level noise and ototoxic drugs, such as cisplatin or the class of aminoglycosides, share several common features in the inner ear. First, the noise and/or drugs alter the free radical/antioxidant levels in the cochlea (inner ear). The increase in free radicals has been shown to be a causative factor in the apoptotic death of the sensory cells. Guinea pigs (N=7) were used in studies of cisplatin-induced hearing loss. The animals' hearing sensitivity was measured using standard electrophysical techniques before the experimental manipulation. In particular, hearing thresholds were measured through evoked potentials from recording electrodes chronically implanted in the inferior colliculus, following standard laboratory procedures. Animals were anesthetized and treated with cisplatin. Subsequently, the animals' hearing was tested to determine evoked potential threshold shifts.

Figure 43:
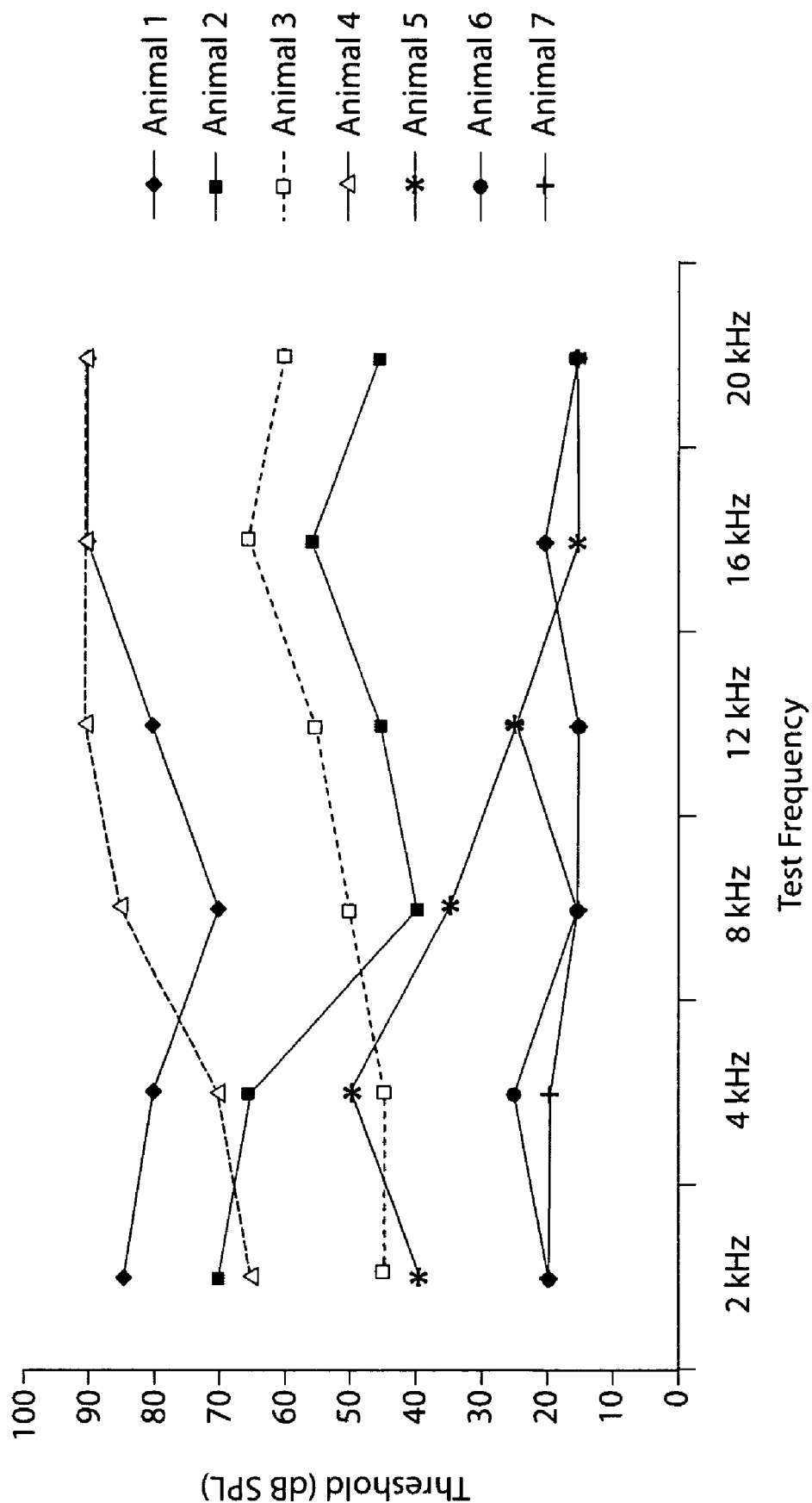
FIG. 43 is a line graph showing the threshold shifts (dB) in guinea pig cochleas after exposure to 2 kHz, 4 kHz, 8 kHz, 12 kHz, 16 kHz and 20 kHz band noise after treatment with cisplatin.
Figure 44:
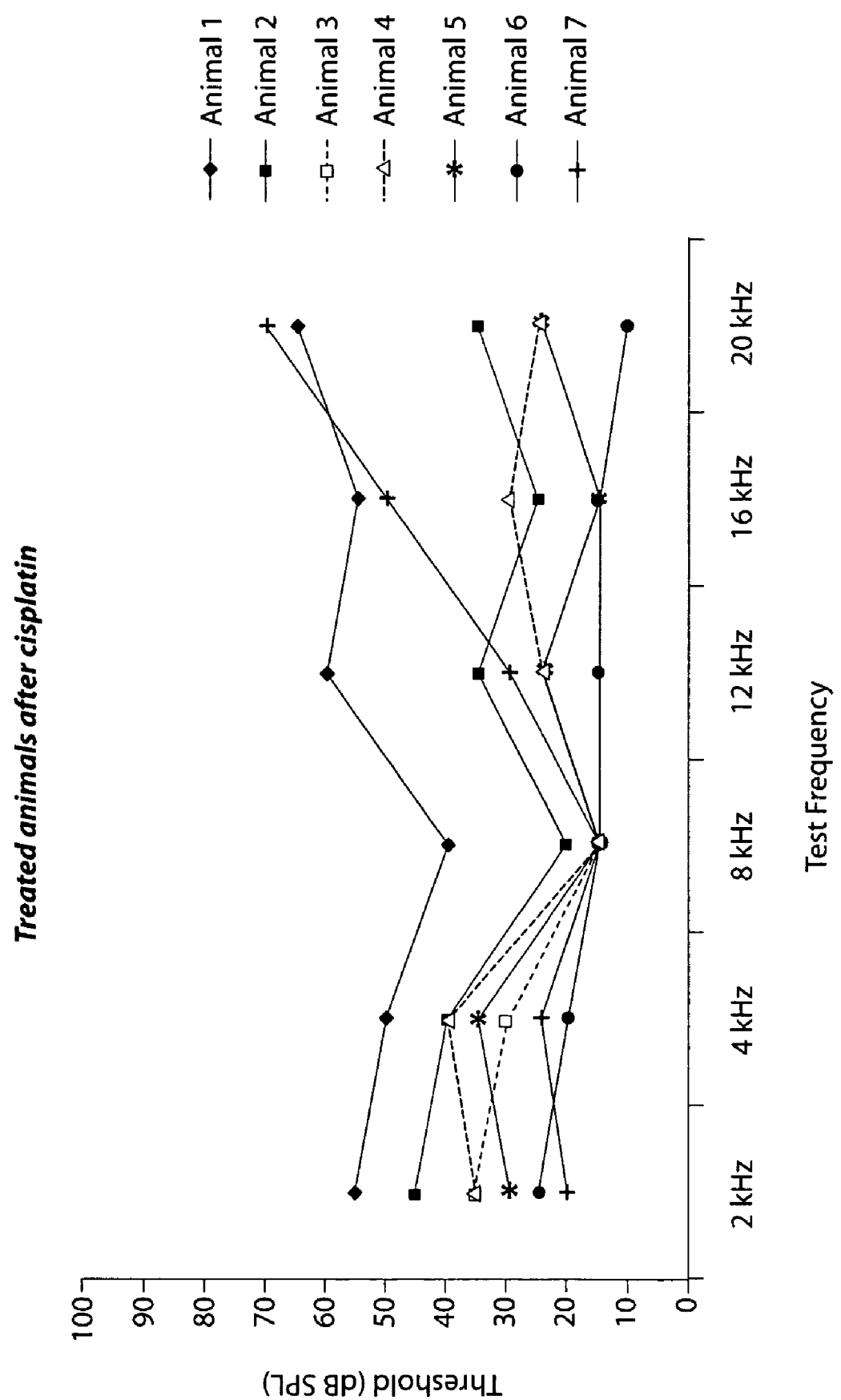
FIG. 44 is a line graph showing the threshold shifts (dB) in KX1-004-treated guinea pig cochleas after exposure to 2 kHz, 4 kHz, 8 kHz, 12 kHz, 16 kHz and 20 kHz band noise after treatment with cisplatin.
Figure 45:
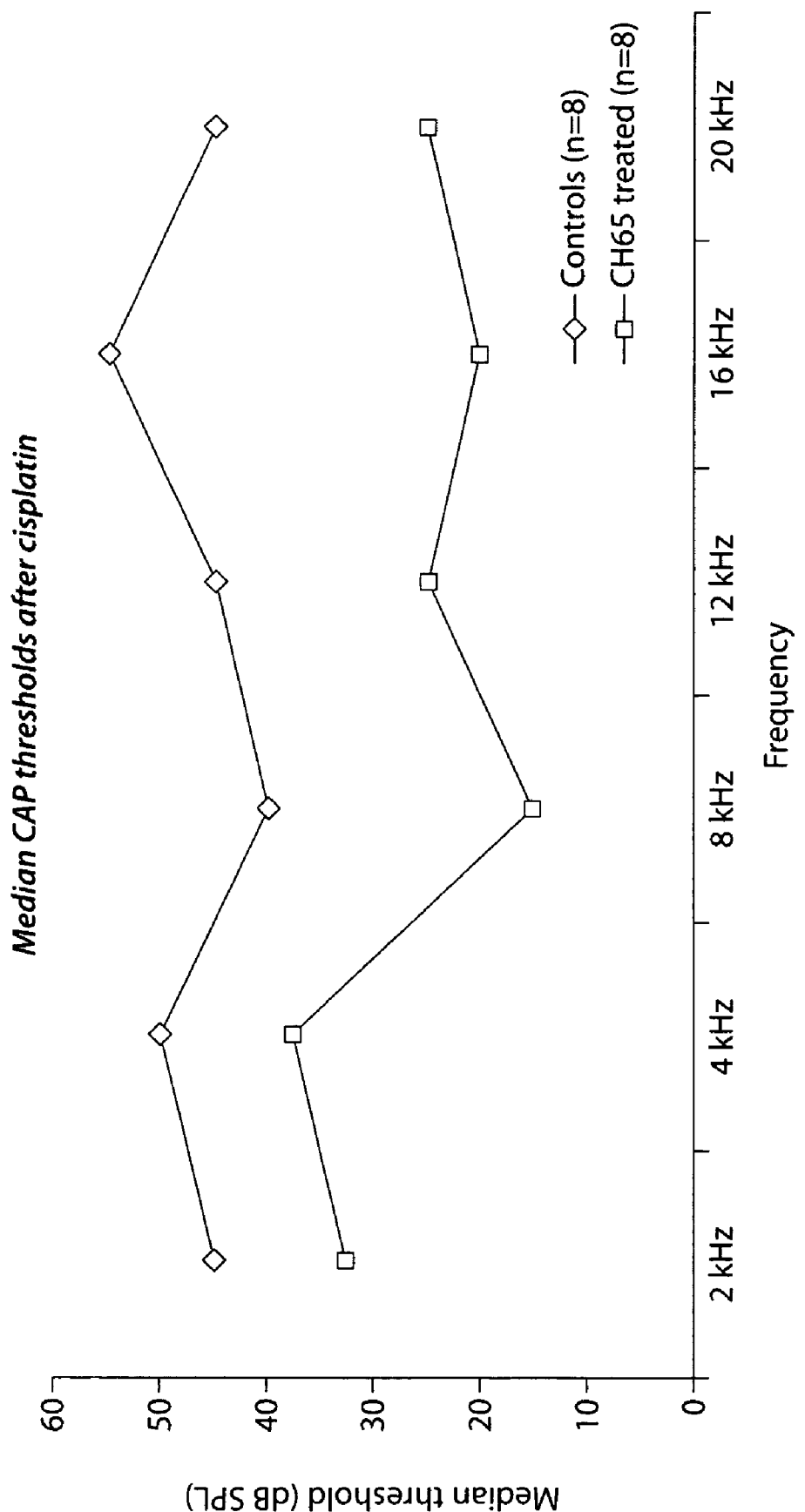
FIG. 45 is a line graph showing the average threshold shifts (dB) in KX1-004-treated guinea pig cochleas and untreated control guinea pig cochleas after exposure to 2 kHz, 4 kHz, 8 kHz, 12 kHz, 16 kHz and 20 kHz band noise after treatment with cisplatin.

FIG. 43 shows threshold shifts for a number of guinea pigs after exposure to 2 kHz, 4 kHz, 8 kHz, 12 kHz, 16 kHz and 20 kHz band noise after treatment with cisplatin. FIG. 44 shows the threshold shifts for animals treated with KX1-004 (CH65). Animals were treated subcutaneously with KX1-004 prior to the cisplatin-induced hearing loss. FIG. 45 shows the median CAP thresholds after cisplatin-induced hearing loss for both the untreated control animals and the KX1-004 (CH65)-treated animals. As shown in FIG. 45, KX1-004 treatment protected against ciplatin-induced hearing loss.

Example 14

Effect of Compounds on Osteoclast Formation

Figure 46:
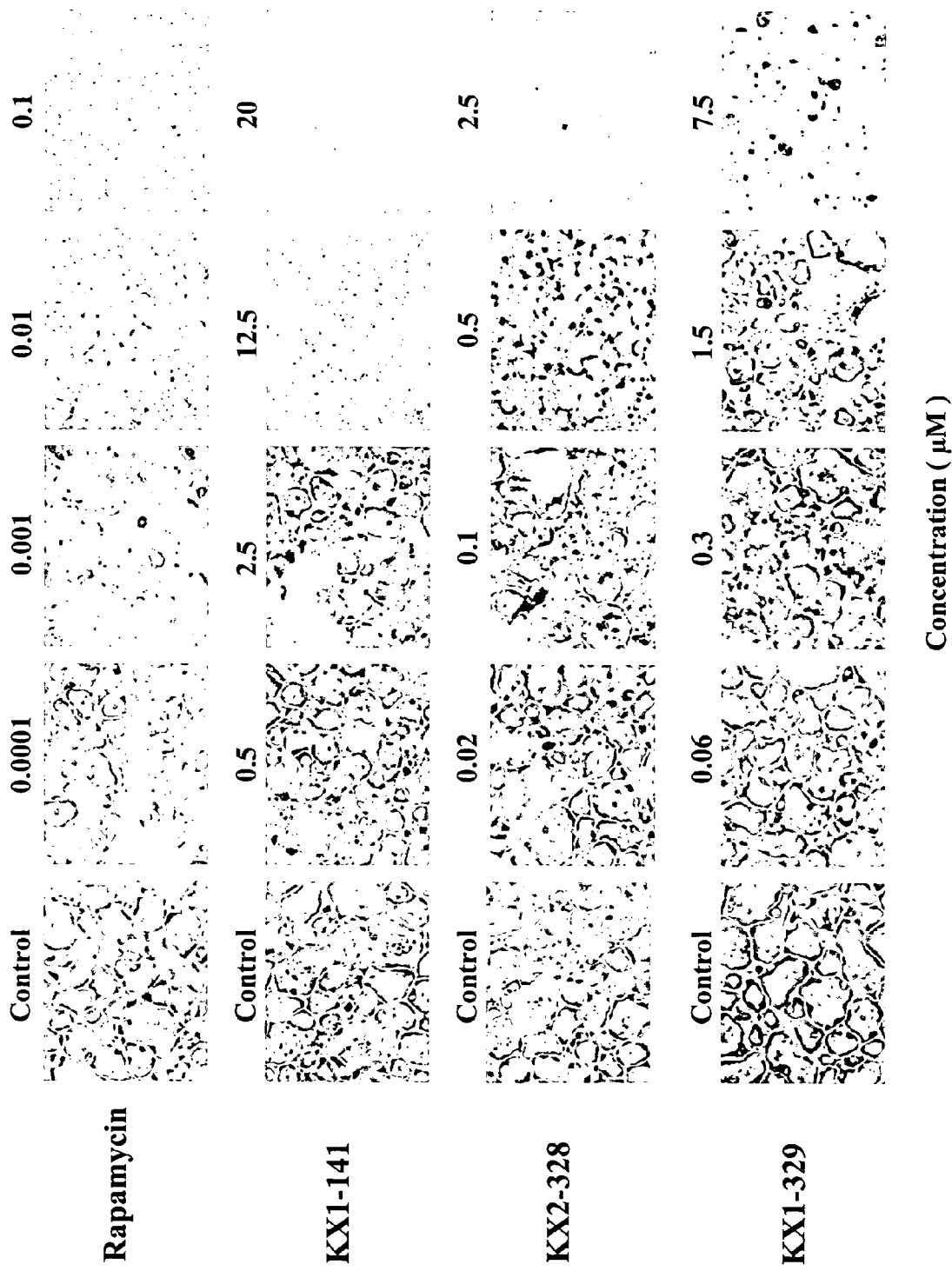
FIG. 46 is a series of illustrations depicting the effect of compounds on osteoclast formation.

To determine the effect of the compounds on osteoclast formation, the compounds were added to osteoclast precursors derived from spleen cells. For the generation of spleen-derived osteoclasts, spleen cells comprising osteoclast precursors were treated with Rapamycin, KX1-141, KX2-328 (Astrazeneca compound), or KX1-329 for 5 days in the presence of receptor activator of nuclear factor-κB ligand (RANKL) and macrophage colony-stimulating factor (M-CSF). In in vitro murine or human osteoclast models, soluble RANKL enables osteoclast precursors to differentiate in the presence of M-CSF (Quinn, et al.; 1998, *Endocrinology*, 139, 4424-4427; Jimi, et al.; 1999, *J. Immunol.*, 163, 434-442). The untreated control cells were incubated in the presence of RANKL and M-CSF alone. Rapamycin was used as a positive control for the inhibition of osteoclast formation. FIG. 46 shows that increasing concentrations of Rapamycin (0.0001 μM, 0.001 μM, 0.01 μM, or 0.1 μM), KX1-141 (0.5 μM, 2.5 μM, 12.5 μM, or 20 μM), KX2-328 (0.02 μM, 0.1 μM, 0.5 μM, or 2.5 μM), or KX1-329 (0.06 μM, 0.3 μM, 1.5 μM or 7.5 μM) were added to the spleen cells. The cells were stained as shown in FIG. 46. All four compounds, including the positive control Rapamycin, inhibited the formation of osteoclasts compared to the untreated control.

Figure 47:
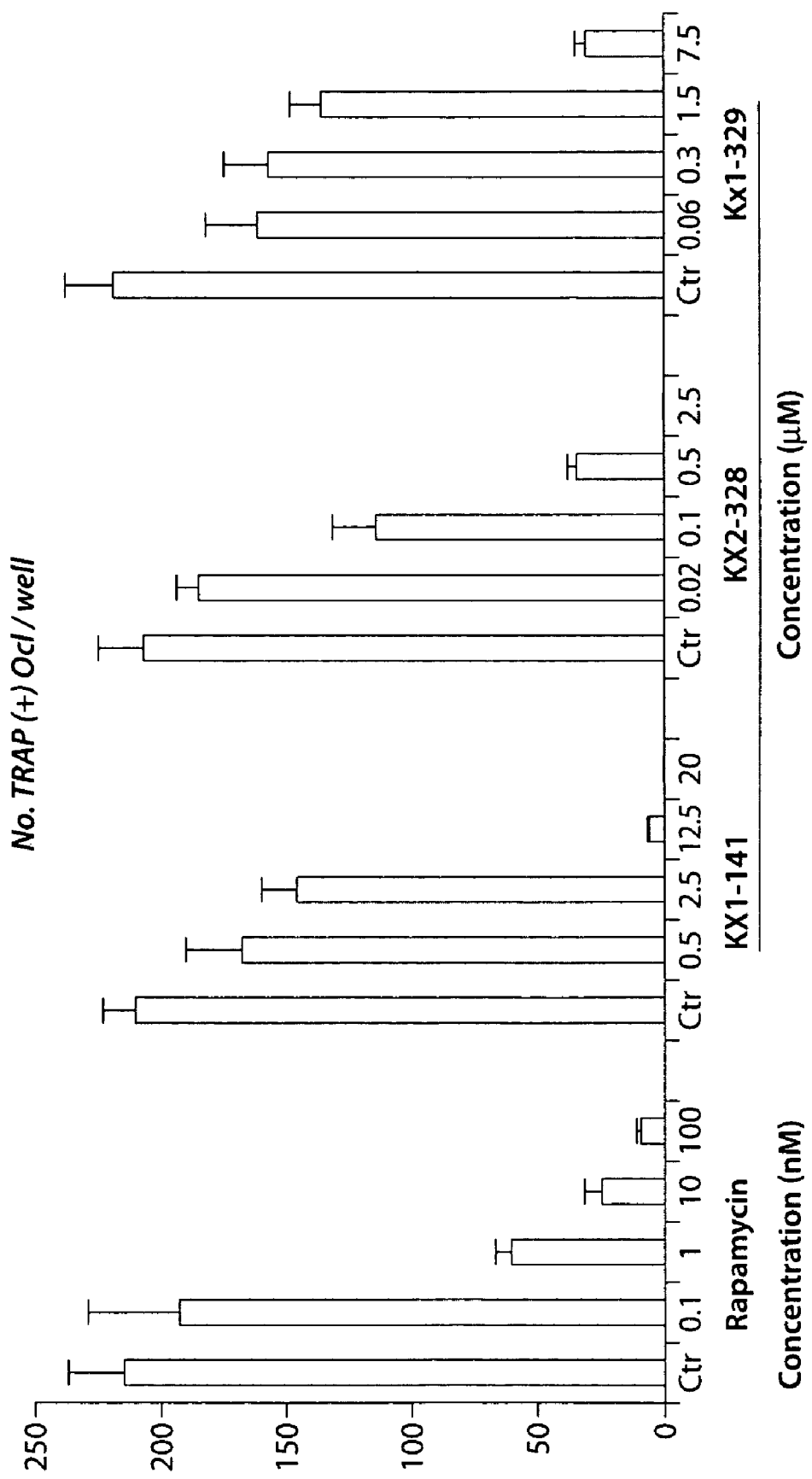
FIG. 47 is a bar chart demonstrating the effect of compounds on osteoclast formation.

For generating spleen-derived osteoclasts, spleen cells were treated as described above. FIG. 47 shows that increasing concentrations of Rapamycin (0.1 nM, 1 nM, 10 nM, or 100 nM), KX1-141 (0.5 μM, 2.5 μM, 12.5 μM, or 20 μM), KX2-328 (0.02 µM, 0.1 µM, 0.5 µM, or 2.5 µM), or KX1-329 (0.06 µM, 0.3 µM, 1.5 µM or 7.5 µM) were added to the spleen cells. Cells were then stained with the osteoclast marker, tartrate-resistant acid phosphatase (TRAP) to visualize differentiated cells. The numbers of TRAP-positive osteoclasts were counted. All four compounds, including the positive control Rapamycin, reduced the number of TRAP-positive osteoclasts compared to the untreated control (Ctr).

Example 15

Effect of Compounds on Osteoclast Survival

Figure 48:
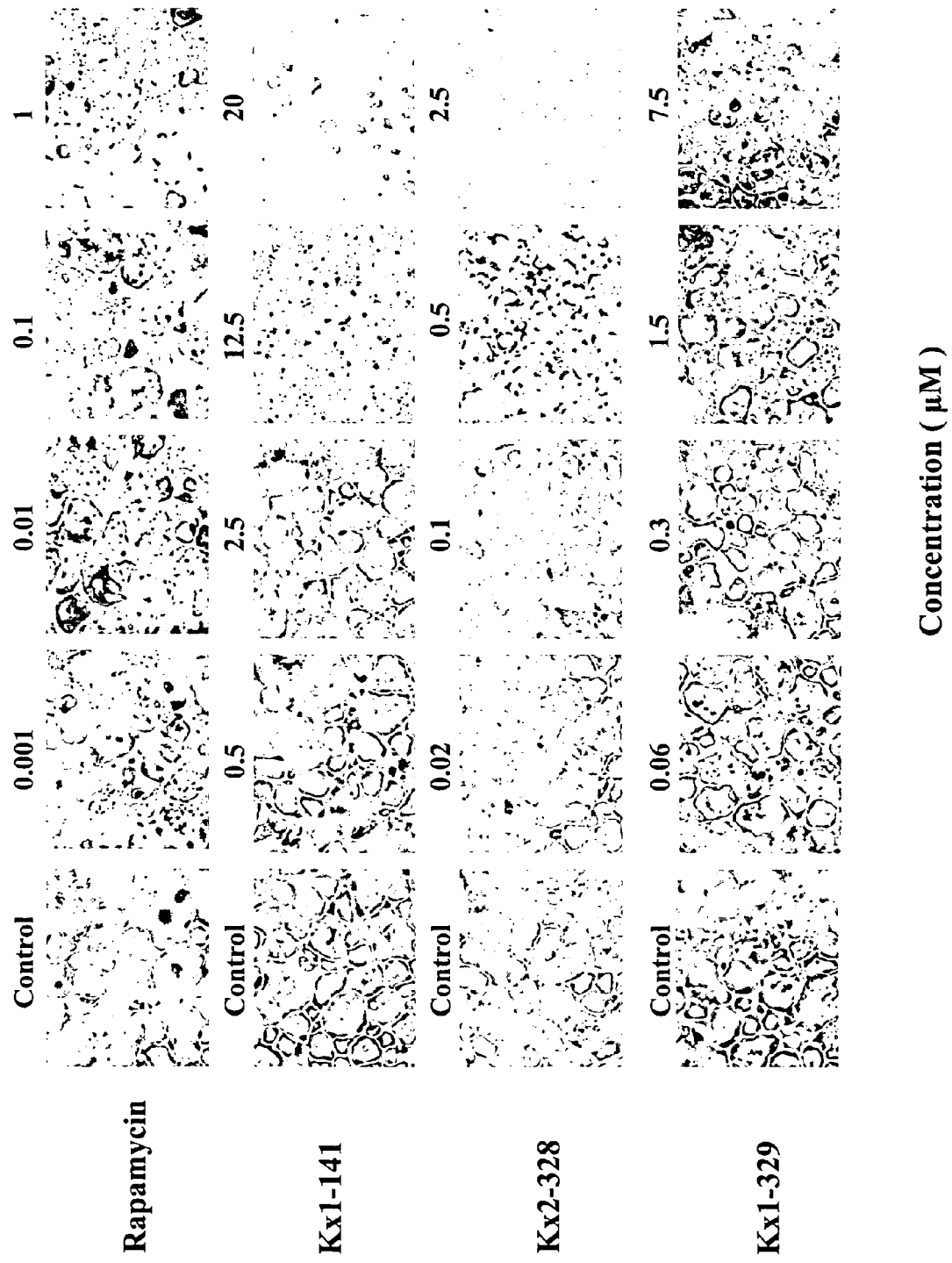
FIG. 48 is a series of illustrations showing the effect of compounds on osteoclast survival.

To determine the effect of the compounds on osteoclast survival, osteoclasts were treated with Rapamycin, KX1-141, KX2-328, or KX10-329 for 48 hours in the presence of RANKL and M-CSF. The untreated, control cells were incubated in the presence of RANKL and M-CSF alone. Rapamycin was used as a positive control for the inhibition of osteoclast survival. FIG. 48 shows that increasing concentrations of Rapamycin (0.001 µM, 0.01 µM, 0.1 µM, or 1 µM), KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) were added to the osteoclasts. The cells were stained as shown in FIG. 48. All four compounds, including the positive control Rapamycin, inhibited the survival of osteoclasts compared to the untreated control.

Figure 49:
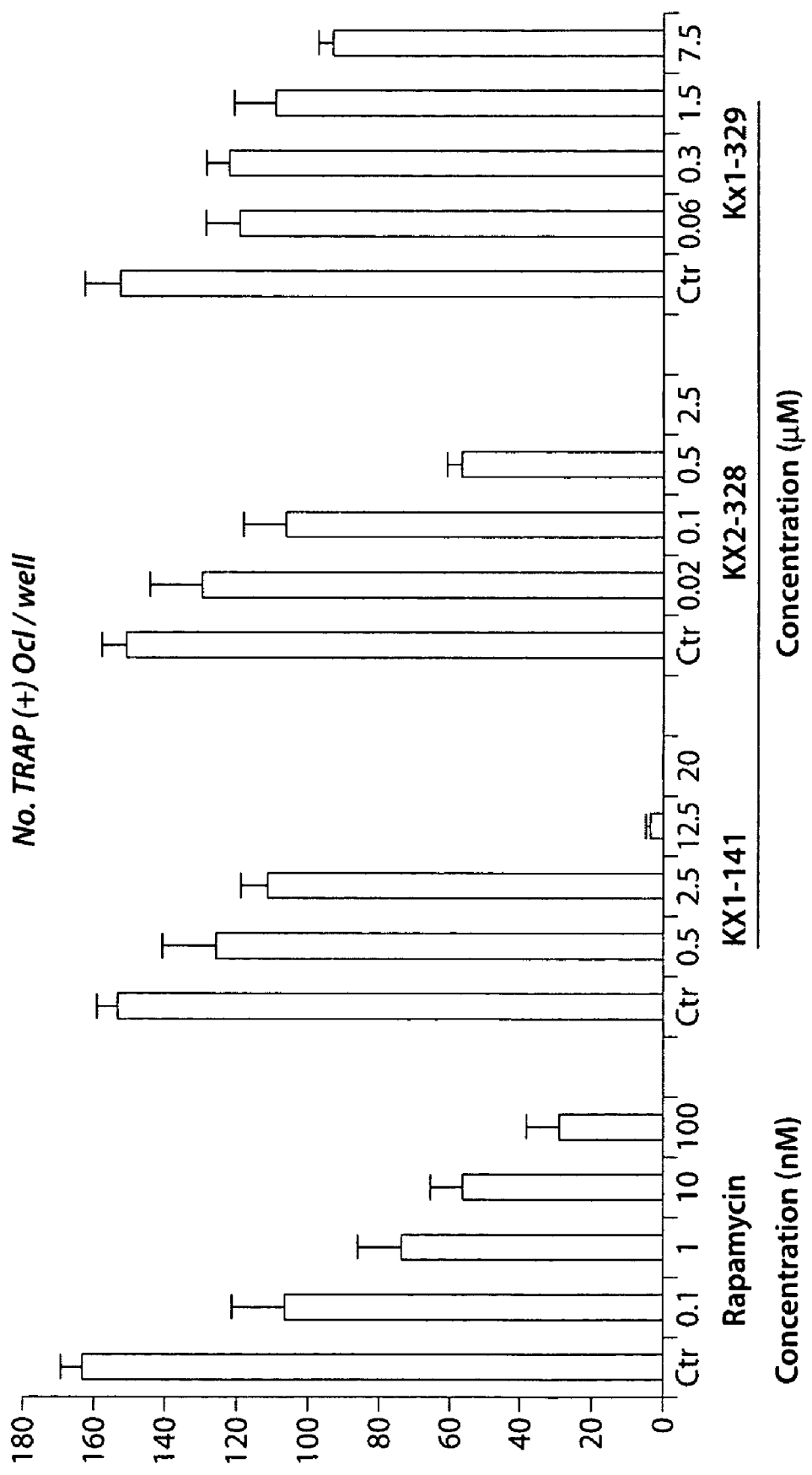
FIG. 49 is a bar chart depicting the effect of compounds on osteoclast survival.

As described above, osteoclasts were treated with Rapamycin, KX1-141, KX2-328, or KX10-329 for 48 hours in the presence of RANKL and M-CSF. FIG. 49 shows that increasing concentrations of Rapamycin (0.1 nM, 1 nM, 10 nM, or 100 nM), KX1-141 (0.5 µM, 2.5 µM, 12.5 µM, or 20 µM), KX2-328 (0.02 µM, 0.1 µM, 0.5 µM, or 2.5 µM), or KX10-329 (0.06 µM, 0.3 µM, 1.5 µM or 7.5 µM) were added to the osteoclasts. Cells were then stained with TRAP and the number of TRAP-positive osteoclasts were counted. All four compounds, including the positive control Rapamycin, reduced the number of TRAP-positive osteoclasts compared to the untreated control.

Example 16

Effect of Compounds on Bone Resorption In Vitro

Figures 50A, 50B:
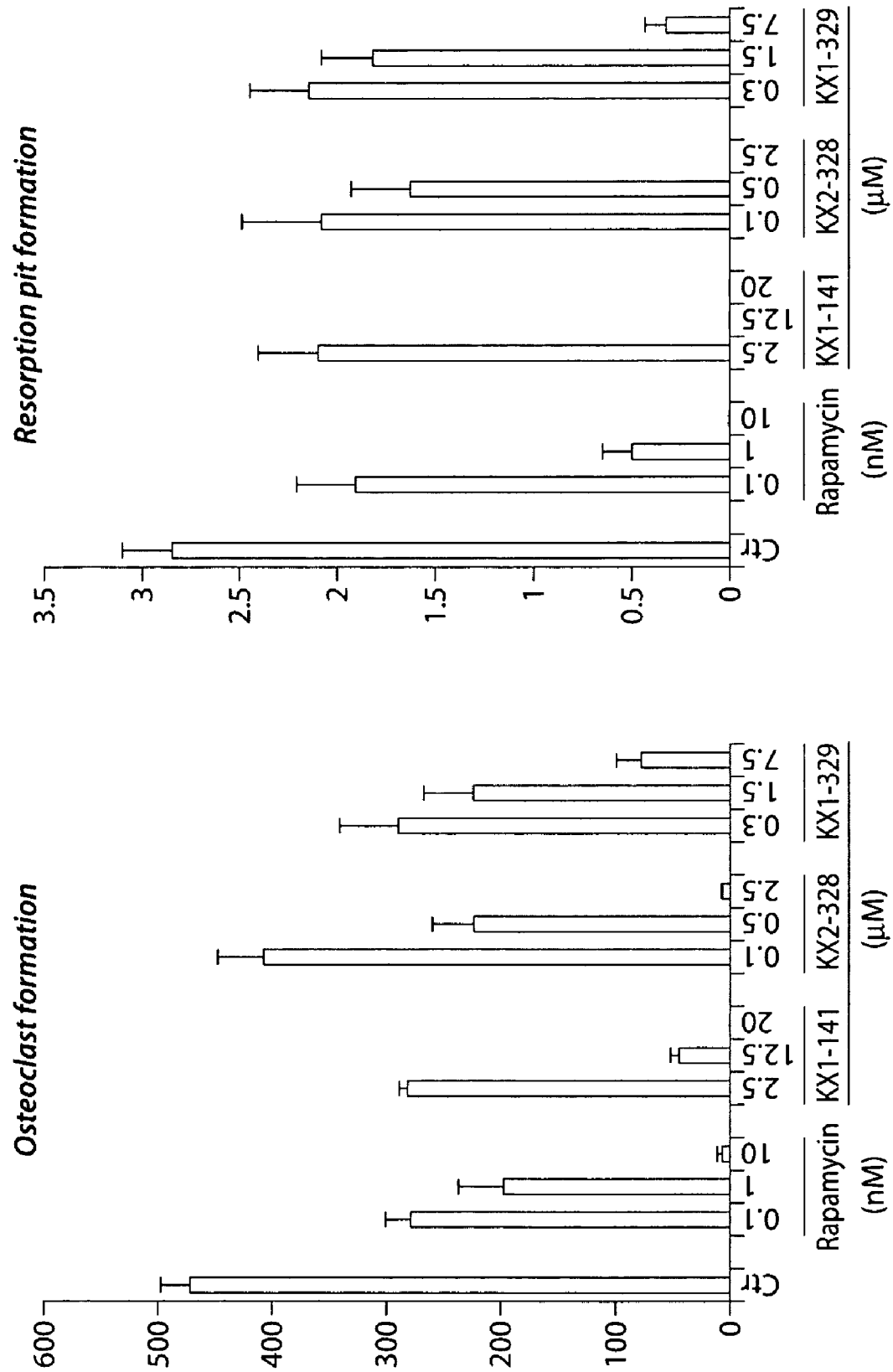
FIG. 50A is a bar chart demonstrating the effect of compounds on bone resorption in vitro.
FIG. 50B is a bar chart showing the effect of compounds on resorption pit formation.

To determine the effects of the compounds on osteoclast formation on bone slices, the bone slices were treated with Rapamycin, KX1-141, KX2-328, or KX1-329. FIG. 50A shows that increasing concentrations of Rapamycin (0.1 nM, 1 nM, or 10 nM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The number of osteoclasts on the bone slices were counted. All four compounds, including the positive control Rapamycin, reduced the number of osteoclasts on the bone slices compared to the untreated control (Ctr).

During the resorption of bone, osteoclasts form resorption pits. To determine the effects of the compounds on resorption pit formation on bone slices, the bone slices were treated with Rapamycin, KX1-141, KX2-328, or KX1-329, as described above. FIG. 50B shows that increasing concentrations of Rapamycin (0.1 nM, 1 nM, or 10 nM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The number of resorption pits on the bone slices was determined. The compounds reduced the number of resorption pits on the bone slices compared to the untreated control (Ctr).

Bone slices were treated as indicated above. FIG. 51A shows that increasing concentrations of Rapamycin (0.001 µM, 0.01 µM, or 0.1 µM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The bone slices were then stained with TRAP. All four compounds, including the positive control Rapamycin, reduced the number of TRAP-positive osteoclasts on the bone slices compared to the untreated control. Notably, 12.5 µM KX1-141 significantly reduced the number of TRAP-positive osteoclasts on the bone slices compared to the untreated control.

Bone slices were treated as indicated above. FIG. 51B shows that increasing concentrations of Rapamycin (0.001 µM, 0.01 µM, or 0.1 µM), KX1-141 (2.5 µM, 12.5 µM, or 20 µM), KX2-328 (0.1 µM, 0.5 µM, or 2.5 µM), or KX1-329 (0.3 µM, 1.5 µM or 7.5 µM) were added to the bone slices. The bone slices were stained with Toluidine Blue to reveal resorption pits, which are indicators of osteoclast-mediated resorption of bone. All four compounds, including the positive control Rapamycin, reduced the number of resorption pits on the bone slices compared to the untreated control.

Example 17

Effect of Compounds on Osteoblasts

Figure 52:
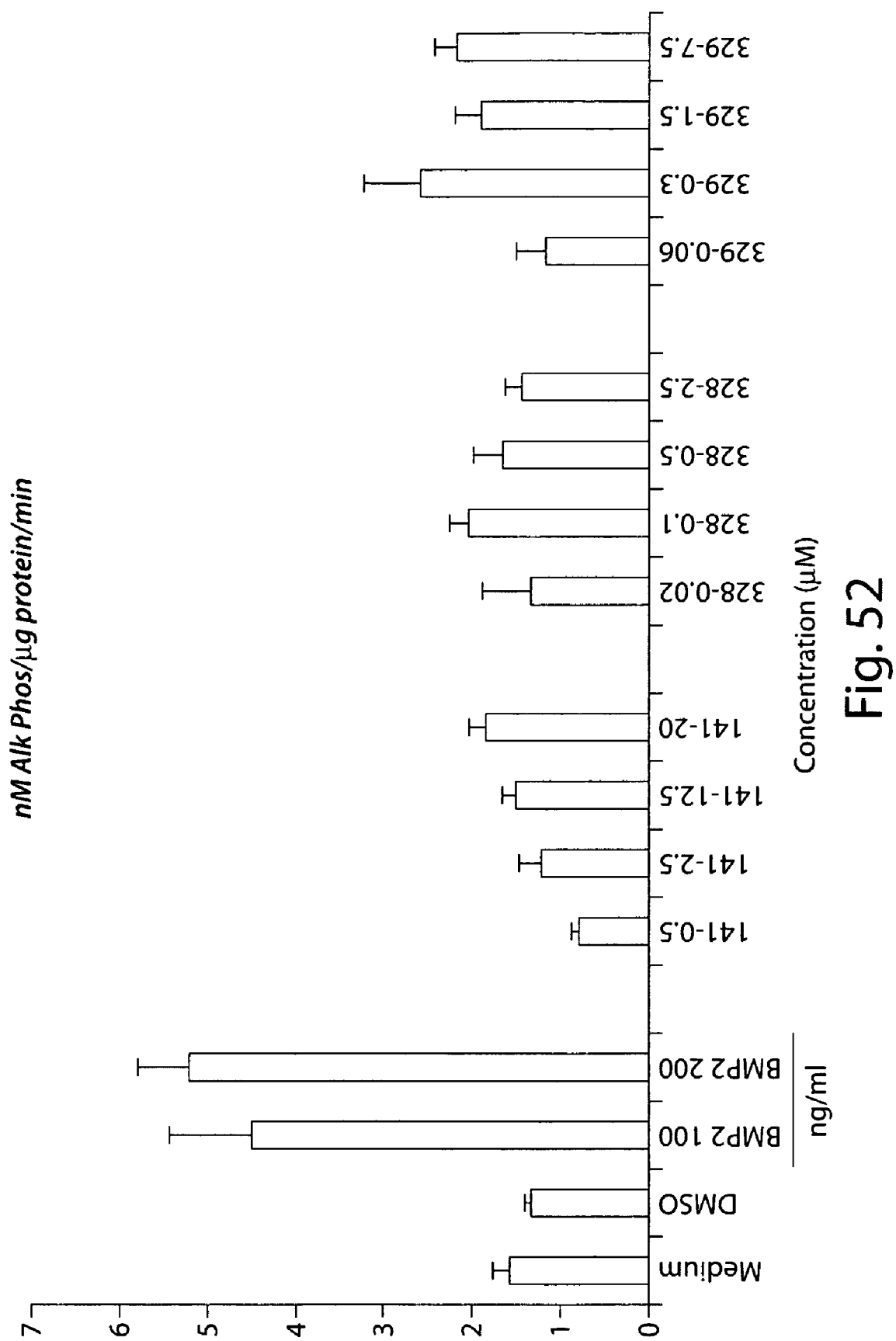
FIG. 52 is a bar chart showing the effect of compounds on alkaline phosphatase expression by osteoblasts.

The enzyme alkaline phosphatase has been used as an indicator of osteoblast activity, as it is involved in making phosphate available for calcification of bone. To determine the effects of the compounds on osteoblast activity, osteoblasts were treated with KX1-141 (0.5 µM, 2.5 µM, 12.5 µM, or 20 µM), KX2-328 (0.02 µM, 0.1 µM, 0.5 µM, or 2.5 µM), or KX1-329 (0.06 µM, 0.3 µM, 1.5 µM or 7.5 µM) and alkaline phosphatase expression was determined (nM alkaline phosphatase/µg protein/min (FIG. 52). As controls, osteoblasts were treated with medium alone, dimethyl sulfoxide (DMSO), or bone morphogenic protein-2 (BMP2). BMPs, defined as osteoinductive by their ability to induce osteogenesis when implanted in extraskeletal sites, are thought to mediate the transformation of undifferentiated mesenchymal cells into bone-producing osteoblasts.

Figure 53:
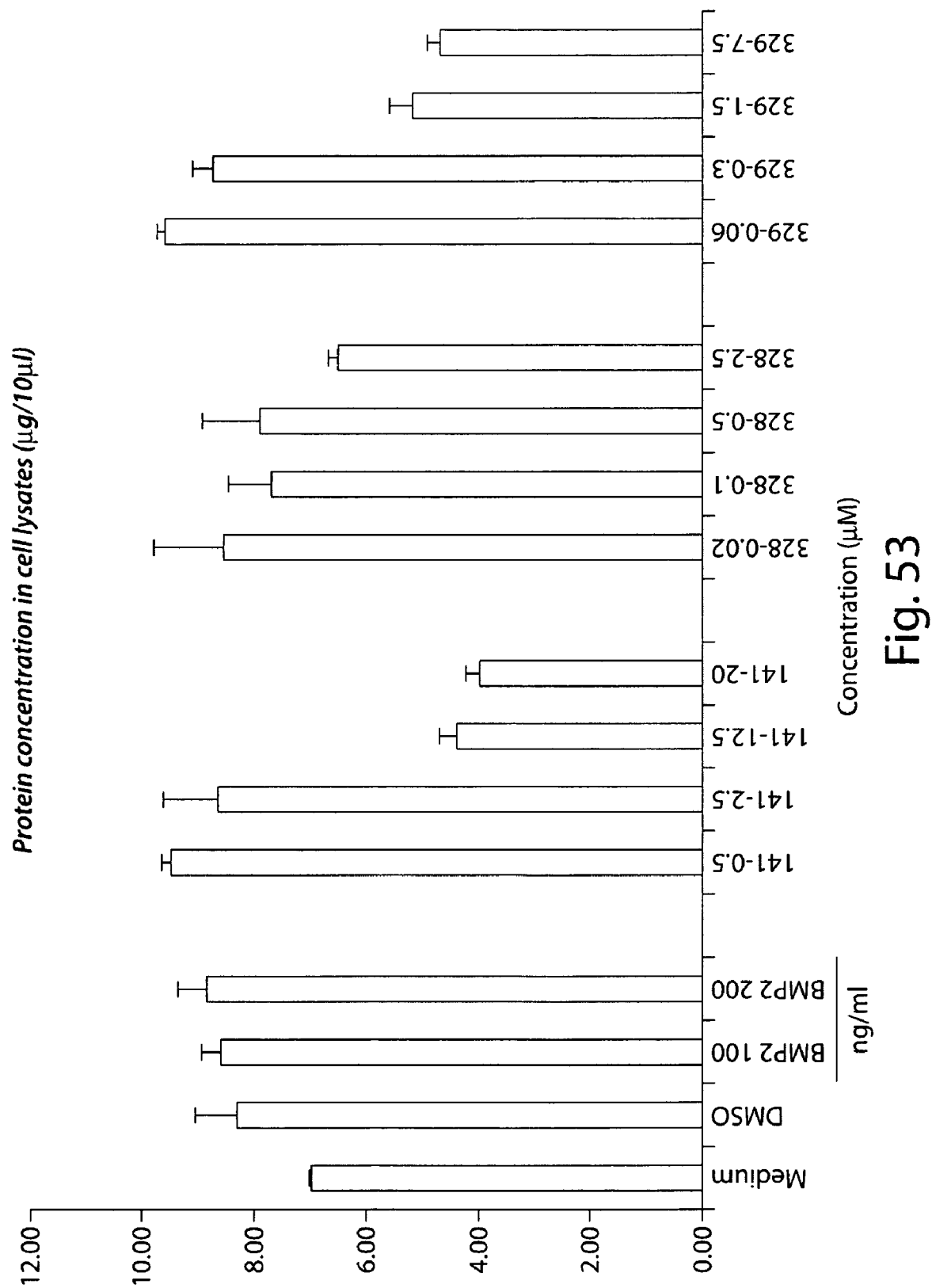
FIG. 53 is a bar chart depicting the effect of compounds on protein expression by osteoblasts.

To determine the effects of the compounds on osteoblast activity and protein expression, osteoblasts were treated with medium, DMSO, BMP2, KX1-141, KX2-328, or KX1-329 as indicated above. The protein concentration in cell lysates was determined (µg/10 µl) (FIG. 53). Notably, KX1-141 increased protein concentration when administered at 0.5 µM and 2.5 µM, but reduced protein concentration in cell lysates when administered at 12.5 µM and 20 µM. Additionally, KX1-329 increased protein concentration when administered at 0.06 µM and 0.3 µM, but reduced protein concentration when administered at 1.5 µM and 7.5 µM.

Example 18

Effect of Compounds on Obesity

The following example illustrates that the compounds of the present invention could be used to treat obesity. The compounds are tested using a method described previously (Minet-Ringuet, et al.; 2006, *Psychopharmacology*, Epub ahead of print, incorporated herein by reference). Thirty male Sprague-Dawley rats initially weighing 175-200 g are housed in individual Plexiglas cages with an artificial 12:12-h light-dark cycle (lights on at 08:00 h) in a room maintained at 24±1° C. and 55±5% humidity. Food and water are available ad libitum throughout. All rats are fed with a medium fat diet (metabolizable energy 17.50 kJ/g) composed of 140 g/kg of whole milk protein, 538.1 g/kg of cornstarch, 87.6 g/kg of sucrose, and 137 g/kg of soya bean oil, and this diet is supplemented with minerals and vitamins (mineral salts 35 g/kg, vitamins 10 g/kg, cellulose 50 g/kg, and choline 2.3 g/kg). This food, named P14-L, which resembles the usual human diet (14% proteins, 31% lipids, and 54% carbohydrates) is prepared in the laboratory in the form of a powder.

Several doses of the compound of the instant invention are tested: 0.01, 0.1, 0.5, and 2 mg/kg, in addition to the control solution. The compound is solubilized in water and then incorporated into the diet. The basal food intake is recorded during the adaptation period and used to determine the daily quantity of the compound of the instant invention incorporated into food. The compound is mixed into the food in the laboratory. After 1 week of adaptation to the laboratory conditions, the rats are separated into five groups (n=6 per group) with homogenous weight and receive the compound of the instant invention in their food for 6 weeks. Weight is recorded three times per week. Body composition is measured at the end of the study by dissection and by weighing the main organs and tissues. Briefly, rats are deeply anesthetized by an intraperitoneal injection of an overdose of anesthetic (sodium pentobarbital 48 mg/kg) and heparinized (100 U heparin/100 g body weight). They are bled (to avoid coagulation in tissues) by sectioning the vena cava and abdominal aorta before removal and weighing of the main fresh organs (liver, spleen, kidneys, and pancreas) and tissues (perirenal and scapular brown adipose tissue, epididymal, retroperitoneal, visceral, and subcutaneous white adipose tissues (WATs), and carcass defined by muscles and skeleton). The compound of the instant invention could reduce the body weight of the animals, indicating that the compound may be used to treat obesity in a subject.

Example 19

Effect of Compounds on Insulin-Induced GLUT4 Translocation in 3T3-L1 Adipocytes

The following example illustrates that the compounds of the present invention could be used to treat diabetes. The compounds are tested using a method described previously (Nakashima, et al.; 2000, *J. Biol. Chem.*, 275, 12889-12895). Either control IgG, or the compound of the instant invention is injected into the nucleus of differentiated 3T3-L1 adipocytes on coverslips. Glutathione S-transferase fusion proteins are each coinjected with 5 mg/ml sheep IgG for detection purposes. Prior to staining, the cells are allowed to recover for a period of 1 h. Cells are starved for 2 hr in serum-free medium, stimulated with or without insulin (0.5 nM or 17 nM) for 20 min and fixed.

Immunostaining is performed using rabbit polyclonal anti-GLUT4 (F349) (1 µg/ml). Each fluorescein isothiocyanate-positive microinjected cell is evaluated for the presence of plasma membrane-associated GLUT4 staining. Control cells are injected with preimmune sheep IgG and then processed in the same way as experimentally injected cells. As quantitated by immunofluorescent GLUT4 staining, insulin leads to an increase in GLUT4 translocation to the plasma membrane. Cells are incubated with wortmannin as a control to block basal and insulin-induced GLUT4 translocation. The compounds of the instant invention could stimulate insulin-induced GLUT4 translocation, which could indicate that administration of the compounds of the invention inhibited kinase activity, e.g., PTEN function, resulting in an increase in intracellular phosphatidylinositol 3,4,5-triphosphate levels, which stimulates GLUT4 translocation.

Example 20

Effect of Compounds on Retinal Neovascularization

The following example illustrates that the compounds of the present invention could be used to treat eye diseases, e.g., macular degeneration, retinopathy and macular edema. The effect of compounds on retinal neovascularization is determined using a model of retinal neovascularization as previously described (Aiello, et al.; 1995, *Proc. Natl. Acad. Sci.*, 92, 10457-10461). Briefly, C57Bl/6J mice are exposed to 75% $O_2$ from postnatal day 7 (P7) to P12 along with nursing mothers. At P12, the mice are returned to room air. Intraocular injections are performed at P12 and sometimes P14 as described below. At P17 the mice are sacrificed by cardiac perfusion of 4% paraformaldehyde in phosphate-buffered saline and the eyes are enucleated and fixed in 4% paraformaldehye overnight at 4° C. before paraffin embedding.

Mice are deeply anesthetized with tribromoethanol for all procedures. The lid fissure is opened (e.g., using a no. 11 scalpel blade) and the eye is proptosed. Intravitreal injections are performed by first entering the left eye with an Ethicon TG140-8 suture needle at the posterior limbus. A 32-gauge Hamilton needle and syringe are used to deliver the compound of the instant invention diluted in Alcon balanced salt solution through the existing entrance site. The eye is then repositioned and the lids are approximated over the cornea. Repeat injections are performed through a previously unmanipulated section of limbus 2 days later. As a control, equal amounts of saline are injected to the right eye.

Over 50 serial 6-µm paraffin-embedded axial sections are obtained starting at the optic nerve head. After staining with periodic acid/Schiff reagent and hematoxylin (Pierce, et al.; 1995, *Proc. Natl. Acad. Sci. USA.*, 92, 905-909; Smith et al.; 1994, *Invest. Ophthal. Vis. Sci.*, 35, 101-111), 10 intact sections of equal length, each 30 µm apart, are evaluated for a span of 300 µm. Eyes exhibiting retinal detachment or endophthalmitis are excluded from evaluation. All retinal vascular cell nuclei anterior to the internal limiting membrane are counted in each section by a fully masked protocol. The mean of all 10 counted sections yield average neovascular cell nuclei per 6-µm section per eye. No vascular cell nuclei anterior to the internal limiting membrane are observed in normal, unmanipulated animals (Smith et al.; 1994, *Invest. Ophthal. Vis. Sci.*, 35, 101-111). Reduced neovascularization could be observed in the eyes treated with the compounds of the instant invention as compared to the eyes in the saline control group.

Example 21

Identification of Compounds that Modulate Kinase Signaling Cascade Associated with Stroke Many animal models for stroke have been developed and characterized, see e.g., Andaluz, et al., Neurosurg. Clin. North Am., vol. 13:385-393 (2002); Ashwal, S. and W. J. Pearce., Curr. Opin. Pediatr., vol 13:506-516 (2001); De Lecinana, et al., Cerebrovasc. Dis., vol. 11 (Suppl. 1):20-30 (2001); Ginsberg and Busto, Stroke, vol. 20:1627-1642 (1989); Lin, et al., J. Neurosci. Methods, vol. 123:89-97 (2003); Macrae, I. M., Br. J. Clin. Pharmacol., vol. 34:302-308 (1992); McAuley, M. A., Cerebrovasc. Brain Metab. Rev., vol. 7:153-180 (1995); Megyesi, et al., Neurosurgery, vol. 46:448-460 (2000); Stefanovich, V. (ed.)., Stroke: animal models. Pergamon Press, Oxford (1983); and Traystman, R. J., ILAR J. 44:85-95 (2003), each of which is hereby incorporated by reference in its entirety. For a review of animal models of focal (stroke) and global (cardiac arrest) cerebral ischemia, see e.g., Traystman, ILAR J., vol. 44(2):85-95 (2003) and Carmichael, NeuroRx®: The Journal of the American Society for Experimental NeuroTherapeutics, vol. 2:396-409 (2005, each of which is hereby incorporated by reference in its entirety.

Compounds that modulate cell death in stroke are identified using any of the art-recognized models for stroke. In the studies described herein, intra-arterial suture occlusion of the middle cerebral artery (MCA), a procedure known as MCAo, through the internal carotid artery is used as a model for cell death in stroke. In the control and test group of rats, the external carotid artery is transected, the common carotid artery is tied off, and the external carotid artery is then used as a pathway to pass a suture through the internal carotid artery, wherein the suture lodges in the junction of the anterior and middle cerebral arteries. To reduce subarachnoid hemorrhage and premature reperfusion, the suture is preferably coated with an agent such as silicone. The suture is used to occlude the MCA, e.g., for a duration of 60, 90, or 120 minutes and to permanently occlude the MCA.

In the test group, rats are administered a compound of the invention at a variety of times prior to, during and after occlusion of the MCA with the suture. The effects of the compound on the test group is compared to the effects observed in the control group, for example, by measuring the extent of cell death in each MCAo group. Typically, in the control group, the pattern of cell death follows a progression from early infarction in the striatum to delayed infarction in the dorsolateral cortex overlying the striatum. Striatal is mostly necrotic and occurs rapidly. The pattern of cell-death in the test group is compared to that of the control group to identify compounds that modulate cell death in stroke.

Example 22

Identification of Compounds that Modulate Kinase Signaling Cascade Associated with Atherosclerosis Many animal models for atherosclerosis have been developed and characterized. For a review of animal models of atherosclerosis, restenosis and endovascular graft research, see e.g., Narayanaswamy et al., JVIR, vol. 11(1): 5-17 (2000), which is hereby incorporated by reference in its entirety. Atherosclerosis is induced in a suitable animal model using a high fat/high cholesterol (HFHC) diet. The test animal is an animal that contains cholesterol ester transferase, such as the rabbit or the swine. The HFHC diet is produced, e.g., using commercial chow supplemented with fat. Cholesterol intake is between 0.5-2.0% of the diet. A test group of animals, e.g., rabbits or swine, receives a compound of the invention. The effect of the test compound is compared to the effects of atherosclerosis in the untreated, control group of animals. Effects that are compared include, for example, the degree of plaque formation, the number and/or frequency of myocardial infarctions observed in each group of animals, and the extent of tissue damage secondary to myocardial infarction exhibited in coronary tissue.

Myocardial infarction is studied using a variety of animal models such as rats and mice. The majority of myocardial infarctions result from acute transbotic occlusion of pre-existing atherosclerotic plaques of coronary arteries, which is mimicked in animal models by ligation of the left coronary artery in e.g., rats and mice. Myocardial infarction induces global changes in the ventricular architecture, a process called ventricular remodeling. The infarcted heart progressively dilates and accelerates the deterioration of ventricular dysfunction that eventually results in heart failure.

Myocardial ischemia is induced in test and control groups of animals, e.g., mice or rats, by ligating the left anterior descending coronary artery. The affected heart tissue is contacted with a compound of the invention, for example, by intraperitoneal (i.p.) injections, after the induction of ischemia. High resolution magnetic resonance imaging (MRI), dry weight measurements, infarct size, heart volume, and area at risk are determined 24 hours postoperatively. Survival rates and echocardiography are determined at various times postoperatively in the rats receiving injections of the compound of the invention. Other effects of the test compound are compared to the control group of rats. For example, changes in left ventricular geometry and function are characterized using echocardiography to compare end-diastolic diameters, relative wall thickness, and the percentage of fractional shortening. In excised hearts, the infarct size calculated and expressed as a percentage of left ventricular surface area.

Example 23

Identification of Compounds that Modulate Kinase Signaling Cascade Associated with Neuropathic Pain Many animal models for neuropathic pain, such as chronic neuropathic pain, have been developed and characterized, see e.g., Bennett & Xie, Pain, vol. 33, 87-107 (1988); Seltzer et al., Pain, vol. 43, 205-18 (1990); Kim & Chung, Pain, vol. 50, 355-63 (1992); Malmberg & Basbaum, Pain, vol. 76, 215-22 (1998); Sung et al., Neurosci Lett., vol. 246, 117-9 (1998); Lee et al., Neuroreport, vol. 11, 657-61 (2000); Decosterd & Woolf, Pain, vol. 87, 149-58 (2000); Vadakkan et al., J Pain, vol. 6, 747-56 (2005), each of which is hereby incorporated by reference in its entirety. For a review of animal models used for neuropathic pain, see e.g., Eaton, J. Rehabilitation Research and Development, vol. 40(4 Supplement):41-54 (2003), the contents of which are hereby incorporated by reference in their entirety.

Compounds that modulate neuropathic pain are identified using any of the art-recognized models for neuropathic pain. For example, the models for neuropathic pain generally involve injury to the sciatic nerve, although the method used to induce injury varies. For example, the sciatic nerve is injured due to partial constriction, complete transection, freezing of the nerve, and metabolic, chemical, or immune insults to the nerve. Animals with these types of nerve injury have been shown to develop abnormal pain sensations similar to those reported by neuropathic pain patients. In the studies described herein, the sciatic nerve of test and control groups of subjects, such as mice, are injured. In the test group, subjects are administered a compound of the invention at a variety of times prior to, during and after injury to the sciatic nerve. The effects of the compound on the test group are compared to the effects observed in the control group, e.g., through physical observation and examination of the subjects. For example, in mice, the subject's hindpaw is used to test the response to non-noxious stimuli, such as tactile stimulation, or to test the subject's response to stimuli that would be noxious in the course of ordinary events, for example, radiant heat delivered to the hindpaw. Evidence of allodynia, a condition in which ordinarily nonpainful stimuli evoke pain, or a hyperalgesia, the excessive sensitiveness or sensibility to pain, in the test subjects indicates that test compound is not effectively modulating neuropathic pain in the test subjects.

Example 24

Identification of Compounds that Modulate Kinase Signaling Cascade Associated with Hepatitis B Many animal models for hepatitis B have been developed and characterized. For a review of animal models of hepatitis B, see e.g., Guha et al., Lab Animal, vol. 33(7):37-46 (2004), which is hereby incorporated by reference in its entirety. Suitable animal models include, for example, the chimpanzee, tree shrews (non-rodent small animals that are phylogenetically close to primates, see Walter et al., Hepatology, vol. 24(1):1-5 (1996), which is hereby incorporated by reference in its entirety), and surrogate models such as the woodchuck, duck and ground squirrel. (See e.g., Tennant and Gerin, ILAR Journal, vol. 42(2):89-102 (2001), which is hereby incorporated by reference in its entirety).

For example, primary hepatocytes are isolated from livers of the tree shrew species tupaia belangeri and are infected with HBV. In vitro infection results in viral DNA and RNA synthesis in hepatocytes and secretion hepatitis B surface antigen (HBsAg) and hepatitis B e antigen (HBeAg) into culture medium. Tupaias can also be infected with HBV in vivo, resulting in viral DNA replication and gene expression in tupaia livers. Similar to acute, self-limited hepatitis B in humans HBsAg is rapidly cleared from serum, followed by seroconversion to anti-HBe and anti-HBs.

Compounds that modulate hepatitis B are identified using any of the art-recognized models for hepatitis B. In the studies described herein, test and control groups of animals, e.g., chimpanzees or tree shrews, are infected with HBV. In the test group, subjects are administered a compound of the invention at a variety of times prior to, during and after exposure to HBV. The effects of the compound on the test group are compared to the effects observed in the control group, e.g., through physical observation and examination of the subjects and through blood or serum analysis to determine at what point in time the infection is cleared from the subject. For example, assays are run to detect the presence and/or amount of hepatitis B virus called surface antigens and fragments thereof. Alternatively or in addition, the subject's liver is analyzed. Liver function tests analyze levels of certain proteins and enzymes, such as, for example, aspartate aminotransferase (AST, formerly serum glutamic-oxaloacetic transaminase (SGOT)) and alanine aminotransferase (ALT, formerly serum glutamate-pyruvate transaminase (SGPT)).

Example 25

The Effect of Compounds on Tyrosine Kinase Inhibition

The following example illustrates that the compounds of the present invention could be used to treat autoimmune diseases. The compounds are tested using a method described previously (Goldberg, et al.; 2003, *J. Med. Chem.*, 46, 1337-1349). The kinase activity is measured using DELFIA (dissociation enhanced lanthanide fluoroimmunoassay), which utilizes europium chelate-labeled anti-phosphotyrosine antibodies to detect phosphate transfer to a random polymer, poly-Glu4-Tyr1 (PGTYR). The kinase assay is performed in a neutravidin-coated 96-well white plate in kinase assay buffer (50 mM HEPES, pH 7.0, 25 mM MgCl2, 5 mM MnCl2, 50 mM KCl, 100 µM Na3VO4, 0.2% BSA, 0.01% CHAPS). Test samples (compounds of the instant invention) initially dissolved in DMSO at 1 mg/mL are prediluted for dose response (10 doses with starting final concentration of 1 µg/mL, 1-3.5 serial dilutions) with the assay buffer. A 25 µL aliquot of this diluted sample and a 25 µL aliquot of diluted enzyme (lck) (0.8 nM final concentration) are sequentially added to each well. The reaction is started with a 50 µL/well of a mixture of substrates containing 2 µM ATP (final ATP concentration is 1 µM) and 7.2 ng/µL PGTYR-biotin in kinase buffer. Background wells are incubated with buffer and substrates only. Following 45 min of incubation at room temperature, the assay plate is washed three times with 300 µL/well DELFIA wash buffer. A 100 µL/well aliquot of europium-labeled anti-phosphotyrosine ($Eu^{3+}$-PT66, 1 nM, Wallac CR04-100) diluted in DELFIA assay buffer is added to each well and incubated for 30 min at room temperature. Upon completion of the incubation, the plate is washed four times with 300 µL/well of wash buffer and 100 µL/well of DELFIA wash buffer. Enhancement solution (Wallac) is added to each well. After 15 min, time resolved fluorescence is measured on the LJL's analyst (excitation at 360 nm, emission at 620 nm, EU 400 dichroic mirror) after a delay time of 250 µs. The compound of the instant invention could inhibit the kinase activity of lck, indicating that the compound may be used to treat autoimmune disease in a subject.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

LITERATURE CITED

The following references which were cited herein, are hereby incorporated by reference in their entirety into this application:

Abram, C. L.; Courtneidge, S. A. (2000) *Src family tyrosine kinases and growth factor signaling*. Experimental Cell Research 254, 1-13.

Ajay, Murcko, M. A. (1995) *Computational Methods to Predict Binding Free Energy in Ligand-Receptor Complexes*. J. Med. Chem., 38, 4953-4967.

Alberts, B., Bray, D., Lewis, J., Raff, M., Roberts, K. & Watson, J. D. (1994) Molecular Biology Of The Cell, 3rd ed., Garland Publishing, Inc., New York, pp. 97, 508 & 667.

Alfaro-Lopez, J., Yuan, W., Phan, B. C., Kamath, J., Lou, Q., Lam, K. S., Hruby, V. J. (1998) *Discovery of a Novel Series of Potent and Selective Substrate-Based Inhibitors of p60c-src Protein Tyrosine Kinase: Conformational and Topographical Constraints in Peptide Design*. J. Med. Chem., 41, 2252-2260.

Backes, B. J., Virgilo, A. A., Ellman, J. A. (1996) *Activation Method to Prepare a Highly Reactive Acylsulfonamide "Safety-Catch" Linker for Solid-Phase Synthesis*. J. Am. Chem. Soc., 118, 3055-3056.

Baggio, R., Elbaum, D., Kanyo, Z. F., Carroll, P. J., Cavalli, C., Ash, D. E., Christianson, D. W. (1997) *Inhibition of Mn2+-Arginase by Borate Leads to the Design of a Transition State Analog Inhibitor, 2(S)-Amino-6-boronohexanoic Acid*. J. Am. Chem. Soc., 119, 8107-8108.

Barnekow, A.; Paul, E.; Schartl, M. (1987) *Expression of the c-src protooncogene in human skin tumors*. Cancer Res., 47, 235-240.

Benson, W. H., Birge, W. J., Dorough, H. W. (1984) Environ. Toxicol. Chem., 3, 209. Chem. Abstr. 101:124626g.

Bhagwat, S. S., Gude, C. (1994) *N-Alkylation of indole ring using Mitsunobu reaction*. Tet. Lett., 35, 1847-1850.

Biscardi, J. S., Tice, D. A.; Parsons, S. J. (1999) *c-Src, Receptor Tyrosine Kinases and Human Cancer*. Advances in Cancer Research, 61-119.

Biscardi, K. S., Ishizawar, R. C.; Silva, C. M.; Parsons, S. J. (2000) *Tyrosine kinase signaling in breast cancer: Epidermal growth factor receptor and c-Src interactions in breast cancer*. Breast Cancer Res. 2, 203-210.

Bjorge, J. D., O'Connor, T. J., Fujita, D. J. (1996) *Activation of human pp60$^{c-src}$*. Biochemistry & Cell Biology, 74, 477-484.

Bjelfman, C.; Hedborg, F.; Johansson, I.; Nordenskjold, M.; Pahlman, S. (1990) *Expression of the neuronal for of pp60c-src in neuroblastoma in relation to clinical stage and prognosis*. Cancer Res, 50, 6908-6914.

Blume-Jensen, P.; Hunter, T. (2001) *Oncogenic kinase signaling*. Nature 411, 355-365.

Bohacek, R. S., McMartin, C., Guida, W. C. (1996) *The Art and Practice of Structure-Based Drug Design: A Molecular Modeling Perspective*. Medicinal Research Reviews, 16, 3-50 (see p. 43).

Boyd, M. R., Paull, K. D. (1995) *Some practical considerations and applications fo the National Cancer Institute in vitro anticancer drug discovery screen*. Drug Development Research, 34, 91-109.

Bridges, A. J. (2001) *Chemical Inhibitors of Protein Kinases*. Chemical Reviews 101(8), 2541-2572.

Brooks, S. P. J. & Storey, K. B. (1992) *Bound and Determined: A Computer Program for Making Buffers of Defined Ion Concentrations*. Analytical Biochemistry, 201, 119-126.

Brown, D. (1997) *Future Pathways for Combinatorial Chemistry*. Molecular Diversity, 2(4), 217-222.

Budde, R. J. A., McMurray, J. S., Saya, H., Gallick, G. E. & Levin, V. A. (1995) *Discovery, Development, and Testing of Substrates and Inhibitors of pp60$^{c-src}$*. International Journal of Pharmacognosy, 33, 27-34.

Budde, R. J. A., Ke, S., Levin, V. A. (1994) *Activity of pp60c-src in 60 different cell lines derived from human tumors*. Cancer Biochem. Biophys., 14, 171-175.

Burger, A. M., Kaur, G., Alley, M. C., Supko, J. G., Malspeis, L., Grever, M. R. & Sausville, E. A. (1995) *Tyrphostin AG17, [(3,5-Di-tert-butyl-4-hydroxybenzylidene)-malonitrile], inhibits cell growth by disrupting mitochondria*. Cancer Research, 55, 2794-2799.

Burke, T. R.; Lim, B.; Marquez, V. E.; Li, Z-H.; Bolen, J. B.; Stefanova, I.; Horak, I. D. (1993) J. Med. Chem. 36, 425.

Choi, S. (1999), Ph.D. Thesis SUNY at Buffalo, Buffalo, N.Y.

Cooper, C. M. (1990) Oncogenes. Jones and Bartlett Publishers, Boston, Mass.

Coughlin, J. R. (1996) *Inorganic borates-chemistry, human exposure, and health and regulatory guidelines*. J. Trace Elements in Experimental Medicine, 9, 137-151.

Courtneidge, S. A. (1994) *Protein tyrosine kinases, with emphasis on the Src family*. Seminars in Cancer Biology, 5, 239-246.

Cox, S., Radzio-Andzelm, E. & Taylor, S. S. (1994) *Domain movements in protein kinases*. Current Opinion in Structural Biology, 4(6), 893-901.

Culver, B. D., Hubbard, S. A. (1996) *Inorganic boron health effects in humans—and aid to risk assessment and clinical judgment*. J. Trace Elements in Experimental Medicine, 9, 175-184.

Davis, P. D.; Hill, C. H.; Keech, E.; Lawton, G.; Nixon, J. S.; Sedgwick, A. D.; Wadsworth, J.; Westmacott, D.; Wilkinson, S. E. (1989) FEBS Lett. 259(1), 61.

Davis, P. D.; Elliott, L. H.; Harris, W.; Hill, C. H.; Hurst, S. A.; Keech, E.; Kumar, M. K. H.; Lawton, G.; Nixon, J. S.; Wilkinson, S. E. (1992) J. Med. Chem. 35, 994.

Ellis, L. M., Staley, C. A., Liu, W., Fleming, R. Y., Parikh, N. U., Bucana, C. D., & Gallick, G. E. (1998) *Down-regulation of vascular endothelial growth factor in a human colon carcinoma cell line transfected with an antisense expression vector specific for c-src*. Journal of Biological Chemistry 273 (2):1052-1057.

Ezquerra, J., Pedregal, C., Lamas, C., Barluenga, J., Perez, M., Garcia-Martin, M. A., Gonzalez, J. M. (1996) *Efficient reagents for the synthesis of 5-, 7-, and 5,7-substituted indoles starting from aromatic amines: scope and limitations*. J. Org. Chem., 61, 5804-5812.

Faltynek, C., et al. (1995) *Damnacanthal is a highly potent, selective inhibitor of p56lck tyrosine kinase activity*. Biochemistry 34, 12404-12410.

Faltynek, C. R.; Wang, S.; Miller, D.; Mauvais, P.; Gauvin, B.; Reid, J.; Xie, W.; Hoekstra, S.; Juniewicz, P.; Sarup, J.; Lehr, R.; Sawutz, D. G.; Murphy, D. J. (1995) Enzyme Inhibition 9, 111.

Fanning, P.; Bulovas, K.; Saini, K. S.; Libertino, J. A.; Joyce, A. D.; Summerhayes, I. C. (1992) *Elevated expression of pp60$^{c-src}$ in low grade human bladder carcinoma*. Cancer Research, 52, 1457-1462.

Frame, M. C. (2002) *Src in cancer: deregulation and consequences for cell behavior*. Biochemica et Biophysica Acta, 1602, 114-130.

Fredenhagen, A.; Mett, H.; Meyer, T.; Buchdunger, E.; Regenass, U.; Roggo, B. E.; Petersen, F. J. (1995) Antibiotics 48, 1355.

Froyen, P. (1997) Tetrahedron Lett. 38(30), 5359.

Fry, D. W., Kraker, A. J., McMichael, A., Ambroso, L. A., Nelson, J. M. Leopold, W. R., Connors, R. W. & Bridges, A. J. (1994) *A Specific Inhibitor of the Epidermal Growth Factor Receptor Tyrosine Kinase*. Science, 265, 1093-1095.

Garcia-Echeverria, C.; Traxler, P.; Evans, D. B. (2000) *ATP Site-directed competitive and irreversible inhibitors of protein kinases*. Med. Res. Rev. 20(1), 28-57.

Glass, D. B., Cheng, H.-C., Mende-Mueller, L., Reed. J. & Walsh, D. A. (1989) *Primary structure determinants essential for potent inhibition of cAMP-dependent protein kinase by inhibitory peptides corresponding to the active portion of the heat-stable inhibitor protein*. J. Biol. Chem., 264, 8802-8810.

Groundwater, P. W., Solomons, K. R. H., Drewe, J. A. & Munawar, M. A. (1996) *Protein Tyrosine Kinase Inhibitors*. Progress in Medicinal Chemistry, 33, 233-329.

Hanks, S. K. & Hunter, T. (1995) Protein kinases. 6. *The eukaryotic protein kinase superfamily: Kinase (catalytic) domain structure and classification*. FASEB J., 9, 576-596.

Hanke, J. H., Gardner, J. P., Dow, R. L., Changelian, P. S., Brissette, W. H., Weringer, E. J., Pollok, B. A. & Connelly, P. A. (1996) *Discovery of a novel, potent, and Src family-selective tyrosine kinase inhibitor*. J. Biol. Chem., 271, 695-701.

Haskell, M. D.; Slack, J. K.; Parsons, J.; Parsons, S. J. (2001) *c-Src tyrosine phosphorylation of epidermal growth factor receptor, p-190 RhoGAP, and focal adhesion kinase regulates diverse cellular processes*. Chemical Reviews 101 (8), 2425-2440.

Hisano, C., Nakano, S., Fujishima, H., Masumoto, N., Tatsumoto, T., & Niho. Y. (1997) *src oncogene inhibits detachment-induced apoptosis through constitutive activation of p125FAK in HAG-1 human epithelial cells*. Proc. Annu. Meet. Am. Assoc. Cancer Res. 38:A1925.

Hsiao, G. K., Hangauer, D. G. (1998) *A Facile Synthesis of tert-Butyl 2-[(Benzyloxycarbonyl)amino]-3-(4,4,5,5-tetramethyl-1,3,2-dioxaborolan-2-yl)propionate: An Orthogonally Protected Boronic Acid Analog of Aspartic Acid*. Synthesis, 1043-1046.

Hsu, C-Y., J., Jacoski, M. V., Maguire, M. P., Spada, A. P. & Zilberstein, A. (1992) *Inhibition Kinetics and Selectivity of the Tyrosine Kinase Inhibitor Erbstatin and a Pyridone-based Analog*. Biochemical Pharmacology, 43, 241-2477.

Huang, C-K., Wu, F-Y., Ai, Y-X. (1995) *Polyhydroxylated 3-(N-phenyl)carbamoyl-2-iminochromene derivatives as potent inhibitors of tyrosine kinase p60c-src*. Bioorg. & Med. Chem. Lett., 5, 2423-2428.

Hubbard, S. R., Wei, L, Ellis, L, & Hendrickson, W. A. (1994) *Crystal structure of the tyrosine kinase domain of the human insulin receptor*, Nature, 372, 746-754.

Hubbard, S. R. (1997) *Crystal structure of the activated insulin receptor tyrosine kinase in complex with peptide substrate and ATP analog*. The EMBO Journal, 16, 5572-5581.

Hughes, R. L., Smith, I. C., Lawless, E. W. (1967) Production of the Boranes and Related Rearch, Holtzman R. T., Ed., Academic Press, New York, pp. 291-294.

Hunter, T. (1987) *A thousand and one protein kinases*. Cell, 50, 823-829.

Hunter, T. (1994) *1001 protein kinases redux-towards 2000*. Seminars in Cell Biology, 5, 367-376.

Hunter, T. (1998) *The Croonian Lecture 1997. The phosphorylation of proteins on tyrosine: its role in cell growth and disease*. Philosophical Transactions of the Royal Society of London—Series B: Biological Sciences 353 (1368): 583-605.

Hutchins, C., Greer, J. (1991) *Comparative modeling of proteins in the design of novel renin inhibitors*. Critical Reviews in Biochemistry & Molecular Biology, 26, 77-127.

Irby, R. B.; Yeatman, T. J. (2000) *Role of Src expression and activation in human cancer*. Oncogene 19, 5536-5642.

Ishiyama, T., Murata, M., Miyaura, N. (1995) *Palladium(0)-catalyzed cross-coupling reaction of alkoxydboron with haloarenes: A direct procedure for arylboronic esters*. J. Org. Chem., 60, 7508-7510.

Ishiyama, T., Itoh, Y., Kitano, T., Miyaura, N. (1997) *Synthesis of arylboronates via the palladium(0)-catalyzed cross-coupling reaction of tetra(alkoxo)diborons with aryl triflates*. Tet. Lett., 38, 3447-3450.

Johnson, T. O., Ermolieff, J., Jirousek, M. R. (2002) *Protein tyrosine phosphatase 1B inhibitors for diabetes*. Nat. Rev. Drug Discov., 1(9), 696-709.

Karni, R., Jove R., & Levitzki A. (1999) *Inhibition of pp60c-src reduces Bcl-X expression and reverses the transformed phenotype of cells overexpressing EGF and HER-2 receptors*. Oncogene 18(33): 4654-4662.

Kelloff, G. J., Fay, J. R., Steele, V. E., Lubet, R. A., Boone, C. W., Crowell, J. A. (1996) *Epidermal growth factor receptor tyrosine kinase inhibitors as potential cancer chemopreventatives*. Cancer Epidemiology, Biomarkers & Prevention, 5, 657-666.

Kennedy, B. P. (1999) *Role of protein tyrosine phosphatase-1B in diabetes and obesity*. Biomedicine & Pharmacotherapy. 53(10), 466-470.

Kettner, C. A., Shenvi, A. B. (1984) *Inhibition of the Serine Proteases Leukocyte Elastase, Pancreatic Elastase, Cathepsin G, and Chymotrypsin by Peptide Boronic Acids*. J. Biol. Chem., 259, 15106-15114.

Kim. M. H., Lai, J. H. & Hangauer, D. G. (1994) *Tetrapeptide tyrosine kinase inhibitors: Enantioselective synthesis of p-hydroxymethyl-L-phenylalanine, incorporation into a tetrapeptide, and subsequent elaboration into p-(R,S-hydroxyphosphonomethyl)-L-phenylalanine*. Int. J. Peptide Protein Res., 44, 457-465.

Kinder, D. H., Frank, S. K., Ames, M. M. (1990) *Analogues of Carbamyl Aspartate as Inhibitors of Dihydroorotase: Preparation of Boronic Acid Transition-State Analogues and a Zinc Chelator Carbamylhomocysteine*. J. Med. Chem., 33, 819-823.

Klein, G. (1990) *Multistep emancipation of tumors from growth control: can it be curbed in a single step*? BioEssays, 12, 347-350.

Knighton, D. R., Cadena, D. L., Zheng, J., Ten Eyck, L. F., Taylor, S. S. & Sowadski, J. M. (1993) *Structural features that specify tyrosine activity deduced from homology modeling of the epidermal growth factor receptor*. Proc. Natl. Acad. Sci. U.S.A., 90(11), 5001-5.

Kolibaba, K. S. & Druker, B. J. (1997) *Protein tyrosine kinases and cancer*. Biochimica et Biophysica Acta, 1333: F217-F248.

Lai, J. H., Marsilje, T. M., Choi, S., Nair, S. A., Hangauer, D. G. (1998) *The design, synthesis and activity of pentapeptide pp60c-src inhibitors containing L-phosphotyrosine mimics*. J. Peptide Res., 51, 271-281.

Lai, J. H., Pham, H. & Hangauer, D. G. (1996) *Synthesis of a Vicinal Tricarbonyl Amide Derivative of L-Phenylalanine*. J. Org. Chem., 61, 1872-1874.

Lam, K. S. (1997) *Application of Combinatorial Library Methods in Cancer Research an Drug Discovery*. Anti-Cancer Drug Design, 12(3), 145-167.

Lawrence, D. S. & Niu, J. (1998) *Protein Kinase Inhibitors: The Tyrosine-Specific Protein Kinases*. Pharmacol. Ther., 77(2), 81-114.

Levitzki, A. (1996a) *Targeting signal transduction for disease therapy*. Current Opinion in Cell Biology, 8, 239-244.

Levitzki, A. (1996b) *SRC as a target for anti-cancer drugs*. Anti-Cancer Drug Design, 11, 175-182.

Levitzki, A.; Gazit, A. (1995) *Tyrosine Kinase Inhibition: An Approach to Drug Development*. Science, 267, 1782-1788.

Li, H., Liu, T. F., Lazrak, A., Peracchia, C., Goldberg, G. S., Lampe, P. D., Johnson, R. G. (1996) *Properties and regulation of gap junctional hemichannels in the plasma membranes of cultured cells*. J. Cell. Biol., 134, 1019-1030.

Loomis, W. D. & Durst, R. W. (1992) *Chemistry and biology of boron*. BioFactors, 3, 229-239.

Lou, Q., Leftwich, M. E., McKay, T., Salmon, S. E., Rychetsky, L. & Lam, K. S. (1997) *Potent Pseudosubstrate-based Peptide Inhibitors for p60$^{c\text{-}src}$ Protein Tyrosine Kinase*. Cancer Research, 57(10), 1877-1881.

Lou, Q., Leftwich, M. E. & Lam, K. S. (1996) *Identification of GIYWHHY as a Novel Peptide Substrate for Human p60c-src Protein Tyrosine Kinase*. Biorganic & Medicinal Chemistry, 4, 677-682. (SEQ. ID. No. 7).

Luttrell, D. K.; Lee, A.; Lansing, T. J.; Crosby, R. M.; Jung, K. D.; Willard, D.; Luther, M.; Rodriguez, M.; Berman, J.; Gilmer, T. M. (1994) *Involvement of pp60$^{c\text{-}src}$ with two major signaling pathways in human breast cancer*. Proc. Natl. Acad. Sci. USA, 91, 83-87.

Lynch, S. A.; Brugge, J. S.; Fromowitz, F.; Glantz, L.; Wang, P.; Caruso, R.; Viola, M. V. (1993) *Increased expression of the src proto-oncogene in hairy cell leukemia and a subgroup of B-cell lymphomas*. Leukemia, 7, 1416-1422.

Madhusudan, Trafny, E. A., Xuong, N-H, Adams, J. A., Ten Eyck, L. F., Taylor, S. S. & Sowadski, J. M. (1994) *cAMP-dependent protein kinase: Crystallographic insights into substrate recognition and phosphotransfer*. Protein Science, 3, 176-187.

Mao, W. G., Irby, R., Coppola, D., Fu, L., Turner, J. (1997) *Activation of c-src by receptor tyrosine kinases in human colon cancer cells with high metastatic potential*. Oncogene, 15, 3083-3090.

Marsilje, T. H., Milkiewicz, K. L., & Hangauer, D. L. (2000) *The design, synthesis and activity of non-ATP competitive inhibitors of pp60c-src tyrosine kinase 1. Hydroxynaphthalene Derivatives*. Bioorganic and Medicinal Chemistry Letters, in press.

Martin, G. S. (2001) *TIMELINE: The hunting of the Src*. Nat. Rev. Mol. Cell Biol., 2, 467-475.

Marx, J. (1990) *Oncogenes evoke new cancer therapies*. Science, 249, 1376-1378.

National Cancer Institute (1989) Survey of Compounds which have been tested for carcinogenic activity. NIH Publication No. 49-468, p. 16.

Matteson, D. S., Kandil, S. A., Soundararajan, R. (1990) *Synthesis of Asymmetrically Deuterated Glycerol and Dibenzylglyceraldehyde via Boronic Esters*. J. Am. Chem. Soc., 112, 3964-3969.

Matteson, D. S. (1988) Acc. Chem. Res., 21, 294-300.

Matteson, D. S., Kandil, A. A. (1987) *Conversion of α-halo boronic esters to inverted α-(methylsulfonyl)oxy boronic esters*. J. Org. Chem., 52, 5121-5124.

Matteson, D. S., Soloway, A. H., Tomlinson, D. W., Campbell, J. D., Nixon, G. A. (1964) J. Med. Chem., 7, 640.

Mazurenko, N. N.; Kogen, E. A.; Zborovskaya, I. B.; Kisseljov, F. L. (1992) *Expression of pp60$^{c-src}$ in human small cell and non-small cell lung carcinomas*. European J. of Cancer, 28, 372-377.

McCluskey, A.; Sim A. T. R.; Sakoff, J. A. (2002a) *Serine-Threonine Protein Phosphatase, Inhibitors: Development of Potential Therapeutic Strategies*. J. Medicinal Chem. 45(6), 1151-1175.

McCluskey, A.; Sakoff, J. A. (2001) *Small molecule inhibitors of serine/threonine protein phosphatases*. Mini-Reviews in Medicinal Chemistry. 1(1), 43-55.

McCluskey, A.; Sim A. T. R.; Sakoff, J. A. (2002b) *Serine-threonine protein phosphatase inhibitors: development of potential therapeutic strategies*. Journal of Medicinal Chemistry. 45(6), 1151-75.

Milkiewicz, K.; Marsilje, T.; Woodward Jr, R.; Bifulco Jr, N.; Hangauer, M.; Hangauer, D. G. (2000) *The design, synthesis and activity of non-ATP competitive inhibitors of pp60c-src tyrosine kinase 2. Hydroxyindole Derivatives*. Bioorganic and Medicinal Chemistry Letters, in press.

Mohammadi, M., Schlessinger, J., Hubbard, S. R. (1996) *Structure of the FGF Receptor Tyrosine Kinase Domain Reveals a Novel Autoinhibitory Mechanism*. Cell, 86, 577-587.

Mohammadi, M., McMahon, G., Li, S., Tang, C., Hirth, P., Yeh, B. K., Hubbard, S. R., Schlessinger, J. (1997) *Structures of the Tyrosine Kinase Domain of Fibroblast Growth Factor Receptor in Complex with Inhibitors*. Science, 276, 955-960.

Moller, N. P. H.; Inversen, L. F.; Andersen, H. S.; McCormack, J. G. (2000) *Protein tyrosine phosphatases (PTPs) as drug targets: inhibitors of PTP-1B for treatment of diabetes*. Current Opinion in Drug Discovery & Development. 3(5), 527-540.

Morin, C. (1994) *The Chemistry of Boron Analogues of Biomolecules*. Tetrahedron, 50, 12521-12569.

Murakami, Y., Otsuka, K. Wada, Y., Morikawa, A. (1990) *The partial oxidation of ethane over a $B_2O_3$-$Al_2O_3$ catalyst*. Bull. Chem. Soc. Jpn., 63, 340-346.

Nair, S. A., Kim, M. K., Warren, S. D., Choi, S., Songyang, Z., Cantley, L. C. & Hangauer, D. G. (1995). *Identification of Efficient Pentapeptide Substrates for the Tyrosine Kinase pp60$^{c-src}$*. J. Med. Chem., 38, 4276-4283.

Nair, S. A., Lee, B. & Hangauer, D. G. (1995b). *Synthesis of Orthogonally Protected L-Homocysteine and L-2-Amino-4-phosphonobutanoic Acid From L-Homoserine*. Synthesis, 7, 810-814.

Nielsen, F. H. (1997) *Boron in human and animal nutrition*. Plant & Soil, 193, 199-208.

Otsuka, K., Uragami, Y., Hatano, M. (1992) *The partial oxidation of ethane to acetaldehyde*. Catalysis Today, 13, 667-672.

Park, B. K, Kitteringham, N. R., O'Neill, P. M. (2001) *Metabolism of Fluorine-Containing Drugs*. Ann. Rev. Pharmacol. Toxicol., 41, 443-470.

Parsons, J. T. & Parsons, S. J. (1997) *Src family protein tyrosine kinases: cooperating with growth factor and adhesion signaling pathways*. Current Opinion in Cell Biology, 9, 187-192.

Patrick, D. R. & Heimbrook, D. C. (1996) *Protein Kinase Inhibitors For The Treatment of Cancer*. Drug Discovery Today, 1, 325-330.

Pavia, M. R., Cohen, M. P., Dilley, G. J., Dubuc, G. R., Durgin, T. L., Forman, F. W., Hediger, M. E., Milot, G., Powers, T. S., Sucholeiki, I., Zhou, S. & Hangauer, D. G. (1996) *The Design and Synthesis of Substituted Biphenyl Libraries*. Biorganic & Medicinal Chemistry, 4, 659-666.

Pestell, K. E.; Ducruet, A. P.; Wipf, P.; Lazo, J. S. (2000) *Small molecule inhibitors of dual specificity protein phosphatases*. Oncogene, 19(56), 6607-6612.

Posner, I., Engel, M., Gazit, A. & Levitzki, A. (1994) *Kinetics of Inhibition by Tyrphostins of the Tyrosine Kinase Activity of the Epidermal Growth Factor Receptor and Analysis by a New Computer Program*. Molecular Pharmacology, 45, 673-683.

Powis, G. (1991) *Signal targets for anticancer drug development*. TIPS, 188-194.

Ramdas, L., Obeyesekere, N. U., McMurray, J. S., Gallick, G. E., Seifert, W. E. Jr. & Budde, R. J. (1995) *A tyrphostin-derived inhibitor of protein tyrosine kinases: isolation and characterization*. Archives of Biochemistry & Biophysics, 323, 237-242.

Ramdas, L., McMurray, J. S. & Budde, R. J. (1994) *The degree of inhibition of protein tyrosine kinase activity by tyrphostin 23 and 25 is related to their instability*. Cancer Research, 54, 867-869.

Rewcastle, G. W., Palmer, B. D., Thompson, A. M., Bridges, A. J., Cody, D. R., Zhou, H. Fry, D. W., McMichael, A. & Denny, W. A. (1996) *Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor*. J. Med. Chem., 39, 1823-1835.

Ripka, W. C. (2000) *Protein tyrosine phosphatase inhibition*. Annual Reports in Medicinal Chemistry. 35, 231-250.

Rudd, C. E.; Janssen, O.; Prasad, K. V. S.; Raab, M.; da Silva, A.; Telfer, J. C.; Yamamoto, M. (1993) *src-related protein tyrosine kinases and their surface receptors*. Biochimica et Biophysica Acta, 1155, 239-266.

Saperstein, R., Vicario, P. P., Strout, H. V., Brady, E., Slater, E. E., Greenlee, W. J., Ondeyka, D. L., Patchett, A. A. & Hangauer, D. G. (1989) *Design of a selective insulin receptor tyrosine kinase inhibitor and its effect on glucose uptake and metabolism in intact cells*. Biochemistry, 28, 5694-5701.

Sawyer, T.; Boyce, B.; Dalgarno, D.; Iulicci, J. (2001) *Src inhibitors: genomics to therapeutics*. Expert Opin. Investg. Drugs 10(7), 1327-1344.

Sawutz, D. G.; Bode, D. C.; Briggs, G. M.; Reid, J. R.; Canniff, P.; Caldwell, L.; Faltynek, C. R.; Miller, D.; Dunn, J. A.; Garavilla, L.; Guiles, J. W.; Weigelt, C.; Michne, W.; Treasurywala, A. M.; Silver, P. J. (1996) Biochem. Pharmacol. 51, 1631.

Schlessinger, J. (2000) *New roles for Src kinases in control of cell survival and angiogenesis*. Cell 100, 293-296.

Schwartzberg, P. L., et al. (1997) *Rescue of osteoclast function by transgenic expression of kinase-deficient Src in src−/− mutant mice*. Genes & Development 11: 2835-2844.

Sedlacek, H. H. (2000) *Kinase inhibitors in cancer therapy*. Drug, 59(3), 435-476.

Shiraishi, T., Owada, M. K., Tatsuka, M., Yamashita, T., Watanabe, K., Kakunaga, T. (1989) *Specific Inhibitors of Tyrosine-specific Protein Kinases: Properties of 4-hydroxycinnamamide derivatives in vitro*. Cancer Research, 49, 2374-2378.

Showalter, H. H. & Kraker, A. J. (1997) *Small molecule inhibitors of the platelet-derived growth factor receptor, the fibroblast growth factor receptor, and src family tyrosine kinases*. Pharmacology & Therapeutics, 76, 55-71.

Sicheri, F., Moarefi, I. & Kuriyan, J. (1997) *Crystal structure of the Src family tyrosine kinase Hck*. Nature, 385, 602-609.

Skordalakes, E., Tyrell, R., Elgendy, S., Goodwin, C. A., Green, D., Dodson, G., Scully, M. F., Freyssinet, J-M. H., Kakkar, V. V., Deadman, J. J. (1997) *Crystallographic Structures of Human α-Thrombin Complexed to Peptide Boronic Acids Lacking a Positive Charge at $P_1$. Evidence of Novel Interactions*. J. Am. Chem. Soc., 119, 9935-9936.

Snyder, H. R., Kuck, J. A., Johnson, J. R. (1938) J. Am. Chem. Soc., 60, 105.

Soloway, A. H., Whitman, B., Messer, J. R. (1962) J. Med. Pharm. Chem., 7, 640.

Soloway, A. H., Whitman, B., Messer, J. R. (1960) J. Pharmacology and Experimental Therapeutics, 129, 310-314.

Soloway, A. H. (1958) Science, 128, 1572.

Songyang, Z, Blechner, S., Hoagland, N., Hoekstra, M. F., Piwnica-Worms, H. & Cantley, L. C. (1994) *Use of an oriented peptide library to determine the optimal substrates of protein kinases*. Current Biology, 4, 973-982.

Songyang, Z., Carraway III, K. L., Eck, M. J., Harrison, S. C., Feldman, R. A., Mohammadl, M., Schlessinger, J., Hubbard, S. R., Smith, D. P., Eng. C., Lorenzo, J. J., Ponder, B. A. J., Mayer, B. J. & Cantley, L. C. (1995) *Protein tyrosine kinases and SH2 domains have overlapping specificities*. Nature, 373, 536-539.

Sridhar, R.; Hanson-Painton, O.; Cooper, D. R. (2000) *Protein kinases as therapeutic targets*. Pharmaceutical Research 17(11), 1345-1353.

Staley, C. A.; Parikh, N. U.; Gallick, G. E. (1997) *Cell Growth & Differentiation* 8(3), 269.

Stanwell, C., Burke, T. R. & Yuspa, S. H. (1995) *Erbstatin Analogue Methyl 2,5-dihydrocinnamate Cross-links Proteins and is Cytotoxic to Normal and Neoplastic Epithelial Cells by a Mechanism Independent of Tyrosine Kinase Inhibition*. Cancer Research, 55, 4950-4956.

Stanwell, C., Ye, B. & Burke, T. R. (1996) *Cell Protein Cross-linking by Erbstatin and Related Compounds*. Biochemical Pharmacology, 52, 475-480.

Susa, M., Teti, A. (2000) *Tyrosine kinase Src inhibitors: Potential Therapeutic Applications*. Drug News Perspect. 13(3), 169-175.

Susa, M., Missbach, M.; Green, J. (2000) *Src inhibitors: drugs for the treatment of osteoporosis, cancer of both*? TIPS 21, 489-495.

Takeshima, E.; Hamaguchi, M.; Watanbe, T.; Akiyama, S.; Kataoka, M.; Ohnishi, Y.; Xiao, H.; Hagai, Y., Taka, H. (1991) *Aberrant elevation of tyrosine-specific phosphorylation in human gastric cancer cells*. Japan J. Cancer Res., 82, 1428-1435.

Talamonti, M. S.; Roh, M. S.; Curley, S. A.; Gallick, G. E. (1993) *Increase in activity and level of $pp60^{c-src}$ in progressive stages of human colorectal cancer*. J. of Clinical Investigation, 91, 53-60.

Taniyama, K., Fujiwara, H., Kuno, T., Saito, N., Shuntoh, H., Sakaue, M. (1989) *Acute and subacute toxicity of 10B-paraboronophenylalanine*. Pigment Cell Research, 2, 291-296.

Taylor, S. J., Shalloway, D. (1996) *Src and the control of cell division*. Bioessays, 18, 9-11.

Taylor, S. S., Knighton, D. R., Zheng, J., Sowadski, J. M., Gibbs, C. S. & Zoller, M. J. (1993) *A template for the protein kinase family*. Trends in Biochemical Sciences, 18(3), 84-9.

Taylor, S. S., Radzio-Andzelm, E. (1994) *Three protein kinase structures define a common motif*. Structure, 2, 345-355.

Thakkar, K., Geahlen, R. L., Cushman, M. (1993) *Synthesis and protein-tyrosine kinase inhibitory activity of polyhydroxylated stilbene analogs of piceatannol*. J. Med. Chem., 36, 2950-2955.

Weinberg, R. A. (1989) *Oncogenes, antioncogenes, and the molecular basis of multistep carcinogenesis*. Cancer Research, 49, 3713-3721.

Wolfe, J. P., Ahman, J., Sadighi, J. P., Singer, R. A., Buchwald, S. L. (1997) *An ammonia equivalent for the palladium-catalyzed amination of aryl halides and triflates*. Tet. Lett., 38, 6367-6370.

Wong, T. W. & Goldberg, A. R. (1984) *Kinetics and mechanism of angiotensin phosphorylation by the transforming gene product of Rous Sarcoma Virus*. J. Biol. Chem., 259, 3127-3131.

Xu, W., Harrison, S. C. & Eck, M. J. (1997) *Three-dimensional structure of the tyrosine kinase c-Src*. Nature, 385, 595-602.

Yamaguchi, H. & Hendrickson, W. A. (1996) *Structural basis for activation of human lymphocyte kinase Lck upon tyrosine phosphorylation*. Nature, 384, 484-489.

Yamamoto, T. (1993) *Molecular Basis of Cancer: Oncogenes and Tumor Suppresor Genes*. Microbiol. Immunol. 37, 11-22.

Zhang, Z. Y. (2002a) *Protein tyrosine phosphatases: structure and function, substrate specificity, and inhibitor development*. Annual Review of Pharmacology and Toxicology, 42, 209-234.

Zhang, Z. Y. (2002b) *Protein tyrosine phosphatases: prospects for therapeutics*. Current Opinion in Chemical Biology. 5(4), 416-423.

Zhanpeisov, N. U., Otsuka, K. (1992) *Cluster quantum chemical study of the mechanism of selective oxidation of ethane to acetaldehyde on boron-phosphorous mixed oxide catalysts*. React. Kinet. Catal. Lett., 48, 301-308.

Zheng, J., Knighton, D. R., Ten Eyck, L. R., Karlsson, R., Xuong, N-H., Taylor, S. S. & Sowadski, J. M. (1993) *Crystal structure of the catalytic subunit of cAMP-dependent protein kinase complexed with MgATP and peptide inhibitor.* Biochemistry, 32, 2154-61.

Zhong-Yin, Shang (2002) *Protein tyrosine phosphatases: structure and function, substrate specificity, and inhibitor development.* Annual Review of Pharmacology and Toxicology 42, 209-234.

What is claimed is:

1. A method of relieving osteoporosis in a subject comprising administering a compound of Formula VII:

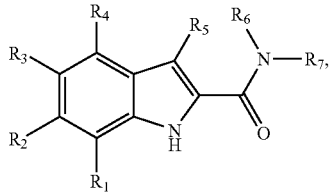

(Formula VII)

or a salt or prodrug thereof, wherein $R_1$, $R_2$, $R_3$, $R_4$, and $R_5$ are the same or different and are independently H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, P, halogen, aryl, benzyl, heteroaryl, biaryl, heterobiaryl, heterocycle, or branched, unbranched, or cyclic alkyl;

one of $R_6$ or $R_7$ is $(CH_2)_t$—Z and the remaining $R_6$ or $R_7$ is H;

Z is aryl, heteroaryl, or biaryl;

t is 1;

$R_a$, $R_b$, and $R_c$ are the same or different and are independently H, aryl, heteroaryl, biaryl, heterobiaryl, or branched, unbranched, or cyclic alkyl;

P is $SO_3H$, $OSO_3H$, $OPO_3H_2$, $OPO_3H_2$, O-lower ($C_1$, $C_2$, $C_3$, $C_4$, $C_5$, or $C_6$) alkyl-K, O—C(O)-lower ($C_1$, $C_2$, $C_3$, $C_4$, $C_5$, or $C_6$) alkyl-L, NH-lower ($C_1$, $C_2$, $C_3$, $C_4$, $C_5$, or $C_6$) alkyl-M, or O-aryl-Q, further wherein lower ($C_1$, $C_2$, $C_3$, $C_4$, $C_5$, or $C_6$) alkyl is linear or branched alkyl;

K is $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

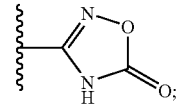

L is aryl, OH, $C(O)NH_2$, COOH, $SO_3H$, $OSO_3H$, $PO_3H_2$, $OPO_3H_2$, $NH_2$, $NHR_{19}$, $NR_{19}R_{20}$, $SO_2R_{21}$, glycoside, lower $C_1$, $C_2$, $C_3$, $C_4$, $C_5$, $C_6$ alkoxy, or

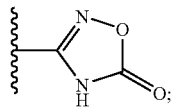

M is aryl, OH, C(O)NH$_2$, COOH, SO$_3$H, OSO$_3$H, PO$_3$H$_2$, OPO$_3$H$_2$, NH$_2$, NHR$_{19}$,
NR$_{19}$R$_{20}$, SO$_2$R$_{21}$, glycoside, lower C$_1$, C$_2$, C$_3$, C$_4$, C$_5$, C$_6$ alkoxy, or

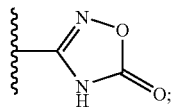

Q is aryl, OH, C(O)NH$_2$, COOH, SO$_3$H, OSO$_3$H, PO$_3$H$_2$, OPO$_3$H$_2$, NH$_2$, NHR$_{19}$,
NR$_{19}$R$_{20}$, SO$_2$R$_{21}$, glycoside, lower C$_1$, C$_2$, C$_3$, C$_4$, C$_5$, C$_6$ alkoxy, or

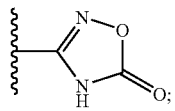

R$_{19}$, R$_{20}$ and R$_{21}$ are independently C$_1$, C$_2$, C$_3$, C$_4$, C$_5$, or C$_6$ alkyl or R$_{19}$ and R$_{20}$ taken together with the attached nitrogen atom form a five membered ring;
wherein any of R$_1$, R$_2$, R$_3$, R$_4$, R$_5$, R$_6$, R$_7$R$_a$, R$_b$, and R$_c$ is substituted or unsubstituted.

2. The method of claim 1, wherein the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes.

3. The method of claim 1, wherein at least one of R$_1$, R$_2$, R$_3$, R$_4$, or R$_5$ is halogen.

4. The method of claim 1, wherein R$_3$ is halogen.

5. The method of claim 4, wherein R$_3$ is fluorine.

6. The method of claim 1, wherein Z is optionally substituted aryl or heteroaryl.

7. The method of claim 6, wherein Z is phenyl.

8. The method of claim 6, wherein aryl is substituted with alkoxy, hydroxyl, halogen, aldehyde, O-benzyl, trifluoromethyl, alkylhydroxy, nitro, —OCF$_3$, or alkoxycarbonyloxy.

9. The method of claim 1, wherein R$_2$ and R$_4$ are each H.

10. The method of claim 1, wherein R$_5$ is H.

11. The method of claim 1, wherein R$_1$ is optionally substituted aryl.

12. The method of claim 11, wherein R$_1$ is phenyl or phenyl substituted with halogen, alkoxy, ethyl, hydroxyl, or alkylhydroxy.

13. The method of claim 11, wherein R$_3$ is fluorine.

14. The method of claim 13, wherein Z is phenyl substituted with fluorine.

15. The method of claim 1, wherein the subject is a human.

16. A method of relieving osteoporosis in a subject comprising administering a compound selected from:

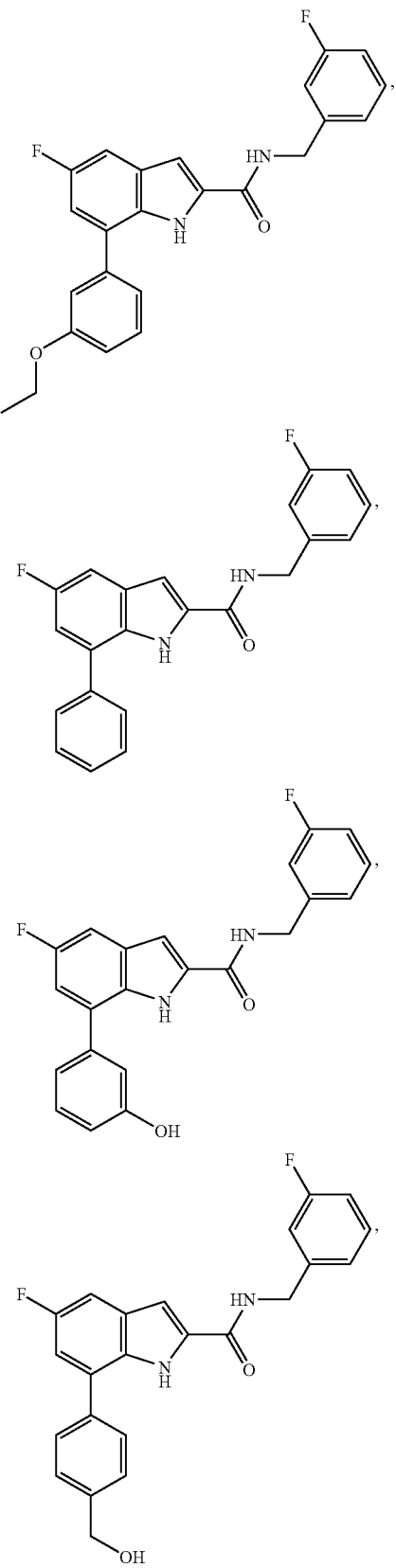

or a salt or prodrug thereof.

17. The method of claim 16, wherein the subject is a human.

18. A method of relieving osteoporosis in a subject comprising administering a compound of the formula:

wherein
- $R_1$ is phenyl or phenyl substituted with halogen, alkoxy, ethyl, hydroxyl, or alkylhydroxy;
- $R_2$, $R_3$, $R_4$, and $R_5$ are the same or different and are independently H, C(O)$R_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$—, P(O)OR$_a$OR$_b$, halogen, or branched, unbranched, or cyclic alkyl;
- $R_a$, $R_b$, and $R_c$ are the same or different and are independently H, aryl, heteroaryl, biaryl, heterobiaryl, or branched, unbranched, or cyclic alkyl;
- Z is phenyl or phenyl substituted with alkoxy, hydroxyl, halogen, aldehyde, O-benzyl, trifluoromethyl, alkylhydroxy, nitro, —OCF$_3$, or alkoxycarbonyloxy.

* * * * *

```
                         SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:  src
      substrate pentapeptide

<400> SEQUENCE: 1

Ile Tyr Gly Glu Phe
 1               5

<210> SEQ ID NO 2
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: Xaa in position 4 is modified Ala or modified
      Ala.
<220> FEATURE:
<223> OTHER INFORMATION: Description of Artificial Sequence: PKA
      pentapeptide scaffold

<400> SEQUENCE: 2

Arg Arg Gly Xaa Ile
 1               5

<210> SEQ ID NO 3
<211> LENGTH: 5
<212> TYPE: PRT
<213> ORGANISM: Artificial Sequence
<220> FEATURE:
<221> NAME/KEY: PEPTIDE
<222> LOCATION: (2)
<223> OTHER INFORMATION: Xaa in position 2 is modifed Tyr.
<220> FEATURE:
<223> OTHER INFORMATION: Description of Artificial Sequence:  src
      pentapeptide scaffold

<400> SEQUENCE: 3

Ile Xaa Gly Glu Phe
 1               5

<210> SEQ ID NO 4
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: Xaa in position 4 is Ala or modified Ala.
<220> FEATURE:
<223> OTHER INFORMATION: Description of Artificial Sequence: Boronic
      acid-containing PKA inhibitor

<400> SEQUENCE: 4

Arg Arg Gly Xaa Ile
 1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Kemptamide

<400> SEQUENCE: 5

Leu Arg Arg Ala Ser Leu Gly
 1               5

<210> SEQ ID NO 6
<211> LENGTH: 7
<212> TYPE: PRT
<213> ORGANISM: Artificial Sequence
<220> FEATURE:
<221> NAME/KEY: MOD_RES
<222> LOCATION: (5)
<223> OTHER INFORMATION: Xaa in position 5 is ALA; PHOSPHORYLATION
<220> FEATURE:
<223> OTHER INFORMATION: Description of Artificial Sequence:
      Phosphorylated Kemptamide

<400> SEQUENCE: 6

Leu Arg Arg Ala Xaa Leu Gly
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Peptide
      substrate for Src

<400> SEQUENCE: 7

Gly Ile Tyr Trp His His Tyr
 1               5
```